(12) United States Patent
Olsen et al.

(10) Patent No.: US 10,106,532 B2
(45) Date of Patent: Oct. 23, 2018

(54) INHIBITORS OF BETA-HYDROXYLASE FOR TREATMENT OF CANCER

(71) Applicant: MIDWESTERN UNIVERSITY, Downers Grove, IL (US)

(72) Inventors: Mark Jon Olsen, Phoenix, AZ (US); John Michael Thomas, Glendale, AZ (US)

(73) Assignee: Midwestern University, Downers Grove, IL (US)

(*) Notice: Subject to any disclaimer, the term of this patent is extended or adjusted under 35 U.S.C. 154(b) by 0 days.

(21) Appl. No.: 15/651,842

(22) Filed: Jul. 17, 2017

(65) Prior Publication Data

US 2018/0009798 A1    Jan. 11, 2018

Related U.S. Application Data

(62) Division of application No. 14/430,101, filed as application No. PCT/US2013/061050 on Sep. 20, 2013, now Pat. No. 9,771,356.

(60) Provisional application No. 61/704,014, filed on Sep. 21, 2012.

(51) Int. Cl.

| | |
|---|---|
| *C07D 307/26* | (2006.01) |
| *C07D 405/04* | (2006.01) |
| *C07D 417/04* | (2006.01) |
| *C12Q 1/26* | (2006.01) |
| *C07D 409/04* | (2006.01) |
| *C07D 405/12* | (2006.01) |
| *C07D 307/32* | (2006.01) |
| *C07D 307/66* | (2006.01) |

(52) U.S. Cl.
CPC ......... *C07D 417/04* (2013.01); *C07D 307/32* (2013.01); *C07D 307/66* (2013.01); *C07D 405/04* (2013.01); *C07D 405/12* (2013.01); *C07D 409/04* (2013.01); *C12Q 1/26* (2013.01)

(58) Field of Classification Search
CPC ........................... C07D 307/26; C07D 405/04
See application file for complete search history.

*Primary Examiner* — Bruck Kifle
(74) *Attorney, Agent, or Firm* — Reed Smith LLP

(57) ABSTRACT

The present invention relates to compounds which modulate (e.g., inhibit) the activity of beta-hydrolase (e.g., ASPH), including novel 2-aryl-5-amino-3(2H)-furanone and 2-heteroaryl-5-amino-3(2H)-furanone compounds, pharmaceutical compositions thereof, methods for their synthesis, and methods of using these compounds to modulate the activity of ASPH in an a cell-free sample, a cell-based assay, and in a subject. Other aspects of the invention relate to use of the compounds disclosed herein to ameliorate or treat cell proliferation disorders.

11 Claims, 11 Drawing Sheets
Specification includes a Sequence Listing.

*; $p<0.05$

FIG. 9A
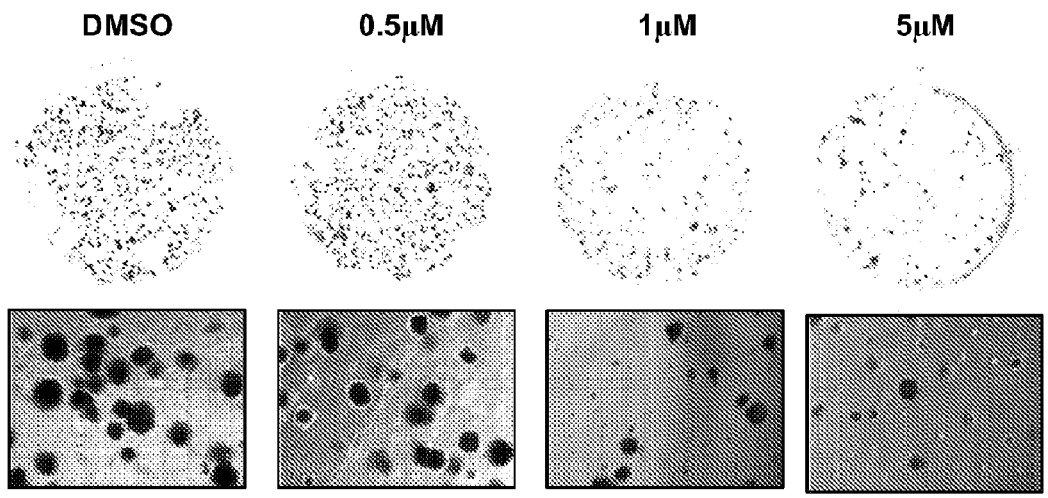
FIG. 9B
FIG. 9C
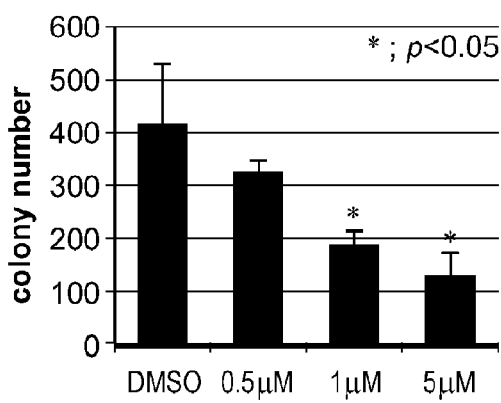
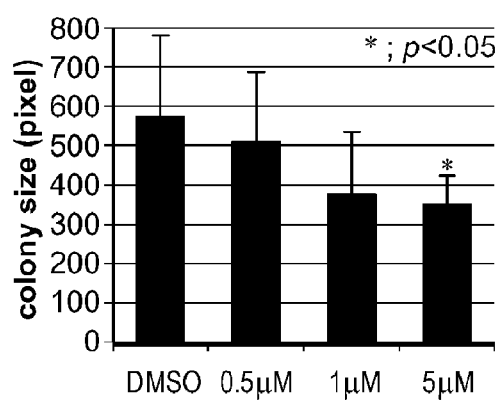
FIG. 10A
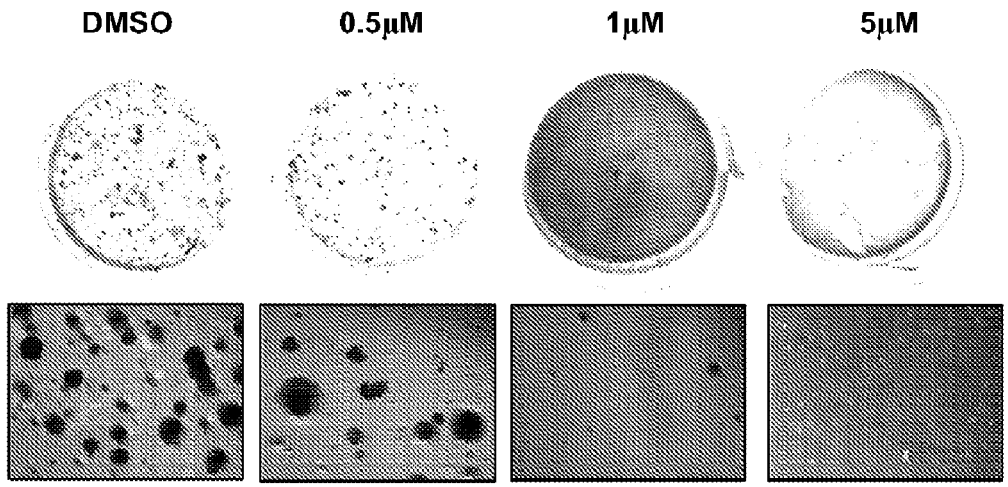

SEQUENCE LISTING

```
<160> NUMBER OF SEQ ID NOS: 4

<210> SEQ ID NO 1
<211> LENGTH: 39
<212> TYPE: PRT
<213> ORGANISM: Homo sapiens

<400> SEQUENCE: 1

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Glu Gly Phe Glu
            20                  25                  30

Gly Lys Asn Cys Glu Leu Phe
        35

<210> SEQ ID NO 2
<211> LENGTH: 31
<212> TYPE: PRT
<213> ORGANISM: Artificial Sequence
<220> FEATURE:
<223> OTHER INFORMATION: Artificial Sequence with EGF-like domain
      comprising a consensus sequence
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 2
```

```
Cys Asp Xaa Xaa Xaa Cys Xaa Xaa Lys Xaa Gly Asn Gly Xaa Cys Asp
 1               5                  10                  15

Xaa Xaa Cys Asn Asn Ala Ala Cys Xaa Xaa Asp Gly Xaa Asp Cys
            20                  25                  30

<210> SEQ ID NO 3
<211> LENGTH: 2324
<212> TYPE: DNA
<213> ORGANISM: Homo sapiens
<220> FEATURE:
<221> NAME/KEY: CDS
<222> LOCATION: (12)..(2288)
<223> OTHER INFORMATION: GenBank Accession No S83325 encoding
      aspartyl(asparaginyl)beta-hydroxylase, HAAH; Protein ID
      AAB50779.1

<400> SEQUENCE: 3
```

| | | | | | | |
|---|---|---|---|---|---|---|
| cggaccgtgc a atg gcc cag cgt aag aat gcc aag agc agc ggc aac agc | | | | | | 50 |
| Met Ala Gln Arg Lys Asn Ala Lys Ser Ser Gly Asn Ser | | | | | | |
| 1               5                  10 | | | | | | |

```
agc agc agc ggc tcc ggc agc ggt agc acg agt gcg ggc agc agc agc      98
Ser Ser Ser Gly Ser Gly Ser Gly Ser Thr Ser Ala Gly Ser Ser Ser
         15                  20                  25 ccc ggg gcc cgg aga gag aca aag cat gga gga cac aag aat ggg agg     146
Pro Gly Ala Arg Arg Glu Thr Lys His Gly Gly His Lys Asn Gly Arg
 30                  35                  40                  45 aaa ggc gga ctc tcg gga act tca ttc ttc acg tgg ttt atg gtg att     194
Lys Gly Gly Leu Ser Gly Thr Ser Phe Phe Thr Trp Phe Met Val Ile
                     50                  55                  60 gca ttg ctg ggc gtc tgg aca tct gta gct gtc gtt tgg ttt gat ctt     242
Ala Leu Leu Gly Val Trp Thr Ser Val Ala Val Val Trp Phe Asp Leu
             65                  70                  75 gtt gac tat gag gaa gtt cta gga aaa cta gga atc tat gat gct gat     290
Val Asp Tyr Glu Glu Val Leu Gly Lys Leu Gly Ile Tyr Asp Ala Asp
         80                  85                  90 ggt gat gga gat ttt gat gtg gat gat gcc aaa gtt tta tta gga ctt     338
Gly Asp Gly Asp Phe Asp Val Asp Asp Ala Lys Val Leu Leu Gly Leu
 95                 100                 105 aaa gag aga tct act tca gag cca gca gtc ccg cca gaa gag gct gag     386
Lys Glu Arg Ser Thr Ser Glu Pro Ala Val Pro Pro Glu Glu Ala Glu
110                 115                 120                 125 cca cac act gag ccc gag gag cag gtt cct gtg gag gca gaa ccc cag     434
Pro His Thr Glu Pro Glu Glu Gln Val Pro Val Glu Ala Glu Pro Gln
                    130                 135                 140 aat atc gaa gat gaa gca aaa gaa caa att cag tcc ctt ctc cat gaa     482
Asn Ile Glu Asp Glu Ala Lys Glu Gln Ile Gln Ser Leu Leu His Glu
                145                 150                 155 atg gta cac gca gaa cat gtt gag gga gaa gac ttg caa caa gaa gat     530
Met Val His Ala Glu His Val Glu Gly Glu Asp Leu Gln Gln Glu Asp
            160                 165                 170 gga ccc aca gga gaa cca caa caa gag gat gat gag ttt ctt atg gcg     578
Gly Pro Thr Gly Glu Pro Gln Gln Glu Asp Asp Glu Phe Leu Met Ala
        175                 180                 185 act gat gta gat gat aga ttt gag acc ctg gaa cct gaa gta tct cat     626
Thr Asp Val Asp Asp Arg Phe Glu Thr Leu Glu Pro Glu Val Ser His
190                 195                 200                 205 gaa gaa acc gag cat agt tac cac gtg gaa gag aca gtt tca caa gac     674
Glu Glu Thr Glu His Ser Tyr His Val Glu Glu Thr Val Ser Gln Asp
                    210                 215                 220 tgt aat cag gat atg gaa gag atg atg tct gag cag gaa aat cca gat     722
Cys Asn Gln Asp Met Glu Glu Met Met Ser Glu Gln Glu Asn Pro Asp
                225                 230                 235
```

-continued

| | | |
|---|---|---|
| tcc agt gaa cca gta gta gaa gat gaa aga ttg cac cat gat aca gat<br>Ser Ser Glu Pro Val Val Glu Asp Glu Arg Leu His His Asp Thr Asp<br>       240                      245                       250 | 770 | |

```
tcc agt gaa cca gta gta gaa gat gaa aga ttg cac cat gat aca gat     770
Ser Ser Glu Pro Val Val Glu Asp Glu Arg Leu His His Asp Thr Asp
        240                 245                 250 gat gta aca tac caa gtc tat gag gaa caa gca gta tat gaa cct cta     818
Asp Val Thr Tyr Gln Val Tyr Glu Glu Gln Ala Val Tyr Glu Pro Leu
    255                 260                 265 gaa aat gaa ggg ata gaa atc aca gaa gta act gct ccc cct gag gat     866
Glu Asn Glu Gly Ile Glu Ile Thr Glu Val Thr Ala Pro Pro Glu Asp
270                 275                 280                 285 aat cct gta gaa gat tca cag gta att gta gaa gaa gta agc att ttt     914
Asn Pro Val Glu Asp Ser Gln Val Ile Val Glu Glu Val Ser Ile Phe
                290                 295                 300 cct gtg gaa gaa cag cag gaa gta cca cca gaa aca aat aga aaa aca     962
Pro Val Glu Glu Gln Gln Glu Val Pro Pro Glu Thr Asn Arg Lys Thr
            305                 310                 315 gat gat cca gaa caa aaa gca aaa gtt aag aaa aag aag cct aaa ctt    1010
Asp Asp Pro Glu Gln Lys Ala Lys Val Lys Lys Lys Lys Pro Lys Leu
        320                 325                 330 tta aat aaa ttt gat aag act att aaa gct gaa ctt gat gct gca gaa    1058
Leu Asn Lys Phe Asp Lys Thr Ile Lys Ala Glu Leu Asp Ala Ala Glu
    335                 340                 345 aaa ctc cgt aaa agg gga aaa att gag gaa gca gtg aat gca ttt aaa    1106
Lys Leu Arg Lys Arg Gly Lys Ile Glu Glu Ala Val Asn Ala Phe Lys
350                 355                 360                 365 gaa cta gta cgc aaa tac cct cag agt cca cga gca aga tat ggg aag    1154
Glu Leu Val Arg Lys Tyr Pro Gln Ser Pro Arg Ala Arg Tyr Gly Lys
                370                 375                 380 gcg cag tgt gag gat gat ttg gct gag aag agg aga agt aat gag gtg    1202
Ala Gln Cys Glu Asp Asp Leu Ala Glu Lys Arg Arg Ser Asn Glu Val
            385                 390                 395 cta cgt gga gcc atc gag acc tac caa gag gtg gcc agc cta cct gat    1250
Leu Arg Gly Ala Ile Glu Thr Tyr Gln Glu Val Ala Ser Leu Pro Asp
        400                 405                 410 gtc cct gca gac ctg ctg aag ctg agt ttg aag cgt cgc tca gac agg    1298
Val Pro Ala Asp Leu Leu Lys Leu Ser Leu Lys Arg Arg Ser Asp Arg
    415                 420                 425 caa caa ttt cta ggt cat atg aga ggt tcc ctg ctt acc ctg cag aga    1346
Gln Gln Phe Leu Gly His Met Arg Gly Ser Leu Leu Thr Leu Gln Arg
430                 435                 440                 445 tta gtt caa cta ttt ccc aat gat act tcc tta aaa aat gac ctt ggc    1394
Leu Val Gln Leu Phe Pro Asn Asp Thr Ser Leu Lys Asn Asp Leu Gly
                450                 455                 460 gtg gga tac ctc ttg ata gga gat aat gac aat gca aag aaa gtt tat    1442
Val Gly Tyr Leu Leu Ile Gly Asp Asn Asp Asn Ala Lys Lys Val Tyr
            465                 470                 475 gaa gag gtg ctg agt gtg aca cct aat gat ggc ttt gct aaa gtc cat    1490
Glu Glu Val Leu Ser Val Thr Pro Asn Asp Gly Phe Ala Lys Val His
        480                 485                 490 tat ggc ttc atc ctg aag gca cag aac aaa att gct gag agc atc cca    1538
Tyr Gly Phe Ile Leu Lys Ala Gln Asn Lys Ile Ala Glu Ser Ile Pro
    495                 500                 505 tat tta aag gaa gga ata gaa tcc gga gat cct ggc act gat gat ggg    1586
Tyr Leu Lys Glu Gly Ile Glu Ser Gly Asp Pro Gly Thr Asp Asp Gly
510                 515                 520                 525 aga ttt tat ttc cac ctg ggg gat gcc atg cag agg gtt ggg aac aaa    1634
Arg Phe Tyr Phe His Leu Gly Asp Ala Met Gln Arg Val Gly Asn Lys
                530                 535                 540 gag gca tat aag tgg tat gag ctt ggg cac aag aga gga cac ttt gca    1682
Glu Ala Tyr Lys Trp Tyr Glu Leu Gly His Lys Arg Gly His Phe Ala
```

```
                        545                 550                 555
tct gtc tgg caa cgc tca ctc tac aat gtg aat gga ctg aaa gca cag       1730
Ser Val Trp Gln Arg Ser Leu Tyr Asn Val Asn Gly Leu Lys Ala Gln
        560                 565                 570 cct tgg tgg acc cca aaa gaa acg ggc tac aca gag tta gta aag tct       1778
Pro Trp Trp Thr Pro Lys Glu Thr Gly Tyr Thr Glu Leu Val Lys Ser
575                 580                 585 tta gaa aga aac tgg aag tta atc cga gat gaa ggc ctt gca gtg atg       1826
Leu Glu Arg Asn Trp Lys Leu Ile Arg Asp Glu Gly Leu Ala Val Met
590                 595                 600                 605 gat aaa gcc aaa ggt ctc ttc ctg cct gag gat gaa aac ctg agg gaa       1874
Asp Lys Ala Lys Gly Leu Phe Leu Pro Glu Asp Glu Asn Leu Arg Glu
            610                 615                 620 aaa ggg gac tgg agc cag ttc acg ctg tgg cag caa gga aga aga aat       1922
Lys Gly Asp Trp Ser Gln Phe Thr Leu Trp Gln Gln Gly Arg Arg Asn
        625                 630                 635 gaa aat gcc tgc aaa gga gct cct aaa acc tgt acc tta cta gaa aag       1970
Glu Asn Ala Cys Lys Gly Ala Pro Lys Thr Cys Thr Leu Leu Glu Lys
            640                 645                 650 ttc ccc gag aca aca gga tgc aga aga gga cag atc aaa tat tcc atc       2018
Phe Pro Glu Thr Thr Gly Cys Arg Arg Gly Gln Ile Lys Tyr Ser Ile
655                 660                 665 atg cac ccc ggg act cac gtg tgg ccg cac aca ggg ccc aca aac tgc       2066
Met His Pro Gly Thr His Val Trp Pro His Thr Gly Pro Thr Asn Cys
670                 675                 680                 685 agg ctc cga atg cac ctg ggc ttg gtg att ccc aag gaa ggc tgc aag       2114
Arg Leu Arg Met His Leu Gly Leu Val Ile Pro Lys Glu Gly Cys Lys
            690                 695                 700 att cga tgt gcc aac gag acc agg acc tgg gag gaa ggc aag gtg ctc       2162
Ile Arg Cys Ala Asn Glu Thr Arg Thr Trp Glu Glu Gly Lys Val Leu
        705                 710                 715 atc ttt gat gac tcc ttt gag cac gag gta tgg cag gat gcc tca tct       2210
Ile Phe Asp Asp Ser Phe Glu His Glu Val Trp Gln Asp Ala Ser Ser
            720                 725                 730 ttc cgg ctg ata ttc atc gtg gat gtg tgg cat ccg gaa ctg aca cca       2258
Phe Arg Leu Ile Phe Ile Val Asp Val Trp His Pro Glu Leu Thr Pro
        735                 740                 745 cag cag aga cgc agc ctt cca gca att tag catgaattca tgcaagcttg         2308
Gln Gln Arg Arg Ser Leu Pro Ala Ile
750                 755 ggaaactctg gagaga                                                     2324

<210> SEQ ID NO 4
<211> LENGTH: 758
<212> TYPE: PRT
<213> ORGANISM: Homo sapiens

<400> SEQUENCE: 4

Met Ala Gln Arg Lys Asn Ala Lys Ser Ser Gly Asn Ser Ser Ser Ser
1               5                   10                  15

Gly Ser Gly Ser Gly Ser Thr Ser Ala Gly Ser Ser Ser Pro Gly Ala
            20                  25                  30

Arg Arg Glu Thr Lys His Gly Gly His Lys Asn Gly Arg Lys Gly Gly
        35                  40                  45

Leu Ser Gly Thr Ser Phe Phe Thr Trp Phe Met Val Ile Ala Leu Leu
    50                  55                  60

Gly Val Trp Thr Ser Val Ala Val Val Trp Phe Asp Leu Val Asp Tyr
65                  70                  75                  80
```

-continued

```
Glu Glu Val Leu Gly Lys Leu Gly Ile Tyr Asp Ala Asp Gly Asp Gly
                 85                  90                  95

Asp Phe Asp Val Asp Asp Ala Lys Val Leu Gly Leu Lys Glu Arg
            100                 105                 110

Ser Thr Ser Glu Pro Ala Val Pro Pro Glu Ala Glu Pro His Thr
        115                 120                 125

Glu Pro Glu Glu Gln Val Pro Val Glu Ala Glu Pro Gln Asn Ile Glu
    130                 135                 140

Asp Glu Ala Lys Glu Gln Ile Gln Ser Leu Leu His Glu Met Val His
145                 150                 155                 160

Ala Glu His Val Glu Gly Glu Asp Leu Gln Gln Glu Asp Gly Pro Thr
                165                 170                 175

Gly Glu Pro Gln Gln Glu Asp Asp Glu Phe Leu Met Ala Thr Asp Val
            180                 185                 190

Asp Asp Arg Phe Glu Thr Leu Glu Pro Glu Val Ser His Glu Glu Thr
        195                 200                 205

Glu His Ser Tyr His Val Glu Glu Thr Val Ser Gln Asp Cys Asn Gln
    210                 215                 220

Asp Met Glu Glu Met Met Ser Glu Gln Glu Asn Pro Asp Ser Ser Glu
225                 230                 235                 240

Pro Val Val Glu Asp Glu Arg Leu His His Asp Thr Asp Asp Val Thr
                245                 250                 255

Tyr Gln Val Tyr Glu Glu Gln Ala Val Tyr Glu Pro Leu Glu Asn Glu
            260                 265                 270

Gly Ile Glu Ile Thr Glu Val Thr Ala Pro Pro Glu Asp Asn Pro Val
        275                 280                 285

Glu Asp Ser Gln Val Ile Val Glu Glu Val Ser Ile Phe Pro Val Glu
    290                 295                 300

Glu Gln Gln Glu Val Pro Pro Glu Thr Asn Arg Lys Thr Asp Asp Pro
305                 310                 315                 320

Glu Gln Lys Ala Lys Val Lys Lys Lys Pro Lys Leu Leu Asn Lys
                325                 330                 335

Phe Asp Lys Thr Ile Lys Ala Glu Leu Asp Ala Ala Glu Lys Leu Arg
            340                 345                 350

Lys Arg Gly Lys Ile Glu Glu Ala Val Asn Ala Phe Lys Glu Leu Val
        355                 360                 365

Arg Lys Tyr Pro Gln Ser Pro Arg Ala Arg Tyr Gly Lys Ala Gln Cys
    370                 375                 380

Glu Asp Asp Leu Ala Glu Lys Arg Arg Ser Asn Glu Val Leu Arg Gly
385                 390                 395                 400

Ala Ile Glu Thr Tyr Gln Glu Val Ala Ser Leu Pro Asp Val Pro Ala
                405                 410                 415

Asp Leu Leu Lys Leu Ser Leu Lys Arg Arg Ser Asp Arg Gln Gln Phe
            420                 425                 430

Leu Gly His Met Arg Gly Ser Leu Leu Thr Leu Gln Arg Leu Val Gln
        435                 440                 445

Leu Phe Pro Asn Asp Thr Ser Leu Lys Asn Asp Leu Gly Val Gly Tyr
    450                 455                 460
```

| | | | | | | | | | | | | | | |
|---|---|---|---|---|---|---|---|---|---|---|---|---|---|---|
| Leu | Leu | Ile | Gly | Asp | Asn | Asp | Asn | Ala | Lys | Lys | Val | Tyr | Glu | Glu | Val |
| 465 | | | | 470 | | | | | 475 | | | | | 480 | |
| Leu | Ser | Val | Thr | Pro | Asn | Asp | Gly | Phe | Ala | Lys | Val | His | Tyr | Gly | Phe |
| | | | | 485 | | | | | 490 | | | | | 495 | |
| Ile | Leu | Lys | Ala | Gln | Asn | Lys | Ile | Ala | Glu | Ser | Ile | Pro | Tyr | Leu | Lys |
| | | | 500 | | | | | 505 | | | | | 510 | | |
| Glu | Gly | Ile | Glu | Ser | Gly | Asp | Pro | Gly | Thr | Asp | Asp | Gly | Arg | Phe | Tyr |
| | | 515 | | | | | 520 | | | | | 525 | | | |
| Phe | His | Leu | Gly | Asp | Ala | Met | Gln | Arg | Val | Gly | Asn | Lys | Glu | Ala | Tyr |
| | 530 | | | | | 535 | | | | | 540 | | | | |
| Lys | Trp | Tyr | Glu | Leu | Gly | His | Lys | Arg | Gly | His | Phe | Ala | Ser | Val | Trp |
| 545 | | | | | 550 | | | | | 555 | | | | | 560 |
| Gln | Arg | Ser | Leu | Tyr | Asn | Val | Asn | Gly | Leu | Lys | Ala | Gln | Pro | Trp | Trp |
| | | | | 565 | | | | | 570 | | | | | 575 | |
| Thr | Pro | Lys | Glu | Thr | Gly | Tyr | Thr | Glu | Leu | Val | Lys | Ser | Leu | Glu | Arg |
| | | | 580 | | | | | 585 | | | | | 590 | | |
| Asn | Trp | Lys | Leu | Ile | Arg | Asp | Glu | Gly | Leu | Ala | Val | Met | Asp | Lys | Ala |
| | | 595 | | | | | 600 | | | | | 605 | | | |
| Lys | Gly | Leu | Phe | Leu | Pro | Glu | Asp | Glu | Asn | Leu | Arg | Glu | Lys | Gly | Asp |
| | 610 | | | | | 615 | | | | | 620 | | | | |
| Trp | Ser | Gln | Phe | Thr | Leu | Trp | Gln | Gln | Gly | Arg | Arg | Asn | Glu | Asn | Ala |
| 625 | | | | | 630 | | | | | 635 | | | | | 640 |
| Cys | Lys | Gly | Ala | Pro | Lys | Thr | Cys | Thr | Leu | Leu | Glu | Lys | Phe | Pro | Glu |
| | | | | 645 | | | | | 650 | | | | | 655 | |
| Thr | Thr | Gly | Cys | Arg | Arg | Gly | Gln | Ile | Lys | Tyr | Ser | Ile | Met | His | Pro |
| | | | 660 | | | | | 665 | | | | | 670 | | |
| Gly | Thr | His | Val | Trp | Pro | His | Thr | Gly | Pro | Thr | Asn | Cys | Arg | Leu | Arg |
| | | 675 | | | | | 680 | | | | | 685 | | | |
| Met | His | Leu | Gly | Leu | Val | Ile | Pro | Lys | Glu | Gly | Cys | Lys | Ile | Arg | Cys |
| | 690 | | | | | 695 | | | | | 700 | | | | |
| Ala | Asn | Glu | Thr | Arg | Thr | Trp | Glu | Glu | Gly | Lys | Val | Leu | Ile | Phe | Asp |
| 705 | | | | | 710 | | | | | 715 | | | | | 720 |
| Asp | Ser | Phe | Glu | His | Glu | Val | Trp | Gln | Asp | Ala | Ser | Ser | Phe | Arg | Leu |
| | | | | 725 | | | | | 730 | | | | | 735 | |
| Ile | Phe | Ile | Val | Asp | Val | Trp | His | Pro | Glu | Leu | Thr | Pro | Gln | Gln | Arg |
| | | | 740 | | | | | 745 | | | | | 750 | | |
| Arg | Ser | Leu | Pro | Ala | Ile | | | | | | | | | | |
| | | | | 755 | | | | | | | | | | | |

INHIBITORS OF BETA-HYDROXYLASE FOR TREATMENT OF CANCER

RELATED APPLICATION

The present application is a divisional of U.S. patent application Ser. No. 14/430,101, now U.S. Pat. No. 9,771,356, filed Mar. 20, 2015 which is the United States national stage of International Application No. PCT/US2013/061050, filed Sep. 20, 2013, which claims priority to U.S. provisional application No. 61/704,014, which was filed on Sep. 21, 2012, all of which are incorporated herein by reference in their entirety.

FIELD OF THE INVENTION

The invention relates to cell proliferation disorders, such as cancer.

BACKGROUND OF THE INVENTION

Hepatocellular carcinoma (HCC) is the fifth most prevalent, and third most fatal type of cancer presently diagnosed in over a half-million people, and which is on the increase globally. Local treatments, which include surgical resection, liver transplantation and radiofrequency ablation, are considered as a first choice for the treatment of HCC. With improvement in these techniques, there has been progress on the early-stage therapy of HCC. Radiofrequency ablation has a demonstrated benefit for early-stage disease, and it can be performed in patients with impaired liver function due to cirrhosis. However, many HCC tumors have highly malignant phenotypes, which aggressively recur after local ablation even if they were discovered at an early stage and have a very poor prognosis. Sorafenib is the only drug having a proven modest clinical benefit and approval as a systemic therapy for HC. Therefore, development of a novel treatment approach for HCC and other Asparatyl (asparaginyl) β-hydroxylase (ASPH)-expressing solid tumors is urgently needed.

SUMMARY OF THE INVENTION

Described herein is a family of compounds that inhibits β-hydroxylase activity of ASPH, which is highly overexpressed in cancers of the liver, pancreas, stomach, colon, breast, prostate, lung, brain as well as many other tumor types. ASPH is necessary and sufficient to promote tumor cell migration, invasion, motility and distant metastatic spread both in vitro and in vivo. Administration of these small molecule inhibitors of β-hydroxylase enzymatic activity reduce tumor development and growth as well as distant metastatic spread to the liver and thus, useful as a drugs to treat a variety of deadly human tumors that overexpress ASPH. The invention encompasses compositions of matter of the small molecules, with and without pharmaceutically-acceptable excipients for administration to human and animal subjects as well as the use of the small molecules in the treatment of human malignancies. The compounds and methods prevent as well as slow the growth rate of established tumors and have low toxicity to normal cells.

In one aspect, this disclosure provides an ASPH inhibitory compound for use in a method of reducing proliferation, migration, invasion, or metastasis of a tumor cell in the treatment of cell proliferative disorder, comprising contacting said tumor cell with the ASPH inhibitory compound, wherein the ASPH inhibitory compound is of Formula Ia or Ib:

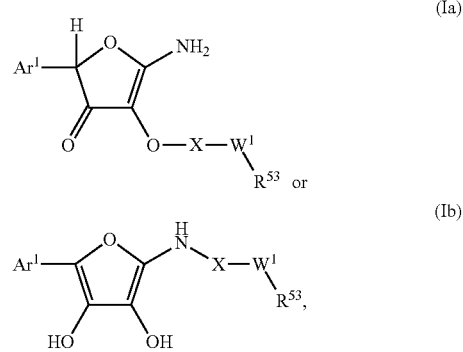

or a salt, ester, metabolite, prodrug, or solvate thereof, wherein $Ar^1$ is substituted or unsubstituted $C_6$-$C_{20}$ aryl or 5 to 20-membered heteroaryl;

X is C(O), C(S), or S(O)$_2$;

$W^1$ is a single bond, O, $CR^{50}R^{51}$, or $NR^{52}$ when X is CO and $W^1$ is a single bond, $CR^{50}R^{51}$, or $NR^{52}$ when X is SO$_2$; and each of $R^{50}$, $R^{51}$, $R^{52}$, and $R^{53}$ independently is selected from the group consisting of hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{20}$ aryl, substituted or unsubstituted $C_7$-$C_{26}$ arylalkyl, substituted or unsubstituted 5 to 20-membered heteroaryl, and substituted or unsubstituted 6-26 membered heteroarylalkyl.

In one embodiment, the compound for said use is of Formula Ia, or a salt, ester, metabolite, prodrug, or solvate thereof. The compound of Formula Ia may have one or more of the following features when applicable.

For example, the compound is of Formula IIa:

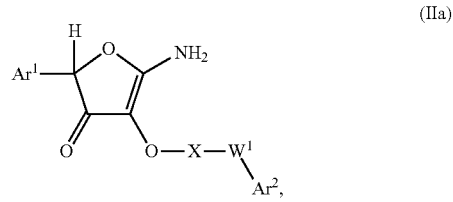

or a salt, ester, metabolite, prodrug, or solvate thereof, wherein each of $Ar^1$ and $Ar^2$ independently is unsubstituted $C_6$-$C_{14}$ aryl, unsubstituted 5 to 14-membered heteroaryl, or $C_6$-$C_{14}$ aryl or 5 to 14-membered heteroaryl each substituted with one or more substituents selected from the group consisting of halo, CN, NO$_2$, NO, N$_3$, OR$_a$, NR$_a$R$_b$, C(O)R$_a$, C(O)OR$_a$, C(O)NR$_a$R$_b$, NR$_b$C(O)R$_a$, —S(O)$_b$R$_a$, —S(O)$_b$NR$_a$R$_b$, or R$_{S1}$, in which R$_{S1}$ is $C_1$-$C_6$ alkyl, $C_2$-$C_6$ alkenyl, $C_2$-$C_6$ alkynyl, $C_1$-$C_8$ cycloalkyl, $C_6$-$C_{10}$ aryl, 5- or 6-membered heteroaryl, or 4 to 12-membered heterocycloalkyl, b is 0, 1, or 2, each of R$_a$ and R$_b$, independently is H or R$_{S2}$, and R$_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; and each of R$_{S1}$ and R$_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, $R^{53}$ is unsubstituted $C_1$-$C_6$ alkyl or $C_1$-$C_6$ alkyl substituted with one or more substituents selected from halo, OH, CN, and amino.

For example, X is $S(O)_2$ and $W^1$ is $CR^{50}R^{51}$.

For example, X is $S(O)_2$ and $W^1$ is a single bond.

For example, X is C(O) and $W^1$ is O, or X is C(S) and $W^1$ is $NR^{52}$.

For example, each of $R^{50}$, $R^{51}$, and $R^{52}$ independently is H, unsubstituted $C_1$-$C_6$ alkyl, or $C_1$-$C_6$ alkyl substituted with one or more substituents selected from halo, OH, CN, and amino.

For example, each of $Ar^1$ and $Ar^2$ independently is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, —$S(O)_bR_a$, —$S(O)_b NR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; and each of $R_{S1}$ and $R_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, each of $Ar^1$ and $Ar^2$ independently is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, or $R_{S1}$, in which $R_{S1}$ is $C_1$-$C_6$ alkyl, each of $R_a$ and $R_b$, independently is H or $R_{S2}$, and $R_{S2}$ is $C_1$-$C_6$ alkyl; and each of $R_{S1}$ and $R_{S2}$, is optionally substituted with one or more substituents selected from the group consisting of halo, OH, $C_1$-$C_6$ alkoxyl, amino, mono-$C_1$-$C_6$ alkylamino, and di-$C_1$-$C_6$ alkylamino.

For example, each of $Ar^1$ and $Ar^2$ independently is selected from phenyl, 1-naphthyl, 2-naphthyl, 2-furanyl, 2-thiazolyl, 2-pyridyl, 3-pyridyl, 4-pyridyl, 2-quinolinyl, 3-quinolinyl, 4-quinolinyl, 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-cyanophenyl, 3-cyanophenyl, 4-cyanophenyl, 3-carboxymethylphenyl, 2-methoxyphenyl, 3-methoxyphenyl, 4-methoxyphenyl, 2,3-dichlorophenyl, 2,4-dichlorophenyl, 2,5-dichlorophenyl, 3,4-dichlorophenyl, 3,5-dichlorophenyl, 2,3-difluorophenyl, 2,4-difluorophenyl, 2,5-difluorophenyl, 3,4-difluorophenyl, 3,5-difluorophenyl, 2,3-dimethoxyphenyl, 2,4-dimethoxyphenyl, 2,5-dimethoxyphenyl, 3,4-dimethoxyphenyl, 3,5-dimethoxyphenyl, 2-chloro-6-fluorophenyl, 3-chloro-4-fluorophenyl, 2-chloro-4-fluorophenyl, 4-chloro-3-fluorophenyl, 3-chloro-2-fluorophenyl, 2-chloro-5-fluorophenyl, 4-chloro-2-fluorophenyl, and 5-chloro-2-fluorophenyl.

In another embodiment, the compound for said use is of Formula Ib, or a salt, ester, metabolite, prodrug, or solvate thereof. The compound of Formula Ib may have one or more of the following features when applicable.

For example, $R^{53}$ is unsubstituted $C_1$-$C_6$ alkyl or $C_1$-$C_6$ alkyl substituted with one or more substituents selected from halo, OH, CN, and amino.

For example, $R^{53}$ is unsubstituted methyl or ethyl.

For example, X is $S(O)_2$ and $W^1$ is $CR^{50}R^{51}$.

For example, X is $S(O)_2$ and $W^1$ is a single bond.

For example, X is C(O) and $W^1$ is O, or X is C(S) and $W^1$ is $NR^{52}$.

For example, each of $R^{50}$, $R^{51}$, and $R^{52}$ independently is H, unsubstituted $C_1$-$C_6$ alkyl, or $C_1$-$C_6$ alkyl substituted with one or more substituents selected from halo, OH, CN, and amino.

For example, $Ar^1$ is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, —$S(O)_bR_a$, —$S(O)_b NR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; and each of $R_{S1}$ and $R_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, $Ar^1$ is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, or $R_{S1}$, in which $R_{S1}$ is $C_1$-$C_6$ alkyl, each of $R_a$ and $R_b$, independently is H or $R_{S2}$, and $R_{S2}$ is $C_1$-$C_6$ alkyl; and each of $R_{S1}$ and $R_{S2}$, is optionally substituted with one or more substituents selected from the group consisting of halo, OH, $C_1$-$C_6$ alkoxyl, amino, mono-$C_1$-$C_6$ alkylamino, and di-$C_1$-$C_6$ alkylamino.

For example, $Ar^1$ is selected from phenyl, 1-naphthyl, 2-naphthyl, 2-furanyl, 2-thiazolyl, 2-pyridyl, 3-pyridyl, 4-pyridyl, 2-quinolinyl, 3-quinolinyl, 4-quinolinyl, 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-cyanophenyl, 3-cyanophenyl, 4-cyanophenyl, 3-carboxymethylphenyl, 2-methoxyphenyl, 3-methoxyphenyl, 4-methoxyphenyl, 2,3-dichlorophenyl, 2,4-dichlorophenyl, 2,5-dichlorophenyl, 3,4-dichlorophenyl, 3,5-dichlorophenyl, 2,3-difluorophenyl, 2,4-difluorophenyl, 2,5-difluorophenyl, 3,4-difluorophenyl, 3,5-difluorophenyl, 2,3-dimethoxyphenyl, 2,4-dimethoxyphenyl, 2,5-dimethoxyphenyl, 3,4-dimethoxyphenyl, 3,5-dimethoxyphenyl, 2-chloro-6-fluorophenyl, 3-chloro-4-fluorophenyl, 2-chloro-4-fluorophenyl, 4-chloro-3-fluorophenyl, 3-chloro-2-fluorophenyl, 2-chloro-5-fluorophenyl, 4-chloro-2-fluorophenyl, and 5-chloro-2-fluorophenyl.

In one embodiment, said tumor cell expresses ASPH.

In certain embodiments, said cell proliferative disorder comprises Pancreatic Cancer, Hepatocellular Cancer, Cholangiocarcinoma, Lung cancer, Colon Cancer, Breast Cancer, Prostatic Cancer, and Glioblastoma.

In one embodiment, said compound is administered intravenously, orally, or subcutaneously.

In one embodiment, said compound is administered at a dose of 0.01 to 50 milligrams/kilogram of body weight.

In another aspect, this disclosure features a compound of Formula Ia:

(Ia)

or a salt, ester, metabolite, prodrug, or solvate thereof, wherein $Ar^1$ is substituted or unsubstituted $C_6$-$C_{20}$ aryl or 5 to 20-membered heteroaryl;

X is C(O), C(S), or $S(O)_2$;

$W^1$ is a single bond, O, $CR^{50}R^{51}$, or $NR^{52}$ when X is CO and $W^1$ is a single bond, $CR^{50}R^{51}$, or $NR^{52}$ when X is $SO_2$; and each of $R^{50}$, $R^{51}$, $R^{52}$, and $R^{53}$ independently is selected from the group consisting of hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{20}$ aryl, substituted or unsubstituted $C_7$-$C_{26}$ arylalkyl, substituted or unsubstituted 5 to 20-membered heteroaryl, and substituted or unsubstituted 6-26 membered heteroarylalkyl, provided that when $Ar^1$ is 4-chlorophenyl, X is C(O), and $W^1$ is a single bond, then $R^{53}$ is not unsubstituted methyl or unsubstituted phenyl.

The compound of Formula Ia may have one or more of the following features when applicable.

For example, the compound is of Formula IIa:

(IIa)

or a salt, ester, metabolite, prodrug, or solvate thereof, wherein each of $Ar^1$ and $Ar^2$ independently is unsubstituted $C_6$-$C_{14}$ aryl, unsubstituted 5 to 14-membered heteroaryl, or $C_6$-$C_{14}$ aryl or 5 to 14-membered heteroaryl each substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, $-S(O)_bR_a$, $-S(O)_bNR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; and each of $R_{S1}$ and $R_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, $R^{53}$ is unsubstituted $C_1$-$C_6$ alkyl or $C_1$-$C_6$ alkyl substituted with one or more substituents selected from halo, OH, CN, and amino.

For example, X is $S(O)_2$ and $W^1$ is $CR^{50}R^{51}$.

For example, X is $S(O)_2$ and $W^1$ is a single bond.

For example, X is C(O) and $W^1$ is O, or X is C(S) and $W^1$ is $NR^{52}$.

For example, each of $R^{50}$, $R^{51}$, and $R^{52}$ independently is H, unsubstituted $C_1$-$C_6$ alkyl, or $C_1$-$C_6$ alkyl substituted with one or more substituents selected from halo, OH, CN, and amino.

For example, each of $Ar^1$ and $Ar^2$ independently is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, $-S(O)_bR_a$, $-S(O)_bNR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; and each of $R_{S1}$ and $R_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, each of $Ar^1$ and $Ar^2$ independently is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, or $R_{S1}$, in which $R_{S1}$ is $C_1$-$C_6$ alkyl, each of $R_a$ and $R_b$, independently is H or $R_{S2}$, and $R_{S2}$ is $C_1$-$C_6$ alkyl; and each of $R_{S1}$ and $R_{S2}$, is optionally substituted with one or more substituents selected from the group consisting of halo, OH, $C_1$-$C_6$ alkoxyl, amino, mono-$C_1$-$C_6$ alkylamino, and di-$C_1$-$C_6$ alkylamino.

For example, each of $Ar^1$ and $Ar^2$ independently is selected from phenyl, 1-naphthyl, 2-naphthyl, 2-furanyl, 2-thiazolyl, 2-pyridyl, 3-pyridyl, 4-pyridyl, 2-quinolinyl, 3-quinolinyl, 4-quinolinyl, 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-cyanophenyl, 3-cyanophenyl, 4-cyanophenyl, 3-carboxymethylphenyl, 2-methoxyphenyl, 3-methoxyphenyl, 4-methoxyphenyl, 2,3-dichlorophenyl, 2,4-dichlorophenyl, 2,5-dichlorophenyl, 3,4-dichlorophenyl, 3,5-dichlorophenyl, 2,3-difluorophenyl, 2,4-difluorophenyl, 2,5-difluorophenyl, 3,4-difluorophenyl, 3,5-difluorophenyl, 2,3-dimethoxyphenyl, 2,4-dimethoxyphenyl, 2,5-dimethoxyphenyl, 3,4-dimethoxyphenyl, 3,5-dimethoxyphenyl, 2-chloro-6-fluorophenyl, 3-chloro-4-fluorophenyl, 2-chloro-4-fluorophenyl, 4-chloro-3-fluorophenyl, 3-chloro-2-fluorophenyl, 2-chloro-5-fluorophenyl, 4-chloro-2-fluorophenyl, and 5-chloro-2-fluorophenyl.

This disclosure also provides a pharmaceutical composition comprising a pharmaceutically acceptable carrier and a compound of Formula Ia or IIa, or a salt, ester, metabolite, prodrug, or solvate thereof.

In yet another aspect, the invention features a method of producing a compound of Formula IIa, wherein X is $S(O)_2$ and $W^1$ is $CR^{50}R^{51}$. The method includes: contacting an amine compound of the formula (IIIa)

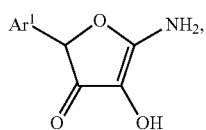

with a sulfonyl chloride of the formula $ClSO_2(CR^{50}R^{51})Ar^2$ under a suitable condition to produce a compound of Formula IIa.

Also provided in the present disclosure is method for treating or preventing a cell proliferative disorder, comprising administering to a subject in need thereof a therapeutically efficient amount of a compound described herein, such as those of Formula Ia or Ib, or a salt, ester, metabolite, prodrug, or solvate thereof described herein. In one embodiment, the compound is of Formula IIa or a salt, ester, metabolite, prodrug, or solvate thereof described herein. In another embodiment, the compound is of Formula Ib or a salt, ester, metabolite, prodrug, or solvate thereof described herein, wherein $R^{53}$ is unsubstituted $C_1$-$C_6$ alkyl or $C_1$-$C_6$ alkyl substituted with one or more substituents selected from halo, OH, CN, and amino.

In embodiments, the methods lead to at least a 10%, 20%, 50%, 2-fold, 5-fold, 10-fold or more reduction in tumor mass, volume, or weight compared to untreated tumors or untreated patients. In some cases, the tumor is completely eradicated. Similarly, the compounds inhibit metastasis, e.g., by inhibiting tumor cell migration or invasion, e.g., by at least 10%, 20%, 50%, 2-fold, 5-fold, 10-fold compared to untreated tumors or tumor cell metastasis in untreated patients.

The small molecule inhibitors are administered to subjects in need of treatment for a cell proliferative disease such as cancer in sufficient amounts of the compounds to reach blood concentrations varying between 0.1 and 100 micro molar. The compound is administered using standard regimens, e.g., daily, every other day, every third day, every fifth day or every seventh day. The compound is administered intravenously, orally, or subcutaneous. The amount given to reach the blood levels described above ranges from 0.01 to 50 milligrams/kilogram of body weight. The compositions and methods are suitable for treatment of subjects diagnosed as suffering from cancer, including those who have undergone another form of treatment for cancer, e.g., other chemotherapeutic agents, radiation, and surgery, and/or are diagnosed with metastatic disease or are at risk of developing metastasis. The mammal can be any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Also described is use of an ASPH inhibitory compound of this invention for the manufacture of a medicament for the use in reduction of proliferation, migration, invasion, or metastasis of a tumor cell in the treatment of cancer.

In yet another aspect, the disclosure provides a method determining ASPH activity by contacting an EGF-like domain peptide with a detectably-labeled α-ketoglutarate and ASPH enzyme and measuring β-hydroxylase activity. In one embodiment, said α-ketoglutarate is $^{14}C$-labelled, and wherein β-hydroxylase activity is measured by detecting liberated $^{14}CO_2$. In one embodiment, said liberated $^{14}CO_2$ is captured on a filter and radioactivity quantified. In one embodiment, the method further includes contacting said ASPH enzyme with a candidate compound, wherein a decrease in β-hydroxylase activity in the presence of said compound compared to the absence of said compound indicates that said compound inhibits ASPH enzyme activity. In one embodiment, said EGF-like domain comprises the amino acid sequence of DGDQCETSPCQNQGKCKDG-LGEYTCTCLEGFEGKNCELF (SEQ ID NO:1). In one embodiment, said EGF-like domain peptide comprises the consensus sequence of CDXXXCXXKXGNGXCDXXCN-NAACXXDGXDC (SEQ ID NO: 2).

Other features and advantages of the invention will be apparent from the following description of the preferred embodiments thereof, and from the claims. All references cited herein are incorporated by reference.

BRIEF DESCRIPTION OF THE DRAWINGS

FIG. 9A is a photograph, and FIGS. 9B-C are bar graphs showing that MO-1-1100 treatment of FOCUS HCC cells reduces the number (A, B) and size (A, C) of colony formation in soft agar thus reducing anchorage independent cell growth as a rigid test of malignant transformation.

FIG. 10A is a photograph.

TERMS AND DEFINITIONS

Figure 1A:
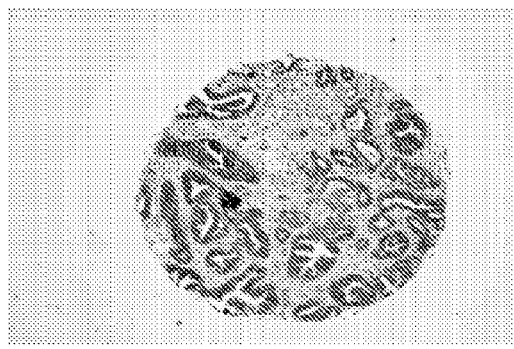
FIGS. 1A-D are photomicrographs.
Figure 1B:
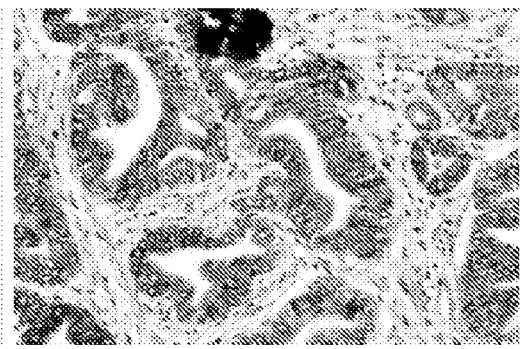
Figure 1C:
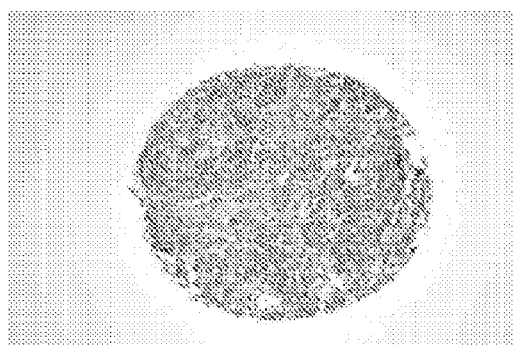
Figure 1D:
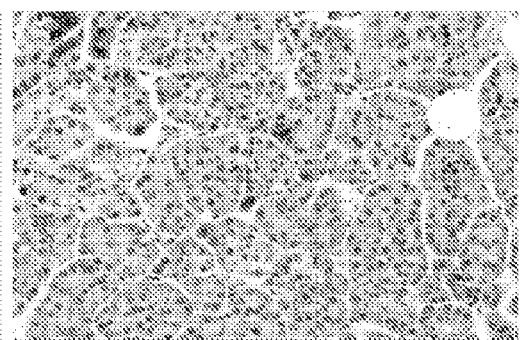
Figure 1E:
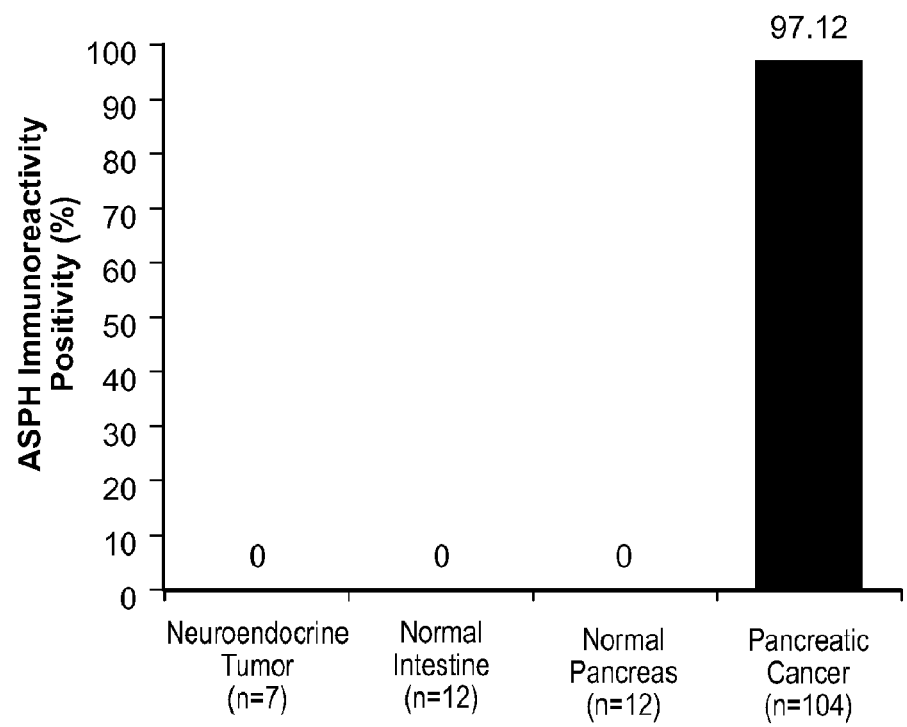
FIG. 1E is a bar graph showing ASPH expression in pancreatic cancer, normal pancreas and neuroendocrine pancreatic tumors. (A) represents ASPH expression in PC at 40× and (B) 400× with mAb RC-50. (C) shows lack of ASPH expression in normal pancreas at 40× and (D) 400×. (E) shows ASPH immunoreactivity.
Figure 2A:
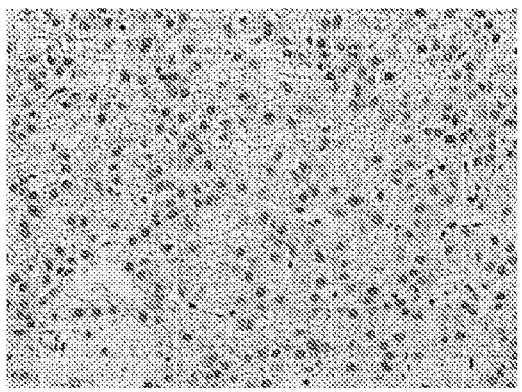
FIGS. 2A-D are photomicrographs showing ASPH expression in human HCC tumors by immunohistochemical staining (HIS) using RC-50 mAb. Note that most if not all tumor cells highly express the ASPH protein. (A) normal liver (B, C and D) human HCC tumors
Figure 2B:
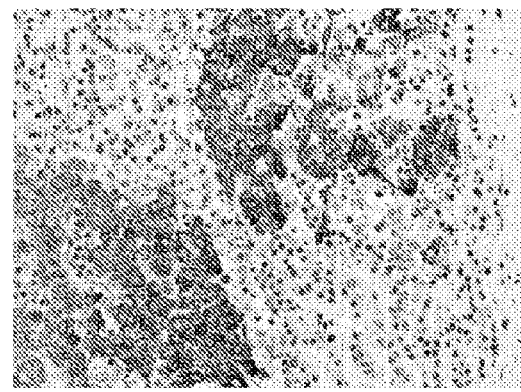
Figure 2C:
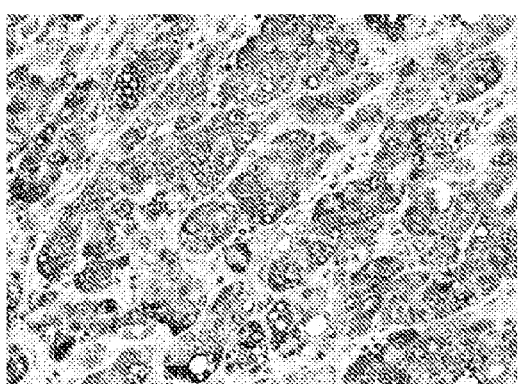
Figure 2D:
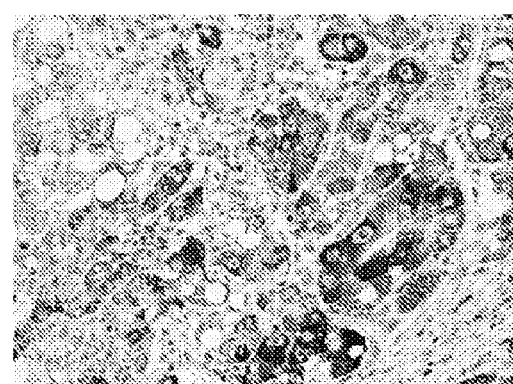

The following is a list of abbreviations, plus terms and their definitions, used throughout the specification and the claims:

General abbreviations and their corresponding meanings include: aa or AA=amino acid; mg=milligram(s); ml or mL=milliliter(s); mm=millimeter(s); mM=millimolar; nmol=nanomole(s); pmol=picomole(s); ppm=parts per million; RT=room temperature; U=units; ug, µg=micro gram(s); ul, µl=micro liter(s); uM, µM=micromolar, TEA=triethylamine, LDA=lithium diisopropyl amine, THF=tetrahydrofuran, DMAP=4-dimethylaminopyridine, DMF=N,N'-dimethylformamide.

The terms "cell" and "cells", which are meant to be inclusive, refer to one or more cells which can be in an isolated or cultured state, as in a cell line comprising a homogeneous or heterogeneous population of cells, or in a tissue sample, or as part of an organism, such as an insect larva or a transgenic mammal.

The term "amino acid" encompasses both naturally occurring and non-naturally occurring amino acids unless otherwise designated.

The term "an effective amount" means an amount of the substance in question which produces a statistically significant effect. For example, an "effective amount" for therapeutic uses is the amount of the composition comprising an active compound herein required to provide a clinically significant alteration in a measurable trait. Such effective amounts will be determined using routine optimization techniques and are dependent on the particular condition to be treated, the condition of the patient, the route of administration, dosage required for the compounds of the invention is manifested as that which induces a statistically significant difference between treatment and control groups.

A "therapeutically effective amount" refers to an amount effective, at dosages and for periods of time necessary, to achieve the desired therapeutic result. A therapeutically effective amount of modulator may vary according to factors such as the disease state, age, sex, and weight of the individual, and the ability of the modulator to elicit a desired response in the individual. Dosage regimens may be adjusted to provide the optimum therapeutic response. A therapeutically-effective amount is also one in which any toxic or detrimental effects of the modulator are outweighed by the therapeutically beneficial effects.

A "prophylactically effective amount" refers to an amount effective, at dosages and for periods of time necessary, to achieve the desired prophylactic result. A prophylactically effective amount can be determined as described above for the therapeutically-effective amount. Typically, since a prophylactic dose is used in subjects prior to or at an earlier stage of disease, the prophylactically effective amount will be less than the therapeutically-effective amount.

As used herein, the term "cell proliferative disorder" refers to conditions in which unregulated or abnormal growth, or both, of cells can lead to the development of an unwanted condition or disease, which may or may not be cancerous. Exemplary cell proliferative disorders that may be treated with the compounds of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. The methods and uses provided herein can be or may be used to treat or alleviate a symptom of cancer or to identify suitable candidates for such purposes. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, prodrug, metabolite, polymorph or solvate thereof, can or may also be used to prevent a relevant disease, condition or disorder, or used to identify suitable candidates for such purposes. As used herein, "preventing," "prevent," or "protecting against" describes reducing or eliminating the onset of the symptoms or complications of such disease, condition or disorder.

As used herein, the term "alleviate" is meant to describe a process by which the severity of a sign or symptom of a disorder is decreased. Importantly, a sign or symptom can be alleviated without being eliminated. The administration of pharmaceutical compositions of the invention can or may lead to the elimination of a sign or symptom, however, elimination is not required. Effective dosages should be expected to decrease the severity of a sign or symptom. For instance, a sign or symptom of a disorder such as cancer, which can occur in multiple locations, is alleviated if the severity of the cancer is decreased within at least one of multiple locations.

As used herein, a "subject" is interchangeable with a "subject in need thereof", both of which refer to a subject having a cell proliferation disorder, or a subject having an increased risk of developing such disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject in need thereof can be one who has been previously diagnosed or identified as having cancer or a precancerous condition. A subject in need thereof can also be one who has (e.g., is suffering from) cancer or a precancerous condition. Alternatively, a subject in need thereof can be one who has an increased risk of developing such disorder relative to the population at large (i.e., a subject who is predisposed to developing such disorder relative to the population at large). A subject in need thereof can have a precancerous condition. The term "animal" includes human beings.

The term "optionally substituted" moiety refers to either unsubstituted chemical moiety (e.g., alkyl, aryl, heteroaryl, etc.) or a chemical moiety having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "substituted aryl or heteroaryl" refers to aromatic or heteroaromatic rings may contain one or more substituents such as —OH, SH, —CN, —F, —Cl, —Br, —R, —NO$_2$—NO, —NH2, —NHR, —NRR, —C(O)R, —C(O)OH, —C(O)OR, —C(O)NH2, —C(O)NHR, —C(O)NRR, and the like where each R is independently ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl or substituted 6-26 membered heteroarylalkyl.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

A "derivative" of a compound X (e.g., a peptide or amino acid) refers to a form of X in which one or more reactive groups on the compound have been derivatized with a substituent group. Peptide derivatives include peptides in which an amino acid side chain, the peptide backbone, or the amino' or carboxy-terminus has been derivatized (e.g., peptidic compounds with 5 methylated amide linkages).

An "analogue" of a compound X refers to a compound which retains chemical structures of X necessary for functional activity of X yet which also contains certain chemical structures which differ from X. An analogue of a naturally-occurring peptide, is a peptide which includes one or more non-naturally-occurring amino acids.

The term "mimetic refers to a compound having similar functional and/or structural properties to another known compound or a particular fragment of that known compound. A "mimetic" of a compound X refers to a compound in which chemical structures of X necessary for functional activity of X have been replaced with other chemical structures which mimic the conformation of X. The term mimetic, and in particular, peptidomimetic, is intended to include isosteres.

The term "cyclic group", as used herein, is intended to include cyclic saturated or unsaturated (i.e., aromatic) group having from about 3 to 10, preferably about 4 to 8, and more preferably about 5 to 7, carbon atoms. Exemplary cyclic groups include cyclopropyl, cyclobutyl, cyclopentyl, cyclohexyl, and cyclooctyl. Cyclic groups may be unsubstituted or substituted at one 35 or more ring positions. Thus, a cyclic group may be substituted with halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates. selenoethers, ketones, aldehydes, esters, 'CF$_3$, 'CN, or the like.

The term "heterocyclic group" is intended to include cyclic saturated or unsaturated (i.e., aromatic) group having from about 3 to 10, preferably about 4 to 8, and more preferably about 5 to 7, carbon atoms, wherein the ring structure includes about one to four heteroatoms. Heterocyclic groups include pyrrolidine, oxolane, thiolane, imidazole, oxazole, piperidine, piperazine, morpholine and pyridine. The heterocyclic ring can be substituted at one or more positions with such substituents as, for example, halogens, alkyls, cycloalkyls, alkenyls, alkynyls, aryls, other heterocycles, hydroxyl, amino, nitro thiol, amines, imines, amides, phosphonates, phosphines, carbonyls, carboxyls, eilyls, ethers, thioethers, sulfonyls, selenoethers, ketones, aldehydes, esters, CF$_3$, CN, or the like. Heterocycles may also be bridged or fused to other cyclic groups as described below.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

The term "polycyclic group" as used herein is intended to refer to two or more saturated or unsaturated (i.e., aromatic) cyclic rings in which two or more carbons are common to two adjoining rings, e.g., the rings are "fused rings". Rings that are joined through non-adjacent atoms are termed "bridged" rings. Each of the rings of the polycyclic group can be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, $CF_3$, CN, or the like.

As used herein, the term "modulating group" and "modifying group" are used interchangeably to describe a chemical group directly or indirectly attached to a peptidic structure. For example, a modifying group(s) can be directly attached by covalent coupling to the peptidic structure or a modifying group(s) can be attached indirectly by a stable non-covalent association.

The compounds described herein include the compounds themselves, as well as their salts, their solvates, and their prodrugs, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

Examples of prodrugs include esters and other pharmaceutically acceptable derivatives, which, upon administration to a subject, are capable of providing active substituted benzene compounds.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

In the present specification, the structural formula of the compound represents a certain isomer for convenience in some cases, but the present invention includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of ketone-enol tautomerism are as shown below.

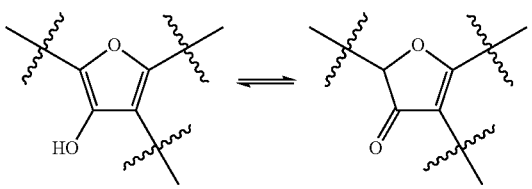 [SMILES: *c1oc(*)c(O)c1* ; *C1=C(*)C(=O)C(*)O1]

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Compounds such as small molecule inhibitors, polynucleotides, polypeptides, or other agents are purified and/or isolated. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. An "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified also defines a degree of sterility that is safe for administration to a human subject, e.g., lacking infectious or toxic agents.

DETAILED DESCRIPTION

ASPH (a.k.a., AAH) is a member of the α-ketoglutarate-dependent dioxygenase family enzyme. It has a predicted molecular mass of ~86 kD and catalyzes the hydroxylation of specific Asp (Asparate) and Asn (Asparagine) residues in EGF-like domains of certain receptor proteins such as Notch. Overexpression of ASPH has been observed in a broad range of malignant neoplasms including hepatocellular carcinoma, cholangiocellular carcinoma, pancreatic cancer, prostate cancer, breast cancer, glioblastoma, lung and colon cancer.

However, ASPH has low or negligible expression in normal adult tissues except for proliferating trophoblastic cells of the placenta. In human HCC cell lines, ASPH promotes the motility and invasiveness of tumor cells through upregulation and activation of the Notch signaling cascade. Indeed, ASPH overexpression is reported to be a poor prognostic factor for patients with HCC and predicts early disease recurrence and reduced survival. Especially in colon cancer, there is a significant association between poor surgical outcome and ASPH expression, which is considered an independent risk factor indicating poor prognosis with this disease. Another tumor with high ASPH expression is pancreatic cancer (PC) which is the fourth leading cause of cancer mortality in the United States with a five-year survival rate of 5-6%. PC is an extremely aggressive tumor refractory to most therapies. There is a need to define the molecular pathogenesis of PC and develop more effective treatment strategies. Signaling pathways mediated by ASPH participate in the growth and metastasis of PC during oncogenesis. This surprising discovery on the role of ASPH overexpression in PC pathogenesis indicates that ASPH is a molecular target for therapy and that inhibition of ASPH in this type of cancer leads to clinical benefit.

Accordingly, in one aspect, the invention features an asparatyl (asparaginyl) beta-hydroxylase (ASPH) inhibitory compound for use in a method of reducing proliferation, migration, invasion, or metastasis of a tumor cell in the treatment of cell proliferative disorder, comprising contacting said tumor cell with the ASPH inhibitory compound, wherein the ASPH inhibitory compound is of Formula Ia or Ib:

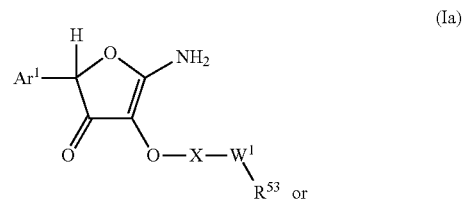

(Ia)

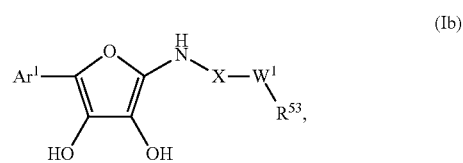

(Ib)

or a salt, ester, metabolite, prodrug, or solvate thereof, wherein $Ar^1$ is substituted or unsubstituted $C_6$-$C_{20}$ aryl or 5 to 20-membered heteroaryl;

X is C(O), C(S), or $S(O)_2$;

$W^1$ is a single bond, O, $CR^{50}R^{51}$, or $NR^{52}$ when X is CO and $W^1$ is a single bond, $CR^{50}R^{51}$, or $NR^{52}$ when X is $SO_2$; and each of $R^{50}$, $R^{51}$, $R^{52}$, and $R^{53}$ independently is selected from the group consisting of hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{20}$ aryl, substituted or unsubstituted $C_7$-$C_{26}$ arylalkyl, substituted or unsubstituted 5 to 20-membered heteroaryl, and substituted or unsubstituted 6-26 membered heteroarylalkyl.

In one embodiment, the compound for said use is of Formula Ia, or a salt, ester, metabolite, prodrug, or solvate thereof. The compound of Formula Ia may have one or more of the following features when applicable.

For example, the compound is of Formula IIa:

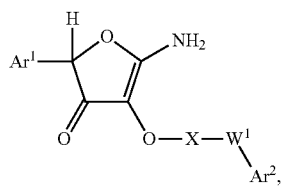

(IIa)

or a salt, ester, metabolite, prodrug, or solvate thereof, wherein each of $Ar^1$ and $Ar^2$ independently is unsubstituted $C_6$-$C_{14}$ aryl, unsubstituted 5 to 14-membered heteroaryl, or $C_6$-$C_{14}$ aryl or 5 to 14-membered heteroaryl each substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, —$S(O)_bR_a$, —$S(O)_bNR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; and each of $R_{S1}$ and $R_{S2}$, is optionally substituted with one or more substituents selected from the group consisting of halo, OH, oxo, $C(O)OH$, $C(O)O$—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, $R^{53}$ is unsubstituted $C_1$-$C_6$ alkyl or $C_1$-$C_6$ alkyl substituted with one or more substituents selected from halo, OH, CN, and amino.

For example, X is $S(O)_2$ and $W^1$ is $CR^{50}R^{51}$.

For example, X is $S(O)_2$ and $W^1$ is a single bond.

For example, X is $C(O)$ and $W^1$ is O, or X is $C(S)$ and $W^1$ is $NR^{52}$.

For example, each of $R^{50}$, $R^{51}$, and $R^{52}$ independently is H, unsubstituted $C_1$-$C_6$ alkyl, or $C_1$-$C_6$ alkyl substituted with one or more substituents selected from halo, OH, CN, and amino.

For example, each of $Ar^1$ and $Ar^2$ independently is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, —$S(O)_bR_a$, —$S(O)_bNR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; and each of $R_{S1}$ and $R_{S2}$, is optionally substituted with one or more substituents selected from the group consisting of halo, OH, oxo, $C(O)OH$, $C(O)O$—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, each of $Ar^1$ and $Ar^2$ independently is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, or $R_{S1}$, in which $R_{S1}$ is $C_1$-$C_6$ alkyl, each of $R_a$ and $R_b$, independently is H or $R_{S2}$, and $R_{S2}$ is $C_1$-$C_6$ alkyl; and each of $R_{S1}$ and $R_{S2}$, is optionally substituted with one or more substituents selected from the group consisting of halo, OH, $C_1$-$C_6$ alkoxyl, amino, mono-$C_1$-$C_6$ alkylamino, and di-$C_1$-$C_6$ alkylamino.

For example, each of $Ar^1$ and $Ar^2$ independently is selected from phenyl, 1-naphthyl, 2-naphthyl, 2-furanyl, 2-thiazolyl, 2-pyridyl, 3-pyridyl, 4-pyridyl, 2-quinolinyl, 3-quinolinyl, 4-quinolinyl, 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-cyanophenyl, 3-cyanophenyl, 4-cyanophenyl, 3-carboxymethylphenyl, 2-methoxyphenyl, 3-methoxyphenyl, 4-methoxyphenyl, 2,3-dichlorophenyl, 2,4-dichlorophenyl, 2,5-dichlorophenyl, 3,4-dichlorophenyl, 3,5-dichlorophenyl, 2,3-difluorophenyl, 2,4-difluorophenyl, 2,5-difluorophenyl, 3,4-difluorophenyl, 3,5-difluorophenyl, 2,3-dimethoxyphenyl, 2,4-dimethoxyphenyl, 2,5-dimethoxyphenyl, 3,4-dimethoxyphenyl, 3,5-dimethoxyphenyl, 2-chloro-6-fluorophenyl, 3-chloro-4-fluorophenyl, 2-chloro-4-fluorophenyl, 4-chloro-3-fluorophenyl, 3-chloro-2-fluorophenyl, 2-chloro-5-fluorophenyl, 4-chloro-2-fluorophenyl, and 5-chloro-2-fluorophenyl.

In another embodiment, the compound for said use is of Formula Ib, or a salt, ester, metabolite, prodrug, or solvate thereof. The compound of Formula Ib may have one or more of the following features when applicable.

For example, $R^{53}$ is unsubstituted $C_1$-$C_6$ alkyl or $C_1$-$C_6$ alkyl substituted with one or more substituents selected from halo, OH, CN, and amino.

For example, $R^{53}$ is unsubstituted methyl or ethyl.

For example, X is $S(O)_2$ and $W^1$ is $CR^{50}R^{51}$.

For example, X is $S(O)_2$ and $W^1$ is a single bond.

For example, X is $C(O)$ and $W^1$ is O, or X is $C(S)$ and $W^1$ is $NR^{52}$.

For example, each of $R^{50}$, $R^{51}$, and $R^{52}$ independently is H, unsubstituted $C_1$-$C_6$ alkyl, or $C_1$-$C_6$ alkyl substituted with one or more substituents selected from halo, OH, CN, and amino.

For example, $Ar^1$ is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, —$S(O)_bR_a$, —$S(O)_b$ $NR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; and each of $R_{S1}$ and $R_{S2}$, is optionally substituted with one or more substituents selected from the group consisting of halo, OH, oxo, $C(O)OH$, $C(O)O$—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, $Ar^1$ is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, or $R_{S1}$, in which $R_{S1}$ is $C_1$-$C_6$ alkyl, each of $R_a$ and $R_b$, independently is H or $R_{S2}$, and $R_{S2}$ is $C_1$-$C_6$ alkyl; and each of $R_{S1}$ and $R_{S2}$, is optionally substituted with one or more substituents selected from the group consisting of halo, OH, $C_1$-$C_6$ alkoxyl, amino, mono-$C_1$-$C_6$ alkylamino, and di-$C_1$-$C_6$ alkylamino.

For example, $Ar^1$ is selected from phenyl, 1-naphthyl, 2-naphthyl, 2-furanyl, 2-thiazolyl, 2-pyridyl, 3-pyridyl, 4-pyridyl, 2-quinolinyl, 3-quinolinyl, 4-quinolinyl, 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-cyanophenyl, 3-cyanophenyl, 4-cyanophenyl, 3-carboxymethylphenyl, 2-methoxyphenyl, 3-methoxyphenyl, 4-methoxyphenyl, 2,3-dichlorophenyl, 2,4-dichlorophenyl, 2,5-dichlorophenyl, 3,4-dichlorophenyl, 3,5-dichlorophenyl, 2,3-difluorophenyl, 2,4-difluorophenyl, 2,5-difluorophenyl, 3,4-difluorophenyl, 3,5-difluorophenyl, 2,3-dimethoxyphenyl, 2,4-dimethoxyphenyl, 2,5-dimethoxyphenyl, 3,4-dimethoxyphenyl, 3,5-dimethoxyphenyl, 2-chloro-6-fluorophenyl, 3-chloro-4-fluorophenyl, 2-chloro-4-fluorophenyl, 4-chloro-3-fluorophenyl, 3-chloro-2-fluorophenyl, 2-chloro-5-fluorophenyl, 4-chloro-2-fluorophenyl, and 5-chloro-2-fluorophenyl.

In one embodiment, said tumor cell expresses ASPH.

In certain embodiments, said cell proliferative disorder comprises Pancreatic Cancer, Hepatocellular Cancer, Cholangiocarcinoma, Lung cancer, Colon Cancer, Breast Cancer, Prostatic Cancer, and Glioblastoma.

In one embodiment, said compound is administered intravenously, orally, or subcutaneously.

In one embodiment, said compound is administered at a dose of 0.01 to 50 milligrams/kilogram of body weight.

ASPH is a highly conserved cell-surface protein in hepatocellular carcinoma (HCC). Both the liver and the pancreas are derived from an early progenitor cell type and ASPH is expressed in embryo but not in adult tissues. ASPH re-expression was observed in human PC tissue microarrays by immunohistochemical staining (IHS) as shown in FIGS. 1A-E. High level cell surface localization of ASPH was present in 101 of 104 (97%) pancreatic ductal adenocarcinoma with negligible expression in normal pancreas, and other adult human tissues. ASPH enhances cell migration, invasion, and metastasis in HCC and also PC. Activation of Notch signaling by ASPH is a final effector mechanism responsible for generation of this highly aggressive and malignant phenotype.

Biologic Properties of ASPH as a Cellular Target.

The regulation, expression, and function of ASPH has been observed in many tumors (U.S. Pat. Nos. 6,835,370; 7,094,556; 6,812,206; 6,815,415; 6,797,696; 6,783,758; and U.S. Published Patent Application No. 2005-0123545; hereby incorporated by reference) and ASPH has been found to be overexpressed in pancreatic ductal adenocarcinoma (PC) indicating that it is a therapeutic target for treatment of PC. ASPH catalyzes post-translational hydroxylation of β-carbons of specific aspartate and asparaginyl residues in epidermal growth factor (EGF)-like domains residing in proteins such as Notch and Jagged (JAG) which are involved in cell growth, differentiation, cellular migration, adhesion, and motility. The catalytic activity resides in the C-terminus and is conferred by the $^{675}$His residue; mutation to an alanine abolishes ASPH enzymatic and transforming activity. ASPH is overexpressed in tumors derived from the endoderm such as liver, pancreas, colon and lung, and translocates from the endoplasmic reticulum (ER) to the plasma membrane where it becomes accessible to the extracellular environment. It has negligible to very low expression in normal human tissue with the notable exception of the placenta which is an invasive tissue, and its expression there is robust.

Compounds are administered directly into a tumor site or systemically to inhibit ASPH hydroxylase activity.

```
Amino acid sequence of human ASPH

MAQRKNAKSS GNSSSSGSGS GSTSAGSSSP GARRETKHGG HKNGRKGGLS GTSFFTWFMV    61

IALLGVWTSV AVVWFDLVDY EEVLGKLGIY DADGDGDFDV DDAKVLLGLK ERSTSEPAVP   121

PEEAEPHTEP EEQVPVEAEP QNIEDEAKEQ IQSLLHEMVH AEHVEGEDLQ QEDGPTGEPQ   181

QEDDEFLMAT DVDDRFETLE PEVSHEETEH SYHVEETVSQ DCNQDMEEMM SEQENPDSSE   241

PVVEDERLHH DTDDVTYQVY EEQAVYEPLE NEGIEITEVT APPEDNPVED SQVIVEEVSI   301

FPVEEQQEVP PETNRKTDDP EQKAKVKKKK PKLLNKFDKT IKAELDAAEK LRKRGKIEEA   361

VNAFKELVRK YPQSPRARYG KAQCEDDLAE KRRSNEVLRG AIETYQEVAS LPDVPADLLK   421

LSLKRRSDRQ QFLGHMRGSL LTLQRLVQLF PNDTSLKNDL GVGYLLIGDN DNAKKVYEEV   481

LSVTPNDGFA KVHYGFILKA QNKIAESIPY LKEGIESGDP GTDDGRFYFH LGDAMQRVGN   541

KEAYKWYELG HKRGEFASVW QRSLYNVNGL KAQPWWTPKE TGYTELVKSL ERNWKLIRDE   601

GLAVMDKAKG LFLPEDENLR EKGDWSQFTL WQQGRRNENA CKGAPKTCTL LEKFPETTGC   661

RRGQIKYSIM HPGTHVWPHT GPTNCRLRMH LGLVIPKEGC KIRCANETRT WEEGKVLIED   721

DSFEHEVWQD ASSFRLIFIV DVWHPELTPQ QRRSLPAI
(SEQ ID NO: 3; GENBANK Accession No. S83325; His motif is underlined;
conserved sequences within the catalytic domain are designated by bold
type) cDNA sequence of human ASPH cggaccgtgc aatggcccag cgtaagaatg ccaagagcag cggcaacagc agcagcagcg    61
gctccggcag cggtagcacg agtgcgggca gcagcagccc cggggcccgg agagagacaa   121
agcatggagg acacaagaat gggaggaaag gcggactctc gggaacttca ttcttcacgt   181
```

-continued

```
ggtttatggt gattgcattg ctgggcgtct ggacatctgt agctgtcgtt tggtttgatc    241
ttgttgacta tgaggaagtt ctaggaaaac taggaatcta tgatgctgat ggtgatggag    301
attttgatgt ggatgatgcc aaagttttat taggacttaa agagagatct acttcagagc    361
cagcagtccc gccagaagag gctgagccac acactgagcc cgaggagcag gttcctgtgg    421
aggcagaacc ccagaatatc gaagatgaag caaaagaaca aattcagtcc cttctccatg    481
aaatggtaca cgcagaacat gttgagggag aagacttgca acaagaagat ggacccacag    541
gagaaccaca acaagaggat gatgagtttc ttatggcgac tgatgtagat gatagatttg    601
agaccctgga acctgaagta tctcatgaag aaaccgagca tagttaccac gtggaagaga    661
cagtttcaca agactgtaat caggatatgg aagagatgat gtctgagcag gaaaatccag    721
attccagtga accagtagta gaagatgaaa gattgcacca tgatacagat gatgtaacat    781
accaagtcta tgaggaacaa gcagtatatg aacctctaga aaatgaaggg atagaaatca    841
cagaagtaac tgctccccct gaggataatc ctgtagaaga ttcacaggta attgtagaag    901
aagtaagcat ttttcctgtg gaagaacagc aggaagtacc accagaaaca aatagaaaaa    961
cagatgatcc agaacaaaaa gcaaagtta agaaaaagaa gcctaaactt ttaaataaat   1021
ttgataagac tattaaagct gaacttgatg ctgcagaaaa actccgtaaa aggggaaaaa   1081
ttgaggaagc agtgaatgca tttaaagaac tagtacgcaa atacccctcag agtccacgag   1141
caagatatgg gaaggcgcag tgtgaggatg atttggctga agaggaga agtaatgagg    1201
tgctacgtgg agccatcgag acctaccaag aggtggccag cctacctgat gtccctgcag   1261
acctgctgaa gctgagtttg aagcgtcgct cagacaggca acaatttcta ggtcatatga   1321
gaggttccct gcttaccctg cagagattag ttcaactatt tcccaatgat acttccttaa   1381
aaaatgacct tggcgtggga tacctcttga taggagataa tgacaatgca aagaaagttt   1441
atgaagaggt gctgagtgtg acacctaatg atggctttgc taaagtccat tatggcttca   1501
tcctgaaggc acagaacaaa attgctgaga gcatcccata tttaaaggaa ggaatagaat   1561
ccggagatcc tggcactgat gatgggagat tttatttcca cctgggggat gccatgcaga   1621
gggttgggaa caaagaggca tataagtggt atgagcttgg gcacaagaga ggacactttg   1681
catctgtctg gcaacgctca ctctacaatg tgaatggact gaaagcacag ccttggtgga   1741
ccccaaaaga aacggggctac acagagttag taaagtcttt agaaagaaac tggaagttaa   1801
tccgagatga aggccttgca gtgatggata aagccaaagg tctcttcctg cctgaggatg   1861
aaaacctgag ggaaaaaggg gactggagcc agttcacgct gtggcagcaa ggaagaagaa   1921
atgaaaatgc ctgcaaagga gctcctaaaa cctgtacctt actagaaaag ttccccgaga   1981
caacaggatg cagaagagga cagatcaaat attccatcat gcaccccggg actcacgtgt   2041
ggccgcacac agggcccaca aactgcaggc tccgaatgca cctgggcttg gtgattccca   2101
aggaaggctg caagattcga tgtgccaacg agaccaggac ctgggaggaa ggcaaggtgc   2161
tcatctttga tgactccttt gagcacgagg tatggcagga tgcctcatct ttccggctga   2221
tattcatcgt ggatgtgtgg catccggaac tgacaccaca gcagagacgc agccttccag   2281
caatttagca tgaattcatg caagcttggg aaactctgga gaga
```
                                                          60

(SEQ ID NO:4; GENBANK Accession No. 583325; codon encoding initiating methionine is underlined).

Methods of inhibiting tumor growth also include administering a compound which inhibits HAAH hydroxylation of a NOTCH polypeptide. For example, the compound inhibits hydroxylation of an EGF-like cysteine-rich repeat sequence in a NOTCH polypeptide, e.g., one containing the consensus sequence CDXXXCXXKXGNGXCDXXCN-NAACXXDGXDC (SEQ ID NO:2). Polypeptides containing an EGF-like cysteine-rich repeat sequence are administered to block hydroxylation of endogenous NOTCH.

ASPH is expressed in many organs during embryogenesis presumably to promote cell motility and migration for cell patterning and organ development; its expression is "shut off" in the adult only to re-emerge during oncogenesis where its function may be required for generation of malignant phenotypes. It appears not to be overexpressed during cell proliferation; however, there is low-level expression in dysplastic ductal cells of pancreatic intraepithelial lesions (PanINs) as well as dysplastic hepatocytes in hepatitis B (HBV) and C (HCV) infected liver. Transcriptional regulation of ASPH is provided by tripartite signaling pathways IN/IGF1/IRS1/MAPK/ERK, IN/IGF1/IRS1/PI3K/AKT, and WNT/β-Catenin. Post-transcriptional regulation of ASPH is mediated by phosphorylation of GSK-3β-related motifs located in the N-terminal region of the molecule. One mechanism by which ASPH exerts its effector function is by activating downstream Notch signaling to promote cell migration and invasion.

ASPH Expression in Human Tumors

Expression of ASPH in Human Tumors Compared to Normal Tissue by IHS and qRT-PCR

| Tumor type | Number | Number Positive (%) |
| --- | --- | --- |
| Pancreatic Cancer | 101 | 98 (97%) |
| Hepatocellular Cancer | 95 | 87 (92%) |
| Cholangiocarcinoma | 20 | 20 (100%) |
| Lung | 16 | 16 (100%) |
| Colon Cancer | 10 | 6 (60%) |
| Breast Cancer | 17 | 17 (100%) |
| Prostatic Cancer | 32 | 30 (94%) |
| Glioblastoma | 5 | 5 (100%) |

The table above details the overexpression of ASPH at the protein and RNA level as determined by IHS and qRT-PCR respectively in various human tumors indicating that it is a therapeutic target for a variety of human solid malignancies with a poor prognosis. FIGS. 1 and 2 show examples of ASPH protein expression by IHS.

Oncogenic Role of ASPH β-Hydroxylase Activity

The C-terminus of ASPH contains amino acid (AA) sequence of the catalytic site ($M^{670}HPGFH^{675}$) and its sequence is identical in human, rat, mouse, and cattle. The $H^{675}AA$ is specifically involved in $Fe^{2+}$ coordination and critical for its enzymatic activity, also highly conserved in the chicken and fly. A $H^{675}R$ mutation reduces β-hydroxylase activity to <1% of wild-type protein while $H^{675}D$ reduces it to 20%. In this context the $H^{675}R$ mutant protein loses the ability to promote cell proliferation, motility, migration, invasion, colony formation in soft agar, as well as metastasis and tumor formation in nude mice compared to the "wild-type" sequence and it also can function as a dominant negative mutant to inhibit the function of the endogenous "Wild-Type" protein. These findings indicate that inhibition of β-hydroxylase activity promotes antitumor effects. The crystal structure of the catalytic site region has been elucidated and is available in the public database (RCSB protein database; code 3RCQ). Small molecule inhibitors for use as anti-tumor agents were identified by their ability to fit into the catalytic site region of ASPH and inhibit ASPH enzymatic activity.

Generation of a Small Molecule Inhibitor (SMI) of ASPH Enzymatic Activity.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; Greene, T. W., Wuts, P. G. M., *Protective Groups in Organic Synthesis*, 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

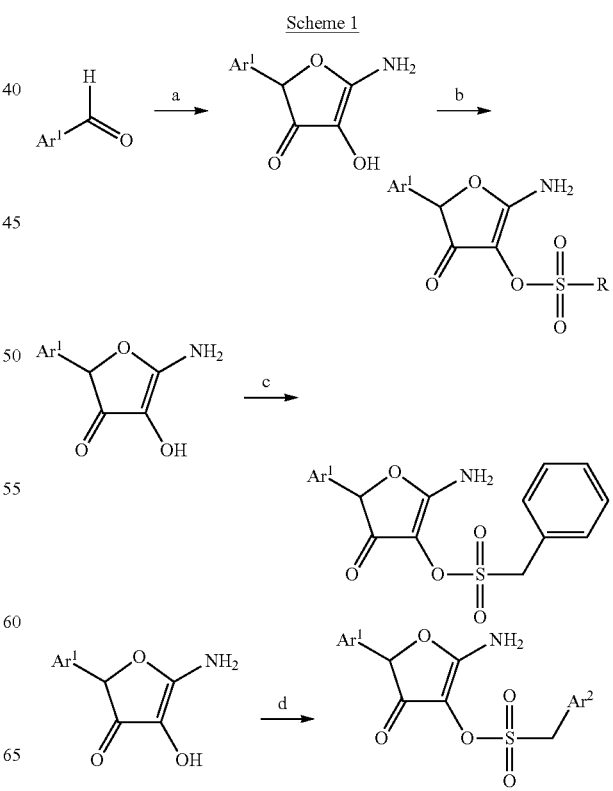

Scheme 1

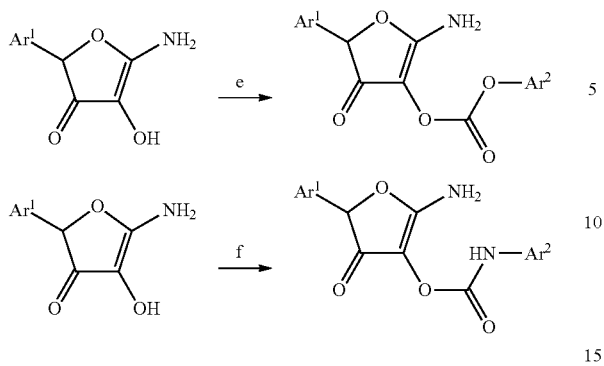

Scheme 1 above shows the synthetic strategies for compounds of Formula Ia. Reactions a-f are as follows: (a) KCN, glyoxal, $Na_2CO_3$, $H_2O$; (b) $ClSO_2R$, TEA, THF; (c) $ClSO_2CH_2Ph$, TEA, THF; (d) $ClSO_2CH_2Ar$, TEA, THF; (e) $ClCO_2Ar$, TEA, THF; (f) RNCS, $Na_2CO_3$, $H_2O$.

a. Synthesis and Characterization of Novel SMI for ASPH.

Based on the crystal structure of the ASPH catalytic site, computer generated drug design was performed that has led to the synthesis of a series of parent compounds and derivatives to fit into the pocket of the catalytic site and inhibit the β-hydroxylase activity. Parent compounds ("MO" series shown below) were synthesized and examined for inhibition of β-hydroxylase activity using a high throughput screening assay. Synthesis of ASPH inhibitors was accomplished in two steps. The first step was a three component reaction including an aromatic aldehyde, glyoxal bisulfate addition product, and potassium cyanide to yield an arylhydroxytetronimide

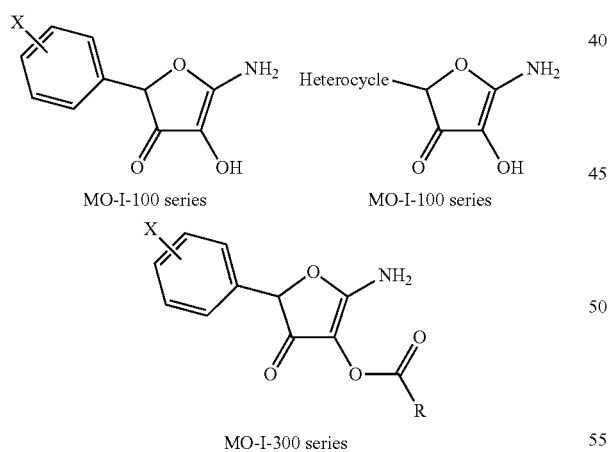

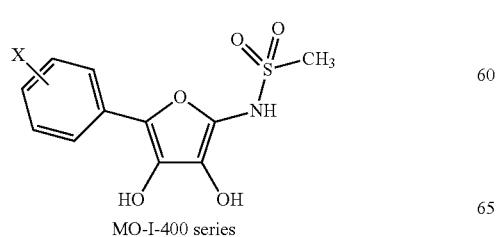

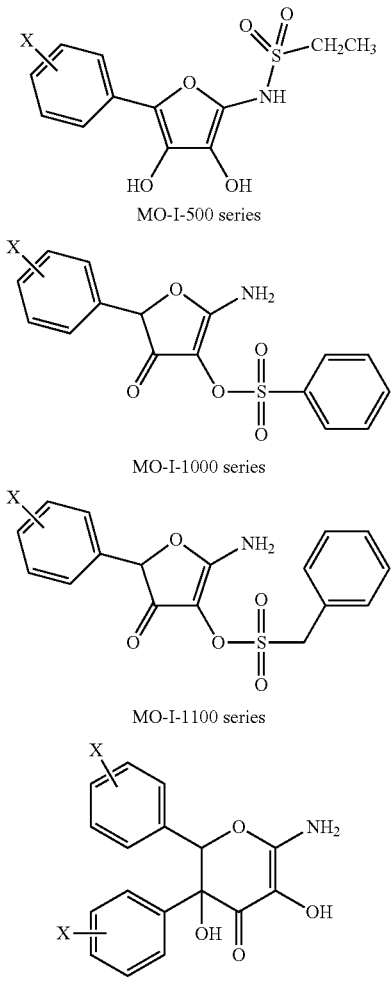

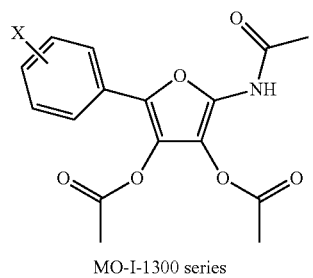

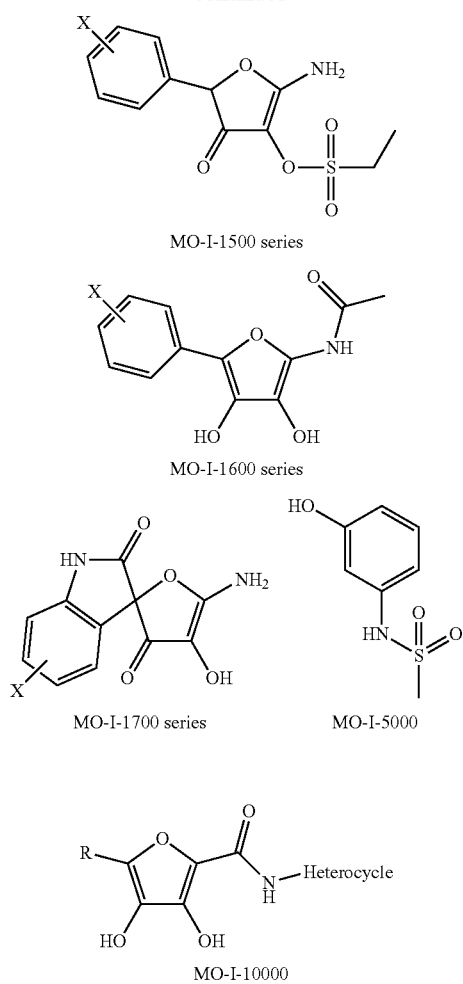

MO-I-1500 series

MO-I-1600 series

MO-I-1700 series

MO-I-5000

MO-I-10000

In the second step arylhydroxytetronimide was sulfonylated with phenylmethansulfonyl chloride in dry tetrahydrofuran to yield compounds of formula 1 (shown below). Compounds were characterized by 1H and 13C nuclear magnetic resonance, high resolution mass spectroscopy, high performance liquid chromatography, infra-red spectroscopy, melting point, elemental analysis and binding to ASPH by isothermal titration calorimetry.

Candidate parent compounds were selected as inhibitors for β-hydroxylase activity based on crystal structure of the catalytic site in the C-terminal region of ASPH and computer assisted drug design. MO-1-400, 500, 1000, and 1100 were then confirmed to demonstrate ASPH binding and ASPH enzymatic inhibitory activity.

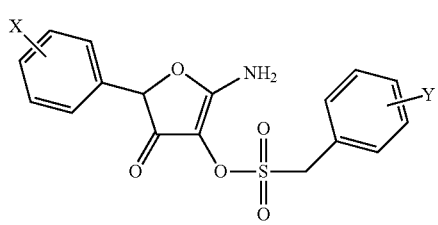

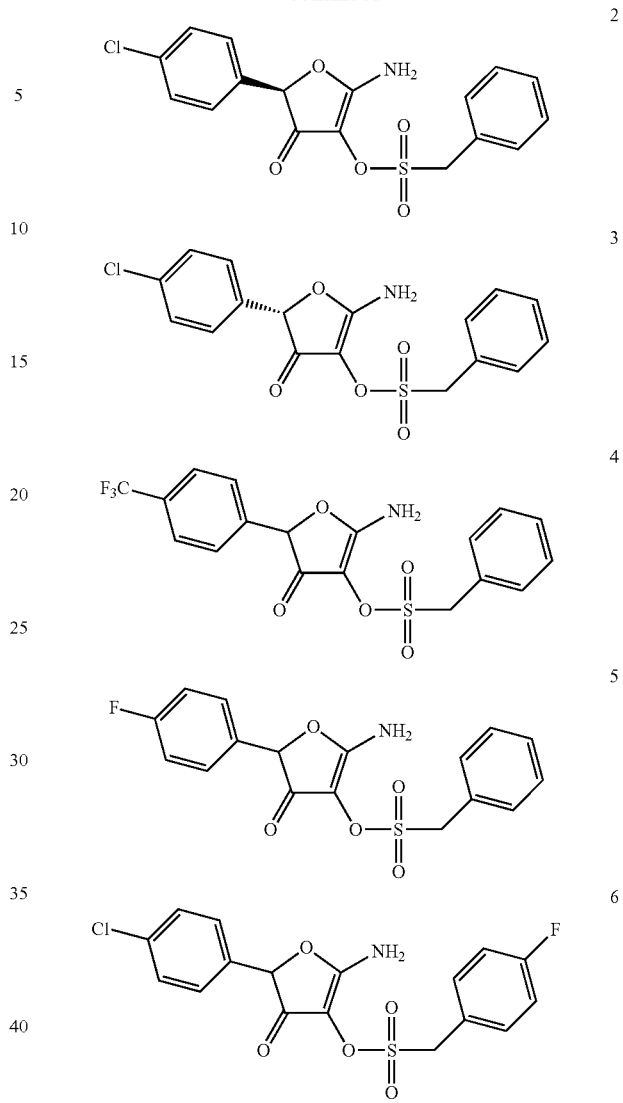

Several compounds of the general structure 1 were synthesized and evaluated for ASPH inhibition. Structure of the lead compounds (2, 3, 4, 5 and 6 shown above) are used as a highly specific ASPH β-hydroxylase inhibitors of PC and other ASPH expressing tumors both in vitro and in vivo. Optical resolution of the lead compound into the (R) 2 and (S) 3 enantiomers is performed to evaluate the impact of the stereocenter on potency. Fluorinated derivatives 4-6 are be prepared to enable MRI visualization of drug penetration and persistence.

Existing Structure Activity Relationship (SAR) Exploration.

The MO-1-1000, MO-1-1100, 400 and 500 compounds were identified as hits. This led to identification of a mixture of enantiomers as the lead compounds 2 and 3 and the additional recognition that the MO-1-500 compound demonstrated biologic activity through its action on ASPH enzymatic activity.

Characterization of a High Throughput Enzymatic Assay for ASPH Activity.

Figure 3A:
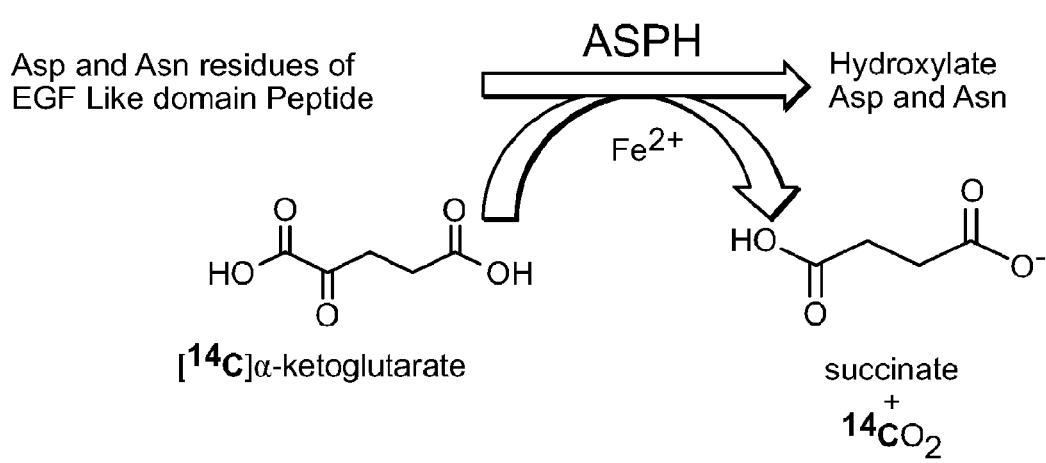
FIG. 3A is a diagram of the biochemical reaction catalyzed by ASPH derived from PC cell lysates.
Figure 3B:
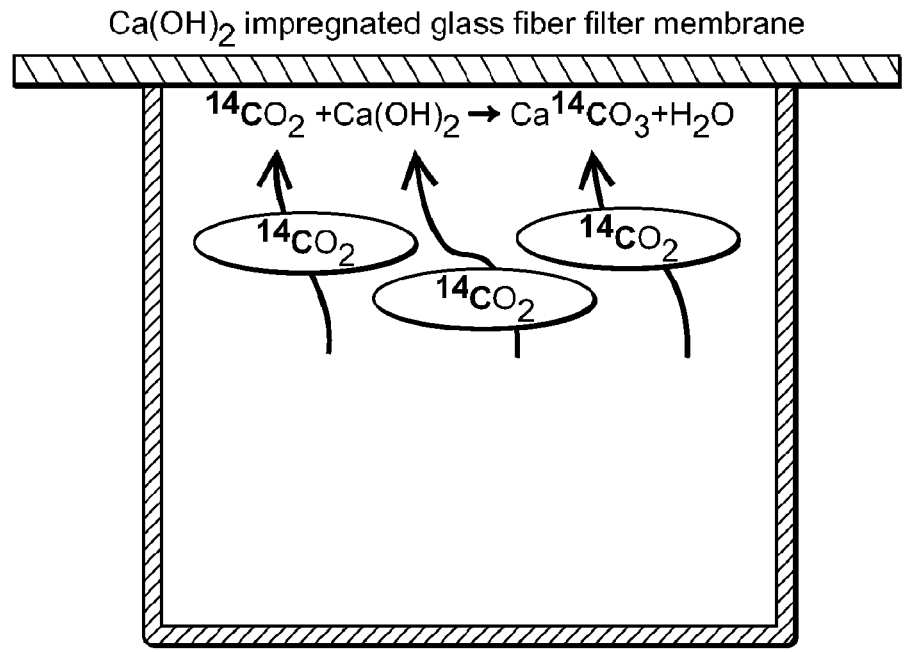
FIG. 3B is a cartoon illustrating the read-out to quantify ASPH activity in PC cells and tumors.
Figure 3C:
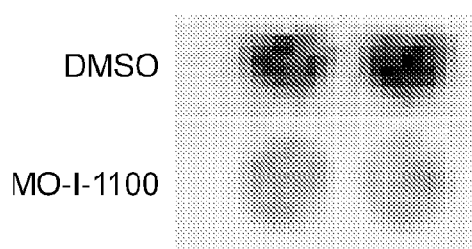
FIG. 3C is an image of membrane was obtained by a phosphor-imager after a 16 hour exposure of the trapping filter to a phospho-screen.
Figure 3D:
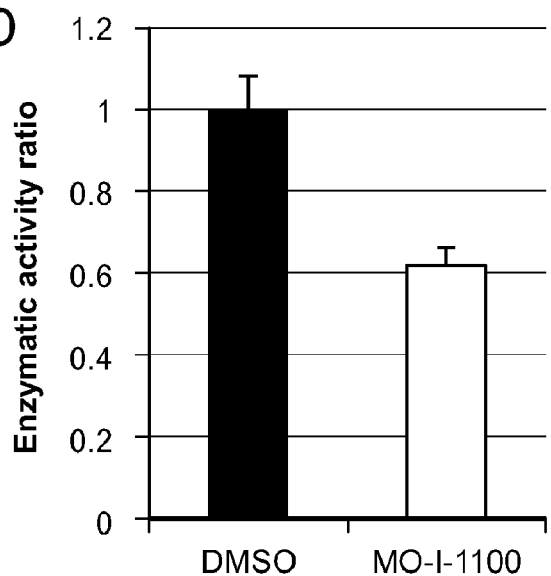
FIG. 3D is a bar graph showing intensities were calculated by Image J software and compared to a DMSO control. Vertical bars represent standard deviation. These figures show methods of measurement and data relating to ASPH catalytic activity.

EGF and EGF-like domains are well known in the art and generally include six cysteine residues which have been shown (in EGF) to be involved in disulfide bonds. The main structure is a two-stranded beta-sheet followed by a loop to a C-terminal short two-stranded sheet. Subdomains between the conserved cysteines vary in length. Examples include those described in Davis, C G, 1990, New Biol. 2(5):410-9; Blomquist et al., 1984, Proc Natl Acad Sci USA. 81(23): 7363-7; Hommel et al., 1002, J Mol Biol. 227(1):271-82; Doolittle et al., 1984, Nature. 307(5951):558-60; Appella et al., 1988, FEBS Lett. 231(1):1-4; Sorkin A., 2001, Biochem Soc Trans. August; 29(Pt 4):480-4; each of which is hereby incorporated by reference). FIGS. 3A-C represents the strategy for development and characterization of the performance of an assay to measure ASPH enzymatic activity. FIG. 3A describes the biochemical reaction catalyzed by ASPH. FIG. 3B depicts the read-out of the assay. Protein lysates were extracted from FOCUS cells (high level of ASPH cell surface expression) treated with 1-10 µM of each parent compound for 24 hours. The lysates were added into 96 well-plates coated with ASPH monoclonal antibodies (mAbs) to add an antigen specific (ASPH) capture step to the assay design. After incubation and washing, only ASPH is captured on each well. The reaction is carried out with 60 µM of an EGF domain containing 39AA peptide, 100 µM $FeCl_2$ and 40 µM $^{14}C$ labeled α-ketoglutarate were added into each well. The $^{14}CO_2$ was captured on a glass fiber membrane soaked in $Ca(OH)_2$. Radioactivity captured was quantified by a phosphor-imager as shown in FIG. 3C. FIG. 3D shows that MO-1-1100 at a concentration of 1 µM substantially inhibits β-hydroxylase activity. The compound was further characterized for clinical use as an anti-tumor agent for PC and HCC and other ASPH-expressing tumors.

PC Growth Inhibition in a Preclinical Murine Model

Figure 4A:
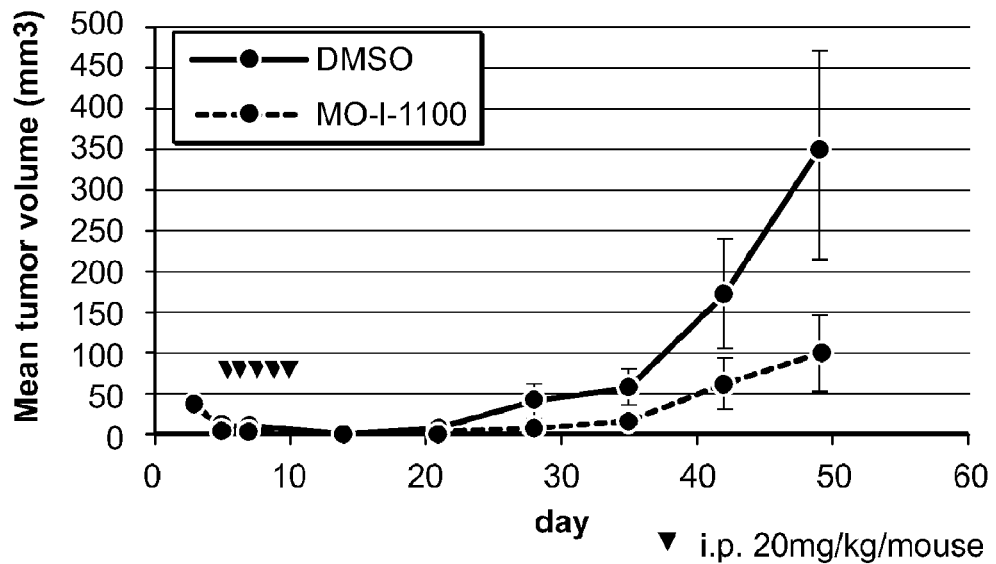
FIG. 4A is a line graph showing tumor volume.
Figure 4B:
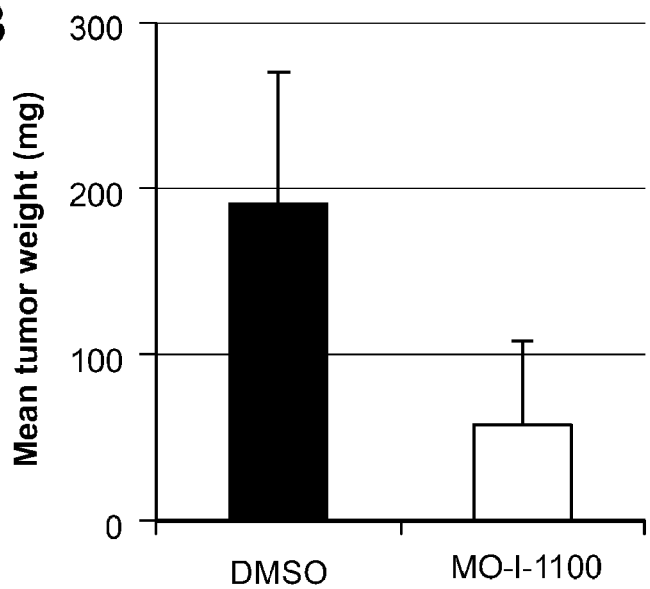
FIG. 4B is a bar graph showing tomor weight. The data show an anti-tumor effect of MO-1-1100 and PC tumor growth initiated with the human pancreatic HPAFH cell line. There were 15 nude mice in each group. i.p. injection (20 mg/kg/mouse). Vertical bars; standard error.

After demonstrating that MO-1-1100 inhibited β-hydroxylase activity using the ASPH specific mAb capture enzymatic assay, its activity as an anti-tumor agent in a nude mouse model of subcutaneous (s.c.) tumor growth was evaluated. The HPAFH AsPC-1 human PC cell line which expresses a high level of ASPH was implanted ($5 \times 10^6$ cells s.c.) into the back of nude mice. Tumors were allowed to grow to approximately 100 $mm^3$ after one week, and MO-1-1100 was then administered intraperitoneal (i.p.) at a concentration of 50 mg/kg. The treatment regimen as shown in FIGS. 4A-B included i.p. injections on a daily basis for five days followed by every other day until the experiment was terminated due to the large size of tumors observed in the control group that received a DMSO vehicle injection. FIGS. 4A-B demonstrates the growth rate and substantial inhibition of HPAFH tumor formation over the course of the study. There were 15 nude mice in each group (control vs. treatment). Therefore, this study demonstrates that the compound (MO-1-1100) was active in vitro inhibiting ASPH β-hydroxylase activity, and performed well in vivo as an anti-tumor agent.

In Vitro Effects of ASPH Inhibitors for Cell Proliferation and Metabolism Studies with MO-1-1100

Figure 5A:
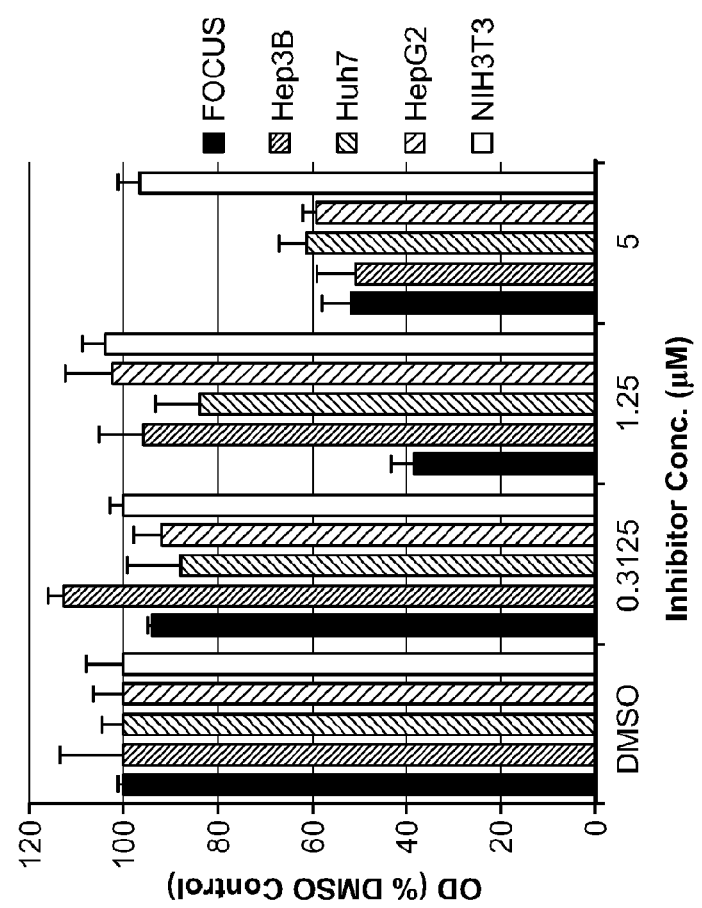
FIGS. 5A-B are line graphs showing the effect of MO1-1100 on metabolic activity (A), and proliferation (B).
Figure 5B:
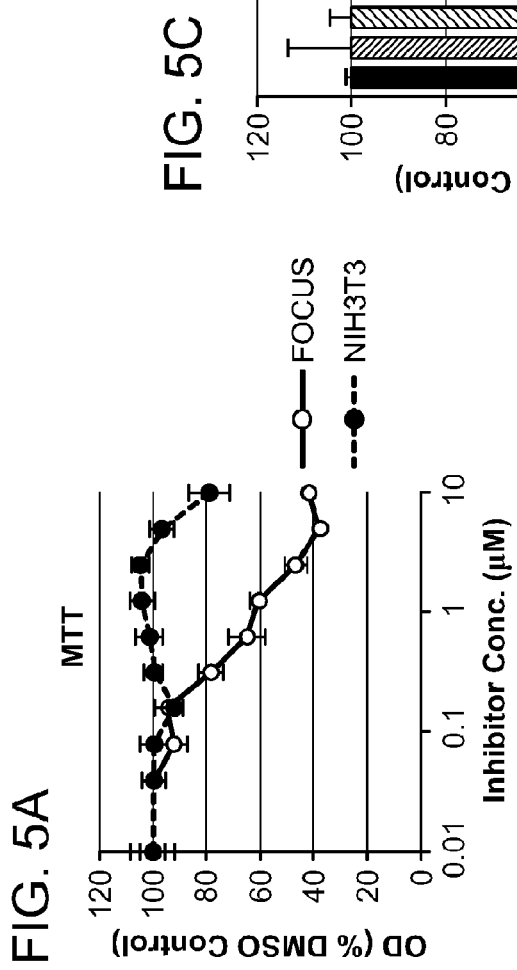
Figure 5C:
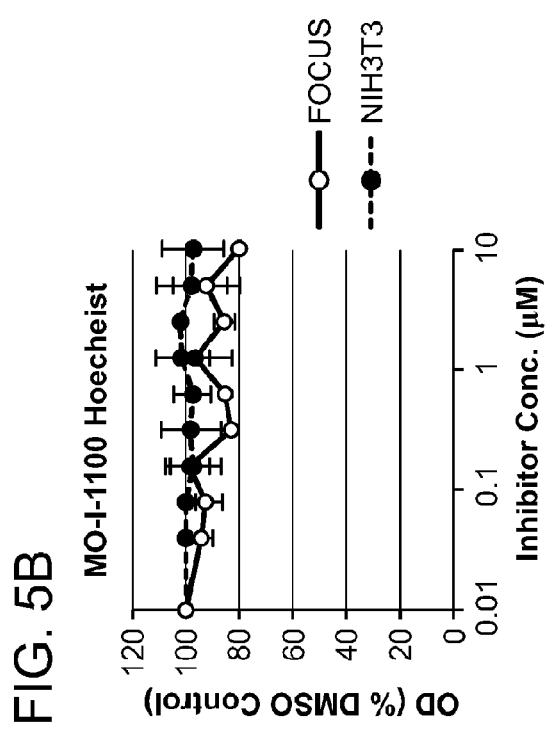
FIG. 5C is a bar graph showing effect of the inhibitor on viability (C). Note that NIH 3T3 cells that lack ASPH expression were resistant to the antitumor activity of MO-1-1100.
Figure 6A:
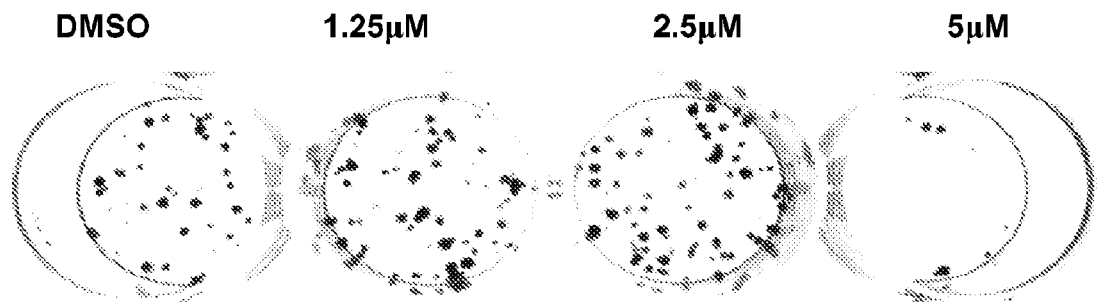
FIG. 6A is a photograph.
Figure 6B:
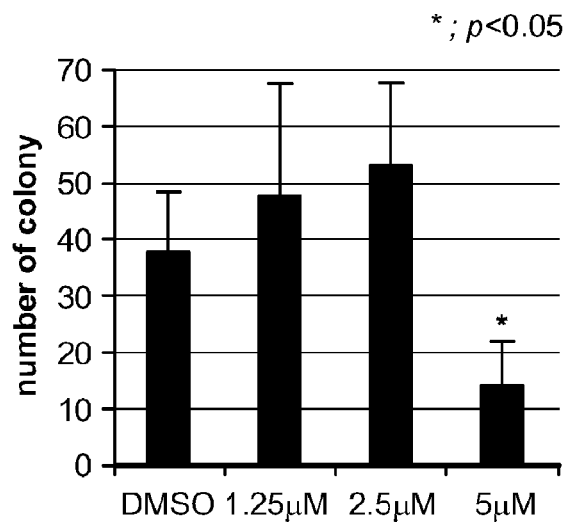
FIG. 6B is a bar graph showing colony formation (a test of malignant potential) produced by FOCUS HCC cells was strikingly inhibited by treatment with 5 μM of MO-1-1100.

A MTT assay was performed to evaluate the effect of MO-1-1100 on cell proliferation and viability. MTT is reduced to purple formazan in living cells. FOCUS cells were used as a high ASPH expressing human HCC cell line. The results shows that treatments with MO-1-1100 for 24 hours dose-dependently decreased the OD (optical density) value in FOCUS cells (FIGS. 5A-B). However, in NIH-3T3 cells, which is a mouse embryo fibroblast cell line not expressing ASPH, MO-1-1100 had no effect on the OD value of MTT indicating that MO-1-1100 is highly specific for the β-hydroxylase activity of ASPH and did not affect cells that lacked ASPH expression. The MTT assay measures cellular metabolic activity via NAD(P)H-dependent cellular oxidoreductase enzymes. However, as shown in FIG. 5C, MO-1-1100 also decreased cell viability in human HCC cell lines at 5 µM (FOCUS, Hep3B, HepG2 and Huh7) which express ASPH (inhibition rate 37.9%, 60%, 59% and 50%, respectively) but not NIH 3T3 cells with no expression of ASPH. In order to evaluate the effect of long-term exposure of MO-1-1100, the colony formation assay (an assay of malignant potential and phenotype) in which cells were treated with inhibitor for 3 weeks was performed. Treatment with MO-1-1100 resulted in reduced colony formation at 5 µM concentration (inhibition rate 36.8%) (FIGS. 6A-B).

Studies on MO-1-500

Figure 7A:
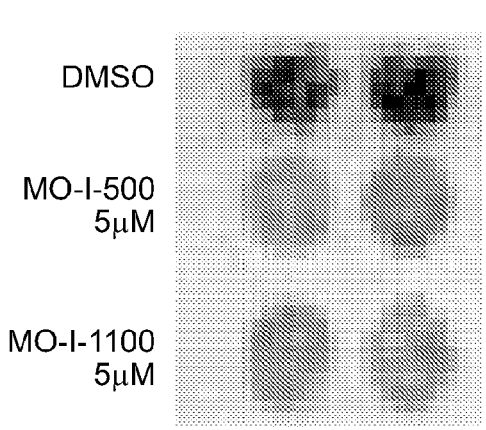
FIG. 7A is an image of membrane was obtained by a phosphor-imager.
Figure 7B:
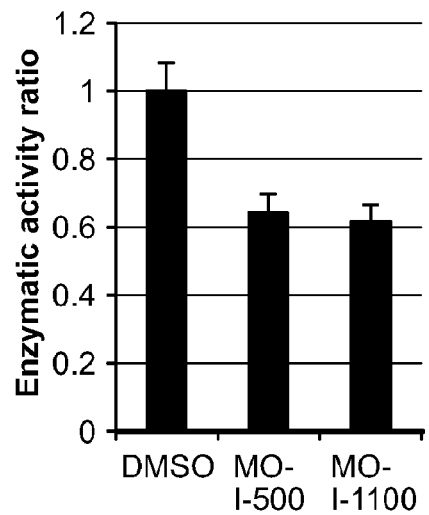
FIG. 7B is a bar graph showing that both MO-1-500 and MO-1-1100 inhibit ASPH enzymatic activity (β-hydroxylase) using the high through-put assay described in FIGS. 3A-D.
Figure 8A:
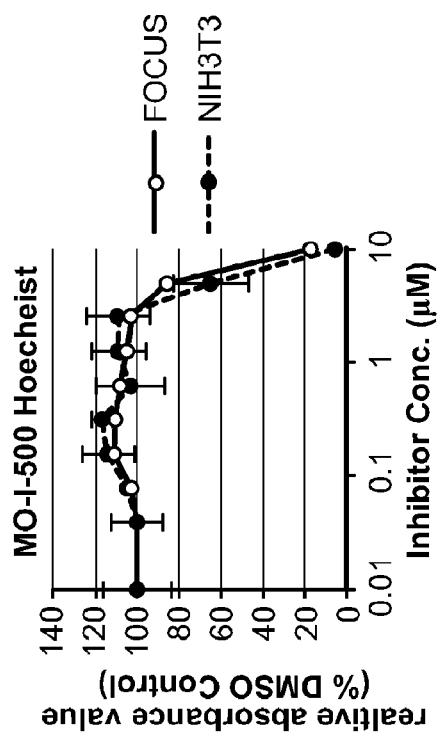
FIGS. 8A-B are bar graphs.
Figure 8B:
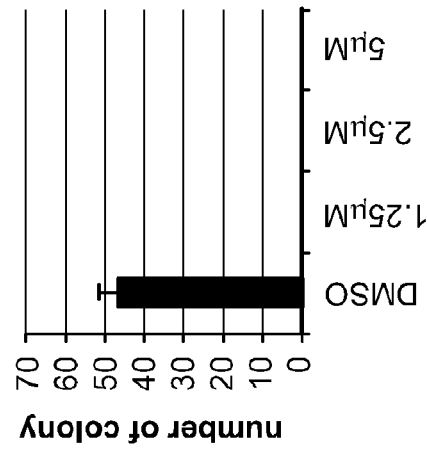
Figure 8C:
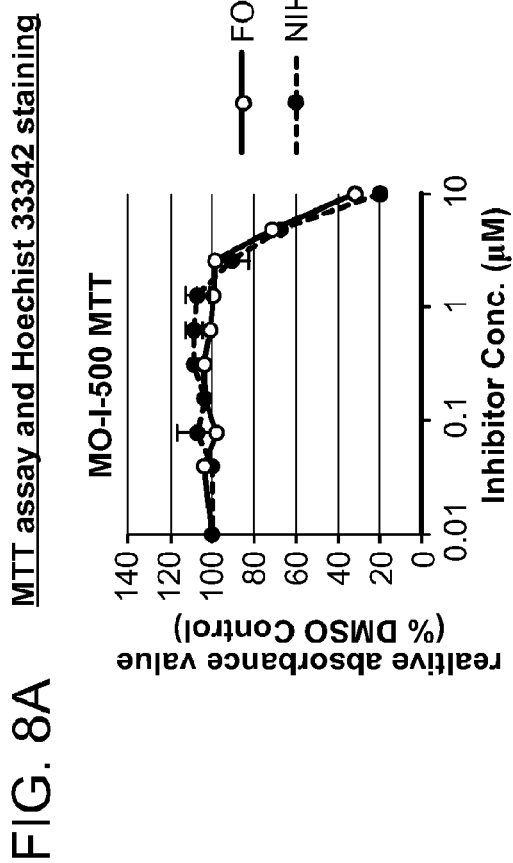
FIG. 8C is a photograph.
Figure 8D:
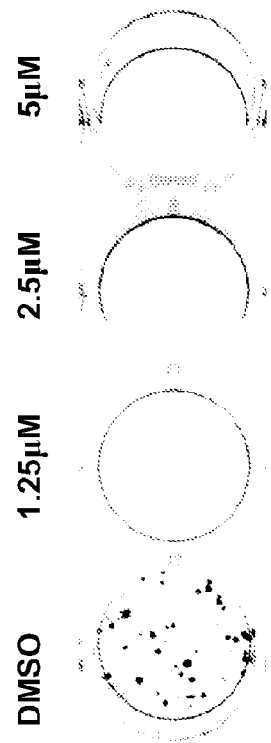
FIG. 8D is a bar graph showing the effect of MO-1-500 on cell metabolism (A), proliferation (B), and colony formation (C, D). Note that both FOCUS HCC cells (express ASPH) and NIH-3T3 cells (do not express ASPH) were growth inhibited indicating that MO-1-500 is not specific for ASPH although it strikingly inhibits colony formation of FOCUS cells at 1.25 µM.

We performed similar studies using the MO-1-500 compound. Similar to the findings in MO-1-1100, we observed that MO-1-500 at 5 µM also inhibited ASPH enzymatic activity as measured by the $^{14}CO2$-ketoglutarate-dependent capture assay. The structure of MO-1-500 is quite different than MO-1-1100 as shown in FIGS. 7A-B. Additional experiments measured the in vitro effects of MO-1-500 on cell proliferation and metabolism as shown in FIGS. 8A-D. In contrast to MO-1-1100 effects, MO-1-500 has striking affects on cell proliferation and metabolic activity at micromolar concentrations in both FOCUS cells (which contain high levels of ASPH cell surface expression) and NIH-3T3 cells which do not. These findings indicate that MO-1-500 has hydroxylase inhibitory activity but also probably inhibits other hydroxylases or proteins that may be important for cell viability and growth as well since NIH 3T3 cells lacking ASPH were susceptible to its inhibitory effects. More striking was the colony formation assay that showed that 1.25 µM concentrations of MO-1-500 had substantial inhibitory effects on colony formation of FOCUS HCC cells indicating high potency in this assay of cellular transformation. In summary both MO-1-1100 and MO-1-500 inhibit ASPH β-hydroxylase activity, cell viability and metabolism, as well as colony formation in soft agar but MO-1-1100 is more highly specific for the β-hydroxylase of ASPH as shown in FIGS. 5A-C.

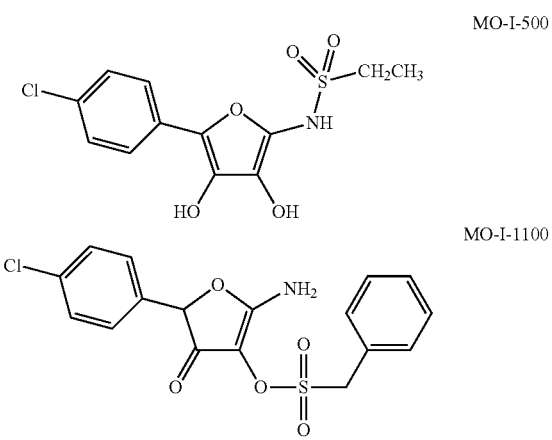

In Vitro Effects of ASPH Inhibitor for Anchorage-Independent Cell Growth.

Studies on MO-1-1100

The effect of MO-1-1100 on anchorage independent growth in soft agar was evaluated. The ability of forming colonosphere in soft agar is considered to be a rigid test for tumorigenic potential. ASPH expression results in cells acquiring the ability to form colonospheres in soft agar.

These results indicated that ASPH plays a key role in establishing tumor, growth, invasion and metastasis in vivo. In order to evaluate the effect of ASPH inhibitor for anchorage independent colony formation, FOCUS cells were incubated in soft agar with or without this ASPH enzymatic inhibitor. After 3 weeks incubation, MO-1-1100 reduced colonosphere formation of FOCUS cells (FIG. 9A). As shown in FIGS. 9B, C treatment with MO-1-1100 produced a dose-dependent and highly significant reduction both in number and size of the colonies after 3 weeks of culture. This assay is a standard method to monitor malignant growth that reflects the ability to form tumors that grow aggressively in vivo. These results confirm that MO-1-1100 impairs the generation of a malignant phenotype in vitro.

Studies With MO-1-500

Figure 10B:
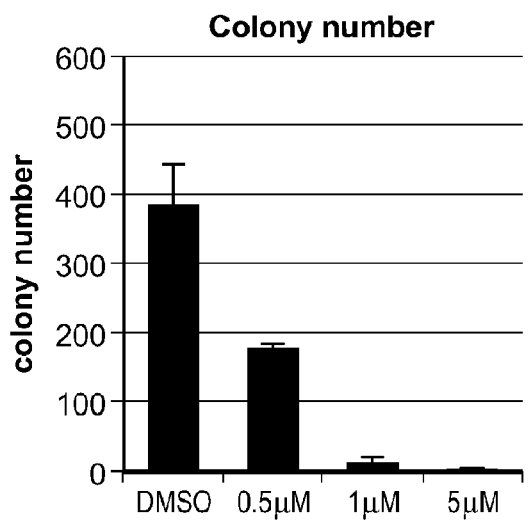
FIGS. 10B-C are bar graphs showing the in vitro effects of MO-1-500 for anchorage independent cell growth. Note the striking reduction in the number and size of FOCUS cell colonies following treatment with 0.5, 1, and 5 µM of MO-1-500.
Figure 10C:
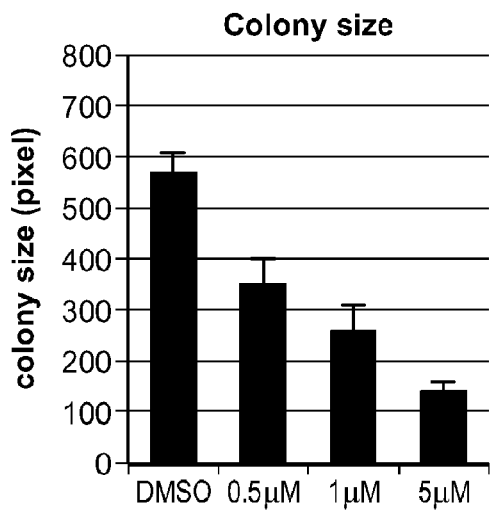

The effect of MO-1-500 on anchorage independent cell growth was evaluated as shown in FIGS. 10A-B. It was striking that 1 µM exposure of HCC cells grown in soft agar dramatically reduced the number of colonies formed, and the colony size in a dose-dependent manner. Thus, MO-1-500 had very similar but more potent effects on anchorage-independent cell growth as did MO-1-1100 for this assay of cellular transformation that correlates well with tumor formation in vivo.

In Vitro Effects of ASPH Inhibitors for Cell Motility and Invasiveness in Human HCC Cell.

Studies With MO-1-1100

Figure 11A:
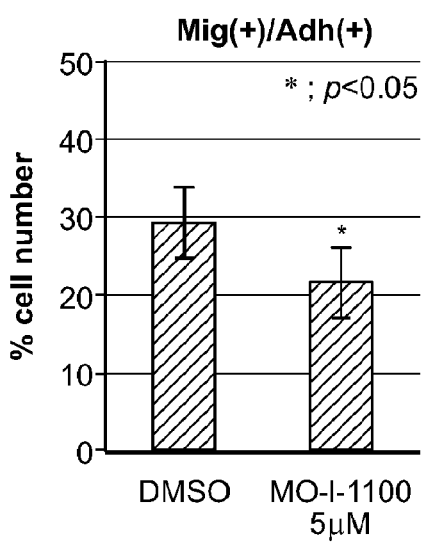
FIGS. 11A-D are bar graphs showing the effect of MO-1-1100 on cell migration and invasion of FOCUS HCC cells. Note that this compound significantly inhibited the migratory (A), and invasion (D), properties of this human liver cancer cell line.
Figure 11B:
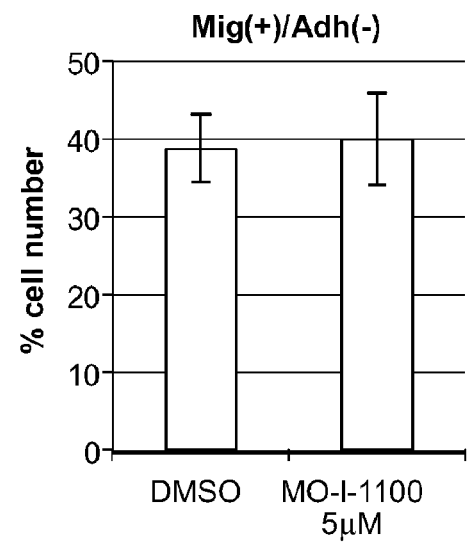
Figure 11C:
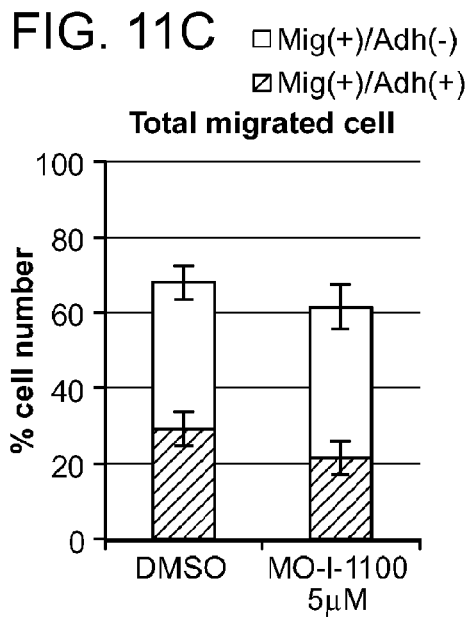
Figure 11D:
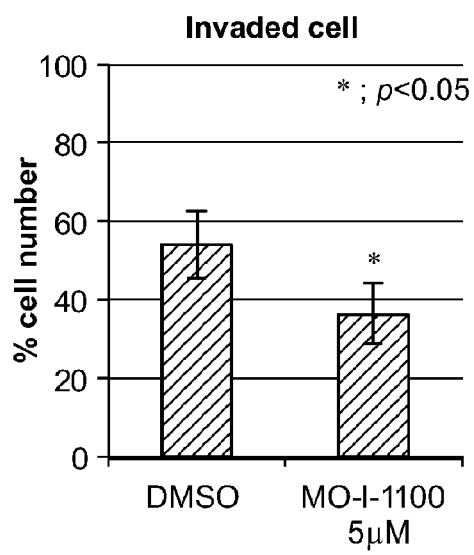

The β-hydroxylase activity is required for ASPH to mediate its effects on cell motility. Directional motility was measured using Boyden chamber-type culture inserts equipped with porous membranes. FOCUS cells were pretreated with 5 µM of MO-1-1100 and MO-1-500 β-hydroxylase inhibitor for 24 hours, and then placed into the upper chamber. Migration was allowed to proceed for 30 min. ATPLite was used to quantify viable cell density. The cells in the upper well and upper surface of membrane reflects the number of non-migrating cells, luminescence measured at the bottom surface of the membrane reflects the number of migrating and non-adherent cells and luminescence measured in the bottom well was reflect migrating and non-adherent cells. As shown in FIGS. 11A-C total migrated cells were reduced following MO-1-1100 treatment but the population of non-adherent cells was unchanged; the migrating and adherent cells were significantly reduced. Cell invasiveness was assessed by invasion assay using matrigel coated membrane, in which cells were allowed to proceed for 6 hours; those found adhered on the bottom surface of membrane were regarded as invading cells. MO-1-1100 treatment FOCUS cells significantly reduced invasiveness compared to cells incubated with DMSO as a control (FIG. 11D). Results demonstrated that MO-1-1100 inhibited cell motility, migration and invasiveness of human HCC cells.

Studies With MO-1-500

Figure 12A:
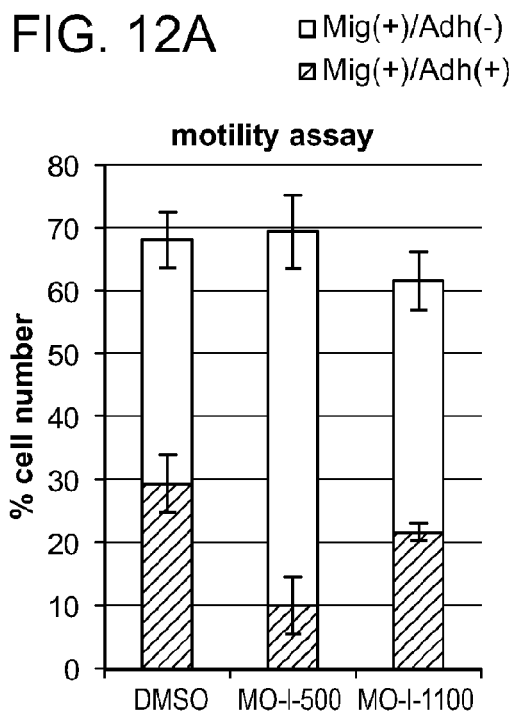
FIGS. 12A-B are bar graphs showing the in vitro effects of ASPH inhibitiors MO-1-500 and MO-1-1100 on cell motility and invasiveness in a human HCC cell line (FOCUS).
Figure 12B:
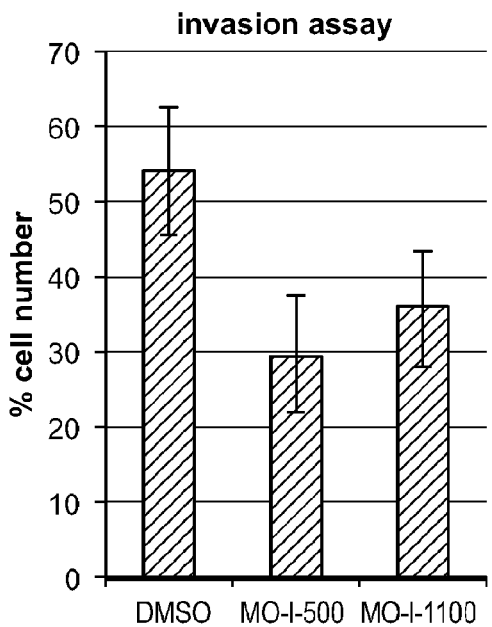

In vivo effects of ASPH inhibitors on cell motility and invasiveness were evaluated using the human HCC FOCUS cell line. As shown in FIGS. 12A-B, MO-1-500 had a pronounced effect on cell motility and invasion as well. Note that MO-1-500 was slightly more potent inhibiting cell motility and invasion than MO-1-1100, but both were highly active in these two assays that characterize the malignant phenotype. Thus, these small molecule inhibitors of ASPH-β-hydroxylase have a profound effect on the function of the metastatic phenotype by reducing the ability of tumor cells to migrate and invade, and thus substantially alter their biologic function and metastatic potential.

In Vivo Effects of an ASPH Inhibitor, MO-1-1100, on Subcutaneous Xenograft Development and Growth of Human Hepatocellular Carcinoma.

Figure 13B:
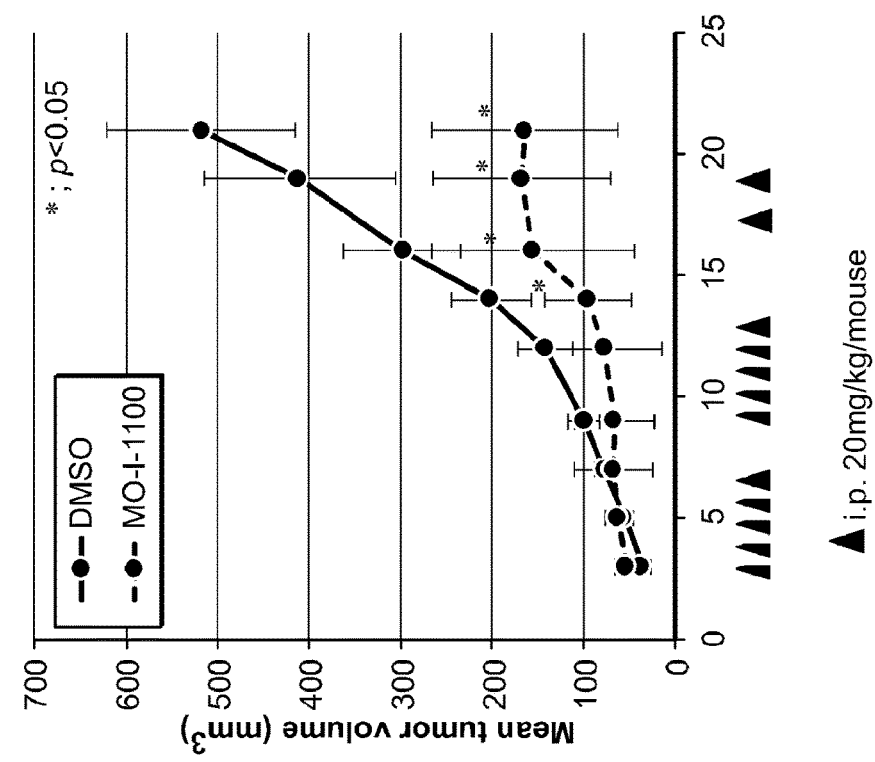
FIG. 13B is a line graph showing that MO-1-1100 treatment strikingly reduces the size and growth of human liver cancer in vivo using an immunodeficient murine subcutaneous xenograft model.
Figure 13A:
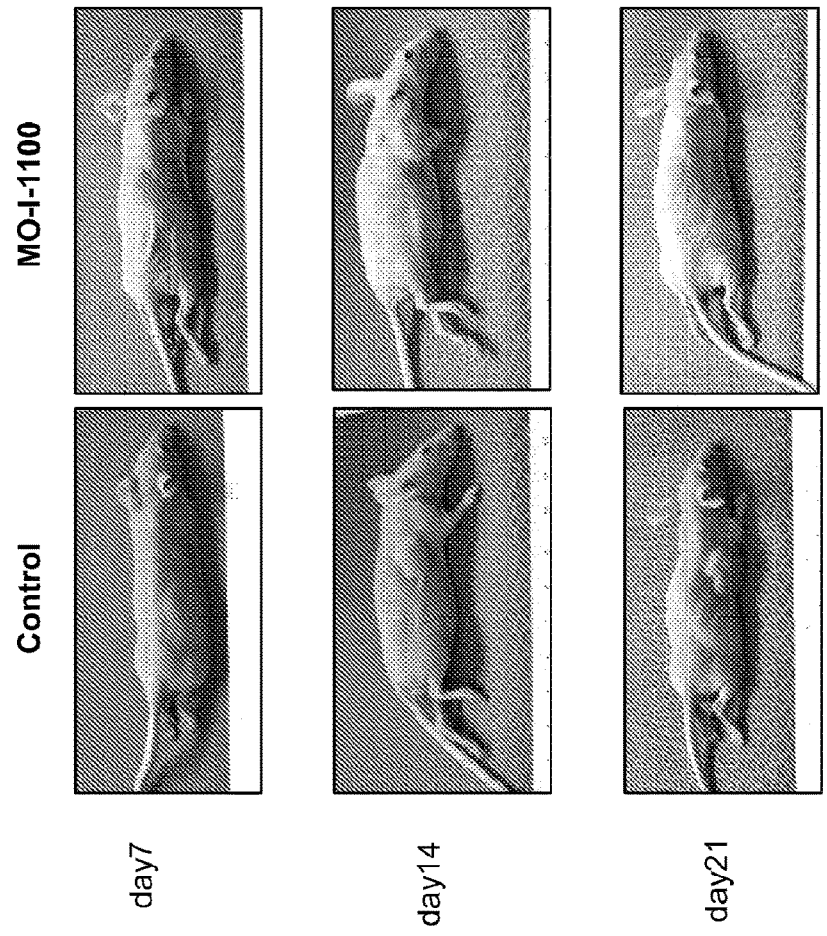
FIG. 13A is a photograph.

The human HCC cell line FOCUS is known to be a highly aggressive tumor forming cell line in vivo. To investigate in vivo anti-tumor efficacy of the ASPH inhibitor, MO-1-1100 at 20 mg/kg per day was administered on 5 consecutive days for 2 weeks and every other day thereafter. As shown in FIGS. 13A-B, the administration of MO-1-1100 significantly reduced HCC subcutaneous xenograft growth. The mean tumor volumes were substantially decreased by treatment with MO-1-1100 on day 12 following treatment, and tumor volumes in treated mice were reduced an average of 31.7% compared to those observed in control mice (FIG. 13B). None of the MO-1-1100 treated mice showed signs of wasting or other adverse effects relative to control mice. Thus, MO-1-1100 was tolerated well at this dose level where striking antitumor efficacy was observed. Thus, a specific β-hydroxylase inhibitor such as MO-1-1100 substantially reduced tumor growth of HCC as shown in FIGS. 13A-B but also inhibited the development and growth of pancreatic cancer as well (FIGS. 4A-B) since the tumor also has high level expression of ASPH. Such findings indicate that any ASPH expressing human tumor are responsive to these specific β-hydroxylase inhibitors. These ASPH inhibitor compounds represent a class of anti-tumor agents that has substantial anti-tumor activity against a large number of solid human tumors known to have a dismal prognosis.

ASPH is overexpressed on the cell surface of human tumor cells within solid tumors and has low or negligible expression in normal human tissues. ASPH expression is present in most, if not all, tumor cells. ASPH is also exposed to the extracellular environment which makes it an excellent therapeutic target since it has easy access to small molecule inhibitors of the catalytic activity through the blood. The data described herein support the following conclusions: ASPH overexpression causes increased motility, migration, invasion and metastasis of HCC cells as well as other human tumor cell lines; many human solid tumors with a dismal prognosis overexpress ASPH on the cell surface including but not limited to pancreatic, hepatocellular, cholangio-, colon, breast, prostate, lung, and glioblastoma cancers; the catalytic site and enzymatic activity are critical for ASPH mediated malignant transformation, and the subsequent generation of an invasive and metastatic tumor phenotype; ASPH exerts its biologic effects on increased migration, invasion, and metastasis of tumor cells by activation of Notch signaling cascade; small molecule inhibitors of the β-hydroxylase activity have been discovered based on the crystal structure of the C-terminal catalytic site of ASPH; tumor cells exposed to these inhibitors such as MO-1-1100 and MO-1-500 have reduced proliferation, migration, invasion, and colony formation in soft agar which impairs the ability of these cells to grow and metastasize; these small molecule inhibitors of ASPH enzymatic activity have striking and unexpected anti-tumor effects in vivo in animal models of human pancreatic and liver cancer growth and development. Thus, these studies demonstrate that compounds which specifically inhibit the β-hydroxylase activity are useful to reduce the growth and/or inhibit metatstases of ASPH expressing human solid tumors, in particular those known to have a dismal clinical prognosis, e.g., Pancreatic Cancer, Hepatocellular Cancer, Cholangiocarcinoma, Lung, Colon Cancer, Breast Cancer, Prostatic Cancer, and Glioblastoma.

In another aspect, this invention features a compound of Formula Ia:

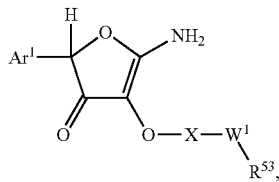

(Ia)

or a salt, ester, metabolite, prodrug, or solvate thereof, wherein $Ar^1$ is substituted or unsubstituted $C_6$-$C_{20}$ aryl or 5 to 20-membered heteroaryl;

X is C(O), C(S), or $S(O)_2$;

$W^1$ is a single bond, O, $CR^{50}R^{51}$, or $NR^{52}$ when X is CO and $W^1$ is a single bond, $CR^{50}R^{51}$, or $NR^{52}$ when X is $SO_2$; and each of $R^{50}$, $R^{51}$, $R^{52}$, and $R^{53}$ independently is selected from the group consisting of hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{20}$ aryl, substituted or unsubstituted $C_7$-$C_{26}$ arylalkyl, substituted or unsubstituted 5 to 20-membered heteroaryl, and substituted or unsubstituted 6-26 membered heteroarylalkyl, provided that when $Ar^1$ is 4-chlorophenyl, X is C(O), and $W^1$ is a single bond, then $R^{53}$ is not unsubstituted methyl or unsubstituted phenyl.

The compound of Formula Ia may have one or more of the following features when applicable.

For example, the compound is of Formula IIa:

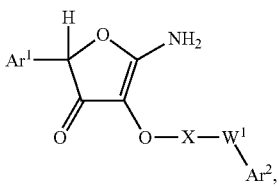

(IIa)

or a salt, ester, metabolite, prodrug, or solvate thereof, wherein each of $Ar^1$ and $Ar^2$ independently is unsubstituted $C_6$-$C_{14}$ aryl, unsubstituted 5 to 14-membered heteroaryl, or $C_6$-$C_{14}$ aryl or 5 to 14-membered heteroaryl each substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, $—S(O)_bR_a$, $—S(O)_bNR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; and each of $R_{S1}$ and $R_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, $R^{53}$ is unsubstituted $C_1$-$C_6$ alkyl or $C_1$-$C_6$ alkyl substituted with one or more substituents selected from halo, OH, CN, and amino.

For example, X is $S(O)_2$ and $W^1$ is $CR^{50}R^{51}$.

For example, X is $S(O)_2$ and $W^1$ is a single bond.

For example, X is C(O) and $W^1$ is O, or X is C(S) and $W^1$ is $NR^{52}$.

For example, each of $R^{50}$, $R^{51}$, and $R^{52}$ independently is H, unsubstituted $C_1$-$C_6$ alkyl, or $C_1$-$C_6$ alkyl substituted with one or more substituents selected from halo, OH, CN, and amino.

For example, each of $Ar^1$ and $Ar^2$ independently is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, $—S(O)_bR_a$, $—S(O)_bNR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 5- or 6-membered heteroaryl, or 4 to 12-membered heterocycloalkyl, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; and each of $R_{S1}$ and $R_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, each of $Ar^1$ and $Ar^2$ independently is phenyl, naphthyl, or 5 to 10-membered heteroaryl, each of which is optionally substituted with one or more substituents selected from the group consisting of halo, CN, $NO_2$, NO, $N_3$, $OR_a$, $NR_aR_b$, $C(O)R_a$, $C(O)OR_a$, or $R_{S1}$, in which $R_{S1}$ is $C_1$-$C_6$ alkyl, each of $R_a$ and $R_b$, independently is H or $R_{S2}$, and $R_{S2}$ is $C_1$-$C_6$ alkyl; and each of $R_{S1}$ and $R_{S2}$, is optionally substituted with one or more substituents selected from the group consisting of halo, OH, $C_1$-$C_6$ alkoxyl, amino, mono-$C_1$-$C_6$ alkylamino, and di-$C_1$-$C_6$ alkylamino.

For example, each of $Ar^1$ and $Ar^2$ independently is selected from phenyl, 1-naphthyl, 2-naphthyl, 2-furanyl, 2-thiazolyl, 2-pyridyl, 3-pyridyl, 4-pyridyl, 2-quinolinyl, 3-quinolinyl, 4-quinolinyl, 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-cyanophenyl, 3-cyanophenyl, 4-cyanophenyl, 3-carboxymethylphenyl, 2-methoxyphenyl, 3-methoxyphenyl, 4-methoxyphenyl, 2,3-dichlorophenyl, 2,4-dichlorophenyl, 2,5-dichlorophenyl, 3,4-dichlorophenyl, 3,5-dichlorophenyl, 2,3-difluorophenyl, 2,4-difluorophenyl, 2,5-difluorophenyl, 3,4-difluorophenyl, 3,5-difluorophenyl, 2,3-dimethoxyphenyl, 2,4-dimethoxyphenyl, 2,5-dimethoxyphenyl, 3,4-dimethoxyphenyl, 3,5-dimethoxyphenyl, 2-chloro-6-fluorophenyl, 3-chloro-4-fluorophenyl, 2-chloro-4-fluorophenyl, 4-chloro-3-fluorophenyl, 3-chloro-2-fluorophenyl, 2-chloro-5-fluorophenyl, 4-chloro-2-fluorophenyl, and 5-chloro-2-fluorophenyl.

For example, the compound of Formula Ia or IIa is an ASPH inhibitory compound.

The present invention also relates to compounds of Formula I, a pharmaceutically-acceptable salt thereof, and mixtures of any of the forgoing:

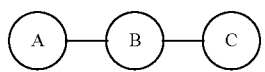 (I)

wherein A is a substituted or unsubstituted single-, fused, or polycyclic, aryl or heteroaryl ring;

wherein said aryl or heteroaryl ring comprises at least one R group selected from the group consisting of —H, —OH, —SH, —CN, —F, —Cl, —Br, —CN, NO$_2$, —NO, —NH$_2$, —NHR, —NRR, —C(O)R, —C(O)OH, —C(O)OR, —C(O)NH$_2$, —C(O)NHR, and —C(O)NRR, —SOR, —SO$_2$R, —SO$_2$NH$_2$, —SO$_2$NHR, —SO$_2$NR$_2$;

wherein each R is independently selected from the group consisting of (C$_1$-C$_5$) alkyl, substituted (C$_1$-C$_6$) alkyl, (C$_2$-C$_6$) alkenyl, substituted (C$_2$-C$_6$) alkenyl, (C$_2$-C$_6$) alkynyl, substituted (C$_2$-C$_6$) alkynyl, (C$_5$-C$_{20}$) aryl, substituted (C$_5$-C$_{20}$) aryl, (C$_6$-C$_{26}$) arylalkyl, substituted (C$_6$-C$_{26}$) arylalkyl, 5-20 membered heteroaryl, substituted 5-20 membered heteroaryl, 6-26 membered heteroarylalkyl, and substituted 6-26 membered heteroarylalkyl;

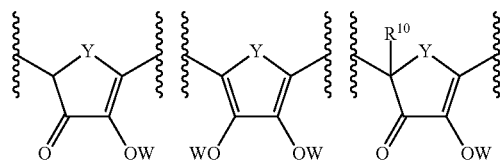

wherein Y is O, S; and wherein R10 is selected from the group consisting of (C$_1$-C$_5$) alkyl, substituted (C$_1$-C$_6$) alkyl, (C$_2$-C$_6$) alkenyl, substituted (C$_2$-C$_6$) alkenyl, (C$_2$-C$_6$) alkynyl, substituted (C$_2$-C$_6$) alkynyl, (C$_5$-C$_{20}$) aryl, substituted (C$_5$-C$_{20}$) aryl, (C$_6$-C$_{26}$) arylalkyl, substituted (C$_6$-C$_{26}$) arylalkyl, 5-20 membered heteroaryl, substituted 5-20 membered heteroaryl, 6-26 membered heteroarylalkyl, and substituted 6-26 membered heteroarylalkyl; and wherein W is selected from the group consisting of hydrogen, alkyl, haloalkyl, —C(O)R, —C(O)OR, —SOR, —SO$_2$R, —C(O)NHR, —C(O)NR$_2$ where R is independently (C$_1$-C$_5$) alkyl, substituted (C$_1$-C$_6$) alkyl, (C$_2$-C$_6$) alkenyl, substituted (C$_2$-C$_6$) alkenyl, (C$_2$-C$_6$) alkynyl, substituted (C$_2$-C$_6$) alkynyl, (C$_5$-C$_{20}$) aryl, substituted (C$_5$-C$_{20}$) aryl, (C$_6$-C$_{26}$) arylalkyl, substituted (C$_6$-C$_{26}$) arylalkyl, 5-20 membered heteroaryl, substituted 5-20 membered heteroaryl, 6-26 membered heteroarylalkyl, and substituted 6-26 membered heteroarylalkyl; and wherein C is selected from the group consisting of —NHSO$_2$R, —N(R)SO$_2$R, —NHC(O)R, —NRC(O)R, —NHC(O)OR, —NRC(O)OR, —NHC(S)R, —NRC(S)R, —NHC(S)OR, —NRC(S)OR, —NH2 where R is independently (C$_1$-C$_5$) alkyl, substituted (C$_1$-C$_6$) alkyl, (C$_2$-C$_6$) alkenyl, substituted (C$_2$-C$_6$) alkenyl, (C$_2$-C$_6$) alkynyl, substituted (C$_2$-C$_6$) alkynyl, (C$_5$-C$_{20}$) aryl, substituted (C$_5$-C$_{20}$) aryl, (C$_6$-C$_{26}$) arylalkyl, substituted (C$_6$-C$_{26}$) arylalkyl, 5-20 membered heteroaryl, substituted 5-20 membered heteroaryl, 6-26 membered heteroarylalkyl, and substituted 6-26 membered heteroarylalkyl;

or wherein C is selected from the group consisting of

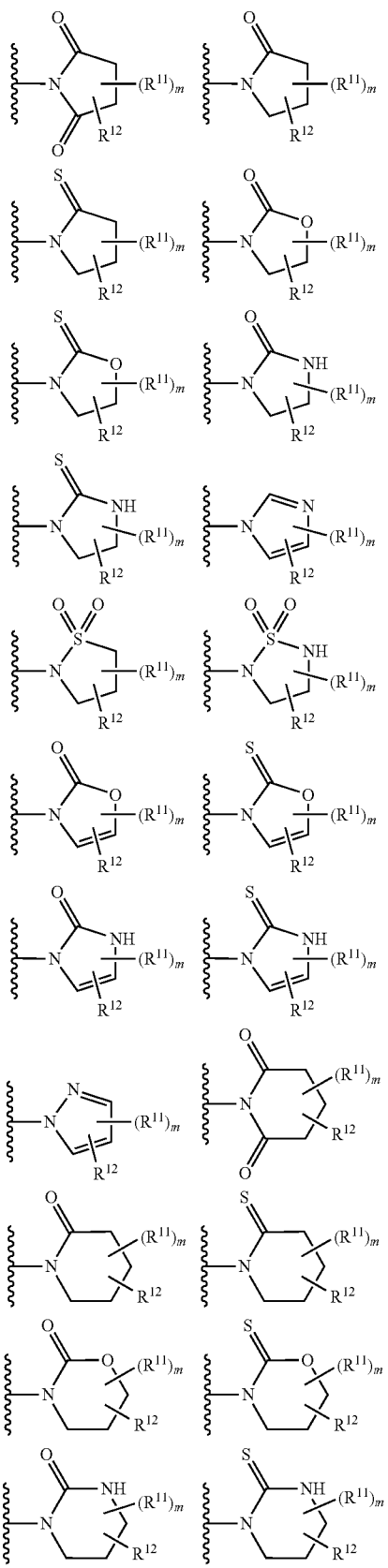

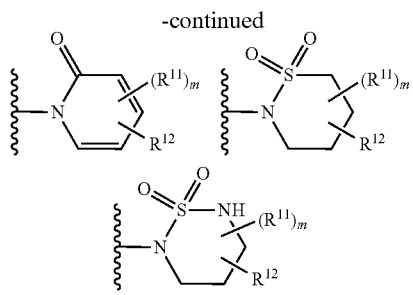

wherein $R^{11}$ and $R^{12}$ are independently selected from the group consisting of hydrogen, —OH, —F, —Cl, —Br, —I, —C(O)R, —CO$_2$R, —CONH$_2$, —CN, —SO2R, ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl;

wherein R is ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl; and wherein C may not be —NH2, unless W contains a sulfur.

Specific Compounds Encompassed by Formula I

The compounds encompassed by Formula I include the following:

2-(2-chlorophenyl)-5-amino-4-hydroxy-3(2H)-furanone; 2-(2-chlorophenyl)-4-(acetoxy)-5-amino-3(2H)-furanone; 2-(2-chlorophenyl)-4-[[phenylsulfonyl]oxy]-5-amino-3(2H)-furanone; N-(3,4-dihydroxy-5-(2-chlorophenyl)-2-furanyl)methanesulfonamide; N-(3,4-dihydroxy-5-(2-chlorophenyl)-2-furanyl) ethanesulfonamide; N-(3,4-dihydroxy-5-(2-chlorophenyl)-2-furanyl) benzenesulfonamide; N-(3,4-dihydroxy-5-(2-chlorophenyl)-2-furanyl) acetamide; N-(3,4-dihydroxy-5-(2-chlorophenyl)-2-furanyl)-carbamic acid ethyl ester; N-(3,4-dihydroxy-5-(2-chlorophenyl)-2-furanyl) benzamide; N-(3-trimethylsilyloxy-4-hydroxy-5-(2-chlorophenyl)-2-furanyl)-4-bromobutanamide; N-(3,4-dihydroxy-5-(2-chlorophenyl)-2-furanyl)-2-pyrrolidinone; N-(3,4-dihydroxy-5-(2-chlorophenyl)-2-furanyl) succinimide; N-(3-trimethylsilyloxy-4-hydroxy-5-(2-chlorophenyl)-2-furanyl)-3-bromopropylsulfonamide; N-(3,4-dihydroxy-5-(2-chlorophenyl)-2-furanyl)-1,1-dioxide-isothiazolidine; N-methyl-N'-(3,4-dihydroxy-5-(2-chlorophenyl)-2-furanyl) ethanesulfonamide; N-(3-acetoxy-4-hydroxy-5-(2-chlorophenyl)-2-furanyl)methanesulfonamide; N-(3-acetoxy-4-hydroxy-5-(2-chlorophenyl)-2-furanyl)ethanesulfonamide; N-(3-acetoxy-4-hydroxy-5-(2-chlorophenyl)-2-furanyl)benzenesulfonamide; N-(3-acetoxy-4-hydroxy-5-(2-chlorophenyl)-2-furanyl)-acetamide; N-(3-acetoxy-4-hydroxy-5-(2-chlorophenyl)-2-furanyl)-carbamic acid ethyl ester; N-(3-acetoxy-4-hydroxy-5-(2-chlorophenyl)-2-furanyl) benzamide; N-(3-acetoxy-4-hydroxy-5-(2-chlorophenyl)-2-furanyl)-4-bromobutanamide; N-(3-acetoxy-4-hydroxy-5-(2-chlorophenyl)-2-furanyl)-2-pyrrolidinone; N-(3-acetoxy-4-hydroxy-5-(2-chlorophenyl)-2-furanyl)succinimide; N-(3-acetoxy-4-hydroxy-5-(2-chlorophenyl)-2-furanyl)-3-bromopropylsulfonamide; N-(3-acetoxy-4-hydroxy-5-(2-chlorophenyl)-2-furanyl)-1,1-dioxide-isothiazolidine; N-methyl-N'-(3-acetoxy-4-hydroxy-5-(2-chlorophenyl)-2-furanyl)ethanesulfonamide; 2-(2-chlorophenyl)-2-methyl-4-trimethylsilyloxy-5-amino-3(2H)-furanone; 2-(2-chlorophenyl)-2-methyl-4-hydroxy-5-amino-3(2H)-furanone; N-(2-(2-chlorophenyl)-2-methyl-4-hydroxy-3(2H)-furanon-5-yl)-methanesulfonamide; N-(2-(2-chlorophenyl)-2-methyl-4-hydroxy-3(2H)-furanon-5-yl)-ethanesulfonamide; N-(2-(2-chlorophenyl)-2-methyl-4-hydroxy-3(2H)-furanon-5-yl)-benzenesulfonamide; N-(2-(2-chlorophenyl)-2-methyl-4-hydroxy-3(2H)-furanon-5-yl)-acetamide; N-(2-(2-chlorophenyl)-2-methyl-4-hydroxy-3(2H)-furanon-5-yl)-carbamic acid ethyl ester; N-(2-(2-chlorophenyl)-2-methyl-4-hydroxy-3(2H)-furanon-5-yl)-benzamide; N-(2-(2-chlorophenyl)-2-methyl-4-hydroxy-3(2H)-furanon-5-yl)-4-bromobutanamide; N-(2-(2-chlorophenyl)-2-methyl-4-hydroxy-3(2H)-furanon-5-yl)-2-pyrrolidinone; N-(2-(2-chlorophenyl)-2-methyl-4-hydroxy-3(2H)-furanon-5-yl)-succinimide; N-(2-(2-chlorophenyl)-2-methyl-4-hydroxy-3(2H)-furanon-5-yl)-3-bromopropylsulfonamide; N-(2-(2-chlorophenyl)-2-methyl-4-hydroxy-3(2H)-furanon-5-yl)-1,1-dioxide-isothiazolidine; N-methyl-N'-(2-(2-chlorophenyl)-2-methyl-4-hydroxy-3(2H)-furanon-5-yl)-ethanesulfonamide; 2-(2-chlorophenyl)-2-methyl-4-acetoxy-5-amino-3(2H)-furanone; N-(2-(2-chlorophenyl)-2-methyl-4-acetoxy-3(2H)-furanon-5-yl)-methanesulfonamide; N-(2-(2-chlorophenyl)-2-methyl-4-acetoxy-3(2H)-furanon-5-yl)-ethanesulfonamide; N-(2-(2-chlorophenyl)-2-methyl-4-acetoxy-3(2H)-furanon-5-yl)-benzenesulfonamide; N-(2-(2-chlorophenyl)-2-methyl-4-acetoxy-3(2H)-furanon-5-yl)-acetamide; N-(2-(2-chlorophenyl)-2-methyl-4-acetoxy-3(2H)-furanon-5-yl)-carbamic acid ethyl ester; N-(2-(2-chlorophenyl)-2-methyl-4-acetoxy-3(2H)-furanon-5-yl)-benzamide; N-(2-(2-chlorophenyl)-2-methyl-4-acetoxy-3(2H)-furanon-5-yl)-4-bromobutanamide; N-(2-(2-chlorophenyl)-2-methyl-4-acetoxy-3(2H)-furanon-5-yl)-2-pyrrolidinone; N-(2-(2-chlorophenyl)-2-methyl-4-acetoxy-3(2H)-furanon-5-yl)-succinimide; N-(2-(2-chlorophenyl)-2-methyl-4-acetoxy-3(2H)-furanon-5-yl)-3-bromopropylsulfonamide; N-(2-(2-chlorophenyl)-2-methyl-4-acetoxy-3(2H)-furanon-5-yl)-1,1-dioxide-isothiazolidine; N-methyl-N'-(2-(2-chlorophenyl)-2-methyl-4-acetoxy-3(2H)-furanon-5-yl)-ethanesulfonamide; 2-(3-chlorophenyl)-5-amino-4-hydroxy-3(2H)-furanone; 2-(3-chlorophenyl)-4-(acetoxy)-5-amino-3(2H)-furanone; 2-(3-chlorophenyl)-4-[[phenylsulfonyl]oxy]-5-amino-3(2H)-furanone; N-(3,4-dihydroxy-5-(3-chlorophenyl)-2-furanyl) methanesulfonamide; N-(3,4-dihydroxy-5-(3-chlorophenyl)-2-furanyl)ethanesulfonamide; N-(3,4-dihydroxy-5-(3-chlorophenyl)-2-furanyl) benzenesulfonamide; N-(3,4-dihydroxy-5-(3-chlorophenyl)-2-furanyl)acetamide; N-(3,4-dihydroxy-5-(3-chlorophenyl)-2-furanyl)-carbamic acid ethyl ester; N-(3,4-dihydroxy-5-(3-chlorophenyl)-2-furanyl)benzamide; N-(3-trimethylsilyloxy-4-hydroxy-5-(3-chlorophenyl)-2-furanyl)-4-bromobutanamide; N-(3,4-dihydroxy-5-(3-chlorophenyl)-2-furanyl)-2-pyrrolidinone; N-(3,4-dihydroxy-5-(3-chlorophenyl)-2-furanyl)succinimide; N-(3-trimethylsilyloxy-4-hydroxy-5-(3-chlorophenyl)-2-furanyl)-3-bromopropylsulfonamide; N-(3,4-dihydroxy-5-(3-chlorophenyl)-2-furanyl)-1,1-dioxide-isothiazolidine; N-5 methyl-N'-(3,4-dihydroxy-5-(3-chlorophenyl)-2-furanyl)ethanesulfonamide; N-(3-acetoxy-4-hydroxy-5-(3-chlorophenyl)-2-furanyl)methanesulfonamide; N-(3-acetoxy-4-hydroxy-5-(3-chlorophenyl)-2-furanyl)ethanesulfonamide; N-(3-acetoxy-4-hydroxy-5-(3-chlorophenyl)-2-furanyl)benzenesulfonamide; N-(3-acetoxy-4-hydroxy-5-(3-chlorophenyl)-2-furanyl)-acetamide; N-(3-acetoxy-4-hydroxy-5-(3-chlorophenyl)-2-furanyl)-carbamic acid ethyl ester; N-(3-acetoxy-4-hydroxy-5-(3-chlorophenyl)-2-furanyl)

benzamide; N-(3-acetoxy-4-hydroxy-5-(3-chlorophenyl)-2-furanyl)-4-bromobutanamide; N-(3-acetoxy-4-hydroxy-5-(3-chlorophenyl)-2-furanyl)-2-pyrrolidinone; N-(3-acetoxy-4-hydroxy-5-(3-chlorophenyl)-2-furanyl)succinimide; N-(3-acetoxy-4-hydroxy-5-(3-chlorophenyl)-2-furanyl)-3-bromopropylsulfonamide; N-(3-acetoxy-4-hydroxy-5-(3-chlorophenyl)-2-furanyl)-1,1-dioxide-isothiazolidine; N-methyl-N'-(3-acetoxy-4-hydroxy-5-(3-chlorophenyl)-2-furanyl)ethanesulfonamide; 2-(3-chlorophenyl)-2-methyl-4-trimethylsilyloxy-5-amino-3(2H)-furanone; 2-(3-chlorophenyl)-2-methyl-4-hydroxy-5-amino-3(2H)-furanone; N-(2-(3-chlorophenyl)-2-methyl-4-hydroxy-3(2H)-furanon-5-yl)-methanesulfonamide; N-(2-(3-chlorophenyl)-2-methyl-4-hydroxy-3(2H)-furanon-5-yl)-ethanesulfonamide; N-(2-(3-chlorophenyl)-2-methyl-4-hydroxy-3(2H)-furanon-5-yl)-benzenesulfonamide; N-(2-(3-chlorophenyl)-2-methyl-4-hydroxy-3(2H)-furanon-5-yl)-acetamide; N-(2-(3-chlorophenyl)-2-methyl-4-hydroxy-3(2H)-furanon-5-yl)-carbamic acid ethyl ester; N-(2-(3-chlorophenyl)-2-methyl-4-hydroxy-3(2H)-furanon-5-yl)-benzamide; N-(2-3-chlorophenyl)-2-methyl-4-hydroxy-3(2H)-furanon-5-yl)-4-bromobutanamide; N-(2-(3-chlorophenyl)-2-methyl-4-hydroxy-3(2H)-furanon-5-yl)-2-pyrrolidinone; N-(2-(3-chlorophenyl)-2-methyl-4-hydroxy-3(2H)-furanon-5-yl)-succinimide; N-(2-(3-chlorophenyl)-2-methyl-4-hydroxy-3(2H)-furanon-5-yl)-3-bromopropylsulfonamide; N-(2-(3-chlorophenyl)-2-methyl-4-hydroxy-3(2H)-furanon-5-yl)-1,1-dioxide-isothiazolidine; N-methyl-N'-(2-(3-chlorophenyl)-2-methyl-4-hydroxy-3(2H)-furanon-5-yl)-ethanesulfonamide; 2-(3-chlorophenyl)-2-methyl-4-acetoxy-5-amino-3(2H)-furanone; N-(2-(3-chlorophenyl)-2-methyl-4-acetoxy-3(2H)-furanon-5-yl)-methanesulfonamide; N-(2-(3-chlorophenyl)-2-methyl-4-acetoxy-3(2H)-furanon-5-yl)-ethanesulfonamide; N-(2-(3-chlorophenyl)-2-methyl-4-acetoxy-3(2H)-furanon-5-yl)-benzenesulfonamide; N-(2-(3-chlorophenyl)-2-methyl-4-acetoxy-3(2H)-furanon-5-yl)-acetamide; N-(2-(3-chlorophenyl)-2-methyl-4-acetoxy-3(2H)-furanon-5-yl)-carbamic acid ethyl ester; N-(2-(3-chlorophenyl)-2-methyl-4-acetoxy-3(2H)-furanon-5-yl)-benzamide; N-(2-(3-chlorophenyl)-2-methyl-4-acetoxy-3(2H)-furanon-5-yl)-4-bromobutanamide; N-(2-(3-chlorophenyl)-2-methyl-4-acetoxy-3(2H)-furanon-5-yl)-2-pyrrolidinone; N-(2-(3-chlorophenyl)-2-methyl-4-acetoxy-3(2H)-furanon-5-yl)-succinimide; N-(2-(3-chlorophenyl)-2-methyl-4-acetoxy-3(2H)-furanon-5-yl)-3-bromopropylsulfonamide; N-(2-(3-chlorophenyl)-2-methyl-4-acetoxy-3(2H)-furanon-5-yl)-1,1-dioxide-isothiazolidine; N-methyl-N'-(2-(3-chlorophenyl)-2-methyl-4-acetoxy-3(2H)-furanon-5-yl)-ethanesulfonamide; 2-(4-chlorophenyl)-5-amino-4-hydroxy-3(2H)-furanone; 2-(4-chlorophenyl)-4-(acetoxy)-5-amino-3(2H)-furanone; 2-(4-chlorophenyl)-4-[[phenylsulfonyl]oxy]-5-amino-3(2H)-furanone; N-(3,4-dihydroxy-5-(4-chlorophenyl)-2-furanyl)methanesulfonamide; N-(3,4-dihydroxy-5-(4-chlorophenyl)-2-furanyl)ethanesulfonamide; N-(3,4-dihydroxy-5-(4-chlorophenyl)-2-furanyl)benzenesulfonamide; N-(3,4-dihydroxy-5-(4-chlorophenyl)-2-furanyl)acetamide; N-(3,4-dihydroxy-5-(4-chlorophenyl)-2-furanyl)-carbamic acid ethyl ester; N-(3,4-dihydroxy-5-(4-chlorophenyl)-2-furanyl)benzamide; N-(3-trimethylsilyloxy-4-hydroxy-5-(4-chlorophenyl)-2-furanyl)-4-bromobutanamide; N-(3,4-dihydroxy-5-(4-chlorophenyl)-2-furanyl)-2-pyrrolidinone; N-(3,4-dihydroxy-5-(4-chlorophenyl)-2-furanyl)succinimide; N-(3-trimethylsilyloxy-4-hydroxy-5-(4-chlorophenyl)-2-furanyl)-3-bromopropylsulfonamide; N-(3,4-dihydroxy-5-(4-chlorophenyl)-2-furanyl)-1,1-20 dioxide-isothiazolidine; N-methyl-N'-(3,4-dihydroxy-5-(4-chlorophenyl)-2-furanyl)ethanesulfonamide; N-(3-acetoxy-4-hydroxy-5-(4-chlorophenyl)-2-furanyl)methanesulfonamide; N-(3-acetoxy-4-hydroxy-5-(4-chlorophenyl)-2-furanyl)ethanesulfonamide; N-(3-acetoxy-4-hydroxy-5-(4-chlorophenyl)-2-furanyl)benzenesulfonamide; N-(3-acetoxy-4-hydroxy-5-(4-chlorophenyl)-2-furanyl)-acetamide; N-(3-acetoxy-4-hydroxy-5-(4-chlorophenyl)-2-furanyl)-carbamic acid ethyl ester; N-(3-acetoxy-4-hydroxy-5-(4-chlorophenyl)-2-furanyl)benzamide; N-(3-acetoxy-4-hydroxy-5-(4-chlorophenyl)-2-furanyl)-4-bromobutanamide; N-(3-acetoxy-4-hydroxy-5-(4-chlorophenyl)-2-furanyl)-2-pyrrolidinone; N-(3-acetoxy-4-hydroxy-5-(4-chlorophenyl)-2-furanyl)succinimide; N-(3-acetoxy-4-hydroxy-5-(4-chlorophenyl)-2-furanyl)-3-bromopropylsulfonamide; N-(3-acetoxy-4-hydroxy-5-(4-chlorophenyl)-2-furanyl)-1,1-dioxide-isothiazolidine; N-methyl-N'-(3-acetoxy-4-hydroxy-5-(4-chlorophenyl)-2-furanyl)ethanesulfonamide; 2-(4-chlorophenyl)-2-methyl-4-trimethylsilyloxy-5-amino-3(2H)-furanone; 2-(4-chlorophenyl)-2-methyl-4-hydroxy-5-amino-3(2H)-furanone; N-(2-(4-chlorophenyl)-2-methyl-4-hydroxy-3(2H)-furanon-5-yl)-methanesulfonamide; N-(2-(4-chlorophenyl)-2-methyl-4-hydroxy-3(2H)-furanon-5-yl)-ethanesulfonamide; N-(2-(4-chlorophenyl)-2-methyl-4-hydroxy-3(2H)-furanon-5-yl)-benzenesulfonamide; N-(2-(4-chlorophenyl)-2-methyl-4-hydroxy-3(2H)-furanon-5-yl)-acetamide; N-(2-(4-chlorophenyl)-2-methyl-4-hydroxy-3(2H)-furanon-5-yl)-carbamic acid ethyl ester; N-(2-(4-chlorophenyl)-2-methyl-4-hydroxy-3(2H)-furanon-5-yl)-benzamide; N-(2-(4-chlorophenyl)-2-methyl-4-hydroxy-3(2H)-furanon-5-yl)-4-bromobutanamide; N-(2-(4-chlorophenyl)-2-methyl-4-hydroxy-3(2H)-furanon-5-yl)-2-pyrrolidinone; N-(2-(4-chlorophenyl)-2-methyl-4-hydroxy-3(2H)-furanon-5-yl)-succinimide; N-(2-(4-chlorophenyl)-2-methyl-4-hydroxy-3(2H)-furanon-5-yl)-3-bromopropylsulfonamide; N-(2-(4-chlorophenyl)-2-methyl-4-hydroxy-3(2H)-furanon-5-yl)-1,1-dioxide-isothiazolidine; N-methyl-N'-(2-(4-chlorophenyl)-2-methyl-4-hydroxy-3(2H)-furanon-5-yl)-ethanesulfonamide; 2-(4-chlorophenyl)-2-methyl-4-acetoxy-5-amino-3(2H)-furanone; N-(2-(4-chlorophenyl)-2-methyl-4-acetoxy-3(2H)-furanon-5-yl)-methanesulfonamide; N-(2-(4-chlorophenyl)-2-methyl-4-acetoxy-3(2H)-furanon-5-yl)-ethanesulfonamide; N-(2-(4-chlorophenyl)-2-methyl-4-acetoxy-3(2H)-furanon-5-yl)-benzenesulfonamide; N-(2-(4-chlorophenyl)-2-methyl-4-acetoxy-3(2H)-furanon-5-yl)-acetamide; N-(2-(4-chlorophenyl)-2-methyl-4-acetoxy-3(2H)-furanon-5-yl)-carbamic acid ethyl ester; N-(2-(4-chlorophenyl)-2-methyl-4-acetoxy-3(2H)-furanon-5-yl)-benzamide; N-(2-(4-chlorophenyl)-2-methyl-4-acetoxy-3(2H)-furanon-5-yl)-4-bromobutanamide; N-(2-(4-chlorophenyl)-2-methyl-4-acetoxy-3(2H)-furanon-5-yl)-2-pyrrolidinone; N-(2-(4-chlorophenyl)-2-methyl-4-acetoxy-3(2H)-furanon-5-yl)-succinimide; N-(2-(4-chlorophenyl)-2-methyl-4-acetoxy-3(2H)-furanon-5-yl)-3-bromopropylsulfonamide; N-(2-(4-chlorophenyl)-2-methyl-4-acetoxy-3(2H)-furanon-5-yl)-1,1-dioxide-isothiazolidine; N-methyl-N'-(2-(4-chlorophenyl)-2-methyl-4-acetoxy-3(2H)-furanon-5-yl)-ethanesulfonamide; 2-(2,3-dichlorophenyl)-5-amino-4-hydroxy-3(2H)-furanone; 2-(2,3-dichlorophenyl)-4-(acetoxy)-5-amino-3(2H)-furanone; 2-(2,3-dichlorophenyl)-4-[[phenylsulfonyl]oxy]-5-amino-3(2H)-furanone; N-(3,4-dihydroxy-5-(2,3-dichlorophenyl)-2-furanyl)methanesulfonamide; N-(3,4-dihydroxy-5-(2,3-dichlorophenyl)-2-furanyl)ethanesulfonamide; N-(3,4-dihydroxy-5-(2,3-dichlorophenyl)-2-furanyl)

benzenesulfonamide; N-(3,4-dihydroxy-5-(2,3-dichlorophenyl)-2-furanyl)acetamide; N-(3,4-dihydroxy-5-(2,3-dichlorophenyl)-2-furanyl)-carbamic acid ethyl ester; N-(3,4-dihydroxy-5-(2,3-dichlorophenyl)-2-furanyl)benzamide; N-(3-trimethylsilyloxy-4-hydroxy-5-(2,3-dichlorophenyl)-2-furanyl)-4-bromobutanamide; N-(3,4-dihydroxy-5-(2,3-dichlorophenyl)-2-furanyl)-2-pyrrolidinone; N-(3,4-dihydroxy-5-(2,3-dichlorophenyl)-2-furanyl)succinimide; N-(3-trimethylsilyloxy-4-hydroxy-5-(2,3-dichlorophenyl)-2-furanyl)-3-bromopropylsulfonamide; N-(3,4-dihydroxy-5-(2,3-dichlorophenyl)-2-furanyl)-1,1-dioxide-isothiazolidine; N-methyl-N'-(3,4-dihydroxy-5-(2,3-dichlorophenyl)-2-furanyl)ethanesulfonamide; N-(3-acetoxy-4-hydroxy-5-(2,3-dichlorophenyl)-2-furanyl)methanesulfonamide; N-(3-acetoxy-4-hydroxy-5-(2,3-dichlorophenyl)-2-furanyl)ethanesulfonamide; N-(3-acetoxy-4-hydroxy-5-(2,3-dichlorophenyl)-2-furanyl)benzenesulfonamide; N-(3-acetoxy-4-hydroxy-5-(2,3-dichlorophenyl)-2-furanyl)-acetamide; N-(3-acetoxy-4-hydroxy-5-(2,3-dichlorophenyl)-2-furanyl)-carbamic acid ethyl ester; N-(3-acetoxy-4-hydroxy-5-(2,3-dichlorophenyl)-2-furanyl)benzamide; N-(3-acetoxy-4-hydroxy-5-(2,3-dichlorophenyl)-2-furanyl)-4-bromobutanamide; N-(3-acetoxy-4-hydroxy-5-(2,3-dichlorophenyl)-2-furanyl)-2-pyrrolidinone; N-(3-acetoxy-4-hydroxy-5-(2,3-dichlorophenyl)-2-furanyl)succinimide; N-(3-acetoxy-4-hydroxy-5-(2,3-dichlorophenyl)-2-furanyl)-3-bromopropylsulfonamide; N-(3-acetoxy-4-hydroxy-5-(2,3-dichlorophenyl)-2-furanyl)-1,1-dioxide-isothiazolidine; N-methyl-N'-(3-acetoxy-4-hydroxy-5-(2,3-dichlorophenyl)-2-furanyl)ethanesulfonamide; 2-(2,3-dichlorophenyl)-2-methyl-4-trimethylsilyloxy-5-amino-3(2H)-furanone; 2-(2,3-dichlorophenyl)-2-methyl-4-hydroxy-5-amino-3(2H)-furanone; N-(2-(2,3-dichlorophenyl)-2-methyl-4-hydroxy-3(2H)-furanon-5-yl)-methanesulfonamide; N-(2-(2,3-dichlorophenyl)-2-methyl-4-hydroxy-3(2H)-furanon-5-yl)-ethanesulfonamide; N-(2-(2,3-dichlorophenyl)-2-methyl-4-hydroxy-3(2H)-furanon-5-yl)-benzenesulfonamide; N-(2-(2,3-dichlorophenyl)-2-methyl-4-hydroxy-3(2H)-furanon-5-yl)-acetamide; N-(2-(2,3-dichlorophenyl)-2-methyl-4-hydroxy-3(2H)-furanon-5-yl)-carbamic acid ethyl ester; N-(2-(2,3-dichlorophenyl)-2-methyl-4-hydroxy-3(2H)-furanon-5-yl)-benzamide; N-(2-(2,3-dichlorophenyl)-2-methyl-4-hydroxy-3(2H)-furanon-5-yl)-4-5 bromobutanamide; N-(2-(2,3-dichlorophenyl)-2-methyl-4-hydroxy-3(2H)-furanon-5-yl)-2-pyrrolidinone; N-(2-(2,3-dichlorophenyl)-2-methyl-4-hydroxy-3(2H)-furanon-5-yl)-succinimide; N-(2-(2,3-dichlorophenyl)-2-methyl-4-hydroxy-3(2H)-furanon-5-yl)-3-bromopropylsulfonamide; N-(2-(2,3-dichlorophenyl)-2-methyl-4-hydroxy-3(2H)-furanon-5-yl)-1,1-dioxide-isothiazolidine; N-methyl-N'-(2-(2,3-dichlorophenyl)-2-methyl-4-hydroxy-3(2H)-furanon-5-yl)-ethanesulfonamide; 2-(2,3-dichlorophenyl)-2-methyl-4-acetoxy-5-amino-3(2H)-furanone; N-(2-(2,3-dichlorophenyl)-2-methyl-4-acetoxy-3(2H)-furanon-5-yl)-methanesulfonamide; N-(2-(2,3-dichlorophenyl)-2-methyl-4-acetoxy-3(2H)-furanon-5-yl)-ethanesulfonamide; N-(2-(2,3-dichlorophenyl)-2-methyl-4-acetoxy-3(2H)-furanon-5-yl)-benzenesulfonamide; N-(2-(2,3-dichlorophenyl)-2-methyl-4-acetoxy-3(2H)-furanon-5-yl)-acetamide; N-(2-(2,3-dichlorophenyl)-2-methyl-4-acetoxy-3(2H)-furanon-5-yl)-carbamic acid ethyl ester; N-(2-(2,3-dichlorophenyl)-2-methyl-4-acetoxy-3(2H)-furanon-5-yl)-benzamide; N-(2-(2,3-dichlorophenyl)-2-methyl-4-acetoxy-3(2H)-furanon-5-yl)-4-bromobutanamide; N-(2-(2,3-dichlorophenyl)-2-methyl-4-acetoxy-3(2H)-furanon-5-yl)-2-pyrrolidinone; N-(2-(2,3-dichlorophenyl)-2-methyl-4-acetoxy-3(2H)-furanon-5-yl)-succinimide; N-(2-(2,3-dichlorophenyl)-2-methyl-4-acetoxy-3(2H)-furanon-5-yl)-3-bromopropylsulfonamide; N-(2-(2,3-dichlorophenyl)-2-methyl-4-acetoxy-3(2H)-furanon-5-yl)-1,1-dioxide-isothiazolidine; N-methyl-N'-(2-(2,3-dichlorophenyl)-2-methyl-4-acetoxy-3(2H)-furanon-5-yl)-ethanesulfonamide; 2-(2,4-dichlorophenyl)-5-amino-4-hydroxy-3(2H)-furanone; 2-(2,4-dichlorophenyl)-4-(acetoxy)-5-amino-3(2H)-furanone; 2-(2,4-dichlorophenyl)-4-[[phenylsulfonyl]oxy]-5-amino-3(2H)-furanone; N-(3,4-dihydroxy-5-(2,4-dichlorophenyl)-2-furanyl)methanesulfonamide; N-(3,4-dihydroxy-5-(2,4-dichlorophenyl)-2-furanyl)ethanesulfonamide; N-(3,4-dihydroxy-5-(2,4-dichlorophenyl)-2-furanyl)benzenesulfonamide; N-(3,4-dihydroxy-5-(2,4-dichlorophenyl)-2-furanyl)acetamide; N-(3,4-dihydroxy-5-(2,4-dichlorophenyl)-2-furanyl)-carbamic acid ethyl ester; N-(3,4-dihydroxy-5-(2,4-dichlorophenyl)-2-furanyl)benzamide; N-(3-trimethylsilyloxy-4-hydroxy-5-(2,4-dichlorophenyl)-2-furanyl)-4-bromobutanamide; N-(3,4-dihydroxy-5-(2,4-dichlorophenyl)-2-furanyl)-2-pyrrolidinone; N-(3,4-dihydroxy-5-(2,4-dichlorophenyl)-2-furanyl)succinimide; N-(3-trimethylsilyloxy-4-hydroxy-5-(2,4-dichlorophenyl)-2-furanyl)-3-bromopropylsulfonamide; N-(3,4-dihydroxy-5-(2,4-dichlorophenyl)-2-furanyl)-1,1-dioxide-isothiazolidine; N-methyl-N'-(3,4-dihydroxy-5-(2,4-dichlorophenyl)-2-furanyl)ethanesulfonamide; N-(3-acetoxy-4-hydroxy-5-(2,4-dichlorophenyl)-2-furanyl)methanesulfonamide; N-(3-acetoxy-4-hydroxy-5-(2,4-dichlorophenyl)-2-furanyl)ethanesulfonamide; N-(3-acetoxy-4-hydroxy-5-(2,4-dichlorophenyl)-2-furanyl)benzenesulfonamide; N-(3-acetoxy-4-hydroxy-5-(2,4-dichlorophenyl)-2-furanyl)-acetamide; N-(3-acetoxy-4-hydroxy-5-(2,4-dichlorophenyl)-2-furanyl)-carbamic acid ethyl ester; N-(3-acetoxy-4-hydroxy-5-(2,4-dichlorophenyl)-2-furanyl)benzamide; N-(3-acetoxy-4-hydroxy-5-(2,4-dichlorophenyl)-2-furanyl)-4-bromobutanamide; N-(3-acetoxy-4-hydroxy-5-(2,4-dichlorophenyl)-2-furanyl)-2-pyrrolidinone; N-(3-acetoxy-4-hydroxy-5-(2,4-dichlorophenyl)-2-furanyl)succinimide; N-(3-acetoxy-4-hydroxy-5-(2,4-dichlorophenyl)-2-furanyl)-3-bromopropylsulfonamide; N-(3-acetoxy-4-hydroxy-5-(2,4-dichlorophenyl)-2-furanyl)-1,1-dioxide-isothiazolidine; N-methyl-N'-(3-acetoxy-4-hydroxy-5-(2,4-dichlorophenyl)-2-furanyl)ethanesulfonamide; 2-(2,4-dichlorophenyl)-2-methyl-4-trimethylsilyloxy-5-amino-3(2H)-furanone; 2-(2,4-dichlorophenyl)-2-methyl-4-hydroxy-5-amino-3(2H)-furanone; N-(2-(2,4-dichlorophenyl)-2-methyl-4-hydroxy-3(2H)-furanon-5-yl)-methanesulfonamide; N-(2-(2,4-dichlorophenyl)-2-methyl-4-hydroxy-3(2H)-furanon-5-yl)-ethanesulfonamide; N-(2-(2,4-dichlorophenyl)-2-methyl-4-hydroxy-3(2H)-furanon-5-yl)-benzenesulfonamide; N-(2-(2,4-dichlorophenyl)-2-methyl-4-hydroxy-3(2H)-furanon-5-yl)-acetamide; N-(2-(2,4-dichlorophenyl)-2-methyl-4-hydroxy-3(2H)-furanon-5-yl)-carbamic acid ethyl ester; N-(2-(2,4-dichlorophenyl)-2-methyl-4-hydroxy-3(2H)-furanon-5-yl)-benzamide; N-(2-(2,4-dichlorophenyl)-2-methyl-4-hydroxy-3(2H)-furanon-5-yl)-4-bromobutanamide; N-(2-(2,4-dichlorophenyl)-2-methyl-4-hydroxy-3(2H)-furanon-5-yl)-2-pyrrolidinone; N-(2-(2,4-dichlorophenyl)-2-methyl-4-hydroxy-3(2H)-furanon-5-yl)-succinimide; N-(2-(2,4-dichlorophenyl)-2-methyl-4-hydroxy-3(2H)-furanon-5-yl)-3-bromopropylsulfonamide; N-(2-(2,4-dichlorophenyl)-2-methyl-4-hydroxy-3(2H)-furanon-5-yl)-1,1-dioxide-isothiazolidine; N-methyl-N'-(2-(2,4-dichlorophenyl)-2-methyl-4-hydroxy-3(2H)-furanon-5-yl)-ethanesulfonamide; 2-(2,4-dichlorophenyl)-2-methyl-4-acetoxy-5-amino-3(2H)-furanone; N-(2-(2,4-dichlorophenyl)-2-methyl-4-acetoxy-3(2H)-furanon-5-yl)-methanesulfonamide; N-(2-(2,4-dichlorophenyl)-2-methyl-4-acetoxy-3(2H)-furanon-5-yl)-ethanesulfonamide; N-(2-(2,4-dichlorophenyl)-2-methyl-4-acetoxy-3(2H)-furanon-5-yl)-benzenesulfonamide; N-(2-(2,4-dichlorophenyl)-2-methyl-4-acetoxy-3(2H)-furanon-5-yl)-acetamide; N-(2-(2,4-dichlorophenyl)-2-methyl-4-acetoxy-3(2H)-furanon-5-yl)-carbamic acid ethyl ester; N-(2-(2,4-dichlorophenyl)-2-methyl-4-acetoxy-3(2H)-furanon-5-yl)-benzamide; N-(2-(2,4-dichlorophenyl)-2-methyl-4-acetoxy-3(2H)-furanon-5-yl)-4-bromobutanamide; N-(2-(2,4-dichlorophenyl)-2-methyl-4-acetoxy-3(2H)-furanon-5-yl)-2-pyrrolidinone; N-(2-(2,4-dichlorophenyl)-2-methyl-4-acetoxy-3(2H)-furanon-5-yl)-succinimide; N-(2-(2,4-dichlorophenyl)-2-methyl-4-acetoxy-3(2H)-furanon-5-yl)-3-bromopropylsulfonamide; N-(2-(2,4-dichlorophenyl)-2-methyl-4-acetoxy-3(2H)-furanon-5-yl)-1,1-dioxide-isothiazolidine; N-methyl-N'-(2-(2,4-dichlorophenyl)-2-methyl-4-acetoxy-3(2H)-furanon-5-yl)-ethanesulfonamide; 2-(2,5-dichlorophenyl)-5-amino-4-hydroxy-3(2H)-furanone; 2-(2,5-dichlorophenyl)-4-(acetoxy)-5-amino-3(2H)-furanone; 2-(2,5-dichlorophenyl)-4-[[phenylsulfonyl]oxy]-5-amino-3(2H)-furanone; N-(3,4-dihydroxy-5-(2,5-dichlorophenyl)-2-furanyl)methanesulfonamide; N-(3,4-dihydroxy-5-(2,5-dichlorophenyl)-2-furanyl)ethanesulfonamide; N-(3,4-dihydroxy-5-(2,5-dichlorophenyl)-2-furanyl)benzenesulfonamide; N-(3,4-dihydroxy-5-(2,5-dichlorophenyl)-2-furanyl)acetamide; N-(3,4-dihydroxy-5-(2,5-dichlorophenyl)-2-furanyl)-carbamic acid ethyl ester; N-(3,4-dihydroxy-5-(2,5-dichlorophenyl)-2-furanyl)benzamide; N-(3-trimethylsilyloxy-4-hydroxy-5-(2,5-dichlorophenyl)-2-furanyl)-4-bromobutanamide; N-(3,4-dihydroxy-5-(2,5-dichlorophenyl)-2-furanyl)-2-pyrrolidinone; N-(3,4-dihydroxy-5-(2,5-dichlorophenyl)-2-furanyl)succinimide; N-(3-trimethylsilyloxy-4-hydroxy-5-(2,5-dichlorophenyl)-2-furanyl)-3-bromopropylsulfonamide; N-(3,4-dihydroxy-5-(2,5-dichlorophenyl)-2-furanyl)-1,1-dioxide-isothiazolidine; N-methyl-N'-(3,4-dihydroxy-5-(2,5-dichlorophenyl)-2-furanyl)ethanesulfonamide; N-(3-acetoxy-4-hydroxy-5-(2,5-dichlorophenyl)-2-furanyl)methanesulfonamide; N-(3-acetoxy-4-hydroxy-5-(2,5-dichlorophenyl)-2-furanyl)ethanesulfonamide; N-(3-acetoxy-4-hydroxy-5-(2,5-dichlorophenyl)-2-furanyl)benzenesulfonamide; N-(3-acetoxy-4-hydroxy-5-(2,5-dichlorophenyl)-2-furanyl)-acetamide; N-(3-acetoxy-4-hydroxy-5-(2,5-dichlorophenyl)-2-furanyl)-carbamic acid ethyl ester; N-(3-acetoxy-4-hydroxy-5-(2,5-dichlorophenyl)-2-furanyl)benzamide; N-(3-acetoxy-4-hydroxy-5-(2,5-dichlorophenyl)-2-furanyl)-4-bromobutanamide; N-(3-acetoxy-4-hydroxy-5-(2,5-dichlorophenyl)-2-furanyl)-2-pyrrolidinone; N-(3-acetoxy-4-hydroxy-5-(2,5-dichlorophenyl)-2-furanyl)succinimide; N-(3-acetoxy-4-hydroxy-5-(2,5-dichlorophenyl)-2-furanyl)-3-bromopropylsulfonamide; N-(3-acetoxy-4-hydroxy-5-(2,5-dichlorophenyl)-2-furanyl)-1,1-dioxide-isothiazolidine; N-methyl-N'-(3-acetoxy-4-hydroxy-5-(2,5-dichlorophenyl)-2-furanyl)ethanesulfonamide; 2-(2,5-dichlorophenyl)-2-methyl-4-trimethylsilyloxy-5-amino-3(2H)-furanone; 2-(2,5-dichlorophenyl)-2-methyl-4-hydroxy-5-amino-3(2H)-furanone; N-(2-(2,5-dichlorophenyl)-2-methyl-4-hydroxy-3(2H)-furanon-5-yl)-methanesulfonamide; N-(2-(2,5-dichlorophenyl)-2-methyl-4-hydroxy-3(2H)-furanon-5-yl)-ethanesulfonamide; N-(2-(2,5-dichlorophenyl)-2-methyl-4-hydroxy-3(2H)-furanon-5-yl)-benzenesulfonamide; N-(2-(2,5-dichlorophenyl)-2-methyl-4-hydroxy-3(2H)-furanon-5-yl)-acetamide; N-(2-(2,5-dichlorophenyl)-2-methyl-4-hydroxy-3(2H)-furanon-5-yl)-carbamic acid ethyl ester; N-(2-(2,5-dichlorophenyl)-2-methyl-4-hydroxy-3(2H)-furanon-5-yl)-benzamide; N-(2-(2,5-dichlorophenyl)-2-methyl-4-hydroxy-3(2H)-furanon-5-yl)-4-bromobutanamide; N-(2-(2,5-dichlorophenyl)-2-methyl-4-hydroxy-3(2H)-furanon-5-yl)-2-pyrrolidinone; N-(2-(2,5-dichlorophenyl)-2-methyl-4-hydroxy-3(2H)-furanon-5-yl)-succinimide; N-(2-(2,5-dichlorophenyl)-2-methyl-4-hydroxy-3(2H)-furanon-5-yl)-3-bromopropylsulfonamide; N-(2-(2,5-dichlorophenyl)-2-methyl-4-hydroxy-3(2H)-furanon-5-yl)-1,1-dioxide-isothiazolidine; N-methyl-N'-(2-(2,5-dichlorophenyl)-2-methyl-4-hydroxy-3(2H)-furanon-5-yl)-ethanesulfonamide; 2-(2,5-dichlorophenyl)-2-methyl-4-acetoxy-5-amino-3(2H)-furanone; N-(2-(2,5-dichlorophenyl)-2-methyl-4-acetoxy-3(2H)-furanon-5-yl)-methanesulfonamide; N-(2-(2,5-dichlorophenyl)-2-methyl-4-acetoxy-3(2H)-furanon-5-yl)-ethanesulfonamide; N-(2-(2,5-dichlorophenyl)-2-methyl-4-acetoxy-3(2H)-furanon-5-yl)-benzenesulfonamide; N-(2-(2,5-dichlorophenyl)-2-methyl-4-acetoxy-3(2H)-furanon-5-yl)-acetamide; N-(2-(2,5-dichlorophenyl)-2-methyl-4-acetoxy-3(2H)-furanon-5-yl)-carbamic acid ethyl ester; N-(2-(2,5-dichlorophenyl)-2-methyl-4-acetoxy-3(2H)-furanon-5-yl)-benzamide; N-(2-(2,5-dichlorophenyl)-2-methyl-4-acetoxy-3(2H)-furanon-5-yl)-4-bromobutanamide; N-(2-(2,5-dichlorophenyl)-2-methyl-4-acetoxy-3(2H)-furanon-5-yl)-2-pyrrolidinone; N-(2-(2,5-dichlorophenyl)-2-methyl-4-acetoxy-3(2H)-furanon-5-yl)-succinimide; N-(2-(2,5-dichlorophenyl)-2-methyl-4-acetoxy-3(2H)-furanon-5-yl)-3-bromopropylsulfonamide; N-(2-(2,5-dichlorophenyl)-2-methyl-4-acetoxy-3(2H)-furanon-5-yl)-1,1-dioxide-isothiazolidine; N-methyl-N'-(2-(2,5-dichlorophenyl)-2-methyl-4-acetoxy-3(2H)-furanon-5-yl)-ethanesulfonamide; 2-(2,6-dichlorophenyl)-5-amino-4-hydroxy-3(2H)-furanone; 2-(2,6-dichlorophenyl)-4-(acetoxy)-5-amino-3(2H)-furanone; 2-(2,6-dichlorophenyl)-4-[[phenylsulfonyl]oxy]-5-amino-3(2H)-furanone; N-(3,4-dihydroxy-5-(2,6-dichlorophenyl)-2-furanyl)methanesulfonamide; N-(3,4-dihydroxy-5-(2,6-dichlorophenyl)-2-furanyl)ethanesulfonamide; N-(3,4-dihydroxy-5-(2,6-dichlorophenyl)-2-furanyl)benzenesulfonamide; N-(3,4-dihydroxy-5-(2,6-dichlorophenyl)-2-furanyl)acetamide; N-(3,4-dihydroxy-5-(2,6-dichlorophenyl)-2-furanyl)-carbamic acid ethyl ester; N-(3,4-dihydroxy-5-(2,6-dichlorophenyl)-2-furanyl)benzamide; N-(3-trimethylsilyloxy-4-hydroxy-5-(2,6-dichlorophenyl)-2-furanyl)-4-bromobutanamide; N-(3,4-dihydroxy-5-(2,6-dichlorophenyl)-2-furanyl)-2-pyrrolidinone; N-(3,4-dihydroxy-5-(2,6-dichlorophenyl)-2-furanyl)succinimide; N-(3-trimethylsilyloxy-4-hydroxy-5-(2,6-dichlorophenyl)-2-furanyl)-3-bromopropylsulfonamide; N-(3,4-dihydroxy-5-(2,6-dichlorophenyl)-2-furanyl)-1,1-dioxide-isothiazolidine; N-methyl-N'-(3,4-dihydroxy-5-(2,6-dichlorophenyl)-2-furanyl)ethanesulfonamide; N-(3-acetoxy-4-hydroxy-5-(2,6-dichlorophenyl)-2-furanyl)methanesulfonamide; N-(3-acetoxy-4-hydroxy-5-(2,6-dichlorophenyl)-2-furanyl)ethanesulfonamide; N-(3-acetoxy-4-hydroxy-5-(2,6-dichlorophenyl)-2-furanyl)benzenesulfonamide; N-(3-acetoxy-4-hydroxy-5-(2,6-dichlorophenyl)-2-furanyl)-acetamide; N-(3-acetoxy-4-hydroxy-5-(2,6-dichlorophenyl)-2-furanyl)-carbamic acid ethyl ester; N-(3-acetoxy-4-hydroxy-5-(2,6-dichlorophenyl)-2-furanyl)benzamide; N-(3-acetoxy-4-hydroxy-5-(2,6-dichlorophenyl)-2-furanyl)-4-bromobutanamide; N-(3-acetoxy-4-hydroxy-5-(2,6-dichlorophenyl)-2-furanyl)-2-pyrrolidinone; N-(3-acetoxy-4-hydroxy-5-(2,6-dichlorophenyl)-2-furanyl)succinimide; N-(3-acetoxy-4-hydroxy-5-(2,6-dichlorophenyl)-2-furanyl)-3-bromopropylsulfonamide; N-(3-acetoxy-4-hydroxy-5-(2,6- dichlorophenyl)-2-furanyl)-1,1-dioxide-isothiazolidine; N-methyl-N'-(3-acetoxy-4-hydroxy-5-(2,6-dichlorophenyl)-2-furanyl)ethanesulfonamide; 2-(2,6-dichlorophenyl)-2-methyl-4-trimethylsilyloxy-5-amino-3(2H)-furanone; 2-(2,6-dichlorophenyl)-2-methyl-4-hydroxy-5-amino-3(2H)-furanone; N-(2-(2,6-dichlorophenyl)-2-methyl-4-hydroxy-3(2H)-furanon-5-yl)-methanesulfonamide; N-(2-(2,6-dichlorophenyl)-2-methyl-4-hydroxy-3(2H)-furanon-5-yl)-ethanesulfonamide; N-(2-(2,6-dichlorophenyl)-2-methyl-4-hydroxy-3(2H)-furanon-5-yl)-benzenesulfonamide; N-(2-(2,6-dichlorophenyl)-2-methyl-4-hydroxy-3(2H)-furanon-5-yl)-acetamide; N-(2-(2,6-dichlorophenyl)-2-methyl-4-hydroxy-3(2H)-furanon-5-yl)-carbamic acid ethyl ester; N-(2-(2,6-dichlorophenyl)-2-methyl-4-hydroxy-3(2H)-furanon-5-yl)-benzamide; N-(2-(2,6-dichlorophenyl)-2-methyl-4-hydroxy-3(2H)-furanon-5-yl)-4-bromobutanamide; N-(2-(2,6-dichlorophenyl)-2-methyl-4-hydroxy-3(2H)-furanon-5-yl)-2-pyrrolidinone; N-(2-(2,6-dichlorophenyl)-2-methyl-4-hydroxy-3(2H)-furanon-5-yl)-succinimide; N-(2-(2,6-dichlorophenyl)-2-methyl-4-hydroxy-3(2H)-furanon-5-yl)-3-bromopropylsulfonamide; N-(2-(2,6-dichlorophenyl)-2-methyl-4-hydroxy-3(2H)-furanon-5-yl)-1,1-dioxide-isothiazolidine; N-methyl-N'-(2-(2,6-dichlorophenyl)-2-methyl-4-hydroxy-3(2H)-furanon-5-yl)-ethanesulfonamide; 2-(2,6-dichlorophenyl)-2-methyl-4-acetoxy-5-amino-3(2H)-furanone; N-(2-(2,6-dichlorophenyl)-2-methyl-4-acetoxy-3(2H)-furanon-5-yl)-methanesulfonamide; N-(2-(2,6-dichlorophenyl)-2-methyl-4-acetoxy-3(2H)-furanon-5-yl)-ethanesulfonamide; N-(2-(2,6-dichlorophenyl)-2-methyl-4-acetoxy-3(2H)-furanon-5-yl)-benzenesulfonamide; N-(2-(2,6-dichlorophenyl)-2-methyl-4-acetoxy-3(2H)-furanon-5-yl)-acetamide; N-(2-(2,6-dichlorophenyl)-2-methyl-4-acetoxy-3(2H)-furanon-5-yl)-carbamic acid ethyl ester; N-(2-(2,6-dichlorophenyl)-2-methyl-4-acetoxy-3(2H)-furanon-5-yl)-benzamide; N-(2-(2,6-dichlorophenyl)-2-methyl-4-acetoxy-3(2H)-furanon-5-yl)-4-bromobutanamide; N-(2-(2,6-dichlorophenyl)-2-methyl-4-acetoxy-3(2H)-furanon-5-yl)-2-pyrrolidinone; N-(2-(2,6-dichlorophenyl)-2-methyl-4-acetoxy-3(2H)-furanon-5-yl)-succinimide; N-(2-(2,6-dichlorophenyl)-2-methyl-4-acetoxy-3(2H)-furanon-5-yl)-3-bromopropylsulfonamide; N-(2-(2,6-dichlorophenyl)-2-methyl-4-acetoxy-3(2H)-furanon-5-yl)-1,1-dioxide-isothiazolidine; N-methyl-N'-(2-(2,6-dichlorophenyl)-2-methyl-4-acetoxy-3(2H)-furanon-5-yl)-ethanesulfonamide; 2-(3,4-dichlorophenyl)-5-amino-4-hydroxy-3(2H)-furanone; 2-(3,4-dichlorophenyl)-4-(acetoxy)-5-amino-3(2H)-furanone; 2-(3,4-dichlorophenyl)-4-[[phenylsulfonyl]oxy]-5-amino-3(2H)-furanone; N-(3,4-dihydroxy-5-(3,4-dichlorophenyl)-2-furanyl)methanesulfonamide; N-(3,4-dihydroxy-5-(3,4-dichlorophenyl)-2-furanyl)ethanesulfonamide; N-(3,4-dihydroxy-5-(3,4-dichlorophenyl)-2-furanyl)benzenesulfonamide; N-(3,4-dihydroxy-5-(3,4-dichlorophenyl)-2-furanyl)acetamide; N-(3,4-dihydroxy-5-(3,4-dichlorophenyl)-2-furanyl)-carbamic acid ethyl ester; N-(3,4-dihydroxy-5-(3,4-dichlorophenyl)-2-furanyl)benzamide; N-(3-trimethylsilyloxy-4-hydroxy-5-(3,4-dichlorophenyl)-2-furanyl)-4-bromobutanamide; N-(3,4-dihydroxy-5-(3,4-dichlorophenyl)-2-furanyl)-2-pyrrolidinone; N-(3,4-dihydroxy-5-(3,4-dichlorophenyl)-2-furanyl)succinimide; N-(3-trimethylsilyloxy-4-hydroxy-5-(3,4-dichlorophenyl)-2-furanyl)-3-bromopropylsulfonamide; N-(3,4-dihydroxy-5-(3,4-dichlorophenyl)-2-furanyl)-1,1-dioxide-isothiazolidine; N-methyl-N'-(3,4-dihydroxy-5-(3,4-dichlorophenyl)-2-furanyl)ethanesulfonamide; N-(3-acetoxy-4-hydroxy-5-(3,4-dichlorophenyl)-2-furanyl)methanesulfonamide; N-(3-acetoxy-4-hydroxy-5-(3,4-dichlorophenyl)-2-furanyl)ethanesulfonamide; N-(3-acetoxy-4-hydroxy-5-(3,4-dichlorophenyl)-2-furanyl)benzenesulfonamide; N-(3-acetoxy-4-hydroxy-5-(3,4-dichlorophenyl)-2-furanyl)acetamide; N-(3-acetoxy-4-hydroxy-5-(3,4-dichlorophenyl)-2-furanyl)-carbamic acid ethyl ester; N-(3-acetoxy-4-hydroxy-5-(3,4-dichlorophenyl)-2-furanyl)benzamide; N-(3-acetoxy-4-hydroxy-5-(3,4-dichlorophenyl)-2-furanyl)-4-bromobutanamide; N-(3-acetoxy-4-hydroxy-5-(3,4-dichlorophenyl)-2-furanyl)-2-pyrrolidinone; N-(3-acetoxy-4-hydroxy-5-(3,4-dichlorophenyl)-2-furanyl)succinimide; N-(3-acetoxy-4-hydroxy-5-(3,4-dichlorophenyl)-2-furanyl)-3-bromopropylsulfonamide; N-(3-acetoxy-4-hydroxy-5-(3,4-dichlorophenyl)-2-furanyl)-1,1-dioxide-isothiazolidine; N-methyl-N'-(3-acetoxy-4-hydroxy-5-(3,4-dichlorophenyl)-2-furanyl)ethanesulfonamide; 2-(3,4-dichlorophenyl)-2-methyl-4-trimethylsilyloxy-5-amino-3(2H)-furanone; 2-(3,4-dichlorophenyl)-2-methyl-4-hydroxy-5-amino-3(2H)-furanone; N-(2-(3,4-dichlorophenyl)-2-methyl-4-hydroxy-3(2H)-furanon-5-yl)-methanesulfonamide; N-(2-(3,4-dichlorophenyl)-2-methyl-4-hydroxy-3(2H)-furanon-5-yl)-ethanesulfonamide; N-(2-(3,4-dichlorophenyl)-2-methyl-4-hydroxy-3(2H)-furanon-5-yl)-benzenesulfonamide; N-(2-(3,4-dichlorophenyl)-2-methyl-4-hydroxy-3(2H)-furanon-5-yl)-acetamide; N-(2-(3,4-dichlorophenyl)-2-methyl-4-hydroxy-3(2H)-furanon-5-yl)-carbamic acid ethyl ester; N-(2-(3,4-dichlorophenyl)-2-methyl-4-hydroxy-3(2H)-furanon-5-yl)-benzamide; N-(2-(3,4-dichlorophenyl)-2-methyl-4-hydroxy-3(2H)-furanon-5-yl)-4-bromobutanamide; N-(2-(3,4-dichlorophenyl)-2-methyl-4-hydroxy-3(2H)-furanon-5-yl)-2-pyrrolidinone; N-(2-(3,4-dichlorophenyl)-2-methyl-4-hydroxy-3(2H)-furanon-5-yl)-succinimide; N-(2-(3,4-dichlorophenyl)-2-methyl-4-hydroxy-3(2H)-furanon-5-yl)-3-bromopropylsulfonamide; N-(2-(3,4-dichlorophenyl)-2-methyl-4-hydroxy-3(2H)-furanon-5-yl)-1,1-dioxide-isothiazolidine; N-methyl-N'-(2-(3,4-dichlorophenyl)-2-methyl-4-hydroxy-3(2H)-furanon-5-yl)-ethanesulfonamide; 2-(3,4-dichlorophenyl)-2-methyl-4-acetoxy-5-amino-3(2H)-furanone; N-(2-(3,4-dichlorophenyl)-2-methyl-4-acetoxy-3(2H)-furanon-5-yl)-methanesulfonamide; N-(2-(3,4-dichlorophenyl)-2-methyl-4-acetoxy-3(2H)-furanon-5-yl)-ethanesulfonamide; N-(2-(3,4-dichlorophenyl)-2-methyl-4-acetoxy-3(2H)-furanon-5-yl)-benzenesulfonamide; N-(2-(3,4-dichlorophenyl)-2-methyl-4-acetoxy-3(2H)-furanon-5-yl)-acetamide; N-(2-(3,4-dichlorophenyl)-2-methyl-4-acetoxy-3(2H)-furanon-5-yl)-carbamic acid ethyl ester; N-(2-(3,4-dichlorophenyl)-2-methyl-4-acetoxy-3(2H)-furanon-5-yl)-benzamide; N-(2-(3,4-dichlorophenyl)-2-methyl-4-acetoxy-3(2H)-furanon-5-yl)-4-bromobutanamide; N-(2-(3,4-dichlorophenyl)-2-methyl-4-acetoxy-3(2H)-furanon-5-yl)-2-pyrrolidinone; N-(2-(3,4-dichlorophenyl)-2-methyl-4-acetoxy-3(2H)-furanon-5-yl)-succinimide; N-(2-(3,4-dichlorophenyl)-2-methyl-4-acetoxy-3(2H)-furanon-5-yl)-3-bromopropylsulfonamide; N-(2-(3,4-dichlorophenyl)-2-methyl-4-acetoxy-3(2H)-furanon-5-yl)-1,1-dioxide-isothiazolidine; N-methyl-N'-(2-(3,4-dichlorophenyl)-2-methyl-4-acetoxy-3(2H)-furanon-5-yl)-ethanesulfonamide; 2-(3,5-dichlorophenyl)-5-amino-4-hydroxy-3(2H)-furanone; 2-(3,5-dichlorophenyl)-4-(acetoxy)-5-amino-3(2H)-furanone; 2-(3,5-dichlorophenyl)-4-[[phenylsulfonyl]oxy]-5-amino-3(2H)-furanone; N-(3,4-dihydroxy-5-(3,5-dichlorophenyl)-2-furanyl)methanesulfonamide; N-(3,4-dihydroxy-5-(3,5-dichlorophenyl)-2-furanyl)ethanesulfonamide; N-(3,4-dihydroxy-5-(3,5-dichlorophenyl)-2-furanyl)benzenesulfonamide; N-(3,4-dihydroxy-5-(3,5-dichlorophenyl)-2-furanyl)acetamide; N-(3,4-dihydroxy-5-(3,5-dichlorophenyl)-2-furanyl)-carbamic acid ethyl ester; N-(3,4-dihydroxy-5-(3,5-dichlorophenyl)-2-furanyl)benzamide; N-(3-trimethylsilyloxy-4-hydroxy-5-(3,5-dichlorophenyl)-2-furanyl)-4-bromobutanamide; N-(3,4-dihydroxy-5-(3,5-dichlorophenyl)-2-furanyl)-2-pyrrolidinone; N-(3,4-dihydroxy-5-(3,5-dichlorophenyl)-2-furanyl)succinimide; N-(3-trimethylsilyloxy-4-hydroxy-5-(3,5-dichlorophenyl)-2-furanyl)-3-bromopropylsulfonamide; N-(3,4-dihydroxy-5-(3,5-dichlorophenyl)-2-furanyl)-1,1-dioxide-isothiazolidine; N-methyl-N'-(3,4-dihydroxy-5-(3,5-dichlorophenyl)-2-furanyl)ethanesulfonamide; N-(3-acetoxy-4-hydroxy-5-(3,5-dichlorophenyl)-2-furanyl)methanesulfonamide; N-(3-acetoxy-4-hydroxy-5-(3,5-dichlorophenyl)-2-furanyl)ethanesulfonamide; N-(3-acetoxy-4-hydroxy-5-(3,5-dichlorophenyl)-2-furanyl)benzenesulfonamide; N-(3-acetoxy-4-hydroxy-5-(3,5-dichlorophenyl)-2-furanyl)-acetamide; N-(3-acetoxy-4-hydroxy-5-(3,5-dichlorophenyl)-2-furanyl)-carbamic acid ethyl ester; N-(3-acetoxy-4-hydroxy-5-(3,5-dichlorophenyl)-2-furanyl)benzamide; N-(3-acetoxy-4-hydroxy-5-(3,5-dichlorophenyl)-2-furanyl)-4-bromobutanamide; N-(3-acetoxy-4-hydroxy-5-(3,5-dichlorophenyl)-2-furanyl)-2-pyrrolidinone; N-(3-acetoxy-4-hydroxy-5-(3,5-dichlorophenyl)-2-furanyl)succinimide; N-(3-acetoxy-4-hydroxy-5-(3,5-dichlorophenyl)-2-furanyl)-3-bromopropylsulfonamide; N-(3-acetoxy-4-hydroxy-5-(3,5-dichlorophenyl)-2-furanyl)-1,1-dioxide-isothiazolidine; N-methyl-N'-(3-acetoxy-4-hydroxy-5-(3,5-dichlorophenyl)-2-furanyl)ethanesulfonamide; 2-(3,5-dichlorophenyl)-2-methyl-4-trimethylsilyloxy-5-amino-3(2H)-furanone; 2-(3,5-dichlorophenyl)-2-methyl-4-hydroxy-5-amino-3(2H)-furanone; N-(2-(3,5-dichlorophenyl)-2-methyl-4-hydroxy-3(2H)-furanon-5-yl)-methanesulfonamide; N-(2-(3,5-dichlorophenyl)-2-methyl-4-hydroxy-3(2H)-furanon-5-yl)-ethanesulfonamide; N-(2-(3,5-dichlorophenyl)-2-methyl-4-hydroxy-3(2H)-furanon-5-yl)-benzenesulfonamide; N-(2-(3,5-dichlorophenyl)-2-methyl-4-hydroxy-3(2H)-furanon-5-yl)-acetamide; N-(2-(3,5-dichlorophenyl)-2-methyl-4-hydroxy-3(2H)-furanon-5-yl)-carbamic acid ethyl ester; N-(2-(3,5-dichlorophenyl)-2-methyl-4-hydroxy-3(2H)-furanon-5-yl)-benzamide; N-(2-(3,5-dichlorophenyl)-2-methyl-4-hydroxy-3(2H)-furanon-5-yl)-4-bromobutanamide; N-(2-(3,5-dichlorophenyl)-2-methyl-4-hydroxy-3(2H)-furanon-5-yl)-2-pyrrolidinone; N-(2-(3,5-dichlorophenyl)-2-methyl-4-hydroxy-3(2H)-furanon-5-yl)-succinimide; N-(2-(3,5-dichlorophenyl)-2-methyl-4-hydroxy-3(2H)-furanon-5-yl)-3-bromopropylsulfonamide; N-(2-(3,5-dichlorophenyl)-2-methyl-4-hydroxy-3(2H)-furanon-5-yl)-1,1-dioxide-isothiazolidine; N-methyl-N'-(2-(3,5-dichlorophenyl)-2-methyl-4-hydroxy-3(2H)-furanon-5-yl)-ethanesulfonamide; 2-(3,5-dichlorophenyl)-2-methyl-4-acetoxy-5-amino-3(2H)-furanone; N-(2-(3,5-dichlorophenyl)-2-methyl-4-acetoxy-3(2H)-furanon-5-yl)-methanesulfonamide; N-(2-(3,5-dichlorophenyl)-2-methyl-4-acetoxy-3(2H)-furanon-5-yl)-ethanesulfonamide; N-(2-(3,5-dichlorophenyl)-2-methyl-4-acetoxy-3(2H)-furanon-5-yl)-benzenesulfonamide; N-(2-(3,5-dichlorophenyl)-2-methyl-4-acetoxy-3(2H)-furanon-5-yl)-acetamide; N-(2-(3,5-dichlorophenyl)-2-methyl-4-acetoxy-3(2H)-furanon-5-yl)-carbamic acid ethyl ester; N-(2-(3,5-dichlorophenyl)-2-methyl-4-acetoxy-3(2H)-furanon-5-yl)-benzamide; N-(2-(3,5-dichlorophenyl)-2-methyl-4-acetoxy-3(2H)-furanon-5-yl)-4-bromobutanamide; N-(2-(3,5-dichlorophenyl)-2-methyl-4-acetoxy-3(2H)-furanon-5-yl)-2-pyrrolidinone; N-(2-(3,5-dichlorophenyl)-2-methyl-4-acetoxy-3(2H)-furanon-5-yl)-succinimide; N-(2-(3,5-dichlorophenyl)-2-methyl-4-acetoxy-3(2H)-furanon-5-yl)-3-bromopropylsulfonamide; N-(2-(3,5-dichlorophenyl)-2-methyl-4-acetoxy-3(2H)-furanon-5-yl)-1,1-dioxide-isothiazolidine; N-methyl-N'-(2-(3,5-dichlorophenyl)-2-methyl-4-acetoxy-3(2H)-furanon-5-yl)-ethanesulfonamide; 2-(2-fluorophenyl)-5-amino-4-hydroxy-3(2H)-furanone; 2-(2-fluorophenyl)-4-(acetoxy)-5-amino-3(2H)-furanone; 2-(2-fluorophenyl)-4-[[phenylsulfonyl]oxy]-5-amino-3(2H)-furanone; N-(3,4-dihydroxy-5-(2-fluorophenyl)-2-furanyl)methanesulfonamide; N-(3,4-dihydroxy-5-(2-fluorophenyl)-2-furanyl)ethanesulfonamide; N-(3,4-dihydroxy-5-(2-fluorophenyl)-2-furanyl)benzenesulfonamide; N-(3,4-dihydroxy-5-(2-fluorophenyl)-2-furanyl)acetamide; N-(3,4-dihydroxy-5-(2-fluorophenyl)-2-furanyl)-carbamic acid ethyl ester; N-(3,4-dihydroxy-5-(2-fluorophenyl)-2-furanyl)benzamide; N-(3-trimethylsilyloxy-4-hydroxy-5-(2-fluorophenyl)-2-furanyl)-4-bromobutanamide; N-(3,4-dihydroxy-5-(2-fluorophenyl)-2-furanyl)-2-pyrrolidinone; N-(3,4-dihydroxy-5-(2-fluorophenyl)-2-furanyl)succinimide; N-(3-trimethylsilyloxy-4-hydroxy-5-(2-fluorophenyl)-2-furanyl)-3-bromopropylsulfonamide; N-(3,4-dihydroxy-5-(2-fluorophenyl)-2-furanyl)-1,1-dioxide-isothiazolidine; N-methyl-N'-(3,4-dihydroxy-5-(2-fluorophenyl)-2-furanyl)ethanesulfonamide; N-(3-acetoxy-4-hydroxy-5-(2-fluorophenyl)-2-furanyl)methanesulfonamide; N-(3-acetoxy-4-hydroxy-5-(2-fluorophenyl)-2-furanyl)ethanesulfonamide; N-(3-acetoxy-4-hydroxy-5-(2-fluorophenyl)-2-furanyl)benzenesulfonamide; N-(3-acetoxy-4-hydroxy-5-(2-fluorophenyl)-2-furanyl)-acetamide; N-(3-acetoxy-4-hydroxy-5-(2-fluorophenyl)-2-furanyl)-carbamic acid ethyl ester; N-(3-acetoxy-4-hydroxy-5-(2-fluorophenyl)-2-furanyl)benzamide; N-(3-acetoxy-4-hydroxy-5-(2-fluorophenyl)-2-furanyl)-4-bromobutanamide; N-(3-acetoxy-4-hydroxy-5-(2-fluorophenyl)-2-furanyl)-2-pyrrolidinone; N-(3-acetoxy-4-hydroxy-5-(2-fluorophenyl)-2-furanyl)succinimide; N-(3-acetoxy-4-hydroxy-5-(2-fluorophenyl)-2-furanyl)-3-bromopropylsulfonamide; N-(3-acetoxy-4-hydroxy-5-(2-fluorophenyl)-2-furanyl)-1,1-dioxide-isothiazolidine; N-methyl-N'-(3-acetoxy-4-hydroxy-5-(2-fluorophenyl)-2-furanyl)ethanesulfonamide; 2-(2-fluorophenyl)-2-methyl-4-trimethylsilyloxy-5-amino-3(2H)-furanone; 2-(2-fluorophenyl)-2-methyl-4-hydroxy-5-amino-3(2H)-furanone; N-(2-(2-fluorophenyl)-2-methyl-4-hydroxy-3(2H)-furanon-5-yl)-methanesulfonamide; N-(2-(2-fluorophenyl)-2-methyl-4-hydroxy-3(2H)-furanon-5-yl)-ethanesulfonamide; N-(2-(2-fluorophenyl)-2-methyl-4-hydroxy-3(2H)-furanon-5-yl)-benzenesulfonamide; N-(2-(2-fluorophenyl)-2-methyl-4-hydroxy-3(2H)-furanon-5-yl)-acetamide; N-(2-(2-fluorophenyl)-2-methyl-4-hydroxy-3(2H)-furanon-5-yl)-carbamic acid ethyl ester; N-(2-(2-fluorophenyl)-2-methyl-4-hydroxy-3(2H)-furanon-5-yl)-benzamide; N-(2-(2-fluorophenyl)-2-methyl-4-hydroxy-3(2H)-furanon-5-yl)-4-bromobutanamide; N-(2-(2-fluorophenyl)-2-methyl-4-hydroxy-3(2H)-furanon-5-yl)-2-pyrrolidinone; N-(2-(2-fluorophenyl)-2-methyl-4-hydroxy-3(2H)-furanon-5-yl)-succinimide; N-(2-(2-fluorophenyl)-2-methyl-4-hydroxy-3(2H)-furanon-5-yl)-3-bromopropylsulfonamide; N-(2-(2-fluorophenyl)-2-methyl-4-hydroxy-3(2H)-furanon-5-yl)-1,1-dioxide-isothiazolidine; N-methyl-N'-(2-(2-fluorophenyl)-2-methyl-4-hydroxy-3(2H)-furanon-5-yl)-ethanesulfonamide; 2-(2-fluorophenyl)-2-methyl-4-acetoxy-5-amino-3(2H)-furanone; N-(2-(2-fluorophenyl)-2-methyl-4-acetoxy-3(2H)-furanon-5-yl)-methanesulfonamide; N-(2-(2-fluorophenyl)-2-methyl-4-acetoxy-3(2H)-furanon-5-yl)-ethanesulfonamide; N-(2-(2-fluorophenyl)-2-methyl-4-acetoxy-3(2H)-furanon-5-yl)-benzenesulfonamide; N-(2-(2-fluorophenyl)-2-methyl-4-acetoxy-3(2H)-furanon-5-yl)-acetamide; N-(2-(2- fluorophenyl)-2-methyl-4-acetoxy-3(2H)-furanon-5-yl)-carbamic acid ethyl ester; N-(2-(2-fluorophenyl)-2-methyl-4-acetoxy-3(2H)-furanon-5-yl)-benzamide; N-(2-(2-fluorophenyl)-2-methyl-4-acetoxy-3(2H)-furanon-5-yl)-4-bromobutanamide; N-(2-(2-fluorophenyl)-2-methyl-4-acetoxy-3(2H)-furanon-5-yl)-2-pyrrolidinone; N-(2-(2-fluorophenyl)-2-methyl-4-acetoxy-3(2H)-furanon-5-yl)-succinimide; N-(2-(2-fluorophenyl)-2-methyl-4-acetoxy-3(2H)-furanon-5-yl)-3-bromopropylsulfonamide; N-(2-(2-fluorophenyl)-2-methyl-4-acetoxy-3(2H)-furanon-5-yl)-1,1-dioxide-isothiazolidine; N-methyl-N'-(2-(2-fluorophenyl)-2-methyl-4-acetoxy-3(2H)-furanon-5-yl)-ethanesulfonamide; 2-(3-fluorophenyl)-5-amino-4-hydroxy-3(2H)-furanone; 2-(3-fluorophenyl)-4-(acetoxy)-5-amino-3(2H)-furanone; 2-(3-fluorophenyl)-4-[[phenylsulfonyl]oxy]-5-amino-3(2H)-furanone; N-(3,4-dihydroxy-5-(3-fluorophenyl)-2-furanyl)methanesulfonamide; N-(3,4-dihydroxy-5-(3-fluorophenyl)-2-furanyl)ethanesulfonamide; N-(3,4-dihydroxy-5-(3-fluorophenyl)-2-furanyl)benzenesulfonamide; N-(3,4-dihydroxy-5-(3-fluorophenyl)-2-furanyl)acetamide; N-(3,4-dihydroxy-5-(3-fluorophenyl)-2-furanyl)-carbamic acid ethyl ester; N-(3,4-dihydroxy-5-(3-fluorophenyl)-2-furanyl)benzamide; N-(3-trimethylsilyloxy-4-hydroxy-5-(3-fluorophenyl)-2-furanyl)-4-bromobutanamide; N-(3,4-dihydroxy-5-(3-fluorophenyl)-2-furanyl)-2-pyrrolidinone; N-(3,4-dihydroxy-5-(3-fluorophenyl)-2-furanyl)succinimide; N-(3-trimethylsilyloxy-4-hydroxy-5-(3-fluorophenyl)-2-furanyl)-3-bromopropylsulfonamide; N-(3,4-dihydroxy-5-(3-fluorophenyl)-2-furanyl)-1,1-dioxide-isothiazolidine; N-methyl-N'-(3,4-dihydroxy-5-(3-fluorophenyl)-2-furanyl)ethanesulfonamide; N-(3-acetoxy-4-hydroxy-5-(3-fluorophenyl)-2-furanyl)methanesulfonamide; N-(3-acetoxy-4-hydroxy-5-(3-fluorophenyl)-2-furanyl)ethanesulfonamide; N-(3-acetoxy-4-hydroxy-5-(3-fluorophenyl)-2-furanyl)benzenesulfonamide; N-(3-acetoxy-4-hydroxy-5-(3-fluorophenyl)-2-furanyl)-acetamide; N-(3-acetoxy-4-hydroxy-5-(3-fluorophenyl)-2-furanyl)-carbamic acid ethyl ester; N-(3-acetoxy-4-hydroxy-5-(3-fluorophenyl)-2-furanyl)benzamide; N-(3-acetoxy-4-hydroxy-5-(3-fluorophenyl)-2-furanyl)-4-bromobutanamide; N-(3-acetoxy-4-hydroxy-5-(3-fluorophenyl)-2-furanyl)-2-pyrrolidinone; N-(3-acetoxy-4-hydroxy-5-(3-fluorophenyl)-2-furanyl)succinimide; N-(3-acetoxy-4-hydroxy-5-(3-fluorophenyl)-2-furanyl)-3-bromopropylsulfonamide; N-(3-acetoxy-4-hydroxy-5-(3-fluorophenyl)-2-furanyl)-1,1-dioxide-isothiazolidine; N-methyl-N'-(3-acetoxy-4-hydroxy-5-(3-fluorophenyl)-2-furanyl)ethanesulfonamide; 2-(3-fluorophenyl)-2-methyl-4-trimethylsilyloxy-5-amino-3(2H)-furanone; 2-(3-fluorophenyl)-2-methyl-4-hydroxy-5-amino-3(2H)-furanone; N-(2-(3-fluorophenyl)-2-methyl-4-hydroxy-3(2H)-furanon-5-yl)-methanesulfonamide; N-(2-(3-fluorophenyl)-2-methyl-4-hydroxy-3(2H)-furanon-5-yl)-ethanesulfonamide; N-(2-(3-fluorophenyl)-2-methyl-4-hydroxy-3(2H)-furanon-5-yl)-benzenesulfonamide; N-(2-(3-fluorophenyl)-2-methyl-4-hydroxy-3(2H)-furanon-5-yl)-acetamide; N-(2-(3-fluorophenyl)-2-methyl-4-hydroxy-3(2H)-furanon-5-yl)-carbamic acid ethyl ester; N-(2-(3-fluorophenyl)-2-methyl-4-hydroxy-3(2H)-furanon-5-yl)-benzamide; N-(2-(3-fluorophenyl)-2-methyl-4-hydroxy-3(2H)-furanon-5-yl)-4-bromobutanamide; N-(2-(3-fluorophenyl)-2-methyl-4-hydroxy-3(2H)-furanon-5-yl)-2-pyrrolidinone; N-(2-(3-fluorophenyl)-2-methyl-4-hydroxy-3(2H)-furanon-5-yl)-succinimide; N-(2-(3-fluorophenyl)-2-methyl-4-hydroxy-3(2H)-furanon-5-yl)-3-bromopropylsulfonamide; N-(2-(3-fluorophenyl)-2-methyl-4-hydroxy-3(2H)-furanon-5-yl)-1,1-dioxide-isothiazolidine; N-methyl-N'-(2-(3-fluorophenyl)-2-methyl-4-hydroxy-3(2H)-furanon-5-yl)-ethanesulfonamide; 2-(3-fluorophenyl)-2-methyl-4-acetoxy-5-amino-3(2H)-furanone; N-(2-(3-fluorophenyl)-2-methyl-4-acetoxy-3(2H)-furanon-5-yl)-methanesulfonamide; N-(2-(3-fluorophenyl)-2-methyl-4-acetoxy-3(2H)-furanon-5-yl)-ethanesulfonamide; N-(2-(3-fluorophenyl)-2-methyl-4-acetoxy-3(2H)-furanon-5-yl)-benzenesulfonamide; N-(2-(3-fluorophenyl)-2-methyl-4-acetoxy-3(2H)-furanon-5-yl)-acetamide; N-(2-(3-fluorophenyl)-2-methyl-4-acetoxy-3(2H)-furanon-5-yl)-carbamic acid ethyl ester; N-(2-(3-fluorophenyl)-2-methyl-4-acetoxy-3(2H)-furanon-5-yl)-benzamide; N-(2-(3-fluorophenyl)-2-methyl-4-acetoxy-3(2H)-furanon-5-yl)-4-bromobutanamide; N-(2-(3-fluorophenyl)-2-methyl-4-acetoxy-3(2H)-furanon-5-yl)-2-pyrrolidinone; N-(2-(3-fluorophenyl)-2-methyl-4-acetoxy-3(2H)-furanon-5-yl)-succinimide; N-(2-(3-fluorophenyl)-2-methyl-4-acetoxy-3(2H)-furanon-5-yl)-3-bromopropylsulfonamide; N-(2-(3-fluorophenyl)-2-methyl-4-acetoxy-3(2H)-furanon-5-yl)-1,1-dioxide-isothiazolidine; N-methyl-N'-(2-(3-fluorophenyl)-2-methyl-4-acetoxy-3(2H)-furanon-5-yl)-ethanesulfonamide; 2-(4-fluorophenyl)-5-amino-4-hydroxy-3(2H)-furanone; 2-(4-fluorophenyl)-4-(acetoxy)-5-amino-3(2H)-furanone; 2-(4-fluorophenyl)-4-[[phenylsulfonyl]oxy]-5-amino-3(2H)-furanone; N-(3,4-dihydroxy-5-(4-fluorophenyl)-2-furanyl)methanesulfonamide; N-(3,4-dihydroxy-5-(4-fluorophenyl)-2-furanyl)ethanesulfonamide; N-(3,4-dihydroxy-5-(4-fluorophenyl)-2-furanyl)benzenesulfonamide; N-(3,4-dihydroxy-5-(4-fluorophenyl)-2-furanyl)acetamide; N-(3,4-dihydroxy-5-(4-fluorophenyl)-2-furanyl)-carbamic-acid ethyl ester; N-(3,4-dihydroxy-5-(4-fluorophenyl)-2-furanyl)benzamide; N-(3-trimethylsilyloxy-4-hydroxy-5-(4-fluorophenyl)-2-furanyl)-4-bromobutanamide; N-(3,4-dihydroxy-5-(4-fluorophenyl)-2-furanyl)-2-pyrrolidinone; N-(3,4-dihydroxy-5-(4-fluorophenyl)-2-furanyl)succinimide; N-(3-trimethylsilyloxy-4-hydroxy-5-(4-fluorophenyl)-2-furanyl)-3-bromopropylsulfonamide; N-(3,4-dihydroxy-5-(4-fluorophenyl)-2-furanyl)-1,1-dioxide-isothiazolidine; N-methyl-N'-(3,4-dihydroxy-5-(4-fluorophenyl)-2-furanyl)ethanesulfonamide; N-(3-acetoxy-4-hydroxy-5-(4-fluorophenyl)-2-furanyl)methanesulfonamide; (3-acetoxy-4-hydroxy-5-(4-fluorophenyl)-2-furanyl)ethanesulfonamide; N-(3-acetoxy-4-hydroxy-5-(4-fluorophenyl)-2-furanyl)benzenesulfonamide; N-(3-acetoxy-4-hydroxy-5-(4-fluorophenyl)-2-furanyl)-acetamide; N-(3-acetoxy-4-hydroxy-5-(4-fluorophenyl)-2-furanyl)-carbamic acid ethyl ester; N-(3-acetoxy-4-hydroxy-5-(4-fluorophenyl)2-furanyl)benzamide; N-(3-acetoxy-4-hydroxy-5-(4-fluorophenyl)-2-furanyl)-4-bromobutanamide; N-(3-acetoxy-4-hydroxy-5-(4-fluorophenyl)-2-furanyl)-2-pyrrolidinone; N-(3-acetoxy-4-hydroxy-5-(4-fluorophenyl)-2-furanyl)succinimide; N-(3-acetoxy-4-hydroxy-5-(4-fluorophenyl)-2-furanyl)-3-bromopropylsulfonamide; N-(3-acetoxy-4-hydroxy-5-(4-fluorophenyl)-2-furanyl)-1,1-dioxide-isothiazolidine; N-methyl-N'-(3-acetoxy-4-hydroxy-5-(4-fluorophenyl)-2-furanyl)ethanesulfonamide; 2-(4-fluorophenyl)-2-methyl-4-trimethylsilyloxy-5-amino-3(2H)-furanone; 2-(4-fluorophenyl)-2-methyl-4-hydroxy-5-amino-3(2H)-furanone; N-(2-(4-fluorophenyl)-2-methyl-4-hydroxy-3(2H)-furanon-5-yl)-methanesulfonamide; N-(2-(4-fluorophenyl)-2-methyl-4-hydroxy-3(2H)-furanon-5-yl)-ethanesulfonamide; N-(2-(4-fluorophenyl)-2-methyl-4-hydroxy-3(2H)-furanon-5-yl)-benzenesulfonamide; N-(2-(4-fluorophenyl)-2-methyl-4-hydroxy-3(2H)-furanon-5-yl)-acetamide; N-(2-(4- fluorophenyl)-2-methyl-4-hydroxy-3(2H)-furanon-5-yl)-carbamic acid ethyl ester; N-(2-(4-fluorophenyl)-2-methyl-4-hydroxy-3(2H)-furanon-5-yl)-benzamide; N-(2-(4-fluorophenyl)-2-methyl-4-hydroxy-3(2H)-furanon-5-yl)-4-bromobutanamide; N-(2-(4-fluorophenyl)-2-methyl-4-hydroxy-3(2H)-furanon-5-yl)-2-pyrrolidinone; N-(2-(4-fluorophenyl)-2-methyl-4-hydroxy-3(2H)-furanon-5-yl)-succinimide; N-(2-(4-fluorophenyl)-2-methyl-4-hydroxy-3(2H)-furanon-5-yl)-3-bromopropylsulfonamide; N-(2-(4-fluorophenyl)-2-methyl-4-hydroxy-3(2H)-furanon-5-yl)-1,1-dioxide-isothiazolidine; N-methyl-N'-(2-(4-fluorophenyl)-2-methyl-4-hydroxy-3(2H)-furanon-5-yl)-ethanesulfonamide; 2-(4-fluorophenyl)-2-methyl-4-acetoxy-5-amino-3(2H)-furanone; N-(2-(4-fluorophenyl)-2-methyl-4-acetoxy-3(2H)-furanon-5-yl)-methanesulfonamide; N-(2-(4-fluorophenyl)-2-methyl-4-acetoxy-3(2H)-furanon-5-yl)-ethanesulfonamide; N-(2-(4-fluorophenyl)-2-methyl-4-acetoxy-3(2H)-furanon-5-yl)-benzenesulfonamide; N-(2-(4-fluorophenyl)-2-methyl-4-acetoxy-3(2H)-furanon-5-yl)-acetamide; N-(2-(4-fluorophenyl)-2-methyl-4-acetoxy-3(2H)-furanon-5-yl)-carbamic acid ethyl ester; N-(2-(4-fluorophenyl)-2-methyl-4-acetoxy-3(2H)-furanon-5-yl)-benzamide; N-(2-(4-fluorophenyl)-2-methyl-4-acetoxy-3(2H)-furanon-5-yl)-4-bromobutanamide; N-(2-(4-fluorophenyl)-2-methyl-4-acetoxy-3(2H)-furanon-5-yl)-2-pyrrolidinone; N-(2-(4-fluorophenyl)-2-methyl-4-acetoxy-3(2H)-furanon-5-yl)-succinimide; N-(2-(4-fluorophenyl)-2-methyl-4-acetoxy-3(2H)-furanon-5-yl)-3-bromopropylsulfonamide; N-(2-(4-fluorophenyl)-2-methyl-4-acetoxy-3(2H)-furanon-5-yl)-1,1-dioxide-isothiazolidine; N-methyl-N'-(2-(4-fluorophenyl)-2-methyl-4-acetoxy-3(2H)-furanon-5-yl)-ethanesulfonamide; 2-(2,3-difluorophenyl)-5-amino-4-hydroxy-3(2H)-furanone; 2-(2,3-difluorophenyl)-4-(acetoxy)-5-amino-3(2H)-furanone; 2-(2,3-difluorophenyl)-4-[[phenylsulfonyl]oxy]-5-amino-3(2H)-furanone; N-(3,4-dihydroxy-5-(2,3-difluorophenyl)-2-furanyl)methanesulfonamide; N-(3,4-dihydroxy-5-(2,3-difluorophenyl)-2-furanyl)ethanesulfonamide; N-(3,4-dihydroxy-5-(2,3-difluorophenyl)-2-furanyl)benzenesulfonamide; N-(3,4-dihydroxy-5-(2,3-difluorophenyl)-2-furanyl)acetamide; N-(3,4-dihydroxy-5-(2,3-difluorophenyl)-2-furanyl)-carbamic acid ethyl ester; N-(3,4-dihydroxy-5-(2,3-difluorophenyl)-2-furanyl)benzamide; N-(3-trimethylsilyloxy-4-hydroxy-5-(2,3-difluorophenyl)-2-furanyl)-4-bromobutanamide; N-(3,4-dihydroxy-5-(2,3-difluorophenyl)-2-furanyl)-2-pyrrolidinone; N-(3,4-dihydroxy-5-(2,3-difluorophenyl)-2-furanyl)succinimide; N-(3-trimethylsilyloxy-4-hydroxy-5-(2,3-difluorophenyl)-2-furanyl)-3-bromopropylsulfonamide; N-(3,4-dihydroxy-5-(2,3-difluorophenyl)-2-furanyl)-1,1-dioxide-isothiazolidine; N-methyl-N'-(3,4-dihydroxy-5-(2,3-difluorophenyl)-2-furanyl)ethanesulfonamide; N-(3-acetoxy-4-hydroxy-5-(2,3-difluorophenyl)-2-furanyl)methanesulfonamide; N-(3-acetoxy-4-hydroxy-5-(2,3-difluorophenyl)-2-furanyl)ethanesulfonamide; N-(3-acetoxy-4-hydroxy-5-(2,3-difluorophenyl)-2-furanyl)benzenesulfonamide; N-(3-acetoxy-4-hydroxy-5-(2,3-difluorophenyl)-2-furanyl)-acetamide; N-(3-acetoxy-4-hydroxy-5-(2,3-difluorophenyl)-2-furanyl)-carbamic acid ethyl ester; N-(3-acetoxy-4-hydroxy-5-(2,3-difluorophenyl)-2-furanyl)benzamide; N-(3-acetoxy-4-hydroxy-5-(2,3-difluorophenyl)-2-furanyl)-4-bromobutanamide; N-(3-acetoxy-4-hydroxy-5-(2,3-difluorophenyl)-2-furanyl)-2-pyrrolidinone; N-(3-acetoxy-4-hydroxy-5-(2,3-difluorophenyl)-2-furanyl)succinimide; N-(3-acetoxy-4-hydroxy-5-(2,3-difluorophenyl)-2-furanyl)-3-bromopropylsulfonamide; N-(3-acetoxy-4-hydroxy-5-(2,3-difluorophenyl)-2-furanyl)-1,1-dioxide-isothiazolidine; N-methyl-N'-(3-acetoxy-4-hydroxy-5-(2,3-difluorophenyl)-2-furanyl)ethanesulfonamide; 2-(2,3-difluorophenyl)-2-methyl-4-trimethylsilyloxy-5-amino-3(2H)-furanone; 2-(2,3-difluorophenyl)-2-methyl-4-hydroxy-5-amino-3(2H)-furanone; N-(2-(2,3-difluorophenyl)-2-methyl-4-hydroxy-3(2H)-furanon-5-yl)-methanesulfonamide; N-(2-(2,3-difluorophenyl)-2-methyl-4-hydroxy-3(2H)-furanon-5-yl)-ethanesulfonamide; N-(2-(2,3-difluorophenyl)-2-methyl-4-hydroxy-3(2H)-furanon-5-yl)-benzenesulfonamide; N-(2-(2,3-difluorophenyl)-2-methyl-4-hydroxy-3(2H)-furanon-5-yl)-acetamide; N-(2-(2,3-difluorophenyl)-2-methyl-4-hydroxy-3(2H)-furanon-5-yl)-carbamic acid ethyl ester; N-(2-(2,3-difluorophenyl)-2-methyl-4-hydroxy-3(2H)-furanon-5-yl)-benzamide; N-(2-(2,3-difluorophenyl)-2-methyl-4-hydroxy-3(2H)-furanon-5-yl)-4-bromobutanamide; N-(2-(2,3-difluorophenyl)-2-methyl-4-hydroxy-3(2H)-furanon-5-yl)-2-pyrrolidinone; N-(2-(2,3-difluorophenyl)-2-methyl-4-hydroxy-3(2H)-furanon-5-yl)-succinimide; N-(2-(2,3-difluorophenyl)-2-methyl-4-hydroxy-3(2H)-furanon-5-yl)-3-bromopropylsulfonamide; N-(2-(2,3-difluorophenyl)-2-methyl-4-hydroxy-3(2H)-furanon-5-yl)-1,1-dioxide-isothiazolidine; N-methyl-N'-(2-(2,3-difluorophenyl)-2-methyl-4-hydroxy-3(2H)-furanon-5-yl)-ethanesulfonamide; 2-(2,3-difluorophenyl)-2-methyl-4-acetoxy-5-amino-3(2H)-furanone; N-(2-(2,3-difluorophenyl)-2-methyl-4-acetoxy-3(2H)-furanon-5-yl)-methanesulfonamide; N-(2-(2,3-difluorophenyl)-2-methyl-4-acetoxy-3(2H)-furanon-5-yl)-ethanesulfonamide; N-(2-(2,3-difluorophenyl)-2-methyl-4-acetoxy-3(2H)-furanon-5-yl)-benzenesulfonamide; N-(2-(2,3-difluorophenyl)-2-methyl-4-acetoxy-3(2H)-furanon-5-yl)-acetamide; N-(2-(2,3-difluorophenyl)-2-methyl-4-acetoxy-3(2H)-furanon-5-yl)-carbamic acid ethyl ester; N-(2-(2,3-difluorophenyl)-2-methyl-4-acetoxy-3(2H)-furanon-5-yl)-benzamide; N-(2-(2,3-difluorophenyl)-2-methyl-4-acetoxy-3(2H)-furanon-5-yl)-4-bromobutanamide; N-(2-(2,3-difluorophenyl)-2-methyl-4-acetoxy-3(2H)-furanon-5-yl)-2-pyrrolidinone; N-(2-(2,3-difluorophenyl)-2-methyl-4-acetoxy-3(2H)-furanon-5-yl)-succinimide; N-(2-(2,3-difluorophenyl)-2-methyl-4-acetoxy-3(2H)-furanon-5-yl)-3-bromopropylsulfonamide; N-(2-(2,3-difluorophenyl)-2-methyl-4-acetoxy-3(2H)-furanon-5-yl)-1,1-dioxide-isothiazolidine; N-methyl-N'-(2-(2,3-difluorophenyl)-2-methyl-4-acetoxy-3(2H)-furanon-5-yl)-ethanesulfonamide; 2-(2,4-difluorophenyl)-5-amino-4-hydroxy-3(2H)-furanone; 2-(2,4-difluorophenyl)-4-(acetoxy)-5-amino-3(2H)-furanone; 2-(2,4-difluorophenyl)-4-[[phenylsulfonyl]oxy]-5-amino-3(2H)-furanone; N-(3,4-dihydroxy-5-(2,4-difluorophenyl)-2-furanyl)methanesulfonamide; N-(3,4-dihydroxy-5-(2,4-difluorophenyl)-2-furanyl)ethanesulfonamide; N-(3,4-dihydroxy-5-(2,4-difluorophenyl)-2-furanyl)benzenesulfonamide; N-(3,4-dihydroxy-5-(2,4-difluorophenyl)-2-furanyl)acetamide; N-(3,4-dihydroxy-5-(2,4-difluorophenyl)-2-furanyl)-carbamic acid ethyl ester; N-(3,4-dihydroxy-5-(2,4-difluorophenyl)-2-furanyl)benzamide; N-(3-trimethylsilyloxy-4-hydroxy-5-(2,4-difluorophenyl)-2-furanyl)-4-bromobutanamide; N-(3,4-dihydroxy-5-(2,4-difluorophenyl)-2-furanyl)-2-pyrrolidinone; N-(3,4-dihydroxy-5-(2,4-difluorophenyl)-2-furanyl)succinimide; N-(3-trimethylsilyloxy-4-hydroxy-5-(2,4-difluorophenyl)-2-furanyl)-3-bromopropylsulfonamide; N-(3,4-dihydroxy-5-(2,4-difluorophenyl)-2-furanyl)-1,1-dioxide-isothiazolidine; N-methyl-N'-(3,4-dihydroxy-5-(2,4-difluorophenyl)-2-furanyl)ethanesulfonamide; N-(3-acetoxy-4-hydroxy-5-(2,4-difluorophenyl)-2-furanyl)methanesulfonamide; N-(3- acetoxy-4-hydroxy-5-(2,4-difluorophenyl)-2-furanyl)ethanesulfonamide; N-(3-acetoxy-4-hydroxy-5-(2,4-difluorophenyl)-2-furanyl)benzenesulfonamide; N-(3-acetoxy-4-hydroxy-5-(2,4-difluorophenyl)-2-furanyl)-acetamide; N-(3-acetoxy-4-hydroxy-5-(2,4-difluorophenyl)-2-furanyl)-carbamic acid ethyl ester; N-(3-acetoxy-4-hydroxy-5-(2,4-difluorophenyl)-2-20 furanyl)benzamide; N-(3-acetoxy-4-hydroxy-5-(2,4-difluorophenyl)-2-furanyl)-4-bromobutanamide; N-(3-acetoxy-4-hydroxy-5-(2,4-difluorophenyl)-2-furanyl)-2-pyrrolidinone; N-(3-acetoxy-4-hydroxy-5-(2,4-difluorophenyl)-2-furanyl)succinimide; N-(3-acetoxy-4-hydroxy-5-(2,4-difluorophenyl)-2-furanyl)-3-bromopropylsulfonamide; N-(3-acetoxy-4-hydroxy-5-(2,4-difluorophenyl)-2-furanyl)-1,1-dioxide-isothiazolidine; N-methyl-N'-(3-acetoxy-4-hydroxy-5-(2,4-difluorophenyl)-2-furanyl)ethanesulfonamide; 2-(2,4-difluorophenyl)-2-methyl-4-trimethylsilyloxy-5-amino-3(2H)-furanone; 2-(2,4-difluorophenyl)-2-methyl-4-hydroxy-5-amino-3(2H)-furanone; N-(2-(2,4-difluorophenyl)-2-methyl-4-hydroxy-3(2H)-furanon-5-yl)-methanesulfonamide; N-(2-(2,4-difluorophenyl)-2-methyl-4-hydroxy-3(2H)-furanon-5-yl)-ethanesulfonamide; N-(2-(2,4-difluorophenyl)-2-methyl-4-hydroxy-3(2H)-furanon-5-yl)-benzenesulfonamide; N-(2-(2,4-difluorophenyl)-2-methyl-4-hydroxy-3(2H)-furanon-5-yl)-acetamide; N-(2-(2,4-difluorophenyl)-2-methyl-4-hydroxy-3(2H)-furanon-5-yl)-carbamic acid ethyl ester; N-(2-(2,4-difluorophenyl)-2-methyl-4-hydroxy-3(2H)-furanon-5-yl)-benzamide; N-(2-(2,4-difluorophenyl)-2-methyl-4-hydroxy-3(2H)-furanon-5-yl)-4-bromobutanamide; N-(2-(2,4-difluorophenyl)-2-methyl-4-hydroxy-3(2H)-furanon-5-yl)-2-pyrrolidinone; N-(2-(2,4-difluorophenyl)-2-methyl-4-hydroxy-3(2H)-furanon-5-yl)-succinimide; N-(2-(2,4-difluorophenyl)-2-methyl-4-hydroxy-3(2H)-furanon-5-yl)-3-bromopropylsulfonamide; N-(2-(2,4-difluorophenyl)-2-methyl-4-hydroxy-3(2H)-furanon-5-yl)-1,1-dioxide-isothiazolidine; N-methyl-N'-(2-(2,4-difluorophenyl)-2-methyl-4-hydroxy-3(2H)-furanon-5-yl)-ethanesulfonamide; 2-(2,4-difluorophenyl)-2-methyl-4-acetoxy-5-amino-3(2H)-furanone; N-(2-(2,4-difluorophenyl)-2-methyl-4-acetoxy-3(2H)-furanon-5-yl)-methanesulfonamide; N-(2-(2,4-difluorophenyl)-2-methyl-4-acetoxy-3(2H)-furanon-5-yl)-ethanesulfonamide; N-(2-(2,4-difluorophenyl)-2-methyl-4-acetoxy-3(2H)-furanon-5-yl)-benzenesulfonamide; N-(2-(2,4-difluorophenyl)-2-methyl-4-acetoxy-3(2H)-furanon-5-yl)-acetamide; N-(2-(2,4-difluorophenyl)-2-methyl-4-acetoxy-3(2H)-furanon-5-yl)-carbamic acid ethyl ester; N-(2-(2,4-difluorophenyl)-2-methyl-4-acetoxy-3(2H)-furanon-5-yl)-benzamide; N-(2-(2,4-difluorophenyl)-2-methyl-4-acetoxy-3(2H)-furanon-5-yl)-4-bromobutanamide; N-(2-(2,4-difluorophenyl)-2-methyl-4-acetoxy-3(2H)-furanon-5-yl)-2-pyrrolidinone; N-(2-(2,4-difluorophenyl)-2-methyl-4-acetoxy-3(2H)-furanon-5-yl)-succinimide; N-(2-(2,4-difluorophenyl)-2-methyl-4-acetoxy-3(2H)-furanon-5-yl)-3-bromopropylsulfonamide; N-(2-(2,4-difluorophenyl)-2-methyl-4-acetoxy-3(2H)-furanon-5-yl)-1,1-dioxide-isothiazolidine; N-methyl-N'-(2-(2,4-difluorophenyl)-2-methyl-4-acetoxy-3(2H)-furanon-5-yl)-ethanesulfonamide; 2-(2,5-difluorophenyl)-5-amino-4-hydroxy-3(2H)-furanone; 2-(2,5-difluorophenyl)-4-(acetoxy)-5-amino-3(2H)-furanone; 2-(2,5-difluorophenyl)-4-[[phenylsulfonyl]oxy]-5-amino-3(2H)-furanone; N-(3,4-dihydroxy-5-(2,5-difluorophenyl)-2-furanyl)methanesulfonamide; N-(3,4-dihydroxy-5-(2,5-difluorophenyl)-2-furanyl)ethanesulfonamide; N-(3,4-dihydroxy-5-(2,5-difluorophenyl)-2-furanyl)benzenesulfonamide; N-(3,4-dihydroxy-5-(2,5-difluorophenyl)-2-furanyl)acetamide; N-(3,4-dihydroxy-5-(2,5-difluorophenyl)-2-furanyl)-carbamic acid ethyl ester; N-(3,4-dihydroxy-5-(2,5-difluorophenyl)-2-furanyl)benzamide; N-(3-trimethylsilyloxy-4-hydroxy-5-(2,5-difluorophenyl)-2-furanyl)-4-bromobutanamide; N-(3,4-dihydroxy-5-(2,5-difluorophenyl)-2-furanyl)-2-pyrrolidinone; N-(3,4-dihydroxy-5-(2,5-difluorophenyl)-2-furanyl)succinimide; N-(3-trimethylsilyloxy-4-hydroxy-5-(2,5-difluorophenyl)-2-furanyl)-3-bromopropylsulfonamide; N-(3,4-dihydroxy-5-(2,5-difluorophenyl)-2-furanyl)-1,1-dioxide-isothiazolidine; N-methyl-N'-(3,4-dihydroxy-5-(2,5-difluorophenyl)-2-furanyl)ethanesulfonamide; N-(3-acetoxy-4-hydroxy-5-(2,5-difluorophenyl)-2-furanyl)methanesulfonamide; N-(3-acetoxy-4-hydroxy-5-(2,5-difluorophenyl)-2-furanyl)ethanesulfonamide; N-(3-acetoxy-4-hydroxy-5-(2,5-difluorophenyl)-2-furanyl)benzenesulfonamide; N-(3-acetoxy-4-hydroxy-5-(2,5-difluorophenyl)-2-furanyl)-acetamide; N-(3-acetoxy-4-hydroxy-5-(2,5-difluorophenyl)-2-furanyl)-carbamic acid ethyl ester; N-(3-acetoxy-4-hydroxy-5-(2,5-difluorophenyl)-2-furanyl)benzamide; N-(3-acetoxy-4-hydroxy-5-(2,5-difluorophenyl)-2-furanyl)-4-bromobutanamide; N-(3-acetoxy-4-hydroxy-5-(2,5-difluorophenyl)-2-furanyl)-2-pyrrolidinone; N-(3-acetoxy-4-hydroxy-5-(2,5-difluorophenyl)-2-furanyl)succinimide; N-(3-acetoxy-4-hydroxy-5-(2,5-difluorophenyl)-2-furanyl)-3-bromopropylsulfonamide; N-(3-acetoxy-4-hydroxy-5-(2,5-difluorophenyl)-2-furanyl)-1,1-dioxide-isothiazolidine; N-methyl-N'-(3-acetoxy-4-hydroxy-5-(2,5-difluorophenyl)-2-furanyl)ethanesulfonamide; 2-(2,5-difluorophenyl)-2-methyl-4-trimethylsilyloxy-5-amino-3(2H)-furanone; 2-(2,5-difluorophenyl)-2-methyl-4-hydroxy-5-amino-3(2H)-furanone; N-(2-(2,5-difluorophenyl)-2-methyl-4-hydroxy-3(2H)-furanon-5-yl)-methanesulfonamide; N-(2-(2,5-difluorophenyl)-2-methyl-4-hydroxy-3(2H)-furanon-5-yl)-ethanesulfonamide; N-(2-(2,5-difluorophenyl)-2-methyl-4-hydroxy-3(2H)-furanon-5-yl)-benzenesulfonamide; N-(2-(2,5-difluorophenyl)-2-methyl-4-hydroxy-3(2H)-furanon-5-yl)-acetamide; N-(2-(2,5-difluorophenyl)-2-methyl-4-hydroxy-3(2H)-furanon-5-yl)-carbamic acid ethyl ester; N-(2-(2,5-difluorophenyl)-2-methyl-4-hydroxy-3(2H)-furanon-5-yl)-benzamide; N-(2-(2,5-difluorophenyl)-2-methyl-4-hydroxy-3(2H)-furanon-5-yl)-4-bromobutanamide; N-(2-(2,5-difluorophenyl)-2-methyl-4-hydroxy-3(2H)-furanon-5-yl)-2-pyrrolidinone; N-(2-(2,5-difluorophenyl)-2-methyl-4-hydroxy-3(2H)-furanon-5-yl)-succinimide; N-(2-(2,5-difluorophenyl)-2-methyl-4-hydroxy-3(2H)-furanon-5-yl)-3-bromopropylsulfonamide; N-(2-(2,5-difluorophenyl)-2-methyl-4-hydroxy-3(2H)-furanon-5-yl)-1,1-dioxide-isothiazolidine; N-methyl-N'-(2-(2,5-difluorophenyl)-2-methyl-4-hydroxy-3(2H)-furanon-5-yl)-ethanesulfonamide; 2-(2,5-difluorophenyl)-2-methyl-4-acetoxy-5-amino-3(2H)-furanone; N-(2-(2,5-difluorophenyl)-2-methyl-4-acetoxy-3(2H)-furanon-5-yl)-methanesulfonamide; N-(2-(2,5-difluorophenyl)-2-methyl-4-acetoxy-3(2H)-furanon-5-yl)-ethanesulfonamide; N-(2-(2,5-difluorophenyl)-2-methyl-4-acetoxy-3(2H)-furanon-5-yl)-benzenesulfonamide; N-(2-(2,5-difluorophenyl)-2-methyl-4-acetoxy-3(2H)-furanon-5-yl)-acetamide; N-(2-(2,5-difluorophenyl)-2-methyl-4-acetoxy-3(2H)-furanon-5-yl)-carbamic acid ethyl ester; N-(2-(2,5-difluorophenyl)-2-methyl-4-acetoxy-3(2H)-furanon-5-yl)-benzamide; N-(2-(2,5-difluorophenyl)-2-methyl-4-acetoxy-3(2H)-furanon-5-yl)-4-bromobutanamide; N-(2-(2,5-difluorophenyl)-2-methyl-4-acetoxy-3(2H)-furanon-5-yl)-2-pyrrolidinone; N-(2-(2,5-difluorophenyl)-2-methyl-4-acetoxy-3(2H)-furanon-5-yl)-succinimide; N-(2-(2,5-difluorophenyl)-2-methyl-4-acetoxy-3(2H)-furanon-5-yl)-

3-bromopropylsulfonamide; N-(2-(2,5-difluorophenyl)-2-methyl-4-acetoxy-3(2H)-furanon-5-yl)-1,1-dioxide-isothiazolidine; N-methyl-N'-(2-(2,5-difluorophenyl)-2-methyl-4-acetoxy-3(2H)-furanon-5-yl)-ethanesulfonamide; 2-(2,6-difluorophenyl)-5-amino-4-hydroxy-3(2H)-furanone; 2-(2,6-difluorophenyl)-4-(acetoxy)-5-amino-3(2H)-furanone; 2-(2,6-difluorophenyl)-4-[[phenylsulfonyl]oxy]-5-amino-3(2H)-furanone; N-(3,4-dihydroxy-5-(2,6-difluorophenyl)-2-furanyl)methanesulfonamide; N-(3,4-dihydroxy-5-(2,6-difluorophenyl)-2-furanyl)ethanesulfonamide; N-(3,4-dihydroxy-5-(2,6-difluorophenyl)-2-furanyl)benzenesulfonamide; N-(3,4-dihydroxy-5-(2,6-difluorophenyl)-2-furanyl)acetamide; N-(3,4-dihydroxy-5-(2,6-difluorophenyl)-2-furanyl)-carbamic acid ethyl ester; N-(3,4-dihydroxy-5-(2,6-difluorophenyl)-2-furanyl)benzamide; N-(3-trimethylsilyloxy-4-hydroxy-5-(2,6-difluorophenyl)-2-furanyl)-4-bromobutanamide; N-(3,4-dihydroxy-5-(2,6-difluorophenyl)-2-furanyl)-2-pyrrolidinone; N-(3,4-dihydroxy-5-(2,6-difluorophenyl)-2-furanyl)succinimide; N-(3-trimethylsilyloxy-4-hydroxy-5-(2,6-difluorophenyl)-2-furanyl)-3-bromopropylsulfonamide; N-(3,4-dihydroxy-5-(2,6-difluorophenyl)-2-furanyl)-1,1-dioxide-isothiazolidine; N-methyl-N'-(3,4-dihydroxy-5-(2,6-difluorophenyl)-2-furanyl)ethanesulfonamide; N-(3-acetoxy-4-hydroxy-5-(2,6-difluorophenyl)-2-furanyl)methanesulfonamide; N-(3-acetoxy-4-hydroxy-5-(2,6-difluorophenyl)-2-furanyl)ethanesulfonamide; N-(3-acetoxy-4-hydroxy-5-(2,6-difluorophenyl)-2-furanyl)benzenesulfonamide; N-(3-acetoxy-4-hydroxy-5-(2,6-difluorophenyl)-2-furanyl)-acetamide; N-(3-acetoxy-4-hydroxy-5-(2,6-difluorophenyl)-2-furanyl)-carbamic acid ethyl ester; N-(3-acetoxy-4-hydroxy-5-(2,6-difluorophenyl)-2-furanyl)benzamide; N-(3-acetoxy-4-hydroxy-5-(2,6-difluorophenyl)-2-furanyl)-4-bromobutanamide; N-(3-acetoxy-4-hydroxy-5-(2,6-difluorophenyl)-2-furanyl)-2-pyrrolidinone; N-(3-acetoxy-4-hydroxy-5-(2,6-difluorophenyl)-2-furanyl)succinimide; N-(3-acetoxy-4-hydroxy-5-(2,6-difluorophenyl)-2-furanyl)-3-bromopropylsulfonamide; N-(3-acetoxy-4-hydroxy-5-(2,6-difluorophenyl)-2-furanyl)-1,1-dioxide-isothiazolidine; N-methyl-N'-(3-acetoxy-4-hydroxy-5-(2,6-difluorophenyl)-2-furanyl)ethanesulfonamide; 2-(2,6-difluorophenyl)-2-methyl-4-trimethylsilyloxy-5-amino-3(2H)-furanone; 2-(2,6-difluorophenyl)-2-methyl-4-hydroxy-5-amino-3(2H)-furanone; N-(2-(2,6-difluorophenyl)-2-methyl-4-hydroxy-3(2H)-furanon-5-yl)-methanesulfonamide; N-(2-(2,6-difluorophenyl)-2-methyl-4-hydroxy-3(2H)-furanon-5-yl)-ethanesulfonamide; N-(2-(2,6-difluorophenyl)-2-methyl-4-hydroxy-3(2H)-furanon-5-yl)-benzenesulfonamide; N-(2-(2,6-difluorophenyl)-2-methyl-4-hydroxy-3(2H)-furanon-5-yl)-acetamide; N-(2-(2,6-difluorophenyl)-2-methyl-4-hydroxy-3(2H)-furanon-5-yl)-carbamic acid ethyl ester; N-(2-(2,6-difluorophenyl)-2-methyl-4-hydroxy-3(2H)-furanon-5-yl)-benzamide; N-(2-(2,6-difluorophenyl)-2-methyl-4-hydroxy-3(2H)-furanon-5-yl)-4-bromobutanamide; N-(2-(2,6-difluorophenyl)-2-methyl-4-hydroxy-3(2H)-furanon-5-yl)-2-pyrrolidinone; N-(2-(2,6-difluorophenyl)-2-methyl-4-hydroxy-3(2H)-furanon-5-yl)-succinimide; N-(2-(2,6-difluorophenyl)-2-methyl-4-hydroxy-3(2H)-furanon-5-yl)-3-bromopropylsulfonamide; N-(2-(2,6-difluorophenyl)-2-methyl-4-hydroxy-3(2H)-furanon-5-yl)-1,1-dioxide-isothiazolidine; N-methyl-N'-(2-(2,6-difluorophenyl)-2-methyl-4-hydroxy-3(2H)-furanon-5-yl)-ethanesulfonamide; 2-(2,6-difluorophenyl)-2-methyl-4-acetoxy-5-amino-3(2H)-furanone; N-(2-(2,6-difluorophenyl)-2-methyl-4-acetoxy-3(2H)-furanon-5-yl)-methanesulfonamide; N-(2-(2,6-difluorophenyl)-2-methyl-4-acetoxy-3(2H)-furanon-5-yl)-ethanesulfonamide; N-(2-(2,6-difluorophenyl)-2-methyl-4-acetoxy-3(2H)-furanon-5-yl)-benzenesulfonamide; N-(2-(2,6-difluorophenyl)-2-methyl-4-acetoxy-3(2H)-furanon-5-yl)-acetamide; N-(2-(2,6-difluorophenyl)-2-methyl-4-acetoxy-3(2H)-furanon-5-yl)-carbamic acid ethyl ester; N-(2-(2,6-difluorophenyl)-2-methyl-4-acetoxy-3(2H)-furanon-5-yl)-benzamide; N-(2-(2,6-difluorophenyl)-2-methyl-4-acetoxy-3(2H)-furanon-5-yl)-4-bromobutanamide; N-(2-(2,6-difluorophenyl)-2-methyl-4-acetoxy-3(2H)-furanon-5-yl)-2-pyrrolidinone; N-(2-(2,6-difluorophenyl)-2-methyl-4-acetoxy-3(2H)-furanon-5-yl)-succinimide; N-(2-(2,6-difluorophenyl)-2-methyl-4-acetoxy-3(2H)-furanon-5-yl)-3-bromopropylsulfonamide; N-(2-(2,6-difluorophenyl)-2-methyl-4-acetoxy-3(2H)-furanon-5-yl)-1,1-dioxide-isothiazolidine; N-methyl-N'-(2-(2,6-difluorophenyl)-2-methyl-4-acetoxy-3(2H)-furanon-5-yl)-ethanesulfonamide; 2-(3,4-difluorophenyl)-5-amino-4-hydroxy-3(2H)-furanone; 2-(3,4-difluorophenyl)-4-(acetoxy)-5-amino-3(2H)-furanone; 2-(3,4-difluorophenyl)-4-[[phenylsulfonyl]oxy]-5-amino-3(2H)-furanone; N-(3,4-dihydroxy-5-(3,4-difluorophenyl)-2-furanyl)methanesulfonamide; N-(3,4-dihydroxy-5-(3,4-difluorophenyl)-2-furanyl)ethanesulfonamide; N-(3,4-dihydroxy-5-(3,4-difluorophenyl)-2-furanyl)benzenesulfonamide; N-(3,4-dihydroxy-5-(3,4-difluorophenyl)-2-furanyl)acetamide; N-(3,4-dihydroxy-5-(3,4-difluorophenyl)-2-furanyl)-carbamic acid ethyl ester; N-(3,4-dihydroxy-5-(3,4-difluorophenyl)-2-furanyl)benzamide; N-(3-trimethylsilyloxy-4-hydroxy-5-(3,4-difluorophenyl)-2-furanyl)-4-bromobutanamide; N-(3,4-dihydroxy-5-(3,4-difluorophenyl)-2-furanyl)-2-pyrrolidinone; N-(3,4-dihydroxy-5-(3,4-difluorophenyl)-2-furanyl)succinimide; N-(3-trimethylsilyloxy-4-hydroxy-5-(3,4-difluorophenyl)-2-furanyl)-3-bromopropylsulfonamide; N-(3,4-dihydroxy-5-(3,4-difluorophenyl)-2-furanyl)-1,1-dioxide-isothiazolidine; N-methyl-N'-(3,4-dihydroxy-5-(3,4-difluorophenyl)-2-furanyl)ethanesulfonamide; N-(3-acetoxy-4-hydroxy-5-(3,4-difluorophenyl)-2-furanyl)methanesulfonamide; N-(3-acetoxy-4-hydroxy-5-(3,4-difluorophenyl)-2-furanyl)ethanesulfonamide; N-(3-acetoxy-4-hydroxy-5-(3,4-difluorophenyl)-2-furanyl)benzenesulfonamide; N-(3-acetoxy-4-hydroxy-5-(3,4-difluorophenyl)-2-furanyl)-acetamide; N-(3-acetoxy-4-hydroxy-5-(3,4-difluorophenyl)-2-furanyl)-carbamic acid ethyl ester; N-(3-acetoxy-4-hydroxy-5-(3,4-difluorophenyl)-2-furanyl)benzamide; N-(3-acetoxy-4-hydroxy-5-(3,4-difluorophenyl)-2-furanyl)-4-bromobutanamide; N-(3-acetoxy-4-hydroxy-5-(3,4-difluorophenyl)-2-furanyl)-2-pyrrolidinone; N-(3-acetoxy-4-hydroxy-5-(3,4-difluorophenyl)-2-furanyl)succinimide; N-(3-acetoxy-4-hydroxy-5-(3,4-difluorophenyl)-2-furanyl)-3-bromopropylsulfonamide; N-(3-acetoxy-4-hydroxy-5-(3,4-difluorophenyl)-2-furanyl)-1,1-dioxide-isothiazolidine; N-methyl-N'-(3-acetoxy-4-hydroxy-5-(3,4-difluorophenyl)-2-furanyl)ethanesulfonamide; 2-(3,4-difluorophenyl)-2-methyl-4-trimethylsilyloxy-5-amino-3(2H)-furanone; 2-(3,4-difluorophenyl)-2-methyl-4-hydroxy-5-amino-3(2H)-furanone; N-(2-(3,4-difluorophenyl)-2-methyl-4-hydroxy-3(2H)-furanon-5-yl)-methanesulfonamide; N-(2-(3,4-difluorophenyl)-2-methyl-4-hydroxy-3(2H)-furanon-5-yl)-ethanesulfonamide; N-(2-(3,4-difluorophenyl)-2-methyl-4-hydroxy-3(2H)-furanon-5-yl)-benzenesulfonamide; N-(2-(3,4-difluorophenyl)-2-methyl-4-hydroxy-3(2H)-furanon-5-yl)-acetamide; N-(2-(3,4-difluorophenyl)-2-methyl-4-hydroxy-3(2H)-furanon-5-yl)-carbamic acid ethyl ester; N-(2-(3,4-difluorophenyl)-2-methyl-4-hydroxy-3(2H)-furanon-5-yl)-benzamide; N-(2-(3,4-difluorophenyl)-2-methyl-4-hydroxy-3(2H)-furanon-5-yl)-4-bromobutanamide; N-(2-(3,4-difluorophenyl)-2-methyl-4-hydroxy-3(2H)-furanon-5-yl)-2-pyrrolidinone; N-(2-(3,4-difluorophenyl)-2-methyl-4-hydroxy-3(2H)-furanon-5-yl)-succinimide; N-(2-(3,4-difluorophenyl)-2-methyl-4-hydroxy-3(2H)-furanon-5-yl)-3-bromopropylsulfonamide; N-(2-(3,4-difluorophenyl)-2-methyl-4-hydroxy-3(2H)-furanon-5-yl)-1,1-dioxide-isothiazolidine; N-methyl-N'-(2-(3,4-difluorophenyl)-2-methyl-4-hydroxy-3(2H)-furanon-5-yl)-ethanesulfonamide; 2-(3,4-difluorophenyl)-2-methyl-4-acetoxy-5-amino-3(2H)-furanone; N-(2-(3,4-difluorophenyl)-2-methyl-4-acetoxy-3(2H)-furanon-5-yl)-methanesulfonamide; N-(2-(3,4-difluorophenyl)-2-methyl-4-acetoxy-3(2H)-furanon-5-yl)-ethanesulfonamide; N-(2-(3,4-difluorophenyl)-2-methyl-4-acetoxy-3(2H)-furanon-5-yl)-benzenesulfonamide; N-(2-(3,4-difluorophenyl)-2-methyl-4-acetoxy-3(2H)-furanon-5-yl)-acetamide; N-(2-(3,4-difluorophenyl)-2-methyl-4-acetoxy-3(2H)-furanon-5-yl)-carbamic acid ethyl ester; N-(2-(3,4-difluorophenyl)-2-methyl-4-acetoxy-3(2H)-furanon-5-yl)-benzamide; N-(2-(3,4-difluorophenyl)-2-methyl-4-acetoxy-3(2H)-furanon-5-yl)-4-bromobutanamide; N-(2-(3,4-difluorophenyl)-2-methyl-4-acetoxy-3(2H)-furanon-5-yl)-2-pyrrolidinone; N-(2-(3,4-difluorophenyl)-2-methyl-4-acetoxy-3(2H)-furanon-5-yl)-succinimide; N-(2-(3,4-difluorophenyl)-2-methyl-4-acetoxy-3(2H)-furanon-5-yl)-3-bromopropylsulfonamide; N-(2-(3,4-difluorophenyl)-2-methyl-4-acetoxy-3(2H)-furanon-5-yl)-1,1-dioxide-isothiazolidine; N-methyl-N'-(2-(3,4-difluorophenyl)-2-methyl-4-acetoxy-3(2H)-furanon-5-yl)-ethanesulfonamide; 2-(3,5-difluorophenyl)-5-amino-4-hydroxy-3(2H)-furanone; 2-(3,5-difluorophenyl)-4-(acetoxy)-5-amino-3(2H)-furanone; 2-(3,5-difluorophenyl)-4-[[phenylsulfonyl]oxy]-5-amino-3(2H)-furanone; N-(3,4-dihydroxy-5-(3,5-difluorophenyl)-2-furanyl)methanesulfonamide; N-(3,4-dihydroxy-5-(3,5-difluorophenyl)-2-furanyl)ethanesulfonamide; N-(3,4-dihydroxy-5-(3,5-difluorophenyl)-2-furanyl)benzenesulfonamide; N-(3,4-dihydroxy-5-(3,5-difluorophenyl)-2-furanyl)acetamide; N-(3,4-dihydroxy-5-(3,5-difluorophenyl)-2-furanyl)-carbamic acid ethyl ester; N-(3,4-dihydroxy-5-(3,5-difluorophenyl)-2-furanyl)benzamide; N-(3-trimethylsilyloxy-4-hydroxy-5-(3,5-difluorophenyl)-2-furanyl)-4-bromobutanamide; N-(3,4-dihydroxy-5-(3,5-difluorophenyl)-2-furanyl)-2-pyrrolidinone; N-(3,4-dihydroxy-5-(3,5-difluorophenyl)-2-furanyl)succinimide; N-(3-trimethylsilyloxy-4-hydroxy-5-(3,5-difluorophenyl)-2-furanyl)-3-bromopropylsulfonamide; N-(3,4-dihydroxy-5-(3,5-difluorophenyl)-2-furanyl)-1,1-dioxide-isothiazolidine; N-methyl-N'-(3,4-dihydroxy-5-(3,5-difluorophenyl)-2-furanyl)ethanesulfonamide; N-(3-acetoxy-4-hydroxy-5-(3,5-difluorophenyl)-2-furanyl)methanesulfonamide; N-(3-acetoxy-4-hydroxy-5-(3,5-difluorophenyl)-2-furanyl)ethanesulfonamide; N-(3-acetoxy-4-hydroxy-5-(3,5-difluorophenyl)-2-furanyl)benzenesulfonamide; N-(3-acetoxy-4-hydroxy-5-(3,5-difluorophenyl)-2-furanyl)-acetamide; N-(3-acetoxy-4-hydroxy-5-(3,5-difluorophenyl)-2-furanyl)-carbamic acid ethyl ester; N-(3-acetoxy-4-hydroxy-5-(3,5-difluorophenyl)-2-furanyl)benzamide; N-(3-acetoxy-4-hydroxy-5-(3,5-difluorophenyl)-2-furanyl)-4-bromobutanamide; N-(3-acetoxy-4-hydroxy-5-(3,5-difluorophenyl)-2-furanyl)-2-pyrrolidinone; N-(3-acetoxy-4-hydroxy-5-(3,5-difluorophenyl)-2-furanyl)succinimide; N-(3-acetoxy-4-hydroxy-5-(3,5-difluorophenyl)-2-furanyl)-3-bromopropylsulfonamide; N-(3-acetoxy-4-hydroxy-5-(3,5-difluorophenyl)-2-furanyl)-1,1-dioxide-isothiazolidine; N-methyl-N'-(3-acetoxy-4-hydroxy-5-(3,5-difluorophenyl)-2-furanyl)ethanesulfonamide; 2-(3,5-difluorophenyl)-2-methyl-4-trimethylsilyloxy-5-amino-3(2H)-furanone; 2-(3,5-difluorophenyl)-2-methyl-4-hydroxy-5-amino-3(2H)-furanone; N-(2-(3,5-difluorophenyl)-2-methyl-4-hydroxy-3(2H)-furanon-5-yl)-methanesulfonamide; N-(2-(3,5-difluorophenyl)-2-methyl-4-hydroxy-3(2H)-furanon-5-yl)-ethanesulfonamide; N-(2-(3,5-difluorophenyl)-2-methyl-4-hydroxy-3(2H)-furanon-5-yl)-benzenesulfonamide; N-(2-(3,5-difluorophenyl)-2-methyl-4-hydroxy-3(2H)-furanon-5-yl)-acetamide; N-(2-(3,5-difluorophenyl)-2-methyl-4-hydroxy-3(2H)-furanon-5-yl)-carbamic acid ethyl ester; N-(2-(3,5-difluorophenyl)-2-methyl-4-hydroxy-3(2H)-furanon-5-yl)-benzamide; N-(2-(3,5-difluorophenyl)-2-methyl-4-hydroxy-3(2H)-furanon-5-yl)-4-bromobutanamide; N-(2-(3,5-difluorophenyl)-2-methyl-4-hydroxy-3(2H)-furanon-5-yl)-2-pyrrolidinone; N-(2-(3,5-difluorophenyl)-2-methyl-4-hydroxy-3(2H)-furanon-5-yl)-succinimide; N-(2-(3,5-difluorophenyl)-2-methyl-4-hydroxy-3(2H)-furanon-5-yl)-3-bromopropylsulfonamide; N-(2-(3,5-difluorophenyl)-2-methyl-4-hydroxy-3(2H)-furanon-5-yl)-1,1-dioxide-isothiazolidine; N-methyl-N'-(2-(3,5-difluorophenyl)-2-methyl-4-hydroxy-3(2H)-furanon-5-yl)-ethanesulfonamide; 2-(3,5-difluorophenyl)-2-methyl-4-acetoxy-5-amino-3(2H)-furanone; N-(2-(3,5-difluorophenyl)-2-methyl-4-acetoxy-3(2H)-furanon-5-yl)-methanesulfonamide; N-(2-(3,5-difluorophenyl)-2-methyl-4-acetoxy-3(2H)-furanon-5-yl)-ethanesulfonamide; N-(2-(3,5-difluorophenyl)-2-methyl-4-acetoxy-3(2H)-furanon-5-yl)-benzenesulfonamide; N-(2-(3,5-difluorophenyl)-2-methyl-4-acetoxy-3(2H)-furanon-5-yl)-acetamide; N-(2-(3,5-difluorophenyl)-2-methyl-4-acetoxy-3(2H)-furanon-5-yl)-carbamic acid ethyl ester; N-(2-(3,5-difluorophenyl)-2-methyl-4-acetoxy-3(2H)-furanon-5-yl)-benzamide; N-(2-(3,5-difluorophenyl)-2-methyl-4-acetoxy-3(2H)-furanon-5-yl)-4-bromobutanamide; N-(2-(3,5-difluorophenyl)-2-methyl-4-acetoxy-3(2H)-furanon-5-yl)-2-pyrrolidinone; N-(2-(3,5-difluorophenyl)-2-methyl-4-acetoxy-3(2H)-furanon-5-yl)-succinimide; N-(2-(3,5-difluorophenyl)-2-methyl-4-acetoxy-3(2H)-furanon-5-yl)-3-bromopropylsulfonamide; N-(2-(3,5-difluorophenyl)-2-methyl-4-acetoxy-3(2H)-furanon-5-yl)-1,1-dioxide-isothiazolidine; N-methyl-N'-(2-(3,5-difluorophenyl)-2-methyl-4-acetoxy-3(2H)-furanon-5-yl)-ethanesulfonamide; 2-(2-methoxyphenyl)-5-amino-4-hydroxy-3(2H)-furanone; 2-(2-methoxyphenyl)-4-acetoxy)-5-amino-3(2H)-furanone; 2-(2-methoxyphenyl)-4-[[phenylsulfonyl]oxy]-5-amino-3(2H)-furanone; N-(3,4-dihydroxy-5-(2-methoxyphenyl)-2-furanyl)methanesulfonamide; N-(3,4-dihydroxy-5-(2-methoxyphenyl)-2-furanyl)ethanesulfonamide; N-(3,4-dihydroxy-5-(2-methoxyphenyl)-2-furanyl)benzenesulfonamide; N-(3,4-dihydroxy-5-(2-methoxyphenyl)-2-furanyl)acetamide; N-(3,4-dihydroxy-5-(2-methoxyphenyl)-2-furanyl)-carbamic acid ethyl ester; N-(3,4-dihydroxy-5-(2-methoxyphenyl)-2-furanyl)benzamide; N-(3-trimethylsilyloxy-4-hydroxy-5-(2-methoxyphenyl)-2-furanyl)-4-bromobutanamide; N-(3,4-dihydroxy-5-(2-methoxyphenyl)-2-furanyl)-2-pyrrolidinone; N-(3,4-dihydroxy-5-(2-methoxyphenyl)-2-furanyl)succinimide; N-(3-trimethylsilyloxy-4-hydroxy-5-(2-methoxyphenyl)-2-furanyl)-3-bromopropylsulfonamide; N-(3,4-dihydroxy-5-(2-methoxyphenyl)-2-furanyl)-1,1-dioxide-isothiazolidine; N-methyl-N'-(3,4-dihydroxy-5-(2-methoxyphenyl)-2-furanyl)ethanesulfonamide; N-(3-acetoxy-4-hydroxy-5-(2-methoxyphenyl)-2-furanyl)methanesulfonamide; N-(3-acetoxy-4-hydroxy-5-(2-methoxyphenyl)-2-furanyl)ethanesulfonamide; N-(3-acetoxy-4-hydroxy-5-(2-methoxyphenyl)-2-furanyl)benzenesulfonamide; N-(3- acetoxy-4-hydroxy-5-(2-methoxyphenyl)-2-furanyl)-acetamide; N-(3-acetoxy-4-hydroxy-5-(2-methoxyphenyl)-2-furanyl)-carbamic acid ethyl ester; N-(3-acetoxy-4-hydroxy-5-(2-methoxyphenyl)-2-furanyl)benzamide; N-(3-acetoxy-4-hydroxy-5-(2-methoxyphenyl)-2-furanyl)-4-bromobutanamide; N-(3-acetoxy-4-hydroxy-5-(2-methoxyphenyl)-2-furanyl)-2-pyrrolidinone; N-(3-acetoxy-4-hydroxy-5-(2-methoxyphenyl)-2-furanyl)succinimide; N-(3-acetoxy-4-hydroxy-5-(2-methoxyphenyl)-2-furanyl)-3-bromopropylsulfonamide; N-(3-acetoxy-4-hydroxy-5-(2-methoxyphenyl)-2-furanyl)-1,1-dioxide-isothiazolidine; N-methyl-N'-(3-acetoxy-4-hydroxy-5-(2-methoxyphenyl)-2-furanyl)ethanesulfonamide; 2-(2-methoxyphenyl)-2-methyl-4-trimethylsilyloxy-5-amino-3(2H)-furanone; 2-(2-methoxyphenyl)-2-methyl-4-hydroxy-5-amino-3(2H)-furanone; N-(2-(2-methoxyphenyl)-2-methyl-4-hydroxy-3(2H)-furanon-5-yl)-methanesulfonamide; N-(2-(2-methoxyphenyl)-2-methyl-4-hydroxy-3(2H)-furanon-5-yl)-ethanesulfonamide; N-(2-(2-methoxyphenyl)-2-methyl-4-hydroxy-3(2H)-furanon-5-yl)-benzenesulfonamide; N-(2-(2-methoxyphenyl)-2-methyl-4-hydroxy-3(2H)-furanon-5-yl)-acetamide; N-(2-(2-methoxyphenyl)-2-methyl-4-hydroxy-3(2H)-furanon-5-yl)-carbamic acid ethyl ester; N-(2-(2-methoxyphenyl)-2-methyl-4-hydroxy-3(2H)-furanon-5-yl)-benzamide; N-(2-(2-methoxyphenyl)-2-methyl-4-hydroxy-3(2H)-furanon-5-yl)-4-bromobutanamide; N-(2-(2-methoxyphenyl)-2-methyl-4-hydroxy-3(2H)-furanon-5-yl)-2-pyrrolidinone; N-(2-(2-methoxyphenyl)-2-methyl-4-hydroxy-3(2H)-furanon-5-yl)-succinimide; N-(2-(2-methoxyphenyl)-2-methyl-4-hydroxy-3(2H)-furanon-5-yl)-3-bromopropylsulfonamide; N-(2-(2-methoxyphenyl)-2-methyl-4-hydroxy-3(2H)-furanon-5-yl)-1,1-dioxide-isothiazolidine; N-methyl-N'-(2-(2-methoxyphenyl)-2-methyl-4-hydroxy-3(2H)-furanon-5-yl)-ethanesulfonamide; 2-(2-methoxyphenyl)-2-methyl-4-acetoxy-5-amino-3(2H)-furanone; N-(2-(2-methoxyphenyl)-2-methyl-4-acetoxy-3(2H)-furanon-5-yl)-methanesulfonamide; N-(2-(2-methoxyphenyl)-2-methyl-4-acetoxy-3(2H)-furanon-5-yl)-ethanesulfonamide; N-(2-(2-methoxyphenyl)-2-methyl-4-acetoxy-3(2H)-furanon-5-yl)-benzenesulfonamide; N-(2-(2-methoxyphenyl)-2-methyl-4-acetoxy-3(2H)-furanon-5-yl)-acetamide; N-(2-(2-methoxyphenyl)-2-methyl-4-acetoxy-3(2H)-furanon-5-yl)-carbamic acid ethyl ester; N-(2-(2-methoxyphenyl)-2-methyl-4-acetoxy-3(2H)-furanon-5-yl)-benzamide; N-(2-(2-methoxyphenyl)-2-methyl-4-acetoxy-3(2H)-furanon-5-yl)-4-bromobutanamide; N-(2-(2-methoxyphenyl)-2-methyl-4-acetoxy-3(2H)-furanon-5-yl)-2-pyrrolidinone; N-(2-(2-methoxyphenyl)-2-methyl-4-acetoxy-3(2H)-furanon-5-yl)-succinimide; N-(2-(2-methoxyphenyl)-2-methyl-4-acetoxy-3(2H)-furanon-5-yl)-3-bromopropylsulfonamide; N-(2-(2-methoxyphenyl)-2-methyl-4-acetoxy-3(2H)-furanon-5-yl)-1,1-dioxide-isothiazolidine; N-methyl-N'-(2-(2-methoxyphenyl)-2-methyl-4-acetoxy-3(2H)-furanon-5-yl)-ethanesulfonamide; 2-(3-methoxyphenyl)-5-amino-4-hydroxy-3(2H)-furanone; 2-(3-methoxyphenyl)-4-(acetoxy)-5-amino-3(2H)-furanone; 2-(3-methoxyphenyl)-4-[[phenylsulfonyl]oxy]-5-amino-3(2H)-furanone; N-(3,4-dihydroxy-5-(3-methoxyphenyl)-2-furanyl)methanesulfonamide; N-(3,4-dihydroxy-5-(3-methoxyphenyl)-2-furanyl)ethanesulfonamide; N-(3,4-dihydroxy-5-(3-methoxyphenyl)-2-furanyl)benzenesulfonamide; N-(3,4-dihydroxy-5-(3-methoxyphenyl)-2-20furanyl)acetamide; N-(3,4-dihydroxy-5-(3-methoxyphenyl)-2-furanyl)-carbamic acid ethyl ester; N-(3,4-dihydroxy-5-(3-methoxyphenyl)-2-furanyl)benzamide; N-(3-trimethylsilyloxy-4-hydroxy-5-(3-methoxyphenyl)-2-furanyl)-4-bromobutanamide; N-(3,4-dihydroxy-5-(3-methoxyphenyl)-2-furanyl)-2-pyrrolidinone; N-(3,4-dihydroxy-5-(3-methoxyphenyl)-2-furanyl)succinimide; N-(3-trimethylsilyloxy-4-hydroxy-5-(3-methoxyphenyl)-2-furanyl)-3-bromopropylsulfonamide; N-(3,4-dihydroxy-5-(3-methoxyphenyl)-2-furanyl)-1,1-dioxide-isothiazolidine; N-methyl-N'-(3,4-dihydroxy-5-(3-methoxyphenyl)-2-furanyl)ethanesulfonamide; N-(3-acetoxy-4-hydroxy-5-(3-methoxyphenyl)-2-furanyl)methanesulfonamide; N-(3-acetoxy-4-hydroxy-5-(3-methoxyphenyl)-2-furanyl) ethanesulfonamide; N-(3-acetoxy-4-hydroxy-5-(3-methoxyphenyl)-2-furanyl)benzenesulfonamide; N-(3-acetoxy-4-hydroxy-5-(3-methoxyphenyl)-2-furanyl)-acetamide; N-(3-acetoxy-4-hydroxy-5-(3-methoxyphenyl)-2-furanyl)-carbamic acid ethyl ester; N-(3-acetoxy-4-hydroxy-5-(3-methoxyphenyl)-2-furanyl)benzamide; N-(3-acetoxy-4-hydroxy-5-(3-methoxyphenyl)-2-furanyl)-4-bromobutanamide; N-(3-acetoxy-4-hydroxy-5-(3-methoxyphenyl)-2-furanyl)-2-pyrrolidinone; N-(3-acetoxy-4-hydroxy-5-(3-methoxyphenyl)-2-furanyl)succinimide; N-(3-acetoxy-4-hydroxy-5-(3-methoxyphenyl)-2-furanyl)-3-bromopropylsulfonamide; N-(3-acetoxy-4-hydroxy-5-(3-methoxyphenyl)-2-furanyl)-1,1-dioxide-isothiazolidine; N-methyl-N'-(3-acetoxy-4-hydroxy-5-(3-methoxyphenyl)-2-furanyl)ethanesulfonamide; 2-(3-methoxyphenyl)-2-methyl-4-trimethylsilyloxy-5-amino-3(2H)-furanone; 2-(3-methoxyphenyl)-2-methyl-4-hydroxy-5-amino-3(2H)-furanone; N-(2-(3-methoxyphenyl)-2-methyl-4-hydroxy-3(2H)-furanon-5-yl)-methanesulfonamide; N-(2-(3-methoxyphenyl)-2-methyl-4-hydroxy-3(2H)-furanon-5-yl)-ethanesulfonamide; N-(2-(3-methoxyphenyl)-2-methyl-4-hydroxy-3(2H)-furanon-5-yl)-benzenesulfonamide; N-(2-(3-methoxyphenyl)-2-methyl-4-hydroxy-3(2H)-furanon-5-yl)-acetamide; N-(2-(3-methoxyphenyl)-2-methyl-4-hydroxy-3(2H)-furanon-5-yl)-carbamic acid ethyl ester; N-(2-(3-methoxyphenyl)-2-methyl-4-hydroxy-3(2H)-furanon-5-yl)-benzamide; N-(2-(3-methoxyphenyl)-2-methyl-4-hydroxy-3(2H)-furanon-5-yl)-4-bromobutanamide; N-(2-(3-methoxyphenyl)-2-methyl-4-hydroxy-3(2H)-furanon-5-yl)-2-pyrrolidinone; N-(2-(3-methoxyphenyl)-2-methyl-4-hydroxy-3(2H)-furanon-5-yl)-succinimide; N-(2-(3-methoxyphenyl)-2-methyl-4-hydroxy-3(2H)-furanon-5-yl)-3-bromopropylsulfonamide; N-(2-(3-methoxyphenyl)-2-methyl-4-hydroxy-3(2H)-furanon-5-yl)-1,1-dioxide-isothiazolidine; N-methyl-N'-(2-(3-methoxyphenyl)-2-methyl-4-hydroxy-3(2H)-furanon-5-yl)-ethanesulfonamide; 2-(3-methoxyphenyl)-2-methyl-4-acetoxy-5-amino-3(2H)-furanone; N-(2-(3-methoxyphenyl)-2-methyl-4-acetoxy-3(2H)-furanon-5-yl)-methanesulfonamide; N-(2-(3-methoxyphenyl)-2-methyl-4-acetoxy-3(2H)-furanon-5-yl)-ethanesulfonamide; N-(2-(3-methoxyphenyl)-2-methyl-4-acetoxy-3(2H)-furanon-5-yl)-benzenesulfonamide; N-(2-(3-methoxyphenyl)-2-methyl-4-acetoxy-3(2H)-furanon-5-yl)-acetamide; N-(2-(3-methoxyphenyl)-2-methyl-4-acetoxy-3(2H)-furanon-5-yl)-carbamic acid ethyl ester; N-(2-(3-methoxyphenyl)-2-methyl-4-acetoxy-3(2H)-furanon-5-yl)-benzamide; N-(2-(3-methoxyphenyl)-2-methyl-4-acetoxy-3(2H)-furanon-5-yl)-4-bromobutanamide; N-(2-(3-methoxyphenyl)-2-methyl-4-acetoxy-3(2H)-furanon-5-yl)-2-pyrrolidinone; N-(2-(3-methoxyphenyl)-2-methyl-4-acetoxy-3(2H)-furanon-5-yl)-succinimide; N-(2-(3-methoxyphenyl)-2-methyl-4-acetoxy-3(2H)-furanon-5-yl)-3-bromopropylsulfonamide; N-(2-(3-methoxyphenyl)-2-methyl-4-acetoxy-3(2H)-furanon-5-yl)-1,1-dioxide-isothiazolidine; N-methyl-N'-(2-(3-methoxyphenyl)-2-methyl-4-acetoxy-3(2H)-furanon-5-yl)-ethanesulfonamide; 2-(4-methoxyphenyl)-5-amino-4-hydroxy-3(2H)-furanone; 2-(4-methoxyphenyl)-4-(acetoxy)-5-amino-3(2H)-furanone; 2-(4-methoxyphenyl)-4-[[phenylsulfonyl]oxy]-5-amino-3(2H)-furanone; N-(3,4-dihydroxy-5-(4-methoxyphenyl)-2-furanyl)methanesulfonamide; N-(3,4-dihydroxy-5-(4-methoxyphenyl)-2-furanyl)ethanesulfonamide; N-(3,4-dihydroxy-5-(4-methoxyphenyl)-2-furanyl)benzenesulfonamide; N-(3,4-dihydroxy-5-(4-methoxyphenyl)-2-furanyl)acetamide; N-(3,4-dihydroxy-5-(4-methoxyphenyl)-2-furanyl)-carbamic acid ethyl ester; N-(3,4-dihydroxy-5-(4-methoxyphenyl)-2-furanyl)benzamide; N-(3-trimethylsilyloxy-4-hydroxy-5-(4-methoxyphenyl)-2-furanyl)-4-bromobutanamide; N-(3,4-dihydroxy-5-(4-methoxyphenyl)-2-furanyl)-2-pyrrolidinone; N-(3,4-dihydroxy-5-(4-methoxyphenyl)-2-furanyl)succinimide; N-(3-trimethylsilyloxy-4-hydroxy-5-(4-methoxyphenyl)-2-furanyl)-3-bromopropylsulfonamide; N-(3,4-dihydroxy-5-(4-methoxyphenyl)-2-furanyl)-1,1-dioxide-isothiazolidine; N-methyl-N'-(3,4-dihydroxy-5-(4-methoxyphenyl)-2-furanyl)ethanesulfonamide; N-(3-acetoxy-4-hydroxy-5-(4-methoxyphenyl)-2-furanyl)methanesulfonamide; N-(3-acetoxy-4-hydroxy-5-(4-methoxyphenyl)-2-furanyl)ethanesulfonamide; N-(3-acetoxy-4-hydroxy-5-(4-methoxyphenyl)-2-furanyl)benzenesulfonamide; N-(3-acetoxy-4-hydroxy-5-(4-methoxyphenyl)-2-furanyl)-acetamide; N-(3-acetoxy-4-hydroxy-5-(4-methoxyphenyl)-2-furanyl)-carbamic acid ethyl ester; N-(3-acetoxy-4-hydroxy-5-(4-methoxyphenyl)-2-furanyl)benzamide; N-(3-acetoxy-4-hydroxy-5-(4-methoxyphenyl)-2-furanyl)-4-bromobutanamide; N-(3-acetoxy-4-hydroxy-5-(4-methoxyphenyl)-2-furanyl)-2-pyrrolidinone; N-(3-acetoxy-4-hydroxy-5-(4-methoxyphenyl)-2-furanyl)succinimide; N-(3-acetoxy-4-hydroxy-5-(4-methoxyphenyl)-2-furanyl)-3-bromopropylsulfonamide; N-(3-acetoxy-4-hydroxy-5-(4-methoxyphenyl)-2-furanyl)-1,1-dioxide-isothiazolidine; N-methyl-N'-(3-acetoxy-4-hydroxy-5-(4-methoxyphenyl)-2-furanyl)ethanesulfonamide; 2-(4-methoxyphenyl)-2-methyl-4-trimethylsilyloxy-5-amino-3(2H)-furanone; 2-(4-methoxyphenyl)-2-methyl-4-hydroxy-5-amino-3(2H)-furanone; N-(2-(4-methoxyphenyl)-2-methyl-4-hydroxy-3(2H)-furanon-5-yl)-methanesulfonamide; N-(2-(4-methoxyphenyl)-2-methyl-4-hydroxy-3(2H)-furanon-5-yl)-ethanesulfonamide; N-(2-(4-methoxyphenyl)-2-methyl-4-hydroxy-3(2H)-furanon-5-yl)-benzenesulfonamide; N-(2-(4-methoxyphenyl)-2-methyl-4-hydroxy-3(2H)-furanon-5-yl)-acetamide; N-(2-(4-methoxyphenyl)-2-methyl-4-hydroxy-3(2H)-furanon-5-yl)-carbamic acid ethyl ester; N-(2-(4-methoxyphenyl)-2-methyl-4-hydroxy-3(2H)-furanon-5-yl)-benzamide; N-(2-(4-methoxyphenyl)-2-methyl-4-hydroxy-3(2H)-furanon-5-yl)-4-bromobutanamide; N-(2-(4-methoxyphenyl)-2-methyl-4-hydroxy-3(2H)-furanon-5-yl)-2-pyrrolidinone; N-(2-(4-methoxyphenyl)-2-methyl-4-hydroxy-3(2H)-furanon-5-yl)-succinimide; N-(2-(4-methoxyphenyl)-2-methyl-4-hydroxy-3(2H)-furanon-5-yl)-3-bromopropylsulfonamide; N-(2-(4-methoxyphenyl)-2-methyl-4-hydroxy-3(2H)-furanon-5-yl)-1,1-dioxide-isothiazolidine; N-methyl-N'-(2-(4-methoxyphenyl)-2-methyl-4-hydroxy-3(2H)-furanon-5-yl)-ethanesulfonamide; 2-(4-methoxyphenyl)-2-methyl-4-acetoxy-5-amino-3(2H)-furanone; N-(2-(4-methoxyphenyl)-2-methyl-4-acetoxy-3(2H)-furanon-5-yl)-methanesulfonamide; N-(2-(4-methoxyphenyl)-2-methyl-4-acetoxy-3(2H)-furanon-5-yl)-ethanesulfonamide; N-(2-(4-methoxyphenyl)-2-methyl-4-acetoxy-3(2H)-furanon-5-yl)-benzenesulfonamide; N-(2-(4-methoxyphenyl)-2-methyl-4-acetoxy-3(2H)-furanon-5-yl)-acetamide; N-(2-(4-methoxyphenyl)-2-methyl-4-acetoxy-3(2H)-furanon-5-yl)-carbamic acid ethyl ester; N-(2-(4-methoxyphenyl)-2-methyl-4-acetoxy-3(2H)-furanon-5-yl)-benzamide; N-(2-(4-methoxyphenyl)-2-methyl-4-acetoxy-3(2H)-furanon-5-yl)-4-bromobutanamide; N-(2-(4-methoxyphenyl)-2-methyl-4-acetoxy-3(2H)-furanon-5-yl)-2-pyrrolidinone; N-(2-(4-methoxyphenyl)-2-methyl-4-acetoxy-3(2H)-furanon-5-yl)-succinimide; N-(2-(4-methoxyphenyl)-2-methyl-4-acetoxy-3(2H)-furanon-5-yl)-3-bromopropylsulfonamide; N-(2-(4-methoxyphenyl)-2-methyl-4-acetoxy-3(2H)-furanon-5-yl)-1,1-dioxide-isothiazolidine; N-methyl-N'-(2-(4-methoxyphenyl)-2-methyl-4-acetoxy-3(2H)-furanon-5-yl)-ethanesulfonamide; 2-(2,3-dimethoxyphenyl)-5-amino-4-hydroxy-3(2H)-furanone; 2-(2,3-dimethoxyphenyl)-4-(acetoxy)-5-amino-3(2H)-furanone; 2-(2,3-dimethoxyphenyl)-4-[[phenylsulfonyl]oxy]-5-amino-3(2H)-furanone; N-(3,4-dihydroxy-5-(2,3-dimethoxyphenyl)-2-furanyl)methanesulfonamide; N-(3,4-dihydroxy-5-(2,3-dimethoxyphenyl)-2-furanyl)ethanesulfonamide; N-(3,4-dihydroxy-5-(2,3-dimethoxyphenyl)-2-furanyl)benzenesulfonamide; N-(3,4-dihydroxy-5-(2,3-dimethoxyphenyl)-2-furanyl)acetamide; N-(3,4-dihydroxy-5-(2,3-dimethoxyphenyl)-2-furanyl)-carbamic acid ethyl ester; N-(3,4-dihydroxy-5-(2,3-dimethoxyphenyl)-2-furanyl)benzamide; N-(3-trimethylsilyloxy-4-hydroxy-5-(2,3-dimethoxyphenyl)-2-furanyl)-4-bromobutanamide; N-(3,4-dihydroxy-5-(2,3-dimethoxyphenyl)-2-furanyl)-2-pyrrolidinone; N-(3,4-dihydroxy-5-(2,3-dimethoxyphenyl)-2-furanyl)succinimide; N-(3-trimethylsilyloxy-4-hydroxy-5-(2,3-dimethoxyphenyl)-2-furanyl)-3-bromopropylsulfonamide; N-(3,4-dihydroxy-5-(2,3-dimethoxyphenyl)-2-furanyl)-1,1-dioxide-isothiazolidine; N-methyl-N'-(3,4-dihydroxy-5-(2,3-dimethoxyphenyl)-2-furanyl)ethanesulfonamide; N-(3-acetoxy-4-hydroxy-5-(2,3-dimethoxyphenyl)-2-furanyl)methanesulfonamide; N-(3-acetoxy-4-hydroxy-5-(2,3-dimethoxyphenyl)-2-furanyl)ethanesulfonamide; N-(3-acetoxy-4-hydroxy-5-(2,3-dimethoxyphenyl)-2-furanyl)benzenesulfonamide; N-(3-acetoxy-4-hydroxy-5-(2,3-dimethoxyphenyl)-2-furanyl)-acetamide; N-(3-acetoxy-4-hydroxy-5-(2,3-dimethoxyphenyl)-2-furanyl)-carbamic acid ethyl ester; N-(3-acetoxy-4-hydroxy-5-(2,3-dimethoxyphenyl)-2-furanyl)benzamide; N-(3-acetoxy-4-hydroxy-5-(2,3-dimethoxyphenyl)-2-furanyl)-4-bromobutanamide; N-(3-acetoxy-4-hydroxy-5-(2,3-dimethoxyphenyl)-2-furanyl)-2-pyrrolidinone; N-(3-acetoxy-4-hydroxy-5-(2,3-dimethoxyphenyl)-2-furanyl)succinimide; N-(3-acetoxy-4-hydroxy-5-(2,3-dimethoxyphenyl)-2-furanyl)-3-bromopropylsulfonamide; N-(3-acetoxy-4-hydroxy-5-(2,3-dimethoxyphenyl)-2-furanyl)-1,1-dioxide-isothiazolidine; N-methyl-N'-(3-acetoxy-4-hydroxy-5-(2,3-dimethoxyphenyl)-2-furanyl)ethanesulfonamide; 2-(2,3-dimethoxyphenyl)-2-methyl-4-trimethylsilyloxy-5-amino-3(2H)-furanone; 2-(2,3-dimethoxyphenyl)-2-methyl-4-hydroxy-5-amino-3(2H)-furanone; N-(2-(2,3-dimethoxyphenyl)-2-methyl-4-hydroxy-3(2H)-furanon-5-yl)-methanesulfonamide; N-(2-(2,3-dimethoxyphenyl)-2-methyl-4-hydroxy-3(2H)-furanon-5-yl)-ethanesulfonamide; N-(2-(2,3-dimethoxyphenyl)-2-methyl-4-hydroxy-3(2H)-furanon-5-yl)-benzenesulfonamide; N-(2-(2,3-dimethoxyphenyl)-2-methyl-4-hydroxy-3(2H)-furanon-5-yl)-acetamide; N-(2-(2,3-dimethoxyphenyl)-2-methyl-4-hydroxy-3(2H)-furanon-5-yl)-carbamic acid ethyl ester; N-(2-(2,3-dimethoxyphenyl)-2-methyl-4-hydroxy-3(2H)-furanon-5-yl)-benzamide; N-(2-(2,3-dimethoxyphenyl)-2-methyl-4-hydroxy-3(2H)-furanon-5-yl)-4-bromobutanamide; N-(2-(2,3-dimethoxyphenyl)-2-methyl-4-hydroxy-3(2H)-furanon-5-yl)-2-pyrrolidinone; N-(2-(2,3-dimethoxyphenyl)-2-methyl-4-hydroxy-3(2H)-furanon-5-yl)-succinimide; N-(2-(2,3-dimethoxyphenyl)-2-methyl-4-hydroxy-3(2H)-furanon-5-yl)-3-bromopropylsulfonamide; N-(2-(2,3- dimethoxyphenyl)-2-methyl-4-hydroxy-3(2H)-furanon-5-yl)-1,1-dioxide-isothiazolidine; N-methyl-N'-(2-(2,3-dimethoxyphenyl)-2-methyl-4-hydroxy-3(2H)-furanon-5-yl)-ethanesulfonamide; 2-(2,3-dimethoxyphenyl)-2-methyl-4-acetoxy-5-amino-3(2H)-furanone; N-(2-(2,3-dimethoxyphenyl)-2-methyl-4-acetoxy-3(2H)-furanon-5-yl)-methanesulfonamide; N-(2-(2,3-dimethoxyphenyl)-2-methyl-4-acetoxy-3(2H)-furanon-5-yl)-ethanesulfonamide; N-(2-(2,3-dimethoxyphenyl)-2-methyl-4-acetoxy-3(2H)-furanon-5-yl)-benzenesulfonamide; N-(2-(2,3-dimethoxyphenyl)-2-methyl-4-acetoxy-3(2H)-furanon-5-yl)-acetamide; N-(2-(2,3-dimethoxyphenyl)-2-methyl-4-acetoxy-3(2H)-furanon-5-yl)-carbamic acid ethyl ester; N-(2-(2,3-dimethoxyphenyl)-2-methyl-4-acetoxy-3(2H)-furanon-5-yl)-benzamide; N-(2-(2,3-dimethoxyphenyl)-2-methyl-4-acetoxy-3(2H)-furanon-5-yl)-4-bromobutanamide; N-(2-(2,3-dimethoxyphenyl)-2-methyl-4-acetoxy-3(2H)-furanon-5-yl)-2-pyrrolidinone; N-(2-(2,3-dimethoxyphenyl)-2-methyl-4-acetoxy-3(2H)-furanon-5-yl)-succinimide; N-(2-(2,3-dimethoxyphenyl)-2-methyl-4-acetoxy-3(2H)-furanon-5-yl)-3-bromopropylsulfonamide; N-(2-(2,3-dimethoxyphenyl)-2-methyl-4-acetoxy-3(2H)-furanon-5-yl)-1,1-dioxide-isothiazolidine; N-methyl-N'-(2-(2,3-dimethoxyphenyl)-2-methyl-4-acetoxy-3(2H)-furanon-5-yl)-ethanesulfonamide; 2-(2,4-dimethoxyphenyl)-5-amino-4-hydroxy-3(2H)-furanone; 2-(2,4-dimethoxyphenyl)-4-(acetoxy)-5-amino-3(2H)-furanone; 2-(2,4-dimethoxyphenyl)-4-[[phenylsulfonyl]oxy]-5-amino-3(2H)-furanone; N-(3,4-dihydroxy-5-(2,4-dimethoxyphenyl)-2-furanyl)methanesulfonamide; N-(3,4-dihydroxy-5-(2,4-dimethoxyphenyl)-2-furanyl)ethanesulfonamide; N-(3,4-dihydroxy-5-(2,4-dimethoxyphenyl)-2-furanyl)benzenesulfonamide; N-(3,4-dihydroxy-5-(2,4-dimethoxyphenyl)-2-furanyl)acetamide; N-(3,4-dihydroxy-5-(2,4-dimethoxyphenyl)-2-furanyl)-carbamic acid ethyl ester; N-(3,4-dihydroxy-5-(2,4-dimethoxyphenyl)-2-furanyl)benzamide; N-(3-trimethylsilyloxy-4-hydroxy-5-(2,4-dimethoxyphenyl)-2-furanyl)-4-bromobutanamide; N-(3,4-dihydroxy-5-(2,4-dimethoxyphenyl)-2-furanyl)-2-pyrrolidinone; N-(3,4-dihydroxy-5-(2,4-dimethoxyphenyl)-2-furanyl)succinimide; N-(3-trimethylsilyloxy-4-hydroxy-5-(2,4-dimethoxyphenyl)-2-furanyl)-3-bromopropylsulfonamide; N-(3,4-dihydroxy-5-(2,4-dimethoxyphenyl)-2-furanyl)-1,1-dioxide-isothiazolidine; N-methyl-N'-(3,4-dihydroxy-5-(2,4-dimethoxyphenyl)-2-furanyl)ethanesulfonamide; N-(3-acetoxy-4-hydroxy-5-(2,4-dimethoxyphenyl)-2-furanyl)methanesulfonamide; N-(3-acetoxy-4-hydroxy-5-(2,4-dimethoxyphenyl)-2-furanyl)ethanesulfonamide; N-(3-acetoxy-4-hydroxy-5-(2,4-dimethoxyphenyl)-2-furanyl)benzenesulfonamide; N-(3-acetoxy-4-hydroxy-5-(2,4-dimethoxyphenyl)-2-furanyl)-acetamide; N-(3-acetoxy-4-hydroxy-5-(2,4-dimethoxyphenyl)-2-furanyl)-carbamic acid ethyl ester; N-(3-acetoxy-4-hydroxy-5-(2,4-dimethoxyphenyl)-2-furanyl)benzamide; N-(3-acetoxy-4-hydroxy-5-(2,4-dimethoxyphenyl)-2-furanyl)-4-bromobutanamide; N-(3-acetoxy-4-hydroxy-5-(2,4-dimethoxyphenyl)-2-furanyl)-2-pyrrolidinone; N-(3-acetoxy-4-hydroxy-5-(2,4-dimethoxyphenyl)-2-furanyl)succinimide; N-(3-acetoxy-4-hydroxy-5-(2,4-dimethoxyphenyl)-2-furanyl)-3-bromopropylsulfonamide; N-(3-acetoxy-4-hydroxy-5-(2,4-dimethoxyphenyl)-2-furanyl)-1,1-dioxide-isothiazolidine; N-methyl-N'-(3-acetoxy-4-hydroxy-5-(2,4-dimethoxyphenyl)-2-furanyl)ethanesulfonamide; 2-(2,4-dimethoxyphenyl)-2-methyl-4-trimethylsilyloxy-5-amino-3(2H)-furanone; 2-(2,4-dimethoxyphenyl)-2-methyl-4-hydroxy-5-amino-3(2H)-furanone; N-(2-(2,4-dimethoxyphenyl)-2-methyl-4-hydroxy-3(2H)-furanon-5-yl)-methanesulfonamide; N-(2-(2,4-dimethoxyphenyl)-2-methyl-4-hydroxy-3(2H)-furanon-5-yl)-ethanesulfonamide; N-(2-(2,4-dimethoxyphenyl)-2-methyl-4-hydroxy-3(2H)-furanon-5-yl)-benzenesulfonamide; N-(2-(2,4-dimethoxyphenyl)-2-methyl-4-hydroxy-3(2H)-furanon-5-yl)-acetamide; N-(2-(2,4-dimethoxyphenyl)-2-methyl-4-hydroxy-3(2H)-furanon-5-yl)-carbamic acid ethyl ester; N-(2-(2,4-dimethoxyphenyl)-2-methyl-4-hydroxy-3(2H)-furanon-5-yl)-benzamide; N-(2-(2,4-dimethoxyphenyl)-2-methyl-4-hydroxy-3(2H)-furanon-5-yl)-4-bromobutanamide; N-(2-(2,4-dimethoxyphenyl)-2-methyl-4-hydroxy-3(2H)-furanon-5-yl)-2-pyrrolidinone; N-(2-(2,4-dimethoxyphenyl)-2-methyl-4-hydroxy-3(2H)-furanon-5-yl)-succinimide; N-(2-(2,4-dimethoxyphenyl)-2-methyl-4-hydroxy-3(2H)-furanon-5-yl)-3-bromopropylsulfonamide; N-(2-(2,4-dimethoxyphenyl)-2-methyl-4-hydroxy-3(2H)-furanon-5-yl)-1,1-dioxide-isothiazolidine; N-methyl-N'-(2-(2,4-dimethoxyphenyl)-2-methyl-4-hydroxy-3(2H)-furanon-5-yl)-ethanesulfonamide; 2-(2,4-dimethoxyphenyl)-2-methyl-4-acetoxy-5-amino-3(2H)-furanone; N-(2-(2,4-dimethoxyphenyl)-2-methyl-4-acetoxy-3(2H)-furanon-5-yl)-methanesulfonamide; N-(2-(2,4-dimethoxyphenyl)-2-methyl-4-acetoxy-3(2H)-furanon-5-yl)-ethanesulfonamide; N-(2-(2,4-dimethoxyphenyl)-2-methyl-4-acetoxy-3(2H)-furanon-5-yl)-benzenesulfonamide; N-(2-(2,4-dimethoxyphenyl)-2-methyl-4-acetoxy-3(2H)-furanon-5-yl)-acetamide; N-(2-(2,4-dimethoxyphenyl)-2-methyl-4-acetoxy-3(2H)-furanon-5-yl)-carbamic acid ethyl ester; N-(2-(2,4-dimethoxyphenyl)-2-methyl-4-acetoxy-3(2H)-furanon-5-yl)-benzamide; N-(2-(2,4-dimethoxyphenyl)-2-methyl-4-acetoxy-3(2H)-furanon-5-yl)-4-bromobutanamide; N-(2-(2,4-dimethoxyphenyl)-2-methyl-4-acetoxy-3(2H)-furanon-5-yl)-2-pyrrolidinone; N-(2-(2,4-dimethoxyphenyl)-2-methyl-4-acetoxy-3(2H)-furanon-5-yl)-succinimide; N-(2-(2,4-dimethoxyphenyl)-2-methyl-4-acetoxy-3(2H)-furanon-5-yl)-3-bromopropylsulfonamide; N-(2-(2,4-dimethoxyphenyl)-2-methyl-4-acetoxy-3(2H)-furanon-5-yl)-1,1-dioxide-isothiazolidine; N-methyl-N'-(2-(2,4-dimethoxyphenyl)-2-methyl-4-acetoxy-3(2H)-furanon-5-yl)-ethanesulfonamide; 2-(2,5-dimethoxyphenyl)-5-amino-4-hydroxy-3(2H)-furanone; 2-(2,5-dimethoxyphenyl)-4-(acetoxy)-5-amino-3(2H)-furanone; 2-(2,5-dimethoxyphenyl)-4-[[phenylsulfonyl]oxy]-5-amino-3(2H)-furanone; N-(3,4-dihydroxy-5-(2,5-dimethoxyphenyl)-2-furanyl)methanesulfonamide; N-(3,4-dihydroxy-5-(2,5-dimethoxyphenyl)-2-furanyl)ethanesulfonamide; N-(3,4-dihydroxy-5-(2,5-dimethoxyphenyl)-2-furanyl)benzenesulfonamide; N-(3,4-dihydroxy-5-(2,5-dimethoxyphenyl)-2-furanyl)acetamide; N-(3,4-dihydroxy-5-(2,5-dimethoxyphenyl)-2-furanyl)-carbamic acid ethyl ester; N-(3,4-dihydroxy-5-(2,5-dimethoxyphenyl)-2-furanyl)benzamide; N-(3-trimethylsilyloxy-4-hydroxy-5-(2,5-dimethoxyphenyl)-2-furanyl)-4-bromobutanamide; N-(3,4-dihydroxy-5-(2,5-dimethoxyphenyl)-2-furanyl)-2-pyrrolidinone; N-(3,4-dihydroxy-5-(2,5-dimethoxyphenyl)-2-furanyl)succinimide; N-(3-trimethylsilyloxy-4-hydroxy-5-(2,5-dimethoxyphenyl)-2-furanyl)-3-bromopropylsulfonamide; N-(3,4-dihydroxy-5-(2,5-dimethoxyphenyl)-2-furanyl)-1,1-dioxide-isothiazolidine; N-methyl-N'-(3,4-dihydroxy-5-(2,5-dimethoxyphenyl)-2-furanyl)ethanesulfonamide; N-(3-acetoxy-4-hydroxy-5-(2,5-dimethoxyphenyl)-2-furanyl)methanesulfonamide; N-(3-acetoxy-4-hydroxy-5-(2,5-dimethoxyphenyl)-2-furanyl)ethanesulfonamide; N-(3-acetoxy-4-hydroxy-5-(2,5-dimethoxyphenyl)-2-furanyl)benzenesulfonamide; N-(3-acetoxy-4-hydroxy-5-(2,5- dimethoxyphenyl)-2-furanyl)-acetamide; N-(3-acetoxy-4-hydroxy-5-(2,5-dimethoxyphenyl)-2-furanyl)-carbamic acid ethyl ester; N-(3-acetoxy-4-hydroxy-5-(2,5-dimethoxyphenyl)-2-furanyl)benzamide; N-(3-acetoxy-4-hydroxy-5-(2,5-dimethoxyphenyl)-2-furanyl)-4-bromobutanamide; N-(3-acetoxy-4-hydroxy-5-(2,5-dimethoxyphenyl)-2-furanyl)-2-pyrrolidinone; N-(3-acetoxy-4-hydroxy-5-(2,5-dimethoxyphenyl)-2-furanyl)succinimide; N-(3-acetoxy-4-hydroxy-5-(2,5-dimethoxyphenyl)-2-furanyl)-3-bromopropylsulfonamide; N-(3-acetoxy-4-hydroxy-5-(2,5-dimethoxyphenyl)-2-furanyl)-1,1-dioxide-isothiazolidine; N-methyl-N'-(3-acetoxy-4-hydroxy-5-(2,5-dimethoxyphenyl)-2-furanyl)ethanesulfonamide; 2-(2,5-dimethoxyphenyl)-2-methyl-4-trimethylsilyloxy-5-amino-3(2H)-furanone; 2-(2,5-dimethoxyphenyl)-2-methyl-4-hydroxy-5-amino-3(2H)-furanone; N-(2-(2,5-dimethoxyphenyl)-2-methyl-4-hydroxy-3(2H)-furanon-5-yl)-methanesulfonamide; N-(2-(2,5-dimethoxyphenyl)-2-methyl-4-hydroxy-3(2H)-furanon-5-yl)-ethanesulfonamide; N-(2-(2,5-dimethoxyphenyl)-2-methyl-4-hydroxy-3(2H)-furanon-5-yl)-benzenesulfonamide; N-(2-(2,5-dimethoxyphenyl)-2-methyl-4-hydroxy-3(2H)-furanon-5-yl)-acetamide; N-(2-(2,5-dimethoxyphenyl)-2-methyl-4-hydroxy-3(2H)-furanon-5-yl)-carbamic acid ethyl ester; N-(2-(2,5-dimethoxyphenyl)-2-methyl-4-hydroxy-3(2H)-furanon-5-yl)-benzamide; N-(2-(2,5-dimethoxyphenyl)-2-methyl-4-hydroxy-3(2H)-furanon-5-yl)-4-bromobutanamide; N-(2-(2,5-dimethoxyphenyl)-2-methyl-4-hydroxy-3(2H)-furanon-5-yl)-2-pyrrolidinone; N-(2-(2,5-dimethoxyphenyl)-2-methyl-4-hydroxy-3(2H)-furanon-5-yl)-succinimide; N-(2-(2,5-dimethoxyphenyl)-2-methyl-4-hydroxy-3(2H)-furanon-5-yl)-3-bromopropylsulfonamide; N-(2-(2,5-dimethoxyphenyl)-2-methyl-4-hydroxy-3(2H)-furanon-5-yl)-1,1-dioxide-isothiazolidine; N-methyl-N'-(2-(2,5-dimethoxyphenyl)-2-methyl-4-hydroxy-3(2H)-furanon-5-yl)-ethanesulfonamide; 2-(2,5-dimethoxyphenyl)-2-methyl-4-acetoxy-5-amino-3(2H)-furanone; N-(2-(2,5-dimethoxyphenyl)-2-methyl-4-acetoxy-3(2H)-furanon-5-yl)-methanesulfonamide; N-(2-(2,5-dimethoxyphenyl)-2-methyl-4-acetoxy-3(2H)-furanon-5-yl)-ethanesulfonamide; N-(2-(2,5-dimethoxyphenyl)-2-methyl-4-acetoxy-3(2H)-furanon-5-yl)-benzenesulfonamide; N-(2-(2,5-dimethoxyphenyl)-2-methyl-4-acetoxy-3(2H)-furanon-5-yl)-acetamide; N-(2-(2,5-dimethoxyphenyl)-2-methyl-4-acetoxy-3(2H)-furanon-5-yl)-carbamic acid ethyl ester; N-(2-(2,5-dimethoxyphenyl)-2-methyl-4-acetoxy-3(2H)-furanon-5-yl)-benzamide; N-(2-(2,5-dimethoxyphenyl)-2-methyl-4-acetoxy-3(2H)-furanon-5-yl)-4-bromobutanamide; N-(2-(2,5-dimethoxyphenyl)-2-methyl-4-acetoxy-3(2H)-furanon-5-yl)-2-pyrrolidinone; N-(2-(2,5-dimethoxyphenyl)-2-methyl-4-acetoxy-3(2H)-furanon-5-yl)-succinimide; N-(2-(2,5-dimethoxyphenyl)-2-methyl-4-acetoxy-3(2H)-furanon-5-yl)-3-bromopropylsulfonamide; N-(2-(2,5-dimethoxyphenyl)-2-methyl-4-acetoxy-3(2H)-furanon-5-yl)-1,1-dioxide-isothiazolidine; N-methyl-N'-(2-(2,5-dimethoxyphenyl)-2-methyl-4-acetoxy-3(2H)-furanon-5-yl)-ethanesulfonamide; 2-(2,6-dimethoxyphenyl)-5-amino-4-hydroxy-3(2H)-furanone; 2-(2,6-dimethoxyphenyl)-4-(acetoxy)-5-amino-3(2H)-furanone; 2-(2,6-dimethoxyphenyl)-4-[[phenylsulfonyl]oxy]-5-amino-3(2H)-furanone; N-(3,4-dihydroxy-5-(2,6-dimethoxyphenyl)-2-furanyl)methanesulfonamide; N-(3,4-dihydroxy-5-(2,6-dimethoxyphenyl)-2-furanyl)ethanesulfonamide; N-(3,4-dihydroxy-5-(2,6-dimethoxyphenyl)-2-furanyl)benzenesulfonamide; N-(3,4-dihydroxy-5-(2,6-dimethoxyphenyl)-2-furanyl)acetamide; N-(3,4-dihydroxy-5-(2,6-dimethoxyphenyl)-2-furanyl)-carbamic acid ethyl ester; N-(3,4-dihydroxy-5-(2,6-dimethoxyphenyl)-2-furanyl)benzamide; N-(3-trimethylsilyloxy-4-hydroxy-5-(2,6-dimethoxyphenyl)-2-furanyl)-4-bromobutanamide; N-(3,4-dihydroxy-5-(2,6-dimethoxyphenyl)-2-furanyl)-2-pyrrolidinone; N-(3,4-dihydroxy-5-(2,6-dimethoxyphenyl)-2-furanyl) succinimide; N-(3-trimethylsilyloxy-4-hydroxy-5-(2,6-dimethoxyphenyl)-2-furanyl)-3-bromopropylsulfonamide; N-(3,4-dihydroxy-5-(2,6-dimethoxyphenyl)-2-furanyl)-1,1-dioxide-isothiazolidine; N-methyl-N'-(3,4-dihydroxy-5-(2,6-dimethoxyphenyl)-2-furanyl)ethanesulfonamide; N-(3-acetoxy-4-hydroxy-5-(2,6-dimethoxyphenyl)-2-furanyl)methanesulfonamide; N-(3-acetoxy-4-hydroxy-5-(2,6-dimethoxyphenyl)-2-furanyl)ethanesulfonamide; N-(3-acetoxy-4-hydroxy-5-(2,6-dimethoxyphenyl)-2-furanyl)benzenesulfonamide; N-(3-acetoxy-4-hydroxy-5-(2,6-dimethoxyphenyl)-2-furanyl)-acetamide; N-(3-acetoxy-4-hydroxy-5-(2,6-dimethoxyphenyl)-2-furanyl)-carbamic acid ethyl ester; N-(3-acetoxy-4-hydroxy-5-(2,6-dimethoxyphenyl)-2-furanyl)benzamide; N-(3-acetoxy-4-hydroxy-5-(2,6-dimethoxyphenyl)-2-furanyl)-4-bromobutanamide; N-(3-acetoxy-4-hydroxy-5-(2,6-dimethoxyphenyl)-2-furanyl)-2-pyrrolidinone; N-(3-acetoxy-4-hydroxy-5-(2,6-dimethoxyphenyl)-2-furanyl)succinimide; N-(3-acetoxy-4-hydroxy-5-(2,6-dimethoxyphenyl)-2-furanyl)-3-bromopropylsulfonamide; N-(3-acetoxy-4-hydroxy-5-(2,6-dimethoxyphenyl)-2-furanyl)-1,1-dioxide-isothiazolidine; N-methyl-N'-(3-acetoxy-4-hydroxy-5-(2,6-dimethoxyphenyl)-2-furanyl)ethanesulfonamide; 2-(2,6-dimethoxyphenyl)-2-methyl-4-trimethylsilyloxy-5-amino-3(2H)-furanone; 2-(2,6-dimethoxyphenyl)-2-methyl-4-hydroxy-5-amino-3(2H)-furanone; N-(2-(2,6-dimethoxyphenyl)-2-methyl-4-hydroxy-3(2H)-furanon-5-yl)-methanesulfonamide; N-(2-(2,6-dimethoxyphenyl)-2-methyl-4-hydroxy-3(2H)-furanon-5-yl)-ethanesulfonamide; N-(2-(2,6-dimethoxyphenyl)-2-methyl-4-hydroxy-3(2H)-furanon-5-yl)-benzenesulfonamide; N-(2-(2,6-dimethoxyphenyl)-2-methyl-4-hydroxy-3(2H)-furanon-5-yl)-acetamide; N-(2-(2,6-dimethoxyphenyl)-2-methyl-4-hydroxy-3(2H)-furanon-5-yl)-carbamic acid ethyl ester; N-(2-(2,6-dimethoxyphenyl)-2-methyl-4-hydroxy-3(2H)-furanon-5-yl)-benzamide; N-(2-(2,6-dimethoxyphenyl)-2-methyl-4-hydroxy-3(2H)-furanon-5-yl)-4-bromobutanamide; N-(2-(2,6-dimethoxyphenyl)-2-methyl-4-hydroxy-3(2H)-furanon-5-yl)-2-pyrrolidinone; N-(2-(2,6-dimethoxyphenyl)-2-methyl-4-hydroxy-3(2H)-furanon-5-yl)-succinimide; N-(2-(2,6-dimethoxyphenyl)-2-methyl-4-hydroxy-3(2H)-furanon-5-yl)-3-bromopropylsulfonamide; N-(2-(2,6-dimethoxyphenyl)-2-methyl-4-hydroxy-3(2H)-furanon-5-yl)-1,1-dioxide-isothiazolidine; N-methyl-N'-(2-(2,6-dimethoxyphenyl)-2-methyl-4-hydroxy-3(2H)-furanon-5-yl)-ethanesulfonamide; 2-(2,6-dimethoxyphenyl)-2-methyl-4-acetoxy-5-amino-3(2H)-furanone; N-(2-(2,6-dimethoxyphenyl)-2-methyl-4-acetoxy-3(2H)-furanon-5-yl)-methanesulfonamide; N-(2-(2,6-dimethoxyphenyl)-2-methyl-4-acetoxy-3(2H)-furanon-5-yl)-ethanesulfonamide; N-(2-(2,6-dimethoxyphenyl)-2-methyl-4-acetoxy-3(2H)-furanon-5-yl)-benzenesulfonamide; N-(2-(2,6-dimethoxyphenyl)-2-methyl-4-acetoxy-3(2H)-furanon-5-yl)-acetamide; N-(2-(2,6-dimethoxyphenyl)-2-methyl-4-acetoxy-3(2H)-furanon-5-yl)-carbamic acid ethyl ester; N-(2-(2,6-dimethoxyphenyl)-2-methyl-4-acetoxy-3(2H)-furanon-5-yl)-benzamide; N-(2-(2,6-dimethoxyphenyl)-2-methyl-4-acetoxy-3(2H)-furanon-5-yl)-4-bromobutanamide; N-(2-(2,6-dimethoxyphenyl)-2-methyl-4-acetoxy-3(2H)-furanon-5-yl)-2-pyrrolidinone; N-(2-(2,6-dimethoxyphenyl)-2-methyl-4-acetoxy-3(2H)-furanon-5-yl)-succinimide; N-(2-(2,6- dimethoxyphenyl)-2-methyl-4-acetoxy-3(2H)-furanon-5-yl)-3-bromopropylsulfonamide; N-(2-(2,6-dimethoxyphenyl)-2-methyl-4-acetoxy-3(2H)-furanon-5-yl)-1,1-dioxide-isothiazolidine; N-methyl-N'-(2-(2,6-dimethoxyphenyl)-2-methyl-4-acetoxy-3(2H)-furanon-5-yl)-ethanesulfonamide; 2-(3,4-dimethoxyphenyl)-5-amino-4-hydroxy-3(2H)-furanone; 2-(3,4-dimethoxyphenyl)-4-(acetoxy)-5-amino-3(2H)-furanone; 2-(3,4-dimethoxyphenyl)-4-[[phenylsulfonyl]oxy]-5-amino-3 (2H)-furanone; N-(3,4-dihydroxy-5-(3,4-dimethoxyphenyl)-2-furanyl)methanesulfonamide; N-(3,4-dihydroxy-5-(3,4-dimethoxyphenyl)-2-furanyl) ethanesulfonamide; N-(3,4-dihydroxy-5-(3,4-dimethoxyphenyl)-2-furanyl)benzenesulfonamide; N-(3,4-dihydroxy-5-(3,4-dimethoxyphenyl)-2-furanyl)acetamide; N-(3,4-dihydroxy-5-(3,4-dimethoxyphenyl)-2-furanyl)-carbamic acid ethyl ester; N-(3,4-dihydroxy-5-(3,4-dimethoxyphenyl)-2-furanyl)benzamide; N-(3-trimethylsilyloxy-4-hydroxy-5-(3,4-dimethoxyphenyl)-2-furanyl)-4-bromobutanamide; N-(3,4-dihydroxy-5-(3,4-dimethoxyphenyl)-2-furanyl)-2-pyrrolidinone; N-(3,4-dihydroxy-5-(3,4-dimethoxyphenyl)-2-furanyl) succinimide; N-(3-trimethylsilyloxy-4-hydroxy-5-(3,4-dimethoxyphenyl)-2-furanyl)-3-bromopropylsulfonamide; N-(3,4-dihydroxy-5-(3,4-dimethoxyphenyl)-2-furanyl)-1,1-dioxide-isothiazolidine; N-methyl-N'-(3,4-dihydroxy-5-(3,4-dimethoxyphenyl)-2-furanyl)ethanesulfonamide; N-(3-acetoxy-4-hydroxy-5-(3,4-dimethoxyphenyl)-2-furanyl) methanesulfonamide; N-(3-acetoxy-4-hydroxy-5-(3,4-dimethoxyphenyl)-2-furanyl)ethanesulfonamide; N-(3-acetoxy-4-hydroxy-5-(3,4-dimethoxyphenyl)-2-furanyl) benzenesulfonamide; N-(3-acetoxy-4-hydroxy-5-(3,4-dimethoxyphenyl)-2-furanyl)-acetamide; N-(3-acetoxy-4-hydroxy-5-(3,4-dimethoxyphenyl)-2-furanyl)-carbamic acid ethyl ester; N-(3-acetoxy-4-hydroxy-5-(3,4-dimethoxyphenyl)-2-furanyl)benzamide; N-(3-acetoxy-4-hydroxy-5-(3,4-dimethoxyphenyl)-2-furanyl)-4-bromobutanamide; N-(3-acetoxy-4-hydroxy-5-(3,4-dimethoxyphenyl)-2-furanyl)-2-pyrrolidinone; N-(3-acetoxy-4-hydroxy-5-(3,4-dimethoxyphenyl)-2-furanyl)succinimide; N-(3-acetoxy-4-hydroxy-5-(3,4-dimethoxyphenyl)-2-furanyl)-3-bromopropylsulfonamide; N-(3-acetoxy-4-hydroxy-5-(3,4-dimethoxyphenyl)-2-furanyl)-1,1-dioxide-isothiazolidine; N-methyl-N'-(3-acetoxy-4-hydroxy-5-(3,4-dimethoxyphenyl)-2-furanyl)ethanesulfonamide; 2-(3,4-dimethoxyphenyl)-2-methyl-4-trimethylsilyloxy-5-amino-3(2H)-furanone; 2-(3,4-dimethoxyphenyl)-2-methyl-4-hydroxy-5-amino-3(2H)-furanone; N-(2-(3,4-dimethoxyphenyl)-2-methyl-4-hydroxy-3(2H)-furanon-5-yl)-methanesulfonamide; N-(2-(3,4-dimethoxyphenyl)-2-methyl-4-hydroxy-3(2H)-furanon-5-yl)-ethanesulfonamide; N-(2-(3,4-dimethoxyphenyl)-2-methyl-4-hydroxy-3(2H)-furanon-5-yl)-benzenesulfonamide; N-(2-(3,4-dimethoxyphenyl)-2-methyl-4-hydroxy-3(2H)-furanon-5-yl)-acetamide; N-(2-(3,4-dimethoxyphenyl)-2-methyl-4-hydroxy-3 (2H)-furanon-5-yl)-carbamic acid ethyl ester; N-(2-(3,4-dimethoxyphenyl)-2-methyl-4-hydroxy-3(2H)-furanon-5-yl)-benzamide; N-(2-(3,4-dimethoxyphenyl)-2-methyl-4-hydroxy-3(2H)-furanon-5-yl)-4-bromobutanamide; N-(2-(3,4-dimethoxyphenyl)-2-methyl-4-hydroxy-3(2H)-furanon-5-yl)-2-pyrrolidinone; N-(2-(3,4-dimethoxyphenyl)-2-methyl-4-hydroxy-3(2H)-furanon-5-yl)-succinimide; N-(2-(3,4-dimethoxyphenyl)-2-methyl-4-hydroxy-3(2H)-furanon-5-yl)-3-bromopropylsulfonamide; N-(2-(3,4-dimethoxyphenyl)-2-methyl-4-hydroxy-3(2H)-furanon-5-yl)-1,1-dioxide-isothiazolidine; N-methyl-N'-(2-(3,4-dimethoxyphenyl)-2-methyl-4-hydroxy-3(2H)-furanon-5-yl)-ethanesulfonamide; 2-(3,4-dimethoxyphenyl)-2-methyl-4-acetoxy-5-amino-3(2H)-furanone; N-(2-(3,4-dimethoxyphenyl)-2-methyl-4-acetoxy-3(2H)-furanon-5-yl)-methanesulfonamide; N-(2-(3,4-dimethoxyphenyl)-2-methyl-4-acetoxy-3(2H)-furanon-5-yl)-ethanesulfonamide; N-(2-(3,4-dimethoxyphenyl)-2-methyl-4-acetoxy-3(2H)-furanon-5-yl)-benzenesulfonamide; N-(2-(3,4-dimethoxyphenyl)-2-methyl-4-acetoxy-3(2H)-furanon-5-yl)-acetamide; N-(2-(3,4-dimethoxyphenyl)-2-methyl-4-acetoxy-3(2H)-furanon-5-yl)-carbamic acid ethyl ester; N-(2-(3,4-dimethoxyphenyl)-2-methyl-4-acetoxy-3(2H)-furanon-5-yl)-benzamide; N-(2-(3,4-dimethoxyphenyl)-2-methyl-4-acetoxy-3(2H)-furanon-5-yl)-4-bromobutanamide; N-(2-(3,4-dimethoxyphenyl)-2-methyl-4-acetoxy-3(2H)-furanon-5-yl)-2-pyrrolidinone; N-(2-(3,4-dimethoxyphenyl)-2-methyl-4-acetoxy-3(2H)-furanon-5-yl)-succinimide; N-(2-(3,4-dimethoxyphenyl)-2-methyl-4-acetoxy-3(2H)-furanon-5-yl)-3-bromopropylsulfonamide; N-(2-(3,4-dimethoxyphenyl)-2-methyl-4-acetoxy-3(2H)-furanon-5-yl)-1,1-dioxide-isothiazolidine; N-methyl-N'-(2-(3,4-dimethoxyphenyl)-2-methyl-4-acetoxy-3(2H)-furanon-5-yl)-ethanesulfonamide; 2-(3,5-dimethoxyphenyl)-5-amino-4-hydroxy-3(2H)-furanone; 2-(3,5-dimethoxyphenyl)-4-(acetoxy)-5-amino-3(2H)-furanone; 2-(3,5-dimethoxyphenyl)-4-[[phenylsulfonyl]oxy]-5-amino-3(2H)-furanone; N-(3,4-dihydroxy-5-(3,5-dimethoxyphenyl)-2-furanyl)methanesulfonamide; N-(3,4-dihydroxy-5-(3,5-dimethoxyphenyl)-2-furanyl) ethanesulfonamide; N-(3,4-dihydroxy-5-(3,5-dimethoxyphenyl)-2-furanyl)benzenesulfonamide; N-(3,4-dihydroxy-5-(3,5-dimethoxyphenyl)-2-furanyl)acetamide; N-(3,4-dihydroxy-5-(3,5-dimethoxyphenyl)-2-furanyl)-carbamic acid ethyl ester; N-(3,4-dihydroxy-5-(3,5-dimethoxyphenyl)-2-furanyl)benzamide; N-(3-trimethylsilyloxy-4-hydroxy-5-(3,5-dimethoxyphenyl)-2-furanyl)-4-bromobutanamide; N-(3,4-dihydroxy-5-(3,5-dimethoxyphenyl)-2-furanyl)-2-pyrrolidinone; N-(3,4-dihydroxy-5-(3,5-dimethoxyphenyl)-2-furanyl) succinimide; N-(3-trimethylsilyloxy-4-hydroxy-5-(3,5-dimethoxyphenyl)-2-furanyl)-3-bromopropylsulfonamide; N-(3,4-dihydroxy-5-(3,5-dimethoxyphenyl)-2-furanyl)-1,1-dioxide-isothiazolidine; N-methyl-N'-(3,4-dihydroxy-5-(3,5-dimethoxyphenyl)-2-furanyl)ethanesulfonamide; N-(3-acetoxy-4-hydroxy-5-(3,5-dimethoxyphenyl)-2-furanyl) methanesulfonamide; N-(3-acetoxy-4-hydroxy-5-(3,5-dimethoxyphenyl)-2-furanyl)ethanesulfonamide; N-(3-acetoxy-4-hydroxy-5-(3,5-dimethoxyphenyl)-2-furanyl) benzenesulfonamide; N-(3-acetoxy-4-hydroxy-5-(3,5-dimethoxyphenyl)-2-furanyl)-acetamide; N-(3-acetoxy-4-hydroxy-5-(3,5-dimethoxyphenyl)-2-furanyl)-carbamic acid ethyl ester; N-(3-acetoxy-4-hydroxy-5-(3,5-dimethoxyphenyl)-2-furanyl)benzamide; N-(3-acetoxy-4-hydroxy-5-(3,5-dimethoxyphenyl)-2-furanyl)-4-bromobutanamide; N-(3-acetoxy-4-hydroxy-5-(3,5-dimethoxyphenyl)-2-furanyl)-2-pyrrolidinone; N-(3-acetoxy-4-hydroxy-5-(3,5-dimethoxyphenyl)-2-furanyl)succinimide; N-(3-acetoxy-4-hydroxy-5-(3,5-dimethoxyphenyl)-2-furanyl)-3-bromopropylsulfonamide; N-(3-acetoxy-4-hydroxy-5-(3,5-dimethoxyphenyl)-2-furanyl)-1,1-dioxide-isothiazolidine; N-methyl-N'-(3-acetoxy-4-hydroxy-5-(3,5-dimethoxyphenyl)-2-furanyl)ethanesulfonamide; 2-(3,5-dimethoxyphenyl)-2-methyl-4-trimethylsilyloxy-5-amino-3(2H)-furanone; 2-(3,5-dimethoxyphenyl)-2-methyl-4-hydroxy-5-amino-3(2H)-furanone; N-(2-(3,5-dimethoxyphenyl)-2-methyl-4-hydroxy-3(2H)-furanon-5-yl)-methanesulfonamide; N-(2-(3,5-dimethoxyphenyl)-2-methyl-4-hydroxy-3(2H)-furanon-5-yl)-ethanesulfonamide; N-(2-(3,5-dimethoxyphenyl)-2-methyl-4-hydroxy-3(2H)- furanon-5-yl)-benzenesulfonamide; N-(2-(3,5-dimethoxyphenyl)-2-methyl-4-hydroxy-3(2H)-furanon-5-yl)-acetamide; N-(2-(3,5-dimethoxyphenyl)-2-methyl-4-hydroxy-3(2H)-furanon-5-yl)-carbamic acid ethyl ester; N-(2-(3,5-dimethoxyphenyl)-2-methyl-4-hydroxy-3(2H)-furanon-5-yl)-benzamide; N-(2-(3,5-dimethoxyphenyl)-2-methyl-4-hydroxy-3(2H)-furanon-5-yl)-4-bromobutanamide; N-(2-(3,5-dimethoxyphenyl)-2-methyl-4-hydroxy-3(2H)-furanon-5-yl)-2-pyrrolidinone; N-(2-(3,5-dimethoxyphenyl)-2-methyl-4-hydroxy-3(2H)-furanon-5-yl)-succinimide; N-(2-(3,5-dimethoxyphenyl)-2-methyl-4-hydroxy-3(2H)-furanon-5-yl)-3-bromopropylsulfonamide; N-(2-(3,5-dimethoxyphenyl)-2-methyl-4-hydroxy-3(2H)-furanon-5-yl)-1,1-dioxide-isothiazolidine; N-methyl-N'-(2-(3,5-dimethoxyphenyl)-2-methyl-4-hydroxy-3(2H)-furanon-5-yl)-ethanesulfonamide; 2-(3,5-dimethoxyphenyl)-2-methyl-4-acetoxy-5-amino-3(2H)-furanone; N-(2-(3,5-dimethoxyphenyl)-2-methyl-4-acetoxy-3(2H)-furanon-5-yl)-methanesulfonamide; N-(2-(3,5-dimethoxyphenyl)-2-methyl-4-acetoxy-3(2H)-furanon-5-yl)-ethanesulfonamide; N-(2-(3,5-dimethoxyphenyl)-2-methyl-4-acetoxy-3(2H)-furanon-5-yl)-benzenesulfonamide; N-(2-(3,5-dimethoxyphenyl)-2-methyl-4-acetoxy-3(2H)-furanon-5-yl)-acetamide; N-(2-(3,5-dimethoxyphenyl)-2-methyl-4-acetoxy-3(2H)-furanon-5-yl)-carbamic acid ethyl ester; N-(2-(3,5-dimethoxyphenyl)-2-methyl-4-acetoxy-3(2H)-furanon-5-yl)-benzamide; N-(2-(3,5-dimethoxyphenyl)-2-methyl-4-acetoxy-3(2H)-furanon-5-yl)-4-bromobutanamide; N-(2-(3,5-dimethoxyphenyl)-2-methyl-4-acetoxy-3(2H)-furanon-5-yl)-2-pyrrolidinone; N-(2-(3,5-dimethoxyphenyl)-2-methyl-4-acetoxy-3(2H)-furanon-5-yl)-succinimide; N-(2-(3,5-dimethoxyphenyl)-2-methyl-4-acetoxy-3(2H)-furanon-5-yl)-3-bromopropylsulfonamide; N-(2-(3,5-dimethoxyphenyl)-2-methyl-4-acetoxy-3(2H)-furanon-5-yl)-1,1-dioxide-isothiazolidine; N-methyl-N'-(2-(3,5-dimethoxyphenyl)-2-methyl-4-acetoxy-3(2H)-furanon-5-yl)-ethanesulfonamide; 2-(2-chloro-6-fluorophenyl)-5-amino-4-hydroxy-3(2H)-furanone; 2-(2-chloro-6-fluorophenyl)-4-(acetoxy)-5-amino-3(2H)-furanone; 2-(2-chloro-6-fluorophenyl)-4-[[phenylsulfonyl]oxy]-5-amino-3(2H)-furanone; N-(3,4-dihydroxy-5-(2-chloro-6-fluorophenyl)-2-furanyl)methanesulfonamide; N-(3,4-dihydroxy-5-(2-chloro-6-fluorophenyl)-2-furanyl)ethanesulfonamide; N-(3,4-dihydroxy-5-(2-chloro-6-fluorophenyl)-2-furanyl)benzenesulfonamide; N-(3,4-dihydroxy-5-(2-chloro-6-fluorophenyl)-2-furanyl)acetamide; N-(3,4-dihydroxy-5-(2-chloro-6-fluorophenyl)-2-furanyl)-carbamic acid ethyl ester; N-(3,4-dihydroxy-5-(2-chloro-6-fluorophenyl)-2-furanyl)benzamide; N-(3-trimethylsilyloxy-4-hydroxy-5-(2-chloro-6-fluorophenyl)-2-furanyl)-4-bromobutanamide; N-(3,4-dihydroxy-5-(2-chloro-6-fluorophenyl)-2-furanyl)-2-pyrrolidinone; N-(3,4-dihydroxy-5-(2-chloro-6-fluorophenyl)-2-furanyl)succinimide; N-(3-trimethylsilyloxy-4-hydroxy-5-(2-chloro-6-fluorophenyl)-2-furanyl)-3-bromopropylsulfonamide; N-(3,4-dihydroxy-5-(2-chloro-6-fluorophenyl)-2-furanyl)-1,1-dioxide-isothiazolidine; N-methyl-N'-(3,4-dihydroxy-5-(2-chloro-6-fluorophenyl)-2-furanyl)ethanesulfonamide; N-(3-acetoxy-4-hydroxy-5-(2-chloro-6-fluorophenyl)-2-furanyl)methanesulfonamide; N-(3-acetoxy-4-hydroxy-5-(2-chloro-6-fluorophenyl)-2-furanyl)ethanesulfonamide; N-(3-acetoxy-4-hydroxy-5-(2-chloro-6-fluorophenyl)-2-furanyl)benzenesulfonamide; N-(3-acetoxy-4-hydroxy-5-(2-chloro-6-fluorophenyl)-2-furanyl)acetamide; N-(3-acetoxy-4-hydroxy-5-(2-chloro-6-fluorophenyl)-2-furanyl)-carbamic acid ethyl ester; N-(3-acetoxy-4-hydroxy-5-(2-chloro-6-fluorophenyl)-2-furanyl)benzamide; N-(3-acetoxy-4-hydroxy-5-(2-chloro-6-fluorophenyl)-2-furanyl)-4-bromobutanamide; N-(3-acetoxy-4-hydroxy-5-(2-chloro-6-fluorophenyl)-2-furanyl)-2-pyrrolidinone; N-(3-acetoxy-4-hydroxy-5-(2-chloro-6-fluorophenyl)-2-furanyl)succinimide; N-(3-acetoxy-4-hydroxy-5-(2-chloro-6-fluorophenyl)-2-furanyl)-3-bromopropylsulfonamide; N-(3-acetoxy-4-hydroxy-5-(2-chloro-6-fluorophenyl)-2-furanyl)-1,1-dioxide-isothiazolidine; N-methyl-N'-(3-acetoxy-4-hydroxy-5-(2-chloro-6-fluorophenyl)-2-furanyl)ethanesulfonamide; 2-(2-chloro-6-fluorophenyl)-2-methyl-4-trimethylsilyloxy-5-amino-3(2H)-furanone; 2-(2-chloro-6-fluorophenyl)-2-methyl-4-hydroxy-5-amino-3(2H)-furanone; N-(2-(2-chloro-6-fluorophenyl)-2-methyl-4-hydroxy-3(2H)-furanon-5-yl)-methanesulfonamide; N-(2-(2-chloro-6-fluorophenyl)-2-methyl-4-hydroxy-3(2H)-furanon-5-yl)-ethanesulfonamide; N-(2-(2-chloro-6-fluorophenyl)-2-methyl-4-hydroxy-3(2H)-furanon-5-yl)-benzenesulfonamide; N-(2-(2-chloro-6-fluorophenyl)-2-methyl-4-hydroxy-3(2H)-furanon-5-yl)-acetamide; N-(2-(2-chloro-6-fluorophenyl)-2-methyl-4-hydroxy-3(2H)-furanon-5-yl)-carbamic acid ethyl ester; N-(2-(2-chloro-6-fluorophenyl)-2-methyl-4-hydroxy-3(2H)-furanon-5-yl)-benzamide; N-(2-(2-chloro-6-fluorophenyl)-2-methyl-4-hydroxy-3(2H)-furanon-5-yl)-4-bromobutanamide; N-(2-(2-chloro-6-fluorophenyl)-2-methyl-4-hydroxy-3(2H)-furanon-5-yl)-2-pyrrolidinone; N-(2-(2-chloro-6-fluorophenyl)-2-methyl-4-hydroxy-3(2H)-furanon-5-yl)-succinimide; N-(2-(2-chloro-6-fluorophenyl)-2-methyl-4-hydroxy-3(2H)-furanon-5-yl)-3-bromopropylsulfonamide; N-(2-(2-chloro-6-fluorophenyl)-2-methyl-4-hydroxy-3(2H)-furanon-5-yl)-1,1-dioxide-isothiazolidine; N-methyl-N'-(2-(2-chloro-6-fluorophenyl)-2-methyl-4-hydroxy-3(2H)-furanon-5-yl)-ethanesulfonamide; 2-(2-chloro-6-fluorophenyl)-2-methyl-4-acetoxy-5-amino-3(2H)-furanone; N-(2-(2-chloro-6-fluorophenyl)-2-methyl-4-acetoxy-3(2H)-furanon-5-yl)-methanesulfonamide; N-(2-(2-chloro-6-fluorophenyl)-2-methyl-4-acetoxy-3(2H)-furanon-5-yl)-ethanesulfonamide; N-(2-(2-chloro-6-fluorophenyl)-2-methyl-4-acetoxy-3(2H)-furanon-5-yl)-benzenesulfonamide; N-(2-(2-chloro-6-fluorophenyl)-2-methyl-4-acetoxy-3(2H)-furanon-5-yl)-acetamide; N-(2-(2-chloro-6-fluorophenyl)-2-methyl-4-acetoxy-3(2H)-furanon-5-yl)-carbamic acid ethyl ester; N-(2-(2-chloro-6-fluorophenyl)-2-methyl-4-acetoxy-3(2H)-furanon-5-yl)-benzamide; N-(2-(2-chloro-6-fluorophenyl)-2-methyl-4-acetoxy-3(2H)-furanon-5-yl)-4-bromobutanamide; N-(2-(2-chloro-6-fluorophenyl)-2-methyl-4-acetoxy-3(2H)-furanon-5-yl)-2-pyrrolidinone; N-(2-(2-chloro-6-fluorophenyl)-2-methyl-4-acetoxy-3(2H)-furanon-5-yl)-succinimide; N-(2-(2-chloro-6-fluorophenyl)-2-methyl-4-acetoxy-3(2H)-furanon-5-yl)-3-bromopropylsulfonamide; N-(2-(2-chloro-6-fluorophenyl)-2-methyl-4-acetoxy-3(2H)-furanon-5-yl)-1,1-dioxide-isothiazolidine; N-methyl-N'-(2-(2-chloro-6-fluorophenyl)-2-methyl-4-acetoxy-3(2H)-furanon-5-yl)-ethanesulfonamide; 2-(3-chloro-4-fluorophenyl)-5-amino-4-hydroxy-3(2H)-furanone; 2-(3-chloro-4-fluorophenyl)-4-(acetoxy)-5-amino-3(2H)-furanone; 2-(3-chloro-4-fluorophenyl)-4-[[phenylsulfonyl]oxy]-5-amino-3(2H)-furanone; N-(3,4-dihydroxy-5-(3-chloro-4-fluorophenyl)-2-furanyl)methanesulfonamide; N-(3,4-dihydroxy-5-(3-chloro-4-fluorophenyl)-2-furanyl)ethanesulfonamide; N-(3,4-dihydroxy-5-(3-chloro-4-fluorophenyl)-2-furanyl)benzenesulfonamide; N-(3,4-dihydroxy-5-(3-chloro-4-fluorophenyl)-2-furanyl)acetamide; N-(3,4-dihydroxy-5-(3-chloro-4-fluorophenyl)-2-furanyl)-carbamic acid ethyl ester; N-(3,4-dihydroxy-5-(3-chloro-4-fluorophenyl)-2-furanyl)

benzamide; N-(3-trimethylsilyloxy-4-hydroxy-5-(3-chloro-4-fluorophenyl)-2-furanyl)-4-bromobutanamide; N-(3,4-dihydroxy-5-(3-chloro-4-fluorophenyl)-2-furanyl)-2-pyrrolidinone; N-(3,4-dihydroxy-5-(3-chloro-4-fluorophenyl)-2-furanyl)succinimide; N-(3-trimethylsilyloxy-4-hydroxy-5-(3-chloro-4-fluorophenyl)-2-furanyl)-3-bromopropylsulfonamide; N-(3,4-dihydroxy-5-(3-chloro-4-fluorophenyl)-2-furanyl)-1,1-dioxide-isothiazolidine; N-methyl-N'-(3,4-dihydroxy-5-(3-chloro-4-fluorophenyl)-2-furanyl)ethanesulfonamide; N-(3-acetoxy-4-hydroxy-5-(3-chloro-4-fluorophenyl)-2-furanyl)methanesulfonamide; N-(3-acetoxy-4-hydroxy-5-(3-chloro-4-fluorophenyl)-2-furanyl)ethanesulfonamide; N-(3-acetoxy-4-hydroxy-5-(3-chloro-4-fluorophenyl)-2-furanyl)benzenesulfonamide; N-(3-acetoxy-4-hydroxy-5-(3-chloro-4-fluorophenyl)-2-furanyl)-acetamide; N-(3-acetoxy-4-hydroxy-5-(3-chloro-4-fluorophenyl)-2-furanyl)-carbamic acid ethyl ester; N-(3-acetoxy-4-hydroxy-5-(3-chloro-4-fluorophenyl)-2-furanyl)benzamide; N-(3-acetoxy-4-hydroxy-5-(3-chloro-4-fluorophenyl)-2-furanyl)-4-bromobutanamide; N-(3-acetoxy-4-hydroxy-5-(3-chloro-4-fluorophenyl)-2-furanyl)-2-pyrrolidinone; N-(3-acetoxy-4-hydroxy-5-(3-chloro-4-fluorophenyl)-2-furanyl)succinimide; N-(3-acetoxy-4-hydroxy-5-(3-chloro-4-fluorophenyl)-2-furanyl)-3-bromopropylsulfonamide; N-(3-acetoxy-4-hydroxy-5-(3-chloro-4-fluorophenyl)-2-furanyl)-1,1-dioxide-isothiazolidine; N-methyl-N'-(3-acetoxy-4-hydroxy-5-(3-chloro-4-fluorophenyl)-2-furanyl)ethanesulfonamide; 2-(3-chloro-4-fluorophenyl)-2-methyl-4-trimethylsilyloxy-5-amino-3(2H)-furanone; 2-(3-chloro-4-fluorophenyl)-2-methyl-4-hydroxy-5-amino-3(2H)-furanone; N-(2-(3-chloro-4-fluorophenyl)-2-methyl-4-hydroxy-3(2H)-furanon-5-yl)-methanesulfonamide; N-(2-(3-chloro-4-fluorophenyl)-2-methyl-4-hydroxy-3(2H)-furanon-5-yl)-ethanesulfonamide; N-(2-(3-chloro-4-fluorophenyl)-2-methyl-4-hydroxy-3(2H)-furanon-5-yl)-benzenesulfonamide; N-(2-(3-chloro-4-fluorophenyl)-2-methyl-4-hydroxy-3(2H)-furanon-5-yl)-acetamide; N-(2-(3-chloro-4-fluorophenyl)-2-methyl-4-hydroxy-3(2H)-furanon-5-yl)-carbamic acid ethyl ester; N-(2-(3-chloro-4-fluorophenyl)-2-methyl-4-hydroxy-3(2H)-furanon-5-yl)-benzamide; N-(2-(3-chloro-4-fluorophenyl)-2-methyl-4-hydroxy-3(2H)-furanon-5-yl)-4-bromobutanamide; N-(2-(3-chloro-4-fluorophenyl)-2-methyl-4-hydroxy-3(2H)-furanon-5-yl)-2-pyrrolidinone; N-(2-(3-chloro-4-fluorophenyl)-2-methyl-4-hydroxy-3(2H)-furanon-5-yl)-succinimide; N-(2-(3-chloro-4-fluorophenyl)-2-methyl-4-hydroxy-3(2H)-furanon-5-yl)-3-bromopropylsulfonamide; N-(2-(3-chloro-4-fluorophenyl)-2-methyl-4-hydroxy-3(2H)-furanon-5-yl)-1,1-dioxide-isothiazolidine; N-methyl-N'-(2-(3-chloro-4-fluorophenyl)-2-methyl-4-hydroxy-3(2H)-furanon-5-yl)-ethanesulfonamide; 2-(3-chloro-4-fluorophenyl)-2-methyl-4-acetoxy-5-amino-3(2H)-furanone; N-(2-(3-chloro-4-fluorophenyl)-2-methyl-4-acetoxy-3(2H)-furanon-5-yl)-methanesulfonamide; N-(2-(3-chloro-4-fluorophenyl)-2-methyl-4-acetoxy-3(2H)-furanon-5-yl)-ethanesulfonamide; N-(2-(3-chloro-4-fluorophenyl)-2-methyl-4-acetoxy-3(2H)-furanon-5-yl)-benzenesulfonamide; N-(2-(3-chloro-4-fluorophenyl)-2-methyl-4-acetoxy-3(2H)-furanon-5-yl)-acetamide; N-(2-(3-chloro-4-fluorophenyl)-2-methyl-4-acetoxy-3(2H)-furanon-5-yl)-carbamic acid ethyl ester; N-(2-(3-chloro-4-fluorophenyl)-2-methyl-4-acetoxy-3(2H)-furanon-5-yl)-benzamide; N-(2-(3-chloro-4-fluorophenyl)-2-methyl-4-acetoxy-3(2H)-furanon-5-yl)-4-bromobutanamide; N-(2-(3-chloro-4-fluorophenyl)-2-methyl-4-acetoxy-3(2H)-furanon-5-yl)-2-pyrrolidinone; N-(2-(3-chloro-4-fluorophenyl)-2-methyl-4-acetoxy-3(2H)-furanon-5-yl)-succinimide; N-(2-(3-chloro-4-fluorophenyl)-2-methyl-4-acetoxy-3(2H)-furanon-5-yl)-3-bromopropylsulfonamide; N-(2-(3-chloro-4-fluorophenyl)-2-methyl-4-acetoxy-3(2H)-furanon-5-yl)-1,1-dioxide-isothiazolidine; N-methyl-N'-(2-(3-chloro-4-fluorophenyl)-2-methyl-4-acetoxy-3(2H)-furanon-5-yl)-ethanesulfonamide; 2-(2-chloro-4-fluorophenyl)-5-amino-4-hydroxy-3(2H)-furanone; 2-(2-chloro-4-fluorophenyl)-4-(acetoxy)-5-amino-3(2H)-furanone; 2-(2-chloro-4-fluorophenyl)-4-[[phenylsulfonyl]oxy]-5-amino-3(2H)-furanone; N-(3,4-dihydroxy-5-(2-chloro-4-fluorophenyl)-2-furanyl)methanesulfonamide; N-(3,4-dihydroxy-5-(2-chloro-4-fluorophenyl)-2-furanyl)ethanesulfonamide; N-(3,4-dihydroxy-5-(2-chloro-4-fluorophenyl)-2-furanyl)benzenesulfonamide; N-(3,4-dihydroxy-5-(2-chloro-4-fluorophenyl)-2-furanyl)acetamide; N-(3,4-dihydroxy-5-(2-chloro-4-fluorophenyl)-2-furanyl)-carbamic acid ethyl ester; N-(3,4-dihydroxy-5-(2-chloro-4-fluorophenyl)-2-furanyl)benzamide; N-(3-trimethylsilyloxy-4-hydroxy-5-(2-chloro-4-fluorophenyl)-2-furanyl)-4-bromobutanamide; N-(3,4-dihydroxy-5-(2-chloro-4-fluorophenyl)-2-furanyl)-2-pyrrolidinone; N-(3,4-dihydroxy-5-(2-chloro-4-fluorophenyl)-2-furanyl)succinimide; N-(3-trimethylsilyloxy-4-hydroxy-5-(2-chloro-4-fluorophenyl)-2-furanyl)-3-bromopropylsulfonamide; N-(3,4-dihydroxy-5-(2-chloro-4-fluorophenyl)-2-furanyl)-1,1-dioxide-isothiazolidine; N-methyl-N'-(3,4-dihydroxy-5-(2-chloro-4-fluorophenyl)-2-furanyl)ethanesulfonamide; N-(3-acetoxy-4-hydroxy-5-(2-chloro-4-fluorophenyl)-2-furanyl)methanesulfonamide; N-(3-acetoxy-4-hydroxy-5-(2-chloro-4-fluorophenyl)-2-furanyl)ethanesulfonamide; N-(3-acetoxy-4-hydroxy-5-(2-chloro-4-fluorophenyl)-2-furanyl)benzenesulfonamide; N-(3-acetoxy-4-hydroxy-5-(2-chloro-4-fluorophenyl)-2-furanyl)-acetamide; N-(3-acetoxy-4-hydroxy-5-(2-chloro-4-fluorophenyl)-2-furanyl)-carbamic acid ethyl ester; N-(3-acetoxy-4-hydroxy-5-(2-chloro-4-fluorophenyl)-2-furanyl)benzamide; N-(3-acetoxy-4-hydroxy-5-(2-chloro-4-fluorophenyl)-2-furanyl)-4-bromobutanamide; N-(3-acetoxy-4-hydroxy-5-(2-chloro-4-fluorophenyl)-2-furanyl)-2-pyrrolidinone; N-(3-acetoxy-4-hydroxy-5-(2-chloro-4-fluorophenyl)-2-furanyl)succinimide; N-(3-acetoxy-4-hydroxy-5-(2-chloro-4-fluorophenyl)-2-furanyl)-3-bromopropylsulfonamide; N-(3-acetoxy-4-hydroxy-5-(2-chloro-4-fluorophenyl)-2-furanyl)-1,1-dioxide-isothiazolidine; N-methyl-N'-(3-acetoxy-4-hydroxy-5-(2-chloro-4-fluorophenyl)-2-furanyl)ethanesulfonamide; 2-(2-chloro-4-fluorophenyl)-2-methyl-4-trimethylsilyloxy-5-amino-3(2H)-furanone; 2-(2-chloro-4-fluorophenyl)-2-methyl-4-hydroxy-5-amino-3(2H)-furanone; N-(2-(2-chloro-4-fluorophenyl)-2-methyl-4-hydroxy-3(2H)-furanon-5-yl)-methanesulfonamide; N-(2-(2-chloro-4-fluorophenyl)-2-methyl-4-hydroxy-3(2H)-furanon-5-yl)-ethanesulfonamide; N-(2-(2-chloro-4-fluorophenyl)-2-methyl-4-hydroxy-3(2H)-furanon-5-yl)-benzenesulfonamide; N-(2-(2-chloro-4-fluorophenyl)-2-methyl-4-hydroxy-3(2H)-furanon-5-yl)-acetamide; N-(2-(2-chloro-4-fluorophenyl)-2-methyl-4-hydroxy-3(2H)-furanon-5-yl)-carbamic acid ethyl ester; N-(2-(2-chloro-4-fluorophenyl)-2-methyl-4-hydroxy-3(2H)-furanon-5-yl)-benzamide; N-(2-(2-chloro-4-fluorophenyl)-2-methyl-4-hydroxy-3(2H)-furanon-5-yl)-4-bromobutanamide; N-(2-(2-chloro-4-fluorophenyl)-2-methyl-4-hydroxy-3(2H)-furanon-5-yl)-2-pyrrolidinone; N-(2-(2-chloro-4-fluorophenyl)-2-methyl-4-hydroxy-3(2H)-furanon-5-yl)-succinimide; N-(2-(2-chloro-4-fluorophenyl)-2-methyl-4-hydroxy-3(2H)-furanon-5-yl)-3-bromopropylsulfonamide; N-(2-(2-chloro-4-fluorophenyl)-2-methyl-4-hydroxy-3

(2H)-furanon-5-yl)-1,1-dioxide-isothiazolidine; N-methyl-N'-(2-(2-chloro-4-fluorophenyl)-2-methyl-4-hydroxy-3(2H)-furanon-5-yl)-ethanesulfonamide; 2-(2-chloro-4-fluorophenyl)-2-methyl-4-acetoxy-5-amino-3(2H)-furanone; N-(2-(2-chloro-4-fluorophenyl)-2-methyl-4-acetoxy-3(2H)-furanon-5-yl)-methanesulfonamide; N-(2-(2-chloro-4-fluorophenyl)-2-methyl-4-acetoxy-3(2H)-furanon-5-yl)-ethanesulfonamide; N-(2-(2-chloro-4-fluorophenyl)-2-methyl-4-acetoxy-3(2H)-furanon-5-yl)-benzenesulfonamide; N-(2-(2-chloro-4-fluorophenyl)-2-methyl-4-acetoxy-3(2H)-furanon-5-yl)-acetamide; N-(2-(2-chloro-4-fluorophenyl)-2-methyl-4-acetoxy-3(2H)-furanon-5-yl)-carbamic acid ethyl ester; N-(2-(2-chloro-4-fluorophenyl)-2-methyl-4-acetoxy-3(2H)-furanon-5-yl)-benzamide; N-(2-(2-chloro-4-fluorophenyl)-2-methyl-4-acetoxy-3(2H)-furanon-5-yl)-4-bromobutanamide; N-(2-(2-chloro-4-fluorophenyl)-2-methyl-4-acetoxy-3(2H)-furanon-5-yl)-2-pyrrolidinone; N-(2-(2-chloro-4-fluorophenyl)-2-methyl-4-acetoxy-3(2H)-furanon-5-yl)-succinimide; N-(2-(2-chloro-4-fluorophenyl)-2-methyl-4-acetoxy-3(2H)-furanon-5-yl)-3-bromopropylsulfonamide; N-(2-(2-chloro-4-fluorophenyl)-2-methyl-4-acetoxy-3(2H)-furanon-5-yl)-1,1-dioxide-isothiazolidine; N-methyl-N'-(2-(2-chloro-4-fluorophenyl)-2-methyl-4-acetoxy-3(2H)-furanon-5-yl)-ethanesulfonamide; 2-(4-chloro-3-fluorophenyl)-5-amino-4-hydroxy-3(2H)-furanone; 2-(4-chloro-3-fluorophenyl)-4-(acetoxy)-5-amino-3(2H)-furanone; 2-(4-chloro-3-fluorophenyl)-4-[[phenylsulfonyl]oxy]-5-amino-3(2H)-furanone; N-(3,4-dihydroxy-5-(4-chloro-3-fluorophenyl)-2-furanyl)methanesulfonamide; N-(3,4-dihydroxy-5-(4-chloro-3-fluorophenyl)-2-furanyl)ethanesulfonamide; N-(3,4-dihydroxy-5-(4-chloro-3-fluorophenyl)-2-furanyl)benzenesulfonamide; N-(3,4-dihydroxy-5-(4-chloro-3-fluorophenyl)-2-furanyl)acetamide; N-(3,4-dihydroxy-5-(4-chloro-3-fluorophenyl)-2-furanyl)-carbamic acid ethyl ester; N-(3,4-dihydroxy-5-(4-chloro-3-fluorophenyl)-2-furanyl)benzamide; N-(3-trimethylsilyloxy-4-hydroxy-5-(4-chloro-3-fluorophenyl)-2-furanyl)-4-bromobutanamide; N-(3,4-dihydroxy-5-(4-chloro-3-fluorophenyl)-2-furanyl)-2-pyrrolidinone; N-(3,4-dihydroxy-5-(4-chloro-3-fluorophenyl)-2-furanyl)succinimide; N-(3-trimethylsilyloxy-4-hydroxy-5-(4-chloro-3-fluorophenyl)-2-furanyl)-3-bromopropylsulfonamide; N-(3,4-dihydroxy-5-(4-chloro-3-fluorophenyl)-2-furanyl)-1,1-dioxide-isothiazolidine; N-methyl-N'-(3,4-dihydroxy-5-(4-chloro-3-fluorophenyl)-2-furanyl)ethanesulfonamide; N-(3-acetoxy-4-hydroxy-5-(4-chloro-3-fluorophenyl)-2-furanyl)methanesulfonamide; N-(3-acetoxy-4-hydroxy-5-(4-chloro-3-fluorophenyl)-2-furanyl)ethanesulfonamide; N-(3-acetoxy-4-hydroxy-5-(4-chloro-3-fluorophenyl)-2-furanyl)benzenesulfonamide; N-(3-acetoxy-4-hydroxy-5-(4-chloro-3-fluorophenyl)-2-furanyl)-acetamide; N-(3-acetoxy-4-hydroxy-5-(4-chloro-3-fluorophenyl)-2-furanyl)-carbamic acid ethyl ester; N-(3-acetoxy-4-hydroxy-5-(4-chloro-3-fluorophenyl)-2-furanyl)benzamide; N-(3-acetoxy-4-hydroxy-5-(4-chloro-3-fluorophenyl)-2-furanyl)-4-bromobutanamide; N-(3-acetoxy-4-hydroxy-5-(4-chloro-3-fluorophenyl)-2-furanyl)-2-pyrrolidinone; N-(3-acetoxy-4-hydroxy-5-(4-chloro-3-fluorophenyl)-2-furanyl)succinimide; N-(3-acetoxy-4-hydroxy-5-(4-chloro-3-fluorophenyl)-2-furanyl)-3-bromopropylsulfonamide; N-(3-acetoxy-4-hydroxy-5-(4-chloro-3-fluorophenyl)-2-furanyl)-1,1-dioxide-isothiazolidine; N-methyl-N'-(3-acetoxy-4-hydroxy-5-(4-chloro-3-fluorophenyl)-2-furanyl)ethanesulfonamide; 2-(4-chloro-3-fluorophenyl)-2-methyl-4-trimethylsilyloxy-5-amino-3(2H)-furanone; 2-(4-chloro-3-fluorophenyl)-2-methyl-4-hydroxy-5-amino-3(2H)-furanone; N-(2-(4-chloro-3-fluorophenyl)-2-methyl-4-hydroxy-3(2H)-furanon-5-yl)-methanesulfonamide; N-(2-(4-chloro-3-fluorophenyl)-2-methyl-4-hydroxy-3(2H)-furanon-5-yl)-ethanesulfonamide; N-(2-(4-chloro-3-fluorophenyl)-2-methyl-4-hydroxy-3(2H)-furanon-5-yl)-benzenesulfonamide; N-(2-(4-chloro-3-fluorophenyl)-2-methyl-4-hydroxy-3(2H)-furanon-5-yl)-acetamide; N-(2-(4-chloro-3-fluorophenyl)-2-methyl-4-hydroxy-3(2H)-furanon-5-yl)-carbamic acid ethyl ester; N-(2-(4-chloro-3-fluorophenyl)-2-methyl-4-hydroxy-3(2H)-furanon-5-yl)-benzamide; N-(2-(4-chloro-3-fluorophenyl)-2-methyl-4-hydroxy-3(2H)-furanon-5-yl)-4-bromobutanamide; N-(2-(4-chloro-3-fluorophenyl)-2-methyl-4-hydroxy-3(2H)-furanon-5-yl)-2-pyrrolidinone; N-(2-(4-chloro-3-fluorophenyl)-2-methyl-4-hydroxy-3(2H)-furanon-5-yl)-succinimide; N-(2-(4-chloro-3-fluorophenyl)-2-methyl-4-hydroxy-3(2H)-furanon-5-yl)-3-bromopropylsulfonamide; N-(2-(4-chloro-3-fluorophenyl)-2-methyl-4-hydroxy-3(2H)-furanon-5-yl)-1,1-dioxide-isothiazolidine; N-methyl-N'-(2-(4-chloro-3-fluorophenyl)-2-methyl-4-hydroxy-3(2H)-furanon-5-yl)-ethanesulfonamide; 2-(4-chloro-3-fluorophenyl)-2-methyl-4-acetoxy-5-amino-3(2H)-furanone; N-(2-(4-chloro-3-fluorophenyl)-2-methyl-4-acetoxy-3(2H)-furanon-5-yl)-methanesulfonamide; N-(2-(4-chloro-3-fluorophenyl)-2-methyl-4-acetoxy-3(2H)-furanon-5-yl)-ethanesulfonamide; N-(2-(4-chloro-3-fluorophenyl)-2-methyl-4-acetoxy-3(2H)-furanon-5-yl)-benzenesulfonamide; N-(2-(4-chloro-3-fluorophenyl)-2-methyl-4-acetoxy-3(2H)-furanon-5-yl)-acetamide; N-(2-(4-chloro-3-fluorophenyl)-2-methyl-4-acetoxy-3(2H)-furanon-5-yl)-carbamic acid ethyl ester; N-(2-(4-chloro-3-fluorophenyl)-2-methyl-4-acetoxy-3(2H)-furanon-5-yl)-benzamide; N-(2-(4-chloro-3-fluorophenyl)-2-methyl-4-acetoxy-3(2H)-furanon-5-yl)-4-bromobutanamide; N-(2-(4-chloro-3-fluorophenyl)-2-methyl-4-acetoxy-3(2H)-furanon-5-yl)-2-pyrrolidinone; N-(2-(4-chloro-3-fluorophenyl)-2-methyl-4-acetoxy-3(2H)-furanon-5-yl)-succinimide; N-(2-(4-chloro-3-fluorophenyl)-2-methyl-4-acetoxy-3(2H)-furanon-5-yl)-3-bromopropylsulfonamide; N-(2-(4-chloro-3-fluorophenyl)-2-methyl-4-acetoxy-3(2H)-furanon-5-yl)-1,1-dioxide-isothiazolidine; N-methyl-N'-(2-(4-chloro-3-fluorophenyl)-2-methyl-4-acetoxy-3(2H)-furanon-5-yl)-ethanesulfonamide; 2-(3-chloro-2-fluorophenyl)-5-amino-4-hydroxy-3(2H)-furanone; 2-(3-chloro-2-fluorophenyl)-4-(acetoxy)-5-amino-3(2H)-furanone; 2-(3-chloro-2-fluorophenyl)-4-[[phenylsulfonyl]oxy]-5-amino-3(2H)-furanone; N-(3,4-dihydroxy-5-(3-chloro-2-fluorophenyl)-2-furanyl)methanesulfonamide; N-(3,4-dihydroxy-5-(3-chloro-2-fluorophenyl)-2-furanyl)ethanesulfonamide; N-(3,4-dihydroxy-5-(3-chloro-2-fluorophenyl)-2-furanyl)benzenesulfonamide; N-(3,4-dihydroxy-5-(3-chloro-2-fluorophenyl)-2-furanyl)acetamide; N-(3,4-dihydroxy-5-(3-chloro-2-fluorophenyl)-2-furanyl)-carbamic acid ethyl ester; N-(3,4-dihydroxy-5-(3-chloro-2-fluorophenyl)-2-furanyl)benzamide; N-(3-trimethylsilyloxy-4-hydroxy-5-(3-chloro-2-fluorophenyl)-2-furanyl)-4-bromobutanamide; N-(3,4-dihydroxy-5-(3-chloro-2-fluorophenyl)-2-furanyl)-2-pyrrolidinone; N-(3,4-dihydroxy-5-(3-chloro-2-fluorophenyl)-2-furanyl)succinimide; N-(3-trimethylsilyloxy-4-hydroxy-5-(3-chloro-2-fluorophenyl)-2-furanyl)-3-bromopropylsulfonamide; N-(3,4-dihydroxy-5-(3-chloro-2-fluorophenyl)-2-furanyl)-1,1-dioxide-isothiazolidine; N-methyl-N'-(3,4-dihydroxy-5-(3-chloro-2-fluorophenyl)-2-furanyl)ethanesulfonamide; N-(3-acetoxy-4-hydroxy-5-(3-chloro-2-fluorophenyl)-2-furanyl)methanesulfonamide; N-(3-acetoxy-4-hydroxy-5-(3-chloro-2-fluorophenyl)-2-furanyl)ethanesulfonamide; N-(3- acetoxy-4-hydroxy-5-(3-chloro-2-fluorophenyl)-2-furanyl)benzenesulfonamide; N-(3-acetoxy-4-hydroxy-5-(3-chloro-2-fluorophenyl)-2-furanyl)-acetamide; N-(3-acetoxy-4-hydroxy-5-(3-chloro-2-fluorophenyl)-2-furanyl)-carbamic acid ethyl ester; N-(3-acetoxy-4-hydroxy-5-(3-chloro-2-fluorophenyl)-2-furanyl)benzamide; N-(3-acetoxy-4-hydroxy-5-(3-chloro-2-fluorophenyl)-2-furanyl)-4-bromobutanamide; N-(3-acetoxy-4-hydroxy-5-(3-chloro-2-fluorophenyl)-2-furanyl)-2-pyrrolidinone; N-(3-acetoxy-4-hydroxy-5-(3-chloro-2-fluorophenyl)-2-furanyl)succinimide; N-(3-acetoxy-4-hydroxy-5-(3-chloro-2-fluorophenyl)-2-furanyl)-3-bromopropylsulfonamide; N-(3-acetoxy-4-hydroxy-5-(3-chloro-2-fluorophenyl)-2-furanyl)-1,1-dioxide-isothiazolidine; N-methyl-N'-(3-acetoxy-4-hydroxy-5-(3-chloro-2-fluorophenyl)-2-furanyl)ethanesulfonamide; 2-(3-chloro-2-fluorophenyl)-2-methyl-4-trimethylsilyloxy-5-amino-3(2H)-furanone; 2-(3-chloro-2-fluorophenyl)-2-methyl-4-hydroxy-5-amino-3(2H)-furanone; N-(2-(3-chloro-2-fluorophenyl)-2-methyl-4-hydroxy-3(2H)-furanon-5-yl)-methanesulfonamide; N-(2-(3-chloro-2-fluorophenyl)-2-methyl-4-hydroxy-3(2H)-furanon-5-yl)-ethanesulfonamide; N-(2-(3-chloro-2-fluorophenyl)-2-methyl-4-hydroxy-3(2H)-furanon-5-yl)-benzenesulfonamide; N-(2-(3-chloro-2-fluorophenyl)-2-methyl-4-hydroxy-3(2H)-furanon-5-yl)-acetamide; N-(2-(3-chloro-2-fluorophenyl)-2-methyl-4-hydroxy-3(2H)-furanon-5-yl)-carbamic acid ethyl ester; N-(2-(3-chloro-2-fluorophenyl)-2-methyl-4-hydroxy-3(2H)-furanon-5-yl)-benzamide; N-(2-(3-chloro-2-fluorophenyl)-2-methyl-4-hydroxy-3(2H)-furanon-5-yl)-4-bromobutanamide; N-(2-(3-chloro-2-fluorophenyl)-2-methyl-4-hydroxy-3(2H)-furanon-5-yl)-2-pyrrolidinone; N-(2-(3-chloro-2-fluorophenyl)-2-methyl-4-hydroxy-3(2H)-furanon-5-yl)-succinimide; N-(2-(3-chloro-2-fluorophenyl)-2-methyl-4-hydroxy-3(2H)-furanon-5-yl)-3-bromopropylsulfonamide; N-(2-(3-chloro-2-fluorophenyl)-2-methyl-4-hydroxy-3(2H)-furanon-5-yl)-1,1-dioxide-isothiazolidine; N-methyl-N'-(2-(3-chloro-2-fluorophenyl)-2-methyl-4-hydroxy-3(2H)-furanon-5-yl)-ethanesulfonamide; 2-(3-chloro-2-fluorophenyl)-2-methyl-4-acetoxy-5-amino-3(2H)-furanone; N-(2-(3-chloro-2-fluorophenyl)-2-methyl-4-acetoxy-3(2H)-furanon-5-yl)-methanesulfonamide; N-(2-(3-chloro-2-fluorophenyl)-2-methyl-4-acetoxy-3(2H)-furanon-5-yl)-ethanesulfonamide; N-(2-(3-chloro-2-fluorophenyl)-2-methyl-4-acetoxy-3(2H)-furanon-5-yl)-benzenesulfonamide; N-(2-(3-chloro-2-fluorophenyl)-2-methyl-4-acetoxy-3(2H)-furanon-5-yl)-acetamide; N-(2-(3-chloro-2-fluorophenyl)-2-methyl-4-acetoxy-3(2H)-furanon-5-yl)-carbamic acid ethyl ester; N-(2-(3-chloro-2-fluorophenyl)-2-methyl-4-acetoxy-3(2H)-furanon-5-yl)-benzamide; N-(2-(3-chloro-2-fluorophenyl)-2-methyl-4-acetoxy-3(2H)-furanon-5-yl)-4-bromobutanamide; N-(2-(3-chloro-2-fluorophenyl)-2-methyl-4-acetoxy-3(2H)-furanon-5-yl)-2-pyrrolidinone; N-(2-(3-chloro-2-fluorophenyl)-2-methyl-4-acetoxy-3(2H)-furanon-5-yl)-succinimide; N-(2-(3-chloro-2-fluorophenyl)-2-methyl-4-acetoxy-3(2H)-furanon-5-yl)-3-bromopropylsulfonamide; N-(2-(3-chloro-2-fluorophenyl)-2-methyl-4-acetoxy-3(2H)-furanon-5-yl)-1,1-dioxide-isothiazolidine; N-methyl-N'-(2-(3-chloro-2-fluorophenyl)-2-methyl-4-acetoxy-3(2H)-furanon-5-yl)-ethanesulfonamide; 2-(2-chloro-5-fluorophenyl)-5-amino-4-hydroxy-3(2H)-furanone; 2-(2-chloro-5-fluorophenyl)-4-(acetoxy)-5-amino-3(2H)-furanone; 2-(2-chloro-5-fluorophenyl)-4-[[phenylsulfonyl]oxy]-5-amino-3(2H)-furanone; N-(3,4-dihydroxy-5-(2-chloro-5-fluorophenyl)-2-furanyl)methanesulfonamide; N-(3,4-dihydroxy-5-(2-chloro-5-fluorophenyl)-2-furanyl)ethanesulfonamide; N-(3,4-dihydroxy-5-(2-chloro-5-fluorophenyl)-2-furanyl)benzenesulfonamide; N-(3,4-dihydroxy-5-(2-chloro-5-fluorophenyl)-2-furanyl)acetamide; N-(3,4-dihydroxy-5-(2-chloro-5-fluorophenyl)-2-furanyl)-carbamic acid ethyl ester; N-(3,4-dihydroxy-5-(2-chloro-5-fluorophenyl)-2-furanyl)benzamide; N-(3-trimethylsilyloxy-4-hydroxy-5-(2-chloro-5-fluorophenyl)-2-furanyl)-4-bromobutanamide; N-(3,4-dihydroxy-5-(2-chloro-5-fluorophenyl)-2-furanyl)-2-pyrrolidinone; N-(3,4-dihydroxy-5-(2-chloro-5-fluorophenyl)-2-furanyl)succinimide; N-(3-trimethylsilyloxy-4-hydroxy-5-(2-chloro-5-fluorophenyl)-2-furanyl)-3-bromopropylsulfonamide; N-(3,4-dihydroxy-5-(2-chloro-5-fluorophenyl)-2-furanyl)-1,1-dioxide-isothiazolidine; N-methyl-N'-(3,4-dihydroxy-5-(2-chloro-5-fluorophenyl)-2-furanyl)ethanesulfonamide; N-(3-acetoxy-4-hydroxy-5-(2-chloro-5-fluorophenyl)-2-furanyl)methanesulfonamide; N-(3-acetoxy-4-hydroxy-5-(2-chloro-5-fluorophenyl)-2-furanyl)ethanesulfonamide; N-(3-acetoxy-4-hydroxy-5-(2-chloro-5-fluorophenyl)-2-furanyl)benzenesulfonamide; N-(3-acetoxy-4-hydroxy-5-(2-chloro-5-fluorophenyl)-2-furanyl)-acetamide; N-(3-acetoxy-4-hydroxy-5-(2-chloro-5-fluorophenyl)-2-furanyl)-carbamic acid ethyl ester; N-(3-acetoxy-4-hydroxy-5-(2-chloro-5-fluorophenyl)-2-furanyl)benzamide; N-(3-acetoxy-4-hydroxy-5-(2-chloro-5-fluorophenyl)-2-furanyl)-4-bromobutanamide; N-(3-acetoxy-4-hydroxy-5-(2-chloro-5-fluorophenyl)-2-furanyl)-2-pyrrolidinone; N-(3-acetoxy-4-hydroxy-5-(2-chloro-5-fluorophenyl)-2-furanyl)succinimide; N-(3-acetoxy-4-hydroxy-5-(2-chloro-5-fluorophenyl)-2-furanyl)-3-bromopropylsulfonamide; N-(3-acetoxy-4-hydroxy-5-(2-chloro-5-fluorophenyl)-2-furanyl)-1,1-dioxide-isothiazolidine; N-methyl-N'-(3-acetoxy-4-hydroxy-5-(2-chloro-5-fluorophenyl)-2-furanyl)ethanesulfonamide; 2-(2-chloro-5-fluorophenyl)-2-methyl-4-trimethylsilyloxy-5-amino-3(2H)-furanone; 2-(2-chloro-5-fluorophenyl)-2-methyl-4-hydroxy-5-amino-3(2H)-furanone; N-(2-(2-chloro-5-fluorophenyl)-2-methyl-4-hydroxy-3(2H)-furanon-5-yl)-methanesulfonamide; N-(2-(2-chloro-5-fluorophenyl)-2-methyl-4-hydroxy-3(2H)-furanon-5-yl)-ethanesulfonamide; N-(2-(2-chloro-5-fluorophenyl)-2-methyl-4-hydroxy-3(2H)-furanon-5-yl)-benzenesulfonamide; N-(2-(2-chloro-5-fluorophenyl)-2-methyl-4-hydroxy-3(2H)-furanon-5-yl)-acetamide; N-(2-(2-chloro-5-fluorophenyl)-2-methyl-4-hydroxy-3(2H)-furanon-5-yl)-carbamic acid ethyl ester; N-(2-(2-chloro-5-fluorophenyl)-2-methyl-4-hydroxy-3(2H)-furanon-5-yl)-benzamide; N-(2-(2-chloro-5-fluorophenyl)-2-methyl-4-hydroxy-3(2H)-furanon-5-yl)-4-bromobutanamide; N-(2-(2-chloro-5-fluorophenyl)-2-methyl-4-hydroxy-3(2H)-furanon-5-yl)-2-pyrrolidinone; N-(2-(2-chloro-5-fluorophenyl)-2-methyl-4-hydroxy-3(2H)-furanon-5-yl)-succinimide; N-(2-(2-chloro-5-fluorophenyl)-2-methyl-4-hydroxy-3(2H)-furanon-5-yl)-3-bromopropylsulfonamide; N-(2-(2-chloro-5-fluorophenyl)-2-methyl-4-hydroxy-3(2H)-furanon-5-yl)-1,1-dioxide-isothiazolidine; N-methyl-N'-(2-(2-chloro-5-fluorophenyl)-2-methyl-4-hydroxy-3(2H)-furanon-5-yl)-ethanesulfonamide; 2-(2-chloro-5-fluorophenyl)-2-methyl-4-acetoxy-5-amino-3(2H)-furanone; N-(2-(2-chloro-5-fluorophenyl)-2-methyl-4-acetoxy-3(2H)-furanon-5-yl)-methanesulfonamide; N-(2-(2-chloro-5-fluorophenyl)-2-methyl-4-acetoxy-3(2H)-furanon-5-yl)-ethanesulfonamide; N-(2-(2-chloro-5-fluorophenyl)-2-methyl-4-acetoxy-3(2H)-furanon-5-yl)-benzenesulfonamide; N-(2-(2-chloro-5-fluorophenyl)-2-methyl-4-acetoxy-3(2H)-furanon-5-yl)-acetamide; N-(2-(2-chloro-5-fluorophenyl)-2-methyl-4-acetoxy-3(2H)-furanon-5-yl)-carbamic acid ethyl ester; N-(2-(2-chloro-5- fluorophenyl)-2-methyl-4-acetoxy-3(2H)-furanon-5-yl)-benzamide; N-(2-(2-chloro-5-fluorophenyl)-2-methyl-4-acetoxy-3(2H)-furanon-5-yl)-4-bromobutanamide; N-(2-(2-chloro-5-fluorophenyl)-2-methyl-4-acetoxy-3(2H)-furanon-5-yl)-2-pyrrolidinone; N-(2-(2-chloro-5-fluorophenyl)-2-methyl-4-acetoxy-3(2H)-furanon-5-yl)-succinimide; N-(2-(2-chloro-5-fluorophenyl)-2-methyl-4-acetoxy-3(2H)-furanon-5-yl)-3-bromopropylsulfonamide; N-(2-(2-chloro-5-fluorophenyl)-2-methyl-4-acetoxy-3(2H)-furanon-5-yl)-1,1-dioxide-isothiazolidine; N-methyl-N'-(2-(2-chloro-5-fluorophenyl)-2-methyl-4-acetoxy-3(2H)-furanon-5-yl)-ethanesulfonamide; 2-(4-chloro-2-fluorophenyl)-5-amino-4-hydroxy-3(2H)-furanone; 2-(4-chloro-2-fluorophenyl)-4-(acetoxy)-5-amino-3(2H)-furanone; 2-(4-chloro-2-fluorophenyl)-4-[[phenylsulfonyl]oxy]-5-amino-3(2H)-furanone; N-(3,4-dihydroxy-5-(4-chloro-2-fluorophenyl)-2-furanyl)methanesulfonamide; N-(3,4-dihydroxy-5-(4-chloro-2-fluorophenyl)-2-furanyl)ethanesulfonamide; N-(3,4-dihydroxy-5-(4-chloro-2-fluorophenyl)-2-furanyl)benzenesulfonamide; N-(3,4-dihydroxy-5-(4-chloro-2-fluorophenyl)-2-furanyl)acetamide; N-(3,4-dihydroxy-5-(4-chloro-2-fluorophenyl)-2-furanyl)-carbamic acid ethyl ester; N-(3,4-dihydroxy-5-(4-chloro-2-fluorophenyl)-2-furanyl)benzamide; N-(3-trimethylsilyloxy-4-hydroxy-5-(4-chloro-2-fluorophenyl)-2-furanyl)-4-bromobutanamide; N-(3,4-dihydroxy-5-(4-chloro-2-fluorophenyl)-2-furanyl))-2-pyrrolidinone; N-(3,4-dihydroxy-5-(4-chloro-2-fluorophenyl)-2-furanyl)succinimide; N-(3-trimethylsilyloxy-4-hydroxy-5-(4-chloro-2-fluorophenyl)-2-furanyl)-3-bromopropylsulfonamide; N-(3,4-dihydroxy-5-(4-chloro-2-fluorophenyl)-2-furanyl)-1,1-dioxide-isothiazolidine; N-methyl-N'-(3,4-dihydroxy-5-(4-chloro-2-fluorophenyl)-2-furanyl)ethanesulfonamide; N-(3-acetoxy-4-hydroxy-5-(4-chloro-2-fluorophenyl)-2-furanyl)methanesulfonamide; N-(3-acetoxy-4-hydroxy-5-(4-chloro-2-fluorophenyl)-2-furanyl)ethanesulfonamide; N-(3-acetoxy-4-hydroxy-5-(4-chloro-2-fluorophenyl)-2-furanyl)benzenesulfonamide; N-(3-acetoxy-4-hydroxy-5-(4-chloro-2-fluorophenyl)-2-furanyl)-acetamide; N-(3-acetoxy-4-hydroxy-5-(4-chloro-2-fluorophenyl)-2-furanyl)-carbamic acid ethyl ester; N-(3-acetoxy-4-hydroxy-5-(4-chloro-2-fluorophenyl)-2-furanyl)benzamide; N-(3-acetoxy-4-hydroxy-5-(4-chloro-2-fluorophenyl)-2-furanyl)-4-bromobutanamide; N-(3-acetoxy-4-hydroxy-5-(4-chloro-2-fluorophenyl)-2-furanyl)-2-pyrrolidinone; N-(3-acetoxy-4-hydroxy-5-(4-chloro-2-fluorophenyl)-2-furanyl)succinimide; N-(3-acetoxy-4-hydroxy-5-(4-chloro-2-fluorophenyl)-2-furanyl)-3-bromopropylsulfonamide; N-(3-acetoxy-4-hydroxy-5-(4-chloro-2-fluorophenyl)-2-furanyl)-1,1-dioxide-isothiazolidine; N-methyl-N'-(3-acetoxy-4-hydroxy-5-(4-chloro-2-fluorophenyl)-2-furanyl)ethanesulfonamide; 2-(4-chloro-2-fluorophenyl)-2-methyl-4-trimethylsilyloxy-5-amino-3(2H)-furanone; 2-(4-chloro-2-fluorophenyl)-2-methyl-4-hydroxy-5-amino-3(2H)-furanone; N-(2-(4-chloro-2-fluorophenyl)-2-methyl-4-hydroxy-3(2H)-furanon-5-yl)-methanesulfonamide; N-(2-(4-chloro-2-fluorophenyl)-2-methyl-4-hydroxy-3(2H)-furanon-5-yl)-ethanesulfonamide; N-(2-(4-chloro-2-fluorophenyl)-2-methyl-4-hydroxy-3(2H)-furanon-5-yl)-benzenesulfonamide; N-(2-(4-chloro-2-fluorophenyl)-2-methyl-4-hydroxy-3(2H)-furanon-5-yl)-acetamide; N-(2-(4-chloro-2-fluorophenyl)-2-methyl-4-hydroxy-3(2H)-furanon-5-yl)-carbamic acid ethyl ester; N-(2-(4-chloro-2-fluorophenyl)-2-methyl-4-hydroxy-3(2H)-furanon-5-yl)-benzamide; N-(2-(4-chloro-2-fluorophenyl)-2-methyl-4-hydroxy-3(2H)-furanon-5-yl)-4-bromobutanamide; N-(2-(4-chloro-2-fluorophenyl)-2-methyl-4-hydroxy-3(2H)-furanon-5-yl)-2-pyrrolidinone; N-(2-(4-chloro-2-fluorophenyl)-2-methyl-4-hydroxy-3(2H)-furanon-5-yl)-succinimide; N-(2-(4-chloro-2-fluorophenyl)-2-methyl-4-hydroxy-3(2H)-furanon-5-yl)-3-bromopropylsulfonamide; N-(2-(4-chloro-2-fluorophenyl)-2-methyl-4-hydroxy-3(2H)-furanon-5-yl)-1,1-dioxide-isothiazolidine; N-methyl-N'-(2-(4-chloro-2-fluorophenyl)-2-methyl-4-hydroxy-3(2H)-furanon-5-yl)-ethanesulfonamide; 2-(4-chloro-2-fluorophenyl)-2-methyl-4-acetoxy-5-amino-3(2H)-furanone; N-(2-(4-chloro-2-fluorophenyl)-2-methyl-4-acetoxy-3(2H)-furanon-5-yl)-methanesulfonamide; N-(2-(4-chloro-2-fluorophenyl)-2-methyl-4-acetoxy-3(2H)-furanon-5-yl)-ethanesulfonamide; N-(2-(4-chloro-2-fluorophenyl)-2-methyl-4-acetoxy-3(2H)-furanon-5-yl)-benzenesulfonamide; N-(2-(4-chloro-2-fluorophenyl)-2-methyl-4-acetoxy-3(2H)-furanon-5-yl)-acetamide; N-(2-(4-chloro-2-fluorophenyl)-2-methyl-4-acetoxy-3(2H)-furanon-5-yl)-carbamic acid ethyl ester; N-(2-(4-chloro-2-fluorophenyl)-2-methyl-4-acetoxy-3(2H)-furanon-5-yl)-benzamide; N-(2-(4-chloro-2-fluorophenyl)-2-methyl-4-acetoxy-3(2H)-furanon-5-yl)-4-bromobutanamide; N-(2-(4-chloro-2-fluorophenyl)-2-methyl-4-acetoxy-3(2H)-furanon-5-yl)-2-pyrrolidinone; N-(2-(4-chloro-2-fluorophenyl)-2-methyl-4-acetoxy-3(2H)-furanon-5-yl)-succinimide; N-(2-(4-chloro-2-fluorophenyl)-2-methyl-4-acetoxy-3(2H)-furanon-5-yl)-3-bromopropylsulfonamide; N-(2-(4-chloro-2-fluorophenyl)-2-methyl-4-acetoxy-3(2H)-furanon-5-yl)-1,1-dioxide-isothiazolidine; N-methyl-N'-(2-(4-chloro-2-fluorophenyl)-2-methyl-4-acetoxy-3(2H)-furanon-5-yl)-ethanesulfonamide; 2-(5-chloro-2-fluorophenyl)-5-amino-4-hydroxy-3(2H)-furanone; 2-(5-chloro-2-fluorophenyl)-4-(acetoxy)-5-amino-3(2H)-furanone; 2-(5-chloro-2-fluorophenyl)-4-[[phenylsulfonyl]oxy]-5-amino-3(2H)-furanone; N-(3,4-dihydroxy-5-(5-chloro-2-fluorophenyl)-2-furanyl)methanesulfonamide; N-(3,4-dihydroxy-5-(5-chloro-2-fluorophenyl)-2-furanyl)ethanesulfonamide; N-(3,4-dihydroxy-5-(5-chloro-2-fluorophenyl)-2-furanyl)benzenesulfonamide; N-(3,4-dihydroxy-5-(5-chloro-2-fluorophenyl)-2-furanyl)acetamide; N-(3,4-dihydroxy-5-(5-chloro-2-fluorophenyl)-2-furanyl)-carbamic acid ethyl ester; N-(3,4-dihydroxy-5-(5-chloro-2-fluorophenyl)-2-furanyl)benzamide; N-(3-trimethylsilyloxy-4-hydroxy-5-(5-chloro-2-fluorophenyl)-2-furanyl)-4-bromobutanamide; N-(3,4-dihydroxy-5-(5-chloro-2-fluorophenyl)-2-furanyl)-2-pyrrolidinone; N-(3,4-dihydroxy-5-(5-chloro-2-fluorophenyl)-2-furanyl)succinimide; N-(3-trimethylsilyloxy-4-hydroxy-5-(5-chloro-2-fluorophenyl)-2-furanyl)-3-bromopropylsulfonamide; N-(3,4-dihydroxy-5-(5-chloro-2-fluorophenyl)-2-furanyl)-1,1-dioxide-isothiazolidine; N-methyl-N'-(3,4-dihydroxy-5-(5-chloro-2-fluorophenyl)-2-furanyl)ethanesulfonamide; N-(3-acetoxy-4-hydroxy-5-(5-chloro-2-fluorophenyl)-2-furanyl)methanesulfonamide; N-(3-acetoxy-4-hydroxy-5-(5-chloro-2-fluorophenyl)-2-furanyl)ethanesulfonamide; N-(3-acetoxy-4-hydroxy-5-(5-chloro-2-fluorophenyl)-2-furanyl)benzenesulfonamide; N-(3-acetoxy-4-hydroxy-5-(5-chloro-2-fluorophenyl)-2-furanyl)-acetamide; N-(3-acetoxy-4-hydroxy-5-(5-chloro-2-fluorophenyl)-2-furanyl)-carbamic acid ethyl ester; N-(3-acetoxy-4-hydroxy-5-(5-chloro-2-fluorophenyl)-2-furanyl)benzamide; N-(3-acetoxy-4-hydroxy-5-(5-chloro-2-fluorophenyl)-2-furanyl)-4-bromobutanamide; N-(3-acetoxy-4-hydroxy-5-(5-chloro-2-fluorophenyl)-2-furanyl)-2-pyrrolidinone; N-(3-acetoxy-4-hydroxy-5-(5-chloro-2-fluorophenyl)-2-furanyl)succinimide; N-(3-acetoxy-4-hydroxy-5-(5-chloro-2-fluorophenyl)-2-furanyl)-3-bromopropylsulfonamide; N-(3-acetoxy-4-hydroxy-5-(5-chloro-2-fluorophenyl)-2-furanyl)-

1,1-dioxide-isothiazolidine; N-methyl-N'-(3-acetoxy-4-hydroxy-5-(5-chloro-2-fluorophenyl)-2-furanyl)ethanesulfonamide; 2-(5-chloro-2-fluorophenyl)-2-methyl-4-trimethylsilyloxy-5-amino-3(2H)-furanone; 2-(5-chloro-2-fluorophenyl)-2-methyl-4-hydroxy-5-amino-3(2H)-furanone; N-(2-(5-chloro-2-fluorophenyl)-2-methyl-4-hydroxy-3(2H)-furanon-5-yl)-methanesulfonamide; N-(2-(5-chloro-2-fluorophenyl)-2-methyl-4-hydroxy-3(2H)-furanon-5-yl)-ethanesulfonamide; N-(2-(5-chloro-2-fluorophenyl)-2-methyl-4-hydroxy-3(2H)-furanon-5-yl)-benzenesulfonamide; N-(2-(5-chloro-2-fluorophenyl)-2-methyl-4-hydroxy-3(2H)-furanon-5-yl)-acetamide; N-(2-(5-chloro-2-fluorophenyl)-2-methyl-4-hydroxy-3(2H)-furanon-5-yl)-carbamic acid ethyl ester; N-(2-(5-chloro-2-fluorophenyl)-2-methyl-4-hydroxy-3(2H)-furanon-5-yl)-benzamide; N-(2-(5-chloro-2-fluorophenyl)-2-methyl-4-hydroxy-3(2H)-furanon-5-yl)-4-bromobutanamide; N-(2-(5-chloro-2-fluorophenyl)-2-methyl-4-hydroxy-3(2H)-furanon-5-yl)-2-pyrrolidinone; N-(2-(5-chloro-2-fluorophenyl)-2-methyl-4-hydroxy-3(2H)-furanon-5-yl)-succinimide; N-(2-(5-chloro-2-fluorophenyl)-2-methyl-4-hydroxy-3(2H)-furanon-5-yl)-3-bromopropylsulfonamide; N-(2-(5-chloro-2-fluorophenyl)-2-methyl-4-hydroxy-3(2H)-furanon-5-yl)-1,1-dioxide-isothiazolidine; N-methyl-N'-(2-(5-chloro-2-fluorophenyl)-2-methyl-4-hydroxy-3(2H)-furanon-5-yl)-ethanesulfonamide; 2-(5-chloro-2-fluorophenyl)-2-methyl-4-acetoxy-5-amino-3(2H)-furanone; N-(2-(5-chloro-2-fluorophenyl)-2-methyl-4-acetoxy-3(2H)-furanon-5-yl)-methanesulfonamide; N-(2-(5-chloro-2-fluorophenyl)-2-methyl-4-acetoxy-3(2H)-furanon-5-yl)-ethanesulfonamide; N-(2-(5-chloro-2-fluorophenyl)-2-methyl-4-acetoxy-3(2H)-furanon-5-yl)-benzenesulfonamide; N-(2-(5-chloro-2-fluorophenyl)-2-methyl-4-acetoxy-3(2H)-furanon-5-yl)-acetamide; N-(2-(5-chloro-2-fluorophenyl)-2-methyl-4-acetoxy-3(2H)-furanon-5-yl)-carbamic acid ethyl ester; N-(2-(5-chloro-2-fluorophenyl)-2-methyl-4-acetoxy-3(2H)-furanon-5-yl)-benzamide; N-(2-(5-chloro-2-fluorophenyl)-2-methyl-4-acetoxy-3(2H)-furanon-5-yl)-4-bromobutanamide; N-(2-(5-chloro-2-fluorophenyl)-2-methyl-4-acetoxy-3(2H)-furanon-5-yl)-2-pyrrolidinone; N-(2-(5-chloro-2-fluorophenyl)-2-methyl-4-acetoxy-3(2H)-furanon-5-yl)-succinimide; N-(2-(5-chloro-2-fluorophenyl)-2-methyl-4-acetoxy-3(2H)-furanon-5-yl)-3-bromopropylsulfonamide; N-(2-(5-chloro-2-fluorophenyl)-2-methyl-4-acetoxy-3(2H)-furanon-5-yl)-1,1-dioxide-isothiazolidine; N-methyl-N'-(2-(5-chloro-2-fluorophenyl)-2-methyl-4-acetoxy-3(2H)-furanon-5-yl)-ethanesulfonamide; 2-(phenyl)-5-amino-4-hydroxy-3(2H)-furanone; 2-(phenyl)-4-(acetoxy)-5-amino-3(2H)-furanone; -(phenyl)-4-[[phenylsulfonyl]oxy]-5-amino-3(2H)-furanone; N-(3,4-dihydroxy-5-(phenyl)-2-furanyl)methanesulfonamide; N-(3,4-dihydroxy-5-(phenyl)-2-furanyl)ethanesulfonamide; N-(3,4-dihydroxy-5-(phenyl)-2-furanyl)benzenesulfonamide; N-(3,4-dihydroxy-5-(phenyl)-2-furanyl)acetamide; N-(3,4-dihydroxy-5-(phenyl)-2-furanyl)-carbamic acid ethyl ester; N-(3,4-dihydroxy-5-(phenyl)-2-furanyl)benzamide; N-(3-trimethylsilyloxy-4-hydroxy-5-(phenyl)-2-furanyl)-4-bromobutanamide; N-(3,4-dihydroxy-5-(phenyl)-2-furanyl)-2-pyrrolidinone; N-(3,4-dihydroxy-5-(phenyl)-2-furanyl)succinimide; N-(3-trimethylsilyloxy-4-hydroxy-5-(phenyl)-2-furanyl)-3-bromopropylsulfonamide; N-(3,4-dihydroxy-5-(phenyl)-2-furanyl)-1,1-dioxide-isothiazolidine; N-methyl-N'-(3,4-dihydroxy-5-(phenyl)-2-furanyl)ethanesulfonamide; N-(3-acetoxy-4-hydroxy-5-(phenyl)-2-furanyl) methanesulfonamide; N-(3-acetoxy-4-hydroxy-5-(phenyl)-2-furanyl)ethanesulfonamide; N-(3-acetoxy-4-hydroxy-5-(phenyl)-2-furanyl)benzenesulfonamide; N-(3-acetoxy-4-hydroxy-5-(phenyl)-2-furanyl)-acetamide; N-(3-acetoxy-4-hydroxy-5-(phenyl)-2-furanyl)-carbamic acid ethyl ester; N-(3-acetoxy-4-hydroxy-5-(phenyl)-2-furanyl)benzamide; N-(3-acetoxy-4-hydroxy-5-(phenyl)-2-furanyl)-4-bromobutanamide; N-(3-acetoxy-4-hydroxy-5-(phenyl)-2-furanyl)-2-pyrrolidinone; N-(3-acetoxy-4-hydroxy-5-(phenyl)-2-furanyl)succinimide; N-(3-acetoxy-4-hydroxy-5-(phenyl)-2-furanyl)-3-bromopropylsulfonamide; N-(3-acetoxy-4-hydroxy-5-(phenyl)-2-furanyl)-1,1-dioxide-isothiazolidine; N-methyl-N'-(3-acetoxy-4-hydroxy-5-(phenyl)-2-furanyl)ethanesulfonamide; 2-(phenyl)-2-methyl-4-trimethylsilyloxy-5-amino-3(2H)-furanone; 2-(phenyl)-2-methyl-4-hydroxy-5-amino-3(2H)-furanone; N-(2-(phenyl)-2-methyl-4-hydroxy-3(2H)-furanon-5-yl)-methanesulfonamide; N-(2-(phenyl)-2-methyl-4-hydroxy-3(2H)-furanon-5-yl)-ethanesulfonamide; N-(2-(phenyl)-2-methyl-4-hydroxy-3(2H)-furanon-5-yl)-benzenesulfonamide; N-(2-(phenyl)-2-methyl-4-hydroxy-3(2H)-furanon-5-yl)-acetamide; N-(2-(phenyl)-2-methyl-4-hydroxy-3(2H)-furanon-5-yl)-carbamic acid ethylester; N-(2-(phenyl)-2-methyl-4-hydroxy-3(2H)-furanon-5-yl)-benzamide; N-(2-(phenyl)-2-methyl-4-hydroxy-3(2H)-furanon-5-yl)-4-bromobutanamide; N-(2-(phenyl)-2-methyl-4-hydroxy-3(2H)-furanon-5-yl)-2-pyrrolidinone; N-(2-(phenyl)-2-methyl-4-hydroxy-3(2H)-furanon-5-yl)-succinimide; N-(2-(phenyl)-2-methyl-4-hydroxy-3(2H)-furanon-5-yl)-3-bromopropylsulfonamide; N-(2-(phenyl)-2-methyl-4-hydroxy-3(2H)-furanon-5-yl)-1,1-dioxide-isothiazolidine; N-methyl-N'-(2-(phenyl)-2-methyl-4-hydroxy-3(2H)-furanon-5-yl)-ethanesulfonamide; 2-(phenyl)-2-methyl-4-acetoxy-5-amino-3(2H)-furanone; N-(2-(phenyl)-2-methyl-4-acetoxy-3(2H)-furanon-5-yl)-methanesulfonamide; N-(2-(phenyl)-2-methyl-4-acetoxy-3(2H)-furanon-5-yl)-ethanesulfonamide; N-(2-(phenyl)-2-methyl-4-acetoxy-3(2H)-furanon-5-yl)-benzenesulfonamide; N-(2-(phenyl)-2-methyl-4-acetoxy-3(2H)-furanon-5-yl)-acetamide; N-(2-(phenyl)-2-methyl-4-acetoxy-3(2H)-furanon-5-yl)-carbamic acid ethyl ester; N-(2-(phenyl)-2-methyl-4-acetoxy-3(2H)-furanon-5-yl)-benzamide; N-(2-(phenyl)-2-methyl-4-acetoxy-3(2H)-furanon-5-yl)-4-bromobutanamide; N-(2-(phenyl)-2-methyl-4-acetoxy-3(2H)-furanon-5-yl)-2-pyrrolidinone; N-(2-(phenyl)-2-methyl-4-acetoxy-3(2H)-furanon-5-yl)-succinimide; N-(2-(phenyl)-2-methyl-4-acetoxy-3(2H)-furanon-5-yl)-3-bromopropylsulfonamide; N-(2-(phenyl)-2-methyl-4-acetoxy-3(2H)-furanon-5-yl)-1,1-dioxide-isothiazolidine; N-methyl-N'-(2-(phenyl)-2-methyl-4-acetoxy-3(2H)-furanon-5-yl)-ethanesulfonamide; 2-(2-thiophenyl)-5-amino-4-hydroxy-3(2H)-furanone; 2-(2-thiophenyl)-4-(acetoxy)-5-amino-3(2H)-furanone; 2-(2-thiophenyl)-4-[[phenylsulfonyl]oxy]-5-amino-3(2H)-furanone; N-(3,4-dihydroxy-5-(2-thiophenyl)-2-furanyl) methanesulfonamide; N-(3,4-dihydroxy-5-(2-thiophenyl)-2-furanyl)ethanesulfonamide; N-(3,4-dihydroxy-5-(2-thiophenyl)-2-furanyl)benzenesulfonamide; N-(3,4-dihydroxy-5-(2-thiophenyl)-2-furanyl)acetamide; N-(3,4-dihydroxy-5-(2-thiophenyl)-2-furanyl)-carbamic acid ethyl ester; N-(3,4-dihydroxy-5-(2-thiophenyl)-2-furanyl)benzamide; N-(3-trimethylsilyloxy-4-hydroxy-5-(2-thiophenyl)-2-furanyl)-4-bromobutanamide; N-(3,4-dihydroxy-5-(2-thiophenyl)-2-furanyl)-2-pyrrolidinone; N-(3,4-dihydroxy-5-(2-thiophenyl)-2-furanyl)succinimide; N-(3-trimethylsilyloxy-4-hydroxy-5-(2-thiophenyl)-2-furanyl)-3-bromopropylsulfonamide; N-(3,4-dihydroxy-5-(2-thiophenyl)-2-furanyl)-1,1-dioxide-isothiazolidine; N-methyl-N'-(3,4-dihydroxy-5-(2-thiophenyl)-2-furanyl)

ethanesulfonamide; N-(3-acetoxy-4-hydroxy-5-(2-thiophenyl)-2-furanyl)methanesulfonamide; N-(3-acetoxy-4-hydroxy-5-(2-thiophenyl)-2-furanyl)ethanesulfonamide; N-(3-acetoxy-4-hydroxy-5-(2-thiophenyl)-2-furanyl)benzenesulfonamide; N-(3-acetoxy-4-hydroxy-5-(2-thiophenyl)-2-furanyl)-acetamide; N-(3-acetoxy-4-hydroxy-5-(2-thiophenyl)-2-furanyl)-carbamic acid ethyl ester; N-(3-acetoxy-4-hydroxy-5-(2-thiophenyl)-2-furanyl)benzamide; N-(3-acetoxy-4-hydroxy-5-(2-thiophenyl)-2-furanyl)-4-bromobutanamide; N-(3-acetoxy-4-hydroxy-5-(2-thiophenyl)-2-furanyl)-2-pyrrolidinone; N-(3-acetoxy-4-hydroxy-5-(2-thiophenyl)-2-furanyl)succinimide; N-(3-acetoxy-4-hydroxy-5-(2-thiophenyl)-2-furanyl)-3-bromopropylsulfonamide; N-(3-acetoxy-4-hydroxy-5-(2-thiophenyl)-2-furanyl)-1,1-dioxide-isothiazolidine; N-methyl-N'-(3-acetoxy-4-hydroxy-5-(2-thiophenyl)-2-furanyl)ethanesulfonamide; 2-(2-thiophenyl)-2-methyl-4-trimethylsilyloxy-5-amino-3(2H)-furanone; 2-(2-thiophenyl)-2-methyl-4-hydroxy-5-amino-3(2H)-furanone; N-(2-(2-thiophenyl)-2-methyl-4-hydroxy-3(2H)-furanon-5-yl)-methanesulfonamide; N-(2-(2-thiophenyl)-2-methyl-4-hydroxy-3(2H)-furanon-5-yl)-ethanesulfonamide; N-(2-(2-thiophenyl)-2-methyl-4-hydroxy-3(2H)-furanon-5-yl)-benzenesulfonamide; N-(2-(2-thiophenyl)-2-methyl-4-hydroxy-3(2H)-furanon-5-yl)-acetamide; N-(2-(2-thiophenyl)-2-methyl-4-hydroxy-3(2H)-furanon-5-yl)-carbamic acid ethyl ester; N-(2-(2-thiophenyl)-2-methyl-4-hydroxy-3(2H)-furanon-5-yl)-benzamide; N-(2-(2-thiophenyl)-2-methyl-4-hydroxy-3(2H)-furanon-5-yl)-4-bromobutanamide; N-(2-(2-thiophenyl)-2-methyl-4-hydroxy-3(2H)-furanon-5-yl)-2-pyrrolidinone; N-(2-(2-thiophenyl)-2-methyl-4-hydroxy-3(2H)-furanon-5-yl)-succinimide; N-(2-(2-thiophenyl)-2-methyl-4-hydroxy-3(2H)-furanon-5-yl)-3-bromopropylsulfonamide; N-(2-(2-thiophenyl)-2-methyl-4-hydroxy-3(2H)-furanon-5-yl)-1,1-dioxide-isothiazolidine; N-methyl-N'-(2-(2-thiophenyl)-2-methyl-4-hydroxy-3(2H)-furanon-5-yl)-ethanesulfonamide; 2-(2-thiophenyl)-2-methyl-4-acetoxy-5-amino-3(2H)-furanone; N-(2-(2-thiophenyl)-2-methyl-4-acetoxy-3(2H)-furanon-5-yl)-methanesulfonamide; N-(2-(2-thiophenyl)-2-methyl-4-acetoxy-3(2H)-furanon-5-yl)-ethanesulfonamide; N-(2-(2-thiophenyl)-2-methyl-4-acetoxy-3(2H)-furanon-5-yl)-benzenesulfonamide; N-(2-(2-thiophenyl)-2-methyl-4-acetoxy-3(2H)-furanon-5-yl)-acetamide; N-(2-(2-thiophenyl)-2-methyl-4-acetoxy-3(2H)-furanon-5-yl)-carbamic acid ethyl ester; N-(2-(2-thiophenyl)-2-methyl-4-acetoxy-3(2H)-furanon-5-yl)-benzamide; N-(2-(2-thiophenyl)-2-methyl-4-acetoxy-3(2H)-furanon-5-yl)-4-bromobutanamide; N-(2-(2-thiophenyl)-2-methyl-4-acetoxy-3(2H)-furanon-5-yl)-2-pyrrolidinone; N-(2-(2-thiophenyl)-2-methyl-4-acetoxy-3(2H)-furanon-5-yl)-succinimide; N-(2-(2-thiophenyl)-2-methyl-4-acetoxy-3(2H)-furanon-5-yl)-3-bromopropylsulfonamide; N-(2-(2-thiophenyl)-2-methyl-4-acetoxy-3(2H)-furanon-5-yl)-1,1-dioxide-isothiazolidine; N-methyl-N'-(2-(2-thiophenyl)-2-methyl-4-acetoxy-3(2H)-furanon-5-yl)-ethanesulfonamide; 2-(2-furanyl)-5-amino-4-hydroxy-3(2H)-furanone; 2-(2-furanyl)-4-(acetoxy)-5-amino-3(2H)-furanone; 2-(2-furanyl)-4-[[phenylsulfonyl]oxy]-5-amino-3(2H)-furanone; N-(3,4-dihydroxy-5-(2-furanyl)-2-furanyl)methanesulfonamide; N-(3,4-dihydroxy-5-(2-furanyl)-2-furanyl)ethanesulfonamide; N-(3,4-dihydroxy-5-(2-furanyl)-2-furanyl)benzenesulfonamide; N-(3,4-dihydroxy-5-(2-furanyl)-2-furanyl)acetamide; N-(3,4-dihydroxy-5-(2-furanyl)-2-furanyl)-carbamic acid ethyl ester; N-(3,4-dihydroxy-5-(2-furanyl)-2-furanyl)benzamide; N-(3-trimethylsilyloxy-4-hydroxy-5-(2-furanyl)-2-furanyl)-4-bromobutanamide; N-(3,4-dihydroxy-5-(2-furanyl)-2-furanyl)-2-pyrrolidinone; N-(3,4-dihydroxy-5-(2-furanyl)-2-furanyl)succinimide; N-(3-trimethylsilyloxy-4-hydroxy-5-(2-furanyl)-2-furanyl)-3-bromopropylsulfonamide; N-(3,4-dihydroxy-5-(2-furanyl)-2-furanyl)-1,1-dioxide-isothiazolidine; N-methyl-N'-(3,4-dihydroxy-5-(2-furanyl)-2-furanyl)ethanesulfonamide; N-(3-acetoxy-4-hydroxy-5-(2-furanyl)-2-furanyl)methanesulfonamide; N-(3-acetoxy-4-hydroxy-5-(2-furanyl)-2-furanyl)ethanesulfonamide; N-(3-acetoxy-4-hydroxy-5-(2-furanyl)-2-furanyl)benzenesulfonamide; N-(3-acetoxy-4-hydroxy-5-(2-furanyl)-2-furanyl)-acetamide; N-(3-acetoxy-4-hydroxy-5-(2-furanyl)-2-furanyl)-carbamic acid ethyl ester; N-(3-acetoxy-4-hydroxy-5-(2-furanyl)-2-furanyl)benzamide; N-(3-acetoxy-4-hydroxy-5-(2-furanyl)-2-furanyl)-4-bromobutanamide; N-(3-acetoxy-4-hydroxy-5-(2-furanyl)-2-furanyl)-2-pyrrolidinone; N-(3-acetoxy-4-hydroxy-5-(2-furanyl)-2-furanyl)succinimide; N-(3-acetoxy-4-hydroxy-5-(2-furanyl)-2-furanyl)-3-bromopropylsulfonamide; N-(3-acetoxy-4-hydroxy-5-(2-furanyl)-2-furanyl)-1,1-dioxide-isothiazolidine; N-methyl-N'-(3-acetoxy-4-hydroxy-5-(2-furanyl)-2-furanyl)ethanesulfonamide; 2-(2-furanyl)-2-methyl-4-trimethylsilyloxy-5-amino-3(2H)-furanone; 2-(2-furanyl)-2-methyl-4-hydroxy-5-amino-3(2H)-furanone; N-(2-(2-furanyl)-2-methyl-4-hydroxy-3(2H)-furanon-5-yl)-methanesulfonamide; N-(2-(2-furanyl)-2-methyl-4-hydroxy-3(2H)-furanon-5-yl)-ethanesulfonamide; N-(2-(2-furanyl)-2-methyl-4-hydroxy-3(2H)-furanon-5-yl)-benzenesulfonamide; N-(2-(2-furanyl)-2-methyl-4-hydroxy-3(2H)-furanon-5-yl)-acetamide; N-(2-(2-furanyl)-2-methyl-4-hydroxy-3(2H)-furanon-5-yl)-carbamic acid ethyl ester; N-(2-(2-furanyl)-2-methyl-4-hydroxy-3(2H)-furanon-5-yl)-benzamide; N-(2-(2-furanyl)-2-methyl-4-hydroxy-3(2H)-furanon-5-yl)-4-bromobutanamide; N-(2-(2-furanyl)-2-methyl-4-hydroxy-3(2H)-furanon-5-yl)-2-pyrrolidinone; N-(2-(2-furanyl)-2-methyl-4-hydroxy-3(2H)-furanon-5-yl)-succinimide; N-(2-(2-furanyl)-2-methyl-4-hydroxy-3(2H)-furanon-5-yl)-3-bromopropylsulfonamide; N-(2-(2-furanyl)-2-methyl-4-hydroxy-3(2H)-furanon-5-yl)-1,1-dioxide-isothiazolidine; N-methyl-N'-(2-(2-furanyl)-2-methyl-4-hydroxy-3(2H)-furanon-5-yl)-ethanesulfonamide; 2-(2-furanyl)-2-methyl-4-acetoxy-5-amino-3(2H)-furanone; N-(2-(2-furanyl)-2-methyl-4-acetoxy-3(2H)-furanon-5-yl)-methanesulfonamide; N-(2-(2-furanyl)-2-methyl-4-acetoxy-3(2H)-furanon-5-yl)-ethanesulfonamide; N-(2-(2-furanyl)-2-methyl-4-acetoxy-3(2H)-furanon-5-yl)-benzenesulfonamide; N-(2-(2-furanyl)-2-methyl-4-acetoxy-3(2H)-furanon-5-yl)-acetamide; N-(2-(2-furanyl)-2-methyl-4-acetoxy-3(2H)-furanon-5-yl)-carbamic acid ethyl ester; N-(2-(2-furanyl)-2-methyl-4-acetoxy-3(2H)-furanon-5-yl)-benzamide; N-(2-(2-furanyl)-2-methyl-4-acetoxy-3(2H)-furanon-5-yl)-4-bromobutanamide; N-(2-(2-furanyl)-2-methyl-4-acetoxy-3(2H)-furanon-5-yl)-2-pyrrolidinone; N-(2-(2-furanyl)-2-methyl-4-acetoxy-3(2H)-furanon-5-yl)-succinimide; N-(2-(2-furanyl)-2-methyl-4-acetoxy-3(2H)-furanon-5-yl)-3-bromopropylsulfonamide; N-(2-(2-furanyl)-2-methyl-4-acetoxy-3(2H)-furanon-5-yl)-1,1-dioxide-isothiazolidine; N-methyl-N'-(2-(2-furanyl)-2-methyl-4-acetoxy-3(2H)-furanon-5-yl)-ethanesulfonamide; 2-(2-thiazolyl)-5-amino-4-hydroxy-3(2H)-furanone; 2-(2-thiazolyl)-4-(acetoxy)-5-amino-3(2H)-furanone; 2-(2-thiazolyl)-4-[[phenylsulfonyl]oxy]-5-amino-3(2H)-furanone; N-(3,4-dihydroxy-5-(2-thiazolyl)-2-furanyl)methanesulfonamide; N-(3,4-dihydroxy-5-(2-thiazolyl)-2-furanyl)ethanesulfonamide; N-(3,4-dihydroxy-5-(2-thiazolyl)-2-furanyl)benzenesulfonamide; N-(3,4-dihydroxy-5-(2-thiazolyl)-2-furanyl)acetamide; N-(3,4- dihydroxy-5-(2-thiazolyl)-2-furanyl)-carbamic acid ethyl ester; N-(3,4-dihydroxy-5-(2-thiazolyl)-2-furanyl)benzamide; N-(3-trimethylsilyloxy-4-hydroxy-5-(2-thiazolyl)-2-furanyl)-4-bromobutanamide; N-(3,4-dihydroxy-5-(2-thiazolyl)-2-furanyl)-2-pyrrolidinone; N-(3,4-dihydroxy-5-(2-thiazolyl)-2-furanyl)succinimide; N-(3-trimethylsilyloxy-4-hydroxy-5-(2-thiazolyl)-2-furanyl)-3-bromopropylsulfonamide; N-(3,4-dihydroxy-5-(2-thiazolyl)-2-furanyl)-1,1-dioxide-isothiazolidine; N-methyl-N'-(3,4-dihydroxy-5-(2-thiazolyl)-2-furanyl) ethanesulfonamide; N-(3-acetoxy-4-hydroxy-5-(2-thiazolyl)-2-furanyl)methanesulfonamide; N-(3-acetoxy-4-hydroxy-5-(2-thiazolyl)-2-furanyl)ethanesulfonamide; N-(3-acetoxy-4-hydroxy-5-(2-thiazolyl)-2-furanyl)benzenesulfonamide; N-(3-acetoxy-4-hydroxy-5-(2-thiazolyl)-2-furanyl)-acetamide; N-(3-acetoxy-4-hydroxy-5-(2-thiazolyl)-2-furanyl)-carbamic acid ethyl ester; N-(3-acetoxy-4-hydroxy-5-(2-thiazolyl)-2-furanyl)benzamide; N-(3-acetoxy-4-hydroxy-5-(2-thiazolyl)-2-furanyl)-4-bromobutanamide; N-(3-acetoxy-4-hydroxy-5-(2-thiazolyl)-2-furanyl)-2-pyrrolidinone; N-(3-acetoxy-4-hydroxy-5-(2-thiazolyl)-2-furanyl)succinimide; N-(3-acetoxy-4-hydroxy-5-(2-thiazolyl)-2-furanyl)-3-bromopropylsulfonamide; N-(3-acetoxy-4-hydroxy-5-(2-thiazolyl)-2-furanyl)-1,1-dioxide-isothiazolidine; N-methyl-N'-(3-acetoxy-4-hydroxy-5-(2-thiazolyl)-2-furanyl) ethanesulfonamide; 2-(2-thiazolyl)-2-methyl-4-trimethylsilyloxy-5-amino-3(2H)-furanone; 2-(2-thiazolyl)-2-methyl-4-hydroxy-5-amino-3(2H)-furanone; N-(2-(2-thiazolyl)-2-methyl-4-hydroxy-3(2H)-furanon-5-yl)-methanesulfonamide; N-(2-(2-thiazolyl)-2-methyl-4-hydroxy-3(2H)-furanon-5-yl)-ethanesulfonamide; N-(2-(2-thiazolyl)-2-methyl-4-hydroxy-3(2H)-furanon-5-yl)-benzenesulfonamide; N-(2-(2-thiazolyl)-2-methyl-4-hydroxy-3(2H)-furanon-5-yl)-acetamide; N-(2-(2-thiazolyl)-2-methyl-4-hydroxy-3(2H)-furanon-5-yl)-carbamic acid ethyl ester; N-(2-(2-thiazolyl)-2-methyl-4-hydroxy-3(2H)-furanon-5-yl)-benzamide; N-(2-(2-thiazolyl)-2-methyl-4-hydroxy-3(2H)-furanon-5-yl)-4-bromobutanamide; N-(2-(2-thiazolyl)-2-methyl-4-hydroxy-3(2H)-furanon-5-yl)-2-pyrrolidinone; N-(2-(2-thiazolyl)-2-methyl-4-hydroxy-3(2H)-furanon-5-yl)-succinimide; N-(2-(2-thiazolyl)-2-methyl-4-hydroxy-3(2H)-furanon-5-yl)-3-bromopropylsulfonamide; N-(2-(2-thiazolyl)-2-methyl-4-hydroxy-3(2H)-furanon-5-yl)-1,1-dioxide-isothiazolidine; N-methyl-N'-(2-(2-thiazolyl)-2-methyl-4-hydroxy-3(2H)-furanon-5-yl)-ethanesulfonamide; 2-(2-thiazolyl)-2-methyl-4-acetoxy-5-amino-3(2H)-furanone; N-(2-(2-thiazolyl)-2-methyl-4-acetoxy-3(2H)-furanon-5-yl)-methanesulfonamide; N-(2-(2-thiazolyl)-2-methyl-4-acetoxy-3(2H)-furanon-5-yl)-ethanesulfonamide; N-(2-(2-thiazolyl)-2-methyl-4-acetoxy-3(2H)-furanon-5-yl)-benzenesulfonamide; N-(2-(2-thiazolyl)-2-methyl-4-acetoxy-3(2H)-furanon-5-yl)-acetamide; N-(2-(2-thiazolyl)-2-methyl-4-acetoxy-3(2H)-furanon-5-yl)-carbamic acid ethyl ester; N-(2-(2-thiazolyl)-2-methyl-4-acetoxy-3(2H)-furanon-5-yl)-benzamide; N-(2-(2-thiazolyl)-2-methyl-4-acetoxy-3(2H)-furanon-5-yl)-4-bromobutanamide; N-(2-(2-thiazolyl)-2-methyl-4-acetoxy-3(2H)-furanon-5-yl)-2-pyrrolidinone; N-(2-(2-thiazolyl)-2-methyl-4-acetoxy-3(2H)-furanon-5-yl)-succinimide; N-(2-(2-thiazolyl)-2-methyl-4-acetoxy-3(2H)-furanon-5-yl)-3-bromopropylsulfonamide; N-(2-(2-thiazolyl)-2-methyl-4-acetoxy-3(2H)-furanon-5-yl)-1,1-dioxide-isothiazolidine; N-methyl-N'-(2-(2-thiazolyl)-2-methyl-4-acetoxy-3(2H)-furanon-5-yl)-ethanesulfonamide; 2-(1-naphthyl)-5-amino-4-hydroxy-3(2H)-furanone; 2-(1-naphthyl)-4-(acetoxy)-5-amino-3(2H)-furanone; 2-(1-naphthyl)-4-[[phenylsulfonyl]oxy]-5-amino-3(2H)-furanone; N-(3,4-dihydroxy-5-(1-naphthyl)-2-furanyl)methanesulfonamide; N-(3,4-dihydroxy-5-(1-naphthyl)-2-furanyl)ethanesulfonamide; N-(3,4-dihydroxy-5-(1-naphthyl)-2-furanyl)benzenesulfonamide; N-(3,4-dihydroxy-5-(1-naphthyl)-2-furanyl)acetamide; N-(3,4-dihydroxy-5-(1-naphthyl)-2-furanyl)-carbamic acid ethyl ester; N-(3,4-dihydroxy-5-(1-naphthyl)-2-furanyl)benzamide; N-(3-trimethylsilyloxy-4-hydroxy-5-(1-naphthyl)-2-furanyl)-4-bromobutanamide; N-(3,4-dihydroxy-5-(1-naphthyl)-2-furanyl)-2-pyrrolidinone; N-(3,4-dihydroxy-5-(1-naphthyl)-2-furanyl)succinimide; N-(3-trimethylsilyloxy-4-hydroxy-5-(1-naphthyl)-2-furanyl)-3-bromopropylsulfonamide; N-(3,4-dihydroxy-5-(1-naphthyl)-2-furanyl)-1,1-dioxide-isothiazolidine; N-methyl-N'-(3,4-dihydroxy-5-(1-naphthyl)-2-furanyl) ethanesulfonamide; N-(3-acetoxy-4-hydroxy-5-(1-naphthyl)-2-furanyl)methanesulfonamide; N-(3-acetoxy-4-hydroxy-5-(1-naphthyl)-2-furanyl)ethanesulfonamide; N-(3-acetoxy-4-hydroxy-5-(1-naphthyl)-2-furanyl)benzenesulfonamide; N-(3-acetoxy-4-hydroxy-5-(1-naphthyl)-2-furanyl)-acetamide; N-(3-acetoxy-4-hydroxy-5-(1-naphthyl)-2-furanyl)-carbamic acid ethyl ester; N-(3-acetoxy-4-hydroxy-5-(1-naphthyl)-2-furanyl)benzamide; N-(3-acetoxy-4-hydroxy-5-(1-naphthyl)-2-furanyl)-4-bromobutanamide; N-(3-acetoxy-4-hydroxy-5-(1-naphthyl)-2-furanyl)-2-pyrrolidinone; N-(3-acetoxy-4-hydroxy-5-(1-naphthyl)-2-furanyl)succinimide; N-(3-acetoxy-4-hydroxy-5-(1-naphthyl)-2-furanyl)-3-bromopropylsulfonamide; N-(3-acetoxy-4-hydroxy-5-(1-naphthyl)-2-furanyl)-1,1-dioxide-isothiazolidine; N-methyl-N'-(3-acetoxy-4-hydroxy-5-(1-naphthyl)-2-furanyl) ethanesulfonamide; 2-(1-naphthyl)-2-methyl-4-trimethylsilyloxy-5-amino-3(2H)-furanone; 2-(1-naphthyl)-2-methyl-4-hydroxy-5-amino-3(2H)-furanone; N-(2-(1-naphthyl)-2-methyl-4-hydroxy-3(2H)-furanon-5-yl)-methanesulfonamide; N-(2-(1-naphthyl)-2-methyl-4-hydroxy-3(2H)-furanon-5-yl)-ethanesulfonamide; N-(2-(1-naphthyl)-2-methyl-4-hydroxy-3(2H)-furanon-5-yl)-benzenesulfonamide; N-(2-(1-naphthyl)-2-methyl-4-hydroxy-3(2H)-furanon-5-yl)-acetamide; N-(2-(1-naphthyl)-2-methyl-4-hydroxy-3(2H)-furanon-5-yl)-carbamic acid ethyl ester; N-(2-(1-naphthyl)-2-methyl-4-hydroxy-3(2H)-furanon-5-yl)-benzamide; N-(2-(1-naphthyl)-2-methyl-4-hydroxy-3(2H)-furanon-5-yl)-4-bromobutanamide; N-(2-(1-naphthyl)-2-methyl-4-hydroxy-3(2H)-furanon-5-yl)-2-pyrrolidinone; N-(2-(1-naphthyl)-2-methyl-4-hydroxy-3(2H)-furanon-5-yl)-succinimide; N-(2-(1-naphthyl)-2-methyl-4-hydroxy-3(2H)-furanon-5-yl)-3-bromopropylsulfonamide; N-(2-(1-naphthyl)-2-methyl-4-hydroxy-3(2H)-furanon-5-yl)-1,1-dioxide-isothiazolidine; N-methyl-N'-(2-(1-naphthyl)-2-methyl-4-hydroxy-3(2H)-furanon-5-yl)-ethanesulfonamide; 2-(1-naphthyl)-2-methyl-4-acetoxy-5-amino-3(2H)-furanone; N-(2-(1-naphthyl)-2-methyl-4-acetoxy-3(2H)-furanon-5-yl)-methanesulfonamide; N-(2-(1-naphthyl)-2-methyl-4-acetoxy-3(2H)-furanon-5-yl)-ethanesulfonamide; N-(2-(1-naphthyl)-2-methyl-4-acetoxy-3(2H)-furanon-5-yl)-benzenesulfonamide; N-(2-(1-naphthyl)-2-methyl-4-acetoxy-3(2H)-furanon-5-yl)-acetamide; N-(2-(1-naphthyl)-2-methyl-4-acetoxy-3(2H)-furanon-5-yl)-carbamic acid ethyl ester; N-(2-(1-naphthyl)-2-methyl-4-acetoxy-3(2H)-furanon-5-yl)-benzamide; N-(2-(1-naphthyl)-2-methyl-4-acetoxy-3(2H)-furanon-5-yl)-4-bromobutanamide; N-(2-(1-naphthyl)-2-methyl-4-acetoxy-3(2H)-furanon-5-yl)-2-pyrrolidinone; N-(2-(1-naphthyl)-2-methyl-4-acetoxy-3(2H)-furanon-5-yl)-succinimide; N-(2-(1-naphthyl)-2- methyl-4-acetoxy-3(2H)-furanon-5-yl)-3-bromopropylsulfonamide; N-(2-(1-naphthyl)-2-methyl-4-acetoxy-3(2H)-furanon-5-yl)-1,1-dioxide-isothiazolidine; N-methyl-N'-(2-(1-naphthyl)-2-methyl-4-acetoxy-3(2H)-furanon-5-yl)-ethanesulfonamide; 2-(2-naphthyl)-5-amino-4-hydroxy-3(2H)-furanone; 2-(2-naphthyl)-4-(acetoxy)-5-amino-3(2H)-furanone; 2-(2-naphthyl)-4-[[phenylsulfonyl]oxy]-5-amino-3(2H)-furanone; N-(3,4-dihydroxy-5-(2-naphthyl)-2-furanyl)methanesulfonamide; N-(3,4-dihydroxy-5-(2-naphthyl)-2-furanyl)ethanesulfonamide; N-(3,4-dihydroxy-5-(2-naphthyl)-2-furanyl)benzenesulfonamide; N-(3,4-dihydroxy-5-(2-naphthyl)-2-furanyl)acetamide; N-(3,4-dihydroxy-5-(2-naphthyl)-2-furanyl)-carbamic acid ethyl ester; N-(3,4-dihydroxy-5-(2-naphthyl)-2-furanyl)benzamide; N-(3-trimethylsilyloxy-4-hydroxy-5-(2-naphthyl)-2-furanyl)-4-bromobutanamide; N-(3,4-dihydroxy-5-(2-naphthyl)-2-furanyl)-2-pyrrolidinone; N-(3,4-dihydroxy-5-(2-naphthyl)-2-furanyl)succinimide; N-(3-trimethylsilyloxy-4-hydroxy-5-(2-naphthyl)-2-furanyl)-3-bromopropylsulfonamide; N-(3,4-dihydroxy-5-(2-naphthyl)-2-furanyl)-1,1-dioxide-isothiazolidine; N-methyl-N'-(3,4-dihydroxy-5-(2-naphthyl)-2-furanyl)ethanesulfonamide; N-(3-acetoxy-4-hydroxy-5-(2-naphthyl)-2-furanyl)methanesulfonamide; N-(3-acetoxy-4-hydroxy-5-(2-naphthyl)-2-furanyl)ethanesulfonamide; N-(3-acetoxy-4-hydroxy-5-(2-naphthyl)-2-furanyl)benzenesulfonamide; N-(3-acetoxy-4-hydroxy-5-(2-naphthyl)-2-furanyl)-acetamide; N-(3-acetoxy-4-hydroxy-5-(2-naphthyl)-2-furanyl)-carbamic acid ethyl ester; N-(3-acetoxy-4-hydroxy-5-(2-naphthyl)-2-furanyl)benzamide; N-(3-acetoxy-4-hydroxy-5-(2-naphthyl)-2-furanyl)-4-bromobutanamide; N-(3-acetoxy-4-hydroxy-5-(2-naphthyl)-2-furanyl)-2-pyrrolidinone; N-(3-acetoxy-4-hydroxy-5-(2-naphthyl)-2-furanyl)succinimide; N-(3-acetoxy-4-hydroxy-5-(2-naphthyl)-2-furanyl)-3-bromopropylsulfonamide; N-(3-acetoxy-4-hydroxy-5-(2-naphthyl)-2-furanyl)-1,1-dioxide-isothiazolidine; N-methyl-N'-(3-acetoxy-4-hydroxy-5-(2-naphthyl)-2-furanyl)ethanesulfonamide; 2-(2-naphthyl)-2-methyl-4-trimethylsilyloxy-5-amino-3(2H)-furanone; 2-(2-naphthyl)-2-methyl-4-hydroxy-5-amino-3(2H)-furanone; N-(2-(2-naphthyl)-2-methyl-4-hydroxy-3(2H)-furanon-5-yl)-methanesulfonamide; N-(2-(2-naphthyl)-2-methyl-4-hydroxy-3(2H)-furanon-5-yl)-ethanesulfonamide; N-(2-(2-naphthyl)-2-methyl-4-hydroxy-3(2H)-furanon-5-yl)-benzenesulfonamide; N-(2-(2-naphthyl)-2-methyl-4-hydroxy-3(2H)-furanon-5-yl)-acetamide; N-(2-(2-naphthyl)-2-methyl-4-hydroxy-3(2H)-furanon-5-yl)-carbamic acid ethyl ester; N-(2-(2-naphthyl)-2-methyl-4-hydroxy-3(2H)-furanon-5-yl)-benzamide; N-(2-(2-naphthyl)-2-methyl-4-hydroxy-3(2H)-furanon-5-yl)-4-bromobutanamide; N-(2-(2-naphthyl)-2-methyl-4-hydroxy-3(2H)-furanon-5-yl)-2-pyrrolidinone; N-(2-(2-naphthyl)-2-methyl-4-hydroxy-3(2H)-furanon-5-yl)-succinimide; N-(2-(2-naphthyl)-2-methyl-4-hydroxy-3(2H)-furanon-5-yl)-3-bromopropylsulfonamide; N-(2-(2-naphthyl)-2-methyl-4-hydroxy-3(2H)-furanon-5-yl)-1,1-dioxide-isothiazolidine; N-methyl-N'-(2-(2-naphthyl)-2-methyl-4-hydroxy-3(2H)-furanon-5-yl)-ethanesulfonamide; 2-(2-naphthyl)-2-methyl-4-acetoxy-5-amino-3(2H)-furanone; N-(2-(2-naphthyl)-2-methyl-4-acetoxy-3(2H)-furanon-5-yl)-methanesulfonamide; N-(2-(2-naphthyl)-2-methyl-4-acetoxy-3(2H)-furanon-5-yl)-ethanesulfonamide; N-(2-(2-naphthyl)-2-methyl-4-acetoxy-3(2H)-furanon-5-yl)-benzenesulfonamide; N-(2-(2-naphthyl)-2-methyl-4-acetoxy-3(2H)-furanon-5-yl)-acetamide; N-(2-(2-naphthyl)-2-methyl-4-acetoxy-3(2H)-furanon-5-yl)-carbamic acid ethyl ester; N-(2-(2-naphthyl)-2-methyl-4-acetoxy-3(2H)-furanon-5-yl)-benzamide; N-(2-(2-naphthyl)-2-methyl-4-acetoxy-3(2H)-furanon-5-yl)-4-bromobutanamide; N-(2-(2-naphthyl)-2-methyl-4-acetoxy-3(2H)-furanon-5-yl)-2-pyrrolidinone; N-(2-(2-naphthyl)-2-methyl-4-acetoxy-3 (2H)-furanon-5-yl)-succinimide; N-(2-(2-naphthyl)-2-methyl-4-acetoxy-3(2H)-furanon-5-yl)-3-bromopropylsulfonamide; N-(2-(2-naphthyl)-2-methyl-4-acetoxy-3(2H)-furanon-5-yl)-1,1-dioxide-isothiazolidine; N-methyl-N'-(2-(2-naphthyl)-2-methyl-4-acetoxy-3(2H)-furanon-5-yl)-ethanesulfonamide; 2-(2-pyridyl)-5-amino-4-hydroxy-3(2H)-furanone; 2-(2-pyridyl)-4-(acetoxy)-5-amino-3(2H)-furanone; 2-(2-pyridyl)-4-[[phenylsulfonyl]oxy]-5-amino-3(2H)-furanone; N-(3,4-dihydroxy-5-(2-pyridyl)-2-furanyl)methanesulfonamide; N-(3,4-dihydroxy-5-(2-pyridyl)-2-furanyl)ethanesulfonamide; N-(3,4-dihydroxy-5-(2-pyridyl)-2-furanyl)benzenesulfonamide; N-(3,4-dihydroxy-5-(2-pyridyl)-2-furanyl)acetamide; N-(3,4-dihydroxy-5-(2-pyridyl)-2-furanyl)-carbamic acid ethyl ester; N-(3,4-dihydroxy-5-(2-pyridyl)-2-furanyl)benzamide; N-(3-trimethylsilyloxy-4-hydroxy-5-(2-pyridyl)-2-furanyl)-4-bromobutanamide; N-(3,4-dihydroxy-5-(2-pyridyl)-2-furanyl)-2-pyrrolidinone; N-(3,4-dihydroxy-5-(2-pyridyl)-2-furanyl)succinimide; N-(3-trimethylsilyloxy-4-hydroxy-5-(2-pyridyl)-2-furanyl)-3-bromopropylsulfonamide; N-(3,4-dihydroxy-5-(2-pyridyl)-2-furanyl)-1,1-dioxide-isothiazolidine; N-methyl-N'-(3,4-dihydroxy-5-(2-pyridyl)-2-furanyl)ethanesulfonamide; N-(3-acetoxy-4-hydroxy-5-(2-pyridyl)-2-furanyl)methanesulfonamide; N-(3-acetoxy-4-hydroxy-5-(2-pyridyl)-2-furanyl)ethanesulfonamide; N-(3-acetoxy-4-hydroxy-5-(2-pyridyl)-2-furanyl)benzenesulfonamide; N-(3-acetoxy-4-hydroxy-5-(2-pyridyl)-2-furanyl)-acetamide; N-(3-acetoxy-4-hydroxy-5-(2-pyridyl)-2-furanyl)-carbamic acid ethyl ester; N-(3-acetoxy-4-hydroxy-5-(2-pyridyl)-2-furanyl)benzamide; N-(3-acetoxy-4-hydroxy-5-(2-pyridyl)-2-furanyl)-4-bromobutanamide; N-(3-acetoxy-4-hydroxy-5-(2-pyridyl)-2-furanyl)-2-pyrrolidinone; N-(3-acetoxy-4-hydroxy-5-(2-pyridyl)-2-furanyl)succinimide; N-(3-acetoxy-4-hydroxy-5-(2-pyridyl)-2-furanyl)-3-bromopropylsulfonamide; N-(3-acetoxy-4-hydroxy-5-(2-pyridyl)-2-furanyl)-1,1-dioxide-isothiazolidine; N-methyl-N'-(3-acetoxy-4-hydroxy-5-(2-pyridyl)-2-furanyl)ethanesulfonamide; 2-(2-pyridyl)-2-methyl-4-trimethylsilyloxy-5-amino-3(2H)-furanone; 2-(2-pyridyl)-2-methyl-4-hydroxy-5-amino-3(2H)-furanone; N-(2-(2-pyridyl)-2-methyl-4-hydroxy-3(2H)-furanon-5-yl)-methanesulfonamide; N-(2-(2-pyridyl)-2-methyl-4-hydroxy-3(2H)-furanon-5-yl)-ethanesulfonamide; N-(2-(2-pyridyl)-2-methyl-4-hydroxy-3(2H)-furanon-5-yl)-benzenesulfonamide; N-(2-(2-pyridyl)-2-methyl-4-hydroxy-3(2H)-furanon-5-yl)-acetamide; N-(2-(2-pyridyl)-2-methyl-4-hydroxy-3(2H)-furanon-5-yl)-carbamic acid ethyl ester; N-(2-(2-pyridyl)-2-methyl-4-hydroxy-3(2H)-furanon-5-yl)-benzamide; N-(2-(2-pyridyl)-2-methyl-4-hydroxy-3(2H)-furanon-5-yl)-4-bromobutanamide; N-(2-(2-pyridyl)-2-methyl-4-hydroxy-3(2H)-furanon-5-yl)-2-pyrrolidinone; N-(2-(2-pyridyl)-2-methyl-4-hydroxy-3(2H)-furanon-5-yl)-succinimide; N-(2-(2-pyridyl)-2-methyl-4-hydroxy-3(2H)-furanon-5-yl)-3-bromopropylsulfonamide; N-(2-(2-pyridyl)-2-methyl-4-hydroxy-3(2H)-furanon-5-yl)-1,1-dioxide-isothiazolidine; N-methyl-N'-(2-(2-pyridyl)-2-methyl-4-hydroxy-3(2H)-furanon-5-yl)-ethanesulfonamide; 2-(2-pyridyl)-2-methyl-4-acetoxy-5-amino-3(2H)-furanone; N-(2-(2-pyridyl)-2-methyl-4-acetoxy-3(2H)-furanon-5-yl)-methanesulfonamide; N-(2-(2-pyridyl)-2-methyl-4-acetoxy-3(2H)-furanon-5-yl)-ethanesulfonamide; N-(2-(2-pyridyl)-

2-methyl-4-acetoxy-3(2H)-furanon-5-yl)-benzenesulfonamide; N-(2-(2-pyridyl)-2-methyl-4-acetoxy-3(2H)-furanon-5-yl)-acetamide; N-(2-(2-pyridyl)-2-methyl-4-acetoxy-3(2H)-furanon-5-yl)-carbamic acid ethyl ester; N-(2-(2-pyridyl)-2-methyl-4-acetoxy-3(2H)-furanon-5-yl)-benzamide; N-(2-(2-pyridyl)-2-methyl-4-acetoxy-3(2H)-furanon-5-yl)-4-bromobutanamide; N-(2-(2-pyridyl)-2-methyl-4-acetoxy-3(2H)-furanon-5-yl)-2-pyrrolidinone; N-(2-(2-pyridyl)-2-methyl-4-acetoxy-3(2H)-furanon-5-yl)-succinimide; N-(2-(2-pyridyl)-2-methyl-4-acetoxy-3(2H)-furanon-5-yl)-3-bromopropylsulfonamide; N-(2-(2-pyridyl)-2-methyl-4-acetoxy-3(2H)-furanon-5-yl)-1,1-dioxide-isothiazolidine; N-methyl-N'-(2-(2-pyridyl)-2-methyl-4-acetoxy-3(2H)-furanon-5-yl)-ethanesulfonamide; 2-(3-pyridyl)-5-amino-4-hydroxy-3(2H)-furanone; 2-(3-pyridyl)-4-(acetoxy)-5-amino-3(2H)-furanone; 2-(3-pyridyl)-4-[[phenylsulfonyl]oxy]-5-amino-3(2H)-furanone; N-(3,4-dihydroxy-5-(3-pyridyl)-2-furanyl)methanesulfonamide; N-(3,4-dihydroxy-5-(3-pyridyl)-2-furanyl)ethanesulfonamide; N-(3,4-dihydroxy-5-(3-pyridyl)-2-furanyl)benzenesulfonamide; N-(3,4-dihydroxy-5-(3-pyridyl)-2-furanyl)acetamide; N-(3,4-dihydroxy-5-(3-pyridyl)-2-furanyl)-carbamic acid ethyl ester; N-(3,4-dihydroxy-5-(3-pyridyl)-2-furanyl)benzamide; N-(3-trimethylsilyloxy-4-hydroxy-5-(3-pyridyl)-2-furanyl)-4-bromobutanamide; N-(3,4-dihydroxy-5-(3-pyridyl)-2-furanyl)-2-pyrrolidinone; N-(3,4-dihydroxy-5-(3-pyridyl)-2-furanyl)succinimide; N-(3-trimethylsilyloxy-4-hydroxy-5-(3-pyridyl)-2-furanyl)-3-bromopropylsulfonamide; N-(3,4-dihydroxy-5-(3-pyridyl)-2-furanyl)-1,1-dioxide-isothiazolidine; N-methyl-N'-(3,4-dihydroxy-5-(3-pyridyl)-2-furanyl)ethanesulfonamide; N-(3-acetoxy-4-hydroxy-5-(3-pyridyl)-2-furanyl)methanesulfonamide; N-(3-acetoxy-4-hydroxy-5-(3-pyridyl)-2-furanyl)ethanesulfonamide; N-(3-acetoxy-4-hydroxy-5-(3-pyridyl)-2-furanyl)benzenesulfonamide; N-(3-acetoxy-4-hydroxy-5-(3-pyridyl)-2-furanyl)-acetamide; N-(3-acetoxy-4-hydroxy-5-(3-pyridyl)-2-furanyl)-carbamic acid ethyl ester; N-(3-acetoxy-4-hydroxy-5-(3-pyridyl)-2-furanyl)benzamide; N-(3-acetoxy-4-hydroxy-5-(3-pyridyl)-2-furanyl)-4-bromobutanamide; N-(3-acetoxy-4-hydroxy-5-(3-pyridyl)-2-furanyl)-2-pyrrolidinone; N-(3-acetoxy-4-hydroxy-5-(3-pyridyl)-2-furanyl)succinimide; N-(3-acetoxy-4-hydroxy-5-(3-pyridyl)-2-furanyl)-3-bromopropylsulfonamide; N-(3-acetoxy-4-hydroxy-5-(3-pyridyl)-2-furanyl)-1,1-dioxide-isothiazolidine; N-methyl-N'-(3-acetoxy-4-hydroxy-5-(3-pyridyl)-2-furanyl)ethanesulfonamide; 2-(3-pyridyl)-2-methyl-4-trimethylsilyloxy-5-amino-3(2H)-furanone; 2-(3-pyridyl)-2-methyl-4-hydroxy-5-amino-3(2H)-furanone; N-(2-(3-pyridyl)-2-methyl-4-hydroxy-3(2H)-furanon-5-yl)-methanesulfonamide; N-(2-(3-pyridyl)-2-methyl-4-hydroxy-3(2H)-furanon-5-yl)-ethanesulfonamide; N-(2-(3-pyridyl)-2-methyl-4-hydroxy-3(2H)-furanon-5-yl)-benzenesulfonamide; N-(2-(3-pyridyl)-2-methyl-4-hydroxy-3(2H)-furanon-5-yl)-acetamide; N-(2-(3-pyridyl)-2-methyl-4-hydroxy-3(2H)-furanon-5-yl)-carbamic acid ethyl ester; N-(2-(3-pyridyl)-2-methyl-4-hydroxy-3(2H)-furanon-5-yl)-benzamide; N-(2-(3-pyridyl)-2-methyl-4-hydroxy-3(2H)-furanon-5-yl)-4-bromobutanamide; N-(2-(3-pyridyl)-2-methyl-4-hydroxy-3(2H)-furanon-5-yl)-2-pyrrolidinone; N-(2-(3-pyridyl)-2-methyl-4-hydroxy-3(2H)-furanon-5-yl)-succinimide; N-(2-(3-pyridyl)-2-methyl-4-hydroxy-3(2H)-furanon-5-yl)-3-bromopropylsulfonamide; N-(2-(3-pyridyl)-2-methyl-4-hydroxy-3(2H)-furanon-5-yl)-1,1-dioxide-isothiazolidine; N-methyl-N'-(2-(3-pyridyl)-2-methyl-4-hydroxy-3(2H)-furanon-5-yl)-ethanesulfonamide; 2-(3-pyridyl)-2-methyl-4-acetoxy-5-amino-3(2H)-furanone; N-(2-(3-pyridyl)-2-methyl-4-acetoxy-3(2H)-furanon-5-yl)-methanesulfonamide; N-(2-(3-pyridyl)-2-methyl-4-acetoxy-3(2H)-furanon-5-yl)-ethanesulfonamide; N-(2-(3-pyridyl)-2-methyl-4-acetoxy-3(2H)-furanon-5-yl)-benzenesulfonamide; N-(2-(3-pyridyl)-2-methyl-4-acetoxy-3(2H)-furanon-5-yl)-acetamide; N-(2-(3-pyridyl)-2-methyl-4-acetoxy-3(2H)-furanon-5-yl)-carbamic acid ethyl ester; N-(2-(3-pyridyl)-2-methyl-4-acetoxy-3(2H)-furanon-5-yl)-benzamide; N-(2-(3-pyridyl)-2-methyl-4-acetoxy-3(2H)-furanon-5-yl)-4-bromobutanamide; N-(2-(3-pyridyl)-2-methyl-4-acetoxy-3(2H)-furanon-5-yl)-2-pyrrolidinone; N-(2-(3-pyridyl)-2-methyl-4-acetoxy-3(2H)-furanon-5-yl)-succinimide; N-(2-(3-pyridyl)-2-methyl-4-acetoxy-3(2H)-furanon-5-yl)-3-bromopropylsulfonamide; N-(2-(3-pyridyl)-2-methyl-4-acetoxy-3(2H)-furanon-5-yl)-1,1-dioxide-isothiazolidine; N-methyl-N'-(2-(3-pyridyl)-2-methyl-4-acetoxy-3(2H)-furanon-5-yl)-ethanesulfonamide; 2-(4-pyridyl)-5-amino-4-hydroxy-3(2H)-furanone; 2-(4-pyridyl)-4-(acetoxy)-5-amino-3(2H)-furanone; 2-(4-pyridyl)-4-[[phenylsulfonyl]oxy]-5-amino-3(2H)-furanone; N-(3,4-dihydroxy-5-(4-pyridyl)-2-furanyl)methanesulfonamide; N-(3,4-dihydroxy-5-(4-pyridyl)-2-furanyl)ethanesulfonamide; N-(3,4-dihydroxy-5-(4-pyridyl)-2-furanyl)benzenesulfonamide; N-(3,4-dihydroxy-5-(4-pyridyl)-2-furanyl)acetamide; N-(3,4-dihydroxy-5-(4-pyridyl)-2-furanyl)-carbamic acid ethyl ester; N-(3,4-dihydroxy-5-(4-pyridyl)-2-furanyl)benzamide; N-(3-trimethylsilyloxy-4-hydroxy-5-(4-pyridyl)-2-furanyl)-4-bromobutanamide; N-(3,4-dihydroxy-5-(4-pyridyl)-2-furanyl)-2-pyrrolidinone; N-(3,4-dihydroxy-5-(4-pyridyl)-2-furanyl)succinimide; N-(3-trimethylsilyloxy-4-hydroxy-5-(4-pyridyl)-2-furanyl)-3-bromopropylsulfonamide; N-(3,4-dihydroxy-5-(4-pyridyl)-2-furanyl)-1,1-dioxide-isothiazolidine; N-methyl-N'-(3,4-dihydroxy-5-(4-pyridyl)-2-furanyl)ethanesulfonamide; N-(3-acetoxy-4-hydroxy-5-(4-pyridyl)-2-furanyl)methanesulfonamide; N-(3-acetoxy-4-hydroxy-5-(4-pyridyl)-2-furanyl)ethanesulfonamide; N-(3-acetoxy-4-hydroxy-5-(4-pyridyl)-2-furanyl)benzenesulfonamide; N-(3-acetoxy-4-hydroxy-5-(4-pyridyl)-2-furanyl)-acetamide; N-(3-acetoxy-4-hydroxy-5-(4-pyridyl)-2-furanyl)-carbamic acid ethyl ester; N-(3-acetoxy-4-hydroxy-5-(4-pyridyl)-2-furanyl)benzamide; N-(3-acetoxy-4-hydroxy-5-(4-pyridyl)-2-furanyl)-4-bromobutanamide; N-(3-acetoxy-4-hydroxy-5-(4-pyridyl)-2-furanyl)-2-pyrrolidinone; N-(3-acetoxy-4-hydroxy-5-(4-pyridyl)-2-furanyl)succinimide; N-(3-acetoxy-4-hydroxy-5-(4-pyridyl)-2-furanyl)-3-bromopropylsulfonamide; N-(3-acetoxy-4-hydroxy-5-(4-pyridyl)-2-furanyl)-1,1-dioxide-isothiazolidine; N-methyl-N'-(3-acetoxy-4-hydroxy-5-(4-pyridyl)-2-furanyl)ethanesulfonamide; 2-(4-pyridyl)-2-methyl-4-trimethylsilyloxy-5-amino-3(2H)-furanone; 2-(4-pyridyl)-2-methyl-4-hydroxy-5-amino-3(2H)-furanone; N-(2-(4-pyridyl)-2-methyl-4-hydroxy-3(2H)-furanon-5-yl)-methanesulfonamide; N-(2-(4-pyridyl)-2-methyl-4-hydroxy-3(2H)-furanon-5-yl)-ethanesulfonamide; N-(2-(4-pyridyl)-2-methyl-4-hydroxy-3(2H)-furanon-5-yl)-benzenesulfonamide; N-(2-(4-pyridyl)-2-methyl-4-hydroxy-3(2H)-furanon-5-yl)-acetamide; N-(2-(4-pyridyl)-2-methyl-4-hydroxy-3(2H)-furanon-5-yl)-carbamic acid ethyl ester; N-(2-(4-pyridyl)-2-methyl-4-hydroxy-3(2H)-furanon-5-yl)-benzamide; N-(2-(4-pyridyl)-2-methyl-4-hydroxy-3(2H)-furanon-5-yl)-4-bromobutanamide; N-(2-(4-pyridyl)-2-methyl-4-hydroxy-3(2H)-furanon-5-yl)-2-pyrrolidinone; N-(2-(4-pyridyl)-2-methyl-4-hydroxy-3(2H)-furanon-5-yl)-succinimide; N-(2-(4-pyridyl)-2-methyl-4-hydroxy-3(2H)-furanon-5-yl)-3- bromopropylsulfonamide; N-(2-(4-pyridyl)-2-methyl-4-hydroxy-3(2H)-furanon-5-yl)-1,1-dioxide-isothiazolidine; N-methyl-N'-(2-(4-pyridyl)-2-methyl-4-hydroxy-3(2H)-furanon-5-yl)-ethanesulfonamide; 2-(4-pyridyl)-2-methyl-4-acetoxy-5-amino-3(2H)-furanone; N-(2-(4-pyridyl)-2-methyl-4-acetoxy-3(2H)-furanon-5-yl)-methanesulfonamide; N-(2-(4-pyridyl)-2-methyl-4-acetoxy-3(2H)-furanon-5-yl)-ethanesulfonamide; N-(2-(4-pyridyl)-2-methyl-4-acetoxy-3(2H)-furanon-5-yl)-benzenesulfonamide; N-(2-(4-pyridyl)-2-methyl-4-acetoxy-3(2H)-furanon-5-yl)-acetamide; N-(2-(4-pyridyl)-2-methyl-4-acetoxy-3(2H)-furanon-5-yl)-carbamic acid ethyl ester; N-(2-(4-pyridyl)-2-methyl-4-acetoxy-3(2H)-furanon-5-yl)-benzamide; N-(2-(4-pyridyl)-2-methyl-4-acetoxy-3(2H)-furanon-5-yl)-4-bromobutanamide; N-(2-(4-pyridyl)-2-methyl-4-acetoxy-3(2H)-furanon-5-yl)-2-pyrrolidinone; N-(2-(4-pyridyl)-2-methyl-4-acetoxy-3(2H)-furanon-5-yl)-succinimide; N-(2-(4-pyridyl)-2-methyl-4-acetoxy-3(2H)-furanon-5-yl)-3-bromopropylsulfonamide; N-(2-(4-pyridyl)-2-methyl-4-acetoxy-3(2H)-furanon-5-yl)-1,1-dioxide-isothiazolidine; N-methyl-N'-(2-(4-pyridyl)-2-methyl-4-acetoxy-3(2H)-furanon-5-yl)-ethanesulfonamide; 2-(2-quinolinyl)-5-amino-4-hydroxy-3(2H)-furanone; 2-(2-quinolinyl)-4-(acetoxy)-5-amino-3(2H)-furanone; 2-(2-quinolinyl)-4-[[phenylsulfonyl]oxy]-5-amino-3(2H)-furanone; N-(3,4-dihydroxy-5-(2-quinolinyl)-2-furanyl)methanesulfonamide; N-(3,4-dihydroxy-5-(2-quinolinyl)-2-furanyl)ethanesulfonamide; N-(3,4-dihydroxy-5-(2-quinolinyl)-2-furanyl)benzenesulfonamide; N-(3,4-dihydroxy-5-(2-quinolinyl)-2-furanyl)acetamide; N-(3,4-dihydroxy-5-(2-quinolinyl)-2-furanyl)-carbamic acid ethyl ester; N-(3,4-dihydroxy-5-(2-quinolinyl)-2-furanyl)benzamide; N-(3-trimethylsilyloxy-4-hydroxy-5-(2-quinolinyl)-2-furanyl)-4-bromobutanamide; N-(3,4-dihydroxy-5-(2-quinolinyl)-2-furanyl)-2-pyrrolidinone; N-(3,4-dihydroxy-5-(2-quinolinyl)-2-furanyl)succinimide; N-(3-trimethylsilyloxy-4-hydroxy-5-(2-quinolinyl)-2-furanyl)-3-bromopropylsulfonamide; N-(3,4-dihydroxy-5-(2-quinolinyl)-2-furanyl)-1,1-dioxide-isothiazolidine; N-methyl-N'-(3,4-dihydroxy-5-(2-quinolinyl)-2-furanyl)ethanesulfonamide; N-(3-acetoxy-4-hydroxy-5-(2-quinolinyl)-2-furanyl)methanesulfonamide; N-(3-acetoxy-4-hydroxy-5-(2-quinolinyl)-2-furanyl)ethanesulfonamide; N-(3-acetoxy-4-hydroxy-5-(2-quinolinyl)-2-furanyl)benzenesulfonamide; N-(3-acetoxy-4-hydroxy-5-(2-quinolinyl)-2-furanyl)-acetamide; N-(3-acetoxy-4-hydroxy-5-(2-quinolinyl)-2-furanyl)-carbamic acid ethyl ester; N-(3-acetoxy-4-hydroxy-5-(2-quinolinyl)-2-furanyl)benzamide; N-(3-acetoxy-4-hydroxy-5-(2-quinolinyl)-2-furanyl)-4-bromobutanamide; N-(3-acetoxy-4-hydroxy-5-(2-quinolinyl)-2-furanyl)-2-pyrrolidinone; N-(3-acetoxy-4-hydroxy-5-(2-quinolinyl)-2-furanyl)succinimide; N-(3-acetoxy-4-hydroxy-5-(2-quinolinyl)-2-furanyl)-3-bromopropylsulfonamide; N-(3-acetoxy-4-hydroxy-5-(2-quinolinyl)-2-furanyl)-1,1-dioxide-isothiazolidine; N-methyl-N'-(3-acetoxy-4-hydroxy-5-(2-quinolinyl)-2-furanyl)ethanesulfonamide; 2-(2-quinolinyl)-2-methyl-4-trimethylsilyloxy-5-amino-3(2H)-furanone; 2-(2-quinolinyl)-2-methyl-4-hydroxy-5-amino-3(2H)-furanone; N-(2-(2-quinolinyl)-2-methyl-4-hydroxy-3(2H)-furanon-5-yl)-methanesulfonamide; N-(2-(2-quinolinyl)-2-methyl-4-hydroxy-3(2H)-furanon-5-yl)-ethanesulfonamide; N-(2-(2-quinolinyl)-2-methyl-4-hydroxy-3(2H)-furanon-5-yl)-benzenesulfonamide; N-(2-(2-quinolinyl)-2-methyl-4-hydroxy-3(2H)-furanon-5-yl)-acetamide; N-(2-(2-quinolinyl)-2-methyl-4-hydroxy-3(2H)-furanon-5-yl)-carbamic acid ethyl ester; N-(2-(2-quinolinyl)-2-methyl-4-hydroxy-3(2H)-furanon-5-yl)-benzamide; N-(2-(2-quinolinyl)-2-methyl-4-hydroxy-3(2H)-furanon-5-yl)-4-bromobutanamide; N-(2-(2-quinolinyl)-2-methyl-4-hydroxy-3(2H)-furanon-5-yl)-2-pyrrolidinone; N-(2-(2-quinolinyl)-2-methyl-4-hydroxy-3(2H)-furanon-5-yl)-succinimide; N-(2-(2-quinolinyl)-2-methyl-4-hydroxy-3(2H)-furanon-5-yl)-3-bromopropylsulfonamide; N-(2-(2-quinolinyl)-2-methyl-4-hydroxy-3(2H)-furanon-5-yl)-1,1-dioxide-isothiazolidine; N-methyl-N'-(2-(2-quinolinyl)-2-methyl-4-hydroxy-3(2H)-furanon-5-yl)-ethanesulfonamide; 2-(2-quinolinyl)-2-methyl-4-acetoxy-5-amino-3(2H)-furanone; N-(2-(2-quinolinyl)-2-methyl-4-acetoxy-3(2H)-furanon-5-yl)-methanesulfonamide; N-(2-(2-quinolinyl)-2-methyl-4-acetoxy-3(2H)-furanon-5-yl)-ethanesulfonamide; N-(2-(2-quinolinyl)-2-methyl-4-acetoxy-3(2H)-furanon-5-yl)-benzenesulfonamide; N-(2-(2-quinolinyl)-2-methyl-4-acetoxy-3(2H)-furanon-5-yl)-acetamide; N-(2-(2-quinolinyl)-2-methyl-4-acetoxy-3(2H)-furanon-5-yl)-carbamic acid ethyl ester; N-(2-(2-quinolinyl)-2-methyl-4-acetoxy-3(2H)-furanon-5-yl)-benzamide; N-(2-(2-quinolinyl)-2-methyl-4-acetoxy-3(2H)-furanon-5-yl)-4-bromobutanamide; N-(2-(2-quinolinyl)-2-methyl-4-acetoxy-3(2H)-furanon-5-yl)-2-pyrrolidinone; N-(2-(2-quinolinyl)-2-methyl-4-acetoxy-3(2H)-furanon-5-yl)-succinimide; N-(2-(2-quinolinyl)-2-methyl-4-acetoxy-3(2H)-furanon-5-yl)-3-bromopropylsulfonamide; N-(2-(2-quinolinyl)-2-methyl-4-acetoxy-3(2H)-furanon-5-yl)-1,1-dioxide-isothiazolidine; N-methyl-N'-(2-(2-quinolinyl)-2-methyl-4-acetoxy-3(2H)-furanon-5-yl)-ethanesulfonamide; 2-(3-quinolinyl)-5-amino-4-hydroxy-3(2H)-furanone; 2-(3-quinolinyl)-4-(acetoxy)-5-amino-3(2H)-furanone; 2-(3-quinolinyl)-4-[[phenylsulfonyl]oxy]-5-amino-3(2H)-furanone; N-(3,4-dihydroxy-5-(3-quinolinyl)-2-furanyl)methanesulfonamide; N-(3,4-dihydroxy-5-(3-quinolinyl)-2-furanyl)ethanesulfonamide; N-(3,4-dihydroxy-5-(3-quinolinyl)-2-furanyl)benzenesulfonamide; N-(3,4-dihydroxy-5-(3-quinolinyl)-2-furanyl)acetamide; N-(3,4-dihydroxy-5-(3-quinolinyl)-2-furanyl)-carbamic acid ethyl ester; N-(3,4-dihydroxy-5-(3-quinolinyl)-2-furanyl)benzamide; N-(3-trimethylsilyloxy-4-hydroxy-5-(3-quinolinyl)-2-furanyl)-4-bromobutanamide; N-(3,4-dihydroxy-5-(3-quinolinyl)-2-furanyl)-2-pyrrolidinone; N-(3,4-dihydroxy-5-(3-quinolinyl)-2-furanyl)succinimide; N-(3-trimethylsilyloxy-4-hydroxy-5-(3-quinolinyl)-2-furanyl)-3-bromopropylsulfonamide; N-(3,4-dihydroxy-5-(3-quinolinyl)-2-furanyl)-1,1-dioxide-isothiazolidine; N-methyl-N'-(3,4-dihydroxy-5-(3-quinolinyl)-2-furanyl)ethanesulfonamide; N-(3-acetoxy-4-hydroxy-5-(3-quinolinyl)-2-furanyl)methanesulfonamide; N-(3-acetoxy-4-hydroxy-5-(3-quinolinyl)-2-furanyl)ethanesulfonamide; N-(3-acetoxy-4-hydroxy-5-(3-quinolinyl)-2-furanyl)benzenesulfonamide; N-(3-acetoxy-4-hydroxy-5-(3-quinolinyl)-2-furanyl)-acetamide; N-(3-acetoxy-4-hydroxy-5-(3-quinolinyl)-2-furanyl)-carbamic acid ethyl ester; N-(3-acetoxy-4-hydroxy-5-(3-quinolinyl)-2-furanyl)benzamide; N-(3-acetoxy-4-hydroxy-5-(3-quinolinyl)-2-furanyl)-4-bromobutanamide; N-(3-acetoxy-4-hydroxy-5-(3-quinolinyl)-2-furanyl)-2-pyrrolidinone; N-(3-acetoxy-4-hydroxy-5-(3-quinolinyl)-2-furanyl)succinimide; N-(3-acetoxy-4-hydroxy-5-(3-quinolinyl)-2-furanyl)-3-bromopropylsulfonamide; N-(3-acetoxy-4-hydroxy-5-(3-quinolinyl)-2-furanyl)-1,1-dioxide-isothiazolidine; N-methyl-N'-(3-acetoxy-4-hydroxy-5-(3-quinolinyl)-2-furanyl)ethanesulfonamide; 2-(3-quinolinyl)-2-methyl-4-trimethylsilyloxy-5-amino-3(2H)-furanone; 2-(3-quinolinyl)-2-methyl-4-hydroxy-5-amino-3(2H)-furanone; N-(2-(3-quinolinyl)-2-methyl-4-hydroxy-3(2H)-furanon-5-yl)-methanesulfonamide; N-(2-(3-quinolinyl)-2-methyl-4- hydroxy-3(2H)-furanon-5-yl)-ethanesulfonamide; N-(2-(3-quinolinyl)-2-methyl-4-hydroxy-3(2H)-furanon-5-yl)-benzenesulfonamide; N-(2-(3-quinolinyl)-2-methyl-4-hydroxy-3(2H)-furanon-5-yl)-acetamide; N-(2-(3-quinolinyl)-2-methyl-4-hydroxy-3(2H)-furanon-5-yl)-carbamic acid ethyl ester; N-(2-(3-quinolinyl)-2-methyl-4-hydroxy-3(2H)-furanon-5-yl)-benzamide; N-(2-(3-quinolinyl)-2-methyl-4-hydroxy-3(2H)-furanon-5-yl)-4-bromobutanamide; N-(2-(3-quinolinyl)-2-methyl-4-hydroxy-3(2H)-furanon-5-yl)-2-pyrrolidinone; N-(2-(3-quinolinyl)-2-methyl-4-hydroxy-3(2H)-furanon-5-yl)-succinimide; N-(2-(3-quinolinyl)-2-methyl-4-hydroxy-3(2H)-furanon-5-yl)-3-bromopropylsulfonamide; N-(2-(3-quinolinyl)-2-methyl-4-hydroxy-3(2H)-furanon-5-yl)-1,1-dioxide-isothiazolidine; N-methyl-N'-(2-(3-quinolinyl)-2-methyl-4-hydroxy-3(2H)-furanon-5-yl)-ethanesulfonamide; 2-(3-quinolinyl)-2-methyl-4-acetoxy-5-amino-3(2H)-furanone; N-(2-(3-quinolinyl)-2-methyl-4-acetoxy-3(2H)-furanon-5-yl)-methanesulfonamide; N-(2-(3-quinolinyl)-2-methyl-4-acetoxy-3(2H)-furanon-5-yl)-ethanesulfonamide; N-(2-(3-quinolinyl)-2-methyl-4-acetoxy-3(2H)-furanon-5-yl)-benzenesulfonamide; N-(2-(3-quinolinyl)-2-methyl-4-acetoxy-3(2H)-furanon-5-yl)-acetamide; N-(2-(3-quinolinyl)-2-methyl-4-acetoxy-3(2H)-furanon-5-yl)-carbamic acid ethyl ester; N-(2-(3-quinolinyl)-2-methyl-4-acetoxy-3(2H)-furanon-5-yl)-benzamide; N-(2-(3-quinolinyl)-2-methyl-4-acetoxy-3(2H)-furanon-5-yl)-4-bromobutanamide; N-(2-(3-quinolinyl)-2-methyl-4-acetoxy-3(2H)-furanon-5-yl)-2-pyrrolidinone; N-(2-(3-quinolinyl)-2-methyl-4-acetoxy-3(2H)-furanon-5-yl)-succinimide; N-(2-(3-quinolinyl)-2-methyl-4-acetoxy-3(2H)-furanon-5-yl)-3-bromopropylsulfonamide; N-(2-(3-quinolinyl)-2-methyl-4-acetoxy-3(2H)-furanon-5-yl)-1,1-dioxide-isothiazolidine; N-methyl-N'-(2-(3-quinolinyl)-2-methyl-4-acetoxy-3(2H)-furanon-5-yl)-ethanesulfonamide; 2-(4-quinolinyl)-5-amino-4-hydroxy-3(2H)-furanone; 2-(4-quinolinyl)-4-(acetoxy)-5-amino-3(2H)-furanone; 2-(4-quinolinyl)-4-[[phenylsulfonyl]oxy]-5-amino-3(2H)-furanone; N-(3,4-dihydroxy-5-(4-quinolinyl)-2-furanyl)methanesulfonamide; N-(3,4-dihydroxy-5-(4-quinolinyl)-2-furanyl)ethanesulfonamide; N-(3,4-dihydroxy-5-(4-quinolinyl)-2-furanyl)benzenesulfonamide; N-(3,4-dihydroxy-5-(4-quinolinyl)-2-furanyl)acetamide; N-(3,4-dihydroxy-5-(4-quinolinyl)-2-furanyl)-carbamic acid ethyl ester; N-(3,4-dihydroxy-5-(4-quinolinyl)-2-furanyl)benzamide; N-(3-trimethylsilyloxy-4-hydroxy-5-(4-quinolinyl)-2-furanyl)-4-bromobutanamide; N-(3,4-dihydroxy-5-(4-quinolinyl)-2-furanyl)-2-pyrrolidinone; N-(3,4-dihydroxy-5-(4-quinolinyl)-2-furanyl)succinimide; N-(3-trimethylsilyloxy-4-hydroxy-5-(4-quinolinyl)-2-furanyl)-3-bromopropylsulfonamide; N-(3,4-dihydroxy-5-(4-quinolinyl)-2-furanyl)-1,1-dioxide-isothiazolidine; N-methyl-N'-(3,4-dihydroxy-5-(4-quinolinyl)-2-furanyl)ethanesulfonamide; N-(3-acetoxy-4-hydroxy-5-(4-quinolinyl)-2-furanyl)methanesulfonamide; N-(3-acetoxy-4-hydroxy-5-(4-quinolinyl)-2-furanyl)ethanesulfonamide; N-(3-acetoxy-4-hydroxy-5-(4-quinolinyl)-2-furanyl)benzenesulfonamide; N-(3-acetoxy-4-hydroxy-5-(4-quinolinyl)-2-furanyl)-acetamide; N-(3-acetoxy-4-hydroxy-5-(4-quinolinyl)-2-furanyl)-carbamic acid ethyl ester; N-(3-acetoxy-4-hydroxy-5-(4-quinolinyl)-2-furanyl)benzamide; N-(3-acetoxy-4-hydroxy-5-(4-quinolinyl)-2-furanyl)-4-bromobutanamide; N-(3-acetoxy-4-hydroxy-5-(4-quinolinyl)-2-furanyl)-2-pyrrolidinone; N-(3-acetoxy-4-hydroxy-5-(4-quinolinyl)-2-furanyl)succinimide; N-(3-acetoxy-4-hydroxy-5-(4-quinolinyl)-2-furanyl)-3-bromopropylsulfonamide; N-(3-acetoxy-4-hydroxy-5-(4-quinolinyl)-2-furanyl)-1,1-dioxide-isothiazolidine; N-methyl-N'-(3-acetoxy-4-hydroxy-5-(4-quinolinyl)-2-furanyl)ethanesulfonamide; 2-(4-quinolinyl)-2-methyl-4-trimethylsilyloxy-5-amino-3(2H)-furanone; 2-(4-quinolinyl)-2-methyl-4-hydroxy-5-amino-3(2H)-furanone; N-(2-(4-quinolinyl)-2-methyl-4-hydroxy-3(2H)-furanon-5-yl)-methanesulfonamide; N-(2-(4-quinolinyl)-2-methyl-4-hydroxy-3(2H)-furanon-5-yl)-ethanesulfonamide; N-(2-(4-quinolinyl)-2-methyl-4-hydroxy-3(2H)-furanon-5-yl)-benzenesulfonamide; N-(2-(4-quinolinyl)-2-methyl-4-hydroxy-3(2H)-furanon-5-yl)-acetamide; N-(2-(4-quinolinyl)-2-methyl-4-hydroxy-3(2H)-furanon-5-yl)-carbamic acid ethyl ester; N-(2-(4-quinolinyl)-2-methyl-4-hydroxy-3(2H)-furanon-5-yl)-benzamide; N-(2-(4-quinolinyl)-2-methyl-4-hydroxy-3(2H)-furanon-5-yl)-4-bromobutanamide; N-(2-(4-quinolinyl)-2-methyl-4-hydroxy-3(2H)-furanon-5-yl)-2-pyrrolidinone; N-(2-(4-quinolinyl)-2-methyl-4-hydroxy-3(2H)-furanon-5-yl)-succinimide; N-(2-(4-quinolinyl)-2-methyl-4-hydroxy-3(2H)-furanon-5-yl)-3-bromopropylsulfonamide; N-(2-(4-quinolinyl)-2-methyl-4-hydroxy-3(2H)-furanon-5-yl)-1,1-dioxide-isothiazolidine; N-methyl-N'-(2-(4-quinolinyl)-2-methyl-4-hydroxy-3(2H)-furanon-5-yl)-ethanesulfonamide; 2-(4-quinolinyl)-2-methyl-4-acetoxy-5-amino-3(2H)-furanone; N-(2-(4-quinolinyl)-2-methyl-4-acetoxy-3(2H)-furanon-5-yl)-methanesulfonamide; N-(2-(4-quinolinyl)-2-methyl-4-acetoxy-3(2H)-furanon-5-yl)-ethanesulfonamide; N-(2-(4-quinolinyl)-2-methyl-4-acetoxy-3(2H)-furanon-5-yl)-benzenesulfonamide; N-(2-(4-quinolinyl)-2-methyl-4-acetoxy-3(2H)-furanon-5-yl)-acetamide; N-(2-(4-quinolinyl)-2-methyl-4-acetoxy-3(2H)-furanon-5-yl)-carbamic acid ethyl ester; N-(2-(4-quinolinyl)-2-methyl-4-acetoxy-3(2H)-furanon-5-yl)-benzamide; N-(2-(4-quinolinyl)-2-methyl-4-acetoxy-3(2H)-furanon-5-yl)-4-bromobutanamide; N-(2-(4-quinolinyl)-2-methyl-4-acetoxy-3(2H)-furanon-5-yl)-2-pyrrolidinone; N-(2-(4-quinolinyl)-2-methyl-4-acetoxy-3(2H)-furanon-5-yl)-succinimide; N-(2-(4-quinolinyl)-2-methyl-4-acetoxy-3(2H)-furanon-5-yl)-3-bromopropylsulfonamide; N-(2-(4-quinolinyl)-2-methyl-4-acetoxy-3(2H)-furanon-5-yl)-1,1-dioxide-isothiazolidine; N-methyl-N'-(2-(4-quinolinyl)-2-methyl-4-acetoxy-3(2H)-furanon-5-yl)-ethanesulfonamide.

Another aspect of the invention relates to a subset of the compounds represented by the structure of Formula I that are represented by the structure of Formula II:

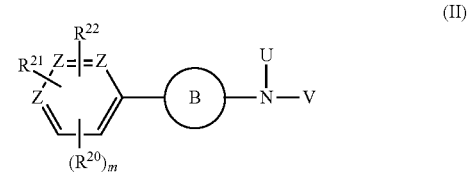

(II)

wherein Z is selected from the group consisting of C and N;

wherein $R^{20}$, $R^{21}$, and $R^{22}$ are independently selected from the group consisting of H, —F, —Cl, —Br, —I, —OH, —SH, —CN, $NO_2$, —NO, $—NH_2$, —NHR, —NRR, —C(O)R, —C(O)OH, —C(O)OR, $—C(O)NH_2$, —C(O)NHR, —C(O)NRR, —SOR, $—SO_2R$, $—SO_2NH_2$, $—SO_2NHR$, and $—SO_2NR_2$;

wherein each R is independently selected from the group consisting of ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-

$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl, and substituted 6-26 membered heteroarylalkyl;

wherein B is selected from the group consisting of

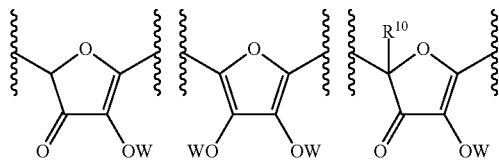

wherein $R^{10}$ is selected from the group consisting of ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl, and substituted 6-26 membered heteroarylalkyl;

wherein W is selected from the group consisting of hydrogen, alkyl, haloalkyl, —C(O)R, —C(O)OR, —SOR, —SO$_2$R, —C(O)NHR, and —C(O)NR$_2$;

wherein R is independently selected from the group consisting of ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl, and substituted 6-26 membered heteroarylalkyl;

wherein U is selected from the group consisting of hydrogen, ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, arylalkyl, substituted ($C_5$-$C_{20}$) aryl, ($C_6$-$C_{26}$) substituted ($C_6$-$C_{26}$) arylalkyl, 5-20 membered heteroaryl, substituted 5-20 membered heteroaryl, 6-26 membered heteroarylalkyl, and substituted 6-26 membered heteroaryl alkyl;

wherein V is selected from the group consisting of —NHSO$_2$R, —N(R)SO$_2$R, —C(O)R, —C(O)OR, —C(S)R, and —C(S)OR;

wherein both U and V are not hydrogen; and wherein U and V can join together to form an unsubstituted or substituted ring.

Another aspect of the invention relates to subset of the compounds represented by the structure of Formula II that are represented by the structure of Formula III:

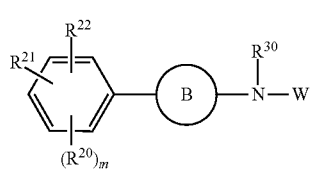

(III)

$R^{20}$, $R^{21}$, and $R^{22}$ are independently selected from the group consisting of H, —F, —Cl, —Br, —I, —OH, —SH, —CN, —CN, NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl, and substituted 6-26 membered heteroarylalkyl;

B is selected from the group consisting of

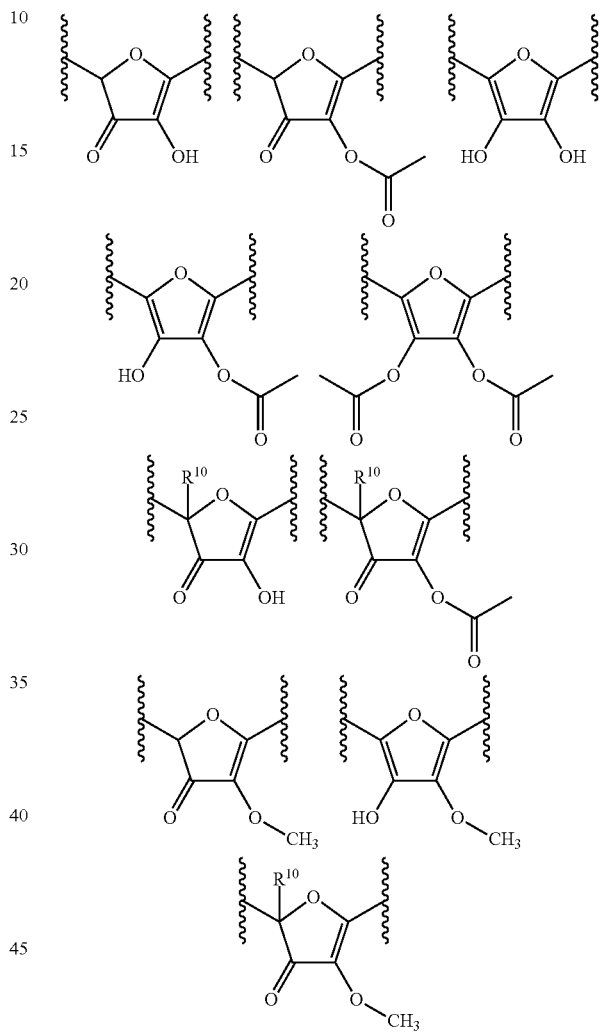

wherein $R^{10}$ is selected from the group consisting of hydrogen, ($C_1$-$C_5$) substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl, and substituted 6-26 membered heteroarylalkyl; and wherein $R^{30}$ is selected from the group consisting of hydrogen, ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl, and substituted 6-26 membered heteroarylalkyl; and wherein W is selected from the group consisting of hydrogen, alkyl, haloalkyl, —C(O)R, —C(O)OR, —SOR, —SO₂R, —C(O)NHR, —C(O)NR₂ where R is independently ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl or substituted 6-26 membered heteroarylalkyl.

Another aspect of the invention relates to subset of the compounds represented by the structure of Formula III that are represented by the structure of Formula IV:

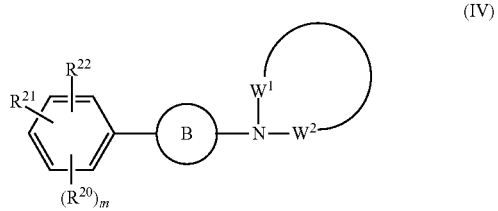

(IV)

wherein $R^{20}$, $R^{21}$, and $R^{22}$ are independently selected from the group consisting of H, —F, —Cl, —Br, —I, —OH, —SH, —CN, —CN, NO2, —NO, —NH₂, —NHR, —NRR, —C(O)R, —C(O)OH, —C(O)OR, —C(O)NH₂, —C(O)NHR, and —C(O)NRR;

wherein each R is independently selected from the group consisting of ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl or substituted 6-26 membered heteroarylalkyl;

wherein B is selected from the group consisting of

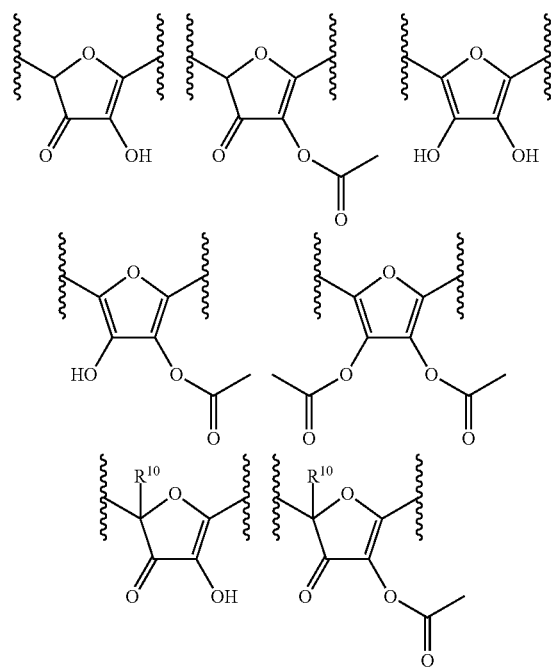

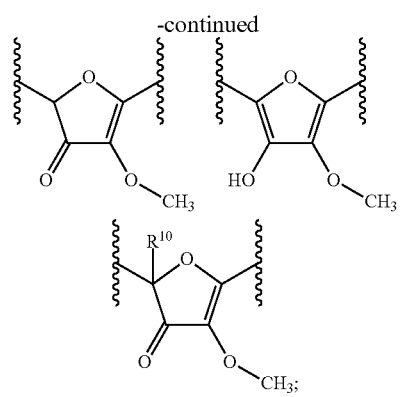

wherein $R^{10}$ is selected from the group consisting of ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl, and substituted 6-26 membered heteroarylalkyl;

wherein $W^1$ and $W^2$ are independently selected from the group consisting of alkyl, haloalkyl, —C(O)R, —C(O)OR, —SOR, —SO₂R, —C(O)NHR, and —C(O)NR₂;

wherein R is independently selected from the group consisting of ($C_1$-$C_5$) alkyl, substituted ($C_1$-$C_6$) alkyl, ($C_2$-$C_6$) alkenyl, substituted ($C_2$-$C_6$) alkenyl, ($C_2$-$C_6$) alkynyl, substituted ($C_2$-$C_6$) alkynyl, ($C_5$-$C_{20}$) aryl, substituted ($C_5$-$C_{20}$) aryl, ($C_6$-$C_{26}$) arylalkyl, substituted ($C_6$-$C_{26}$) arylalkyl, 5-20 membered heteroaryl, substituted 5-20 membered heteroaryl, 6-26 membered heteroarylalkyl, and substituted 6-26 membered heteroarylalkyl.

Another aspect of the invention relates to a subset of the compounds represented by the structure of

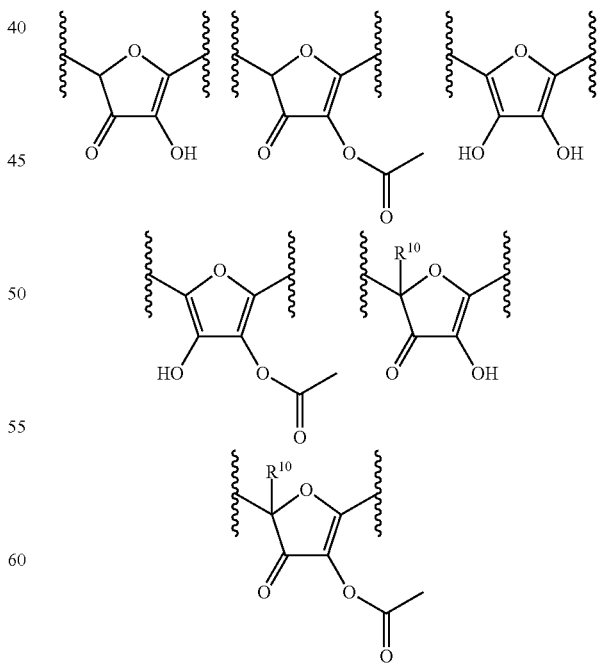

A related aspect of the invention relates to a subset of the compounds represented by the structure of Formula IV, wherein $W^1$ and $W^2$ are joined together to form an unsubstituted or substituted ring selected from the group consisting of

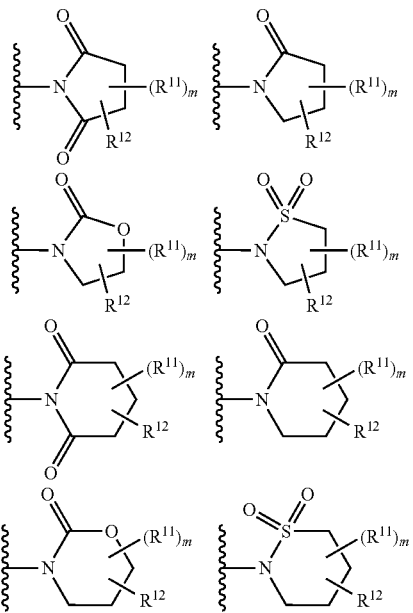

wherein $R^{11}$ and $R^{12}$ are independently selected from the group consisting of hydrogen, —OH, —F, —Cl, —Br, —I, —C(O)R, —CO$_2$R, —CONH2, —CN, —SO$_2$R, (C$_1$-C$_5$) alkyl, substituted (C$_1$-C$_6$) alkyl, (C$_2$-C$_6$) alkenyl, substituted (C$_2$-C$_6$) alkenyl, (C$_2$-C$_6$) alkynyl, substituted (C$_2$-C$_6$) alkynyl, (C$_5$-C$_{20}$) aryl, substituted (C$_5$-C$_{20}$) aryl, (C$_6$-C$_{26}$) arylalkyl, and substituted (C$_6$-C$_{26}$) arylalkyl.

A related aspect of the invention relates to a subset of the compounds represented by the structure of Formula I that are represented by the structure of Formula V:

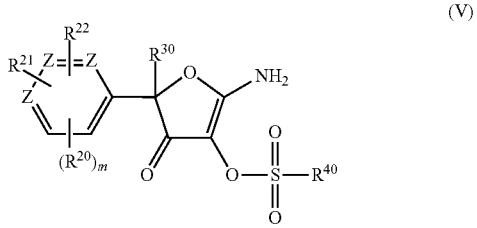

wherein Z is selected from the group consisting of C and N;

wherein $R^{20}$, $R^{21}$, and $R^{22}$ are independently selected from the group consisting of H, —F, —Cl, —Br, —I, —OH, —SH, —CN, —CN, NO$_2$, —NO, —NH$_2$, —NHR, —NRR, —C(O)R, —C(O)OH, —C(O)OR, —C(O)NH$_2$, —C(O)NHR, and —C(O)NRR;

wherein each R is independently selected from the group consisting of (C$_1$-C$_5$) alkyl, substituted (C$_1$-C$_6$) alkyl, (C$_2$-C$_6$) alkenyl, substituted (C$_2$-C$_6$) alkenyl, (C$_2$-C$_6$) alkynyl, substituted (C$_2$-C$_6$) alkynyl, (C$_5$-C$^{20}$) aryl, substituted (C$_5$-C$_{20}$) aryl, (C$_6$-C$_{26}$) arylalkyl, substituted (C$_6$-C$_{26}$) arylalkyl, 5-20 membered heteroaryl, substituted 5-20 membered heteroaryl, 6-26 membered heteroarylalkyl, and substituted 6-26 membered heteroarylalkyl;

wherein $R^{30}$ is selected from the group consisting of hydrogen, (C$_1$-C$_5$) alkyl, substituted (C$_1$-C$_6$) alkyl, (C$_2$-C$_6$) alkenyl, substituted (C2-C$_6$) alkenyl, (C$_2$-C$_6$) alkynyl, substituted (C$_2$-C$_6$) alkynyl, (C$_5$-C$_{20}$) aryl, substituted (C$_5$-C$_{20}$) aryl, (C$_6$-C$_{26}$) arylalkyl, substituted (C$_6$-C$_{26}$) arylalkyl, 5-20 membered heteroaryl, substituted 5-20 membered heteroaryl, 6-26 membered heteroarylalkyl, and substituted 6-26 membered heteroarylalkyl; and wherein $R^{40}$ is selected from the group consisting of (C$_1$-C$_5$) alkyl, substituted (C$_1$-C$_6$) alkyl, (C$_2$-C$_6$) alkenyl, substituted (C$_2$-C$_6$) alkenyl, (C$_2$-C$_6$) alkynyl, substituted (C$_2$-C$_6$) alkynyl, (C$_5$-C$_{20}$) aryl, substituted (C$_5$-C$_{20}$) aryl, (C$_6$-C$_{26}$) arylalkyl, substituted (C$_6$-C$_{26}$) arylalkyl, 5-20 membered heteroaryl, substituted 5-20 membered heteroaryl, 6-26 membered heteroarylalkyl, and substituted 6-26 membered heteroarylalkyl.

One aspect of the invention relates to a method of modulating the level or activity of at least one prolyl hydroxylase in a cell, comprising contacting the cell with an effective amount of the compound or salt described above and encompassed by any of Formulas I-V. Another aspect relates to a method wherein at least one of said prolyl hydroxylases is prolyl-4-hydrolase.

One aspect of the invention relates to a method of modulating the level or activity of at least one prolyl hydroxylase in a subject, which comprises administering a therapeutically-effective amount of an effective amount of the compound or salt described above and encompassed by any of Formulas I-V to said subject. Another aspect relates to a method, wherein at least one of said prolyl hydroxylases is prolyl-4-hydrolase.

Specific aspects of the invention include compounds that are represented by Formula IV selected from the group consisting of N-(3,4-dihydroxy-5-(4-chlorophenyl)-2-furanyl)methanesulfonamide;
N-(3,4-dihydroxy-5-(4-chlorophenyl)-2-furanyl)ethanesulfonamide;
N-(3,4-dihydroxy-5-(4-chlorophenyl)-2-furanyl)benzenesulfonamide;
N-(3,4-dihydroxy-5-(4-chlorophenyl)-2-furanyl)acetamide;
N-(3,4-dihydroxy-5-(4-chlorophenyl)-2-furanyl)-carbamic acid ethyl ester;
N-(3,4-dihydroxy-5-(4-chlorophenyl)-2-furanyl)benzamide;
N-(3-trimethylsilyloxy-4-hydroxy-5-(4-chlorophenyl)-2-furanyl)-4-bromobutanamide;
N-(3,4-dihydroxy-5-(4-chlorophenyl)-2-furanyl)-2-pyrolidinone;
N-(3,4-dihydroxy-5-(4-chlorophenyl)-2-furanyl)succinimide;
N-(3-trimethylsilyloxy-4-hydroxy-5-(4-chlorophenyl)-2-furanyl)-3-bromopropylsulfonamide;
N-(3,4-dihydroxy-5-(4-chlorophenyl)-2-furanyl)-1,1-dioxide-isothiazolidine; and
N-methyl-N'-(3,4-dihydroxy-5-(4-chlorophenyl)-2-furanyl)ethanesulfonamide.

Specific aspects of the invention include compounds that are represented by Formula IV selected from the group consisting of N-(3-acetoxy-4-hydroxy-5-(4-chlorophenyl)-2-furanyl) methanesulfonamide;
N-(3-acetoxy-4-hydroxy-5-(4-chlorophenyl)-2-furanyl) ethanesulfonamide;
N-(3-acetoxy-4-hydroxy-5-(4-chlorophenyl)-2-furanyl) benzenesulfonamide;

N-(3-acetoxy-4-hydroxy-5-(4-chlorophenyl)-2-furanyl)-acetamide;

N-(3-acetoxy-4-hydroxy-5-(4-chlorophenyl)-2-furanyl)-carbamic acid ethyl ester;

N-(3-acetoxy-4-hydroxy-5-(4-chlorophenyl)-2-furanyl) benzamide;

N-(3-acetoxy-4-hydroxy-5-(4-chlorophenyl)-2-furanyl)-4-bromobutanamide;

N-(3-acetoxy-4-hydroxy-5-(4-chlorophenyl)-2-furanyl)-2-pyrrolidinone;

N-(3-acetoxy-4-hydroxy-5-(4-chlorophenyl)-2-furanyl) succinimide;

N-(3-acetoxy-4-hydroxy-5-(4-chlorophenyl)-2-furanyl)-3-bromopropylsulfonamide;

N-(3-acetoxy-4-hydroxy-5-(4-chlorophenyl)-2-furanyl)-1,1-dioxide-isothiazolidine; and N-methyl-N'-(3-acetoxy-4-hydroxy-5-(4-chlorophenyl)-2-furanyl)ethanesulfonamide.

Specific aspects of the invention include compounds that are represented by Formula IV selected from the group consisting of 2-(4-chlorophenyl)-2-methyl-4-trimethylsilyloxy-5-amino-3(2H)-furanone;

2-(4-chlorophenyl)-2-methyl-4-hydroxy-5-amino-3(2H)-furanone;

N-(2-(4-chlorophenyl)-2-methyl-4-hydroxy-3(2H)-furanon-5-yl)-methanesulfonamide;

N-(2-(4-chlorophenyl)-2-methyl-4-hydroxy-3(2H)-furanon-5-yl)-ethanesulfonamide;

N-(2-(4-chlorophenyl)-2-methyl-4-hydroxy-3(2H)-furanon-5-yl)-benzenesulfonamide;

N-(2-(4-chlorophenyl)-2-methyl-4-hydroxy-3(2H)-furanon-5-yl)-acetamide;

N-(2-(4-chlorophenyl)-2-methyl-4-hydroxy-3(2H)-furanon-5-yl)-carbamic acid ethyl ester;

N-(2-(4-chlorophenyl)-2-methyl-4-hydroxy-3(2H)-furanon-5-yl)-benzamide;

N-(2-(4-chlorophenyl)-2-methyl-4-hydroxy-3(2H)-furanon-5-yl)-4-bromobutanamide;

N-(2-(4-chlorophenyl)-2-methyl-4-hydroxy-3(2H)-furanon-5-yl)-2-pyrrolidinone;

N-(2-(4-chlorophenyl)-2-methyl-4-hydroxy-3(2H)-furanon-5-yl)-succinimide;

N-(2-(4-chlorophenyl)-2-methyl-4-hydroxy-3(2H)-furanon-5-yl)-3-bromopropylsulfonamide;

N-(2-(4-chlorophenyl)-2-methyl-4-hydroxy-3(2H)-furanon-5-yl)-1,1-dioxide-isothiazolidine; and N-methyl-N'-(2-(4-chlorophenyl)-2-methyl-4-hydroxy-3(2H)-furanon-5-yl)-ethanesulfonamide.

Specific aspects of the invention include compounds that are represented by Formula IV selected from the group consisting of 2-(4-chlorophenyl)-2-methyl-4-acetoxy-5-amino-3(2H)-furanone;

N-(2-(4-chlorophenyl)-2-methyl-4-acetoxy-3(2H)-furanon-5-yl)-methanesulfonamide;

N-(2-(4-chlorophenyl)-2-methyl-4-acetoxy-3(2H)-furanon-5-yl)-ethanesulfonamide;

N-(2-(4-chlorophenyl)-2-methyl-4-acetoxy-3(2H)-furanon-5-yl)-benzenesulfonamide;

N-(2-(4-chlorophenyl)-2-methyl-4-acetoxy-3(2H)-furanon-5-yl)-acetamide;

N-(2-(4-chlorophenyl)-2-methyl-4-acetoxy-3(2H)-furanon-5-yl)-carbamic acid ethyl ester;

N-(2-(4-chlorophenyl)-2-methyl-4-acetoxy-3(2H)-furanon-5-yl)-benzamide;

N-(2-(4-chlorophenyl)-2-methyl-4-acetoxy-3(2H)-furanon-5-yl)-4-bromobutanamide;

N-(2-(4-chlorophenyl)-2-methyl-4-acetoxy-3(2H)-furanon-5-yl)-2-pyrrolidinone;

N-(2-(4-chlorophenyl)-2-methyl-4-acetoxy-3(2H)-furanon-5-yl)-succinimide;

N-(2-(4-chlorophenyl)-2-methyl-4-acetoxy-3(2H)-furanon-5-yl)-3-bromopropylsulfonamide;

N-(2-(4-chlorophenyl)-2-methyl-4-acetoxy-3(2H)-furanon-5-yl)-1,1-dioxide-isothiazolidine; and N-methyl-N'-(2-(4-chlorophenyl)-2-methyl-4-acetoxy-3(2H)-furanon-5-yl)-ethanesulfonamide.

Therapeutic Uses of Compositions Comprising Compounds of the Invention

In some aspects, this invention provides for the use of a compound as herein described, or its isomer, metabolite, tautomer, pharmaceutically acceptable salt, pharmaceutical product, polymorph, crystal, N-oxide, hydrate, or any combination thereof, for treating, suppressing, preventing, reducing the severity, reducing the risk, or inhibiting a cell proliferation disorder in a subject.

Pharmaceutical Compositions

Related aspects of the invention are directed to compositions, including pharmaceutical compositions, comprising the compounds of the invention, noted above. One aspect of the invention is directed to a pharmaceutical composition comprising at least one pharmaceutically acceptable excipient and a therapeutically effective amount of the compound or salt disclosed above. Still another aspect of the invention relates to a method for pharmaceutical formulation of previously described compounds for use in oral and intravenous applications, and in implantable materials.

Another aspect of the present invention relates to a pharmaceutical composition including a pharmaceutical composition can contain one or more of the above-identified compounds of the present invention.

Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, emulsions, or implantable disc.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

Dosage Forms

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Optional Coatings

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

Excipients

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

Modes of Administration

The active compounds of the present invention may be orally administered, for example, with an inert diluent, or with an assailable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

The pharmaceutical forms suitable for implantable use include sterile wafers of polycarboxyphenoxypropane-sebacic-acid (pCPP:SA) polymers, poly(D,L-lactic acid), polyhydroxybutyrate, lysine diisocyanate (LDI)-glycerol polyurethane, and poly(D-L lactide-co-glycolide). In all cases, the form should be sterile and should be a wafer or disc of suitable dimensions for surgical implantation in the brain. The polymers should be stable under the conditions of manufacture and storage and should be preserved against the contaminating action of microorganisms, such as bacteria and fungi. The wafers should be biodegradable ranging from 24 hours up to 6 months.

In one aspect, the invention provides compounds and compositions, including any aspect described herein, for use in any of the methods of this invention. In one aspect, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

Pharmaceutical Compositions Comprising
Modulator Compounds of the Invention

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, monostearate salts and gelatin. Moreover, the modulators can be administered in a time release formulation, for example in a composition 5 which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

The mode of administration may be oral, for intestinal delivery; intranasal, for nasal delivery; and intravenous for delivery through the blood-brain harrier. Other modes of administration as are known in the art may also be used, including, but not limited to intrathecal, intramuscular, intrabronchial, intrarectal, intraocular, and intravaginal delivery.

The modulator compounds can be administered as oral dosage compositions for small intestinal delivery. Such oral dosage compositions for small intestinal delivery are well-known in the art, and generally comprise gastroresistent tablets or capsules (Remington's Pharmaceutical Sciences, 16th Ed., Eds. Osol, Mack Publishing Co., Chapter 89 (1980); Digenis et al, J. Pharm. Sci., 83:915-921 (1994); Vantini et al, Clinica Terapeutica, 145:445-451 (1993); Yoshitomi et al, Chem. Pharm. Bull., 40:1902'1905 (1992); Thoma et al, Pharmazie, 46:331-336 (1991); Morishita et al, Drug Design and Delivery, 7:309-319 (1991); and Lin et al, Pharmaceutical Res., 8:919'924 (1991)); each of which is incorporated by reference herein in its entirety).

Tablets are made gastroresistant by the addition of compounds such as cellulose acetate phthalate or cellulose acetate terephthalate.

Capsules are solid dosage forms in which the tight junction modulator compound is enclosed in either a hard or soft, soluble container or shell of gelatin. The gelatin used in the manufacture of capsules is obtained from collagenous material by hydrolysis. There are two types of gelatin. Type A, derived from pork skins by acid processing, and Type B, obtained from bones and animal skins by alkaline processing. The use of hard gelatin capsules permit a choice in prescribing a tight junction modulator compound or a combination thereof at the exact dosage level considered best for the individual subject. The hard gelatin capsule consists of two sections, one slipping over the other, thus completely surrounding the tight junction modulator compound. These capsules are filled by introducing the modulator compound, or gastroresistent beads containing the modulator compound, into the longer end of the capsule, and then slipping on the cap. Hard gelatin capsules are made largely from gelatin, FD&C colorants, and sometimes an opacifying agent, such as titanium dioxide. The USP permits the gelatin for this purpose to contain 0.15% (w/v) sulfur dioxide to prevent decomposition during manufacture.

In the context of the present invention, oral dosage compositions for small intestinal delivery also include liquid compositions which contain aqueous buffering agents that prevent the modulator compound from being significantly inactivated by gastric fluids in the stomach, thereby allowing the modulator compound to reach the small intestines in an active form. Examples of such aqueous buffering agents which can be employed in the present invention include bicarbonate buffer (pH 5.5 to 8.7, preferably about pH 7.4).

When the oral dosage composition is a liquid composition, it is preferable that the composition be prepared just prior to administration so as to minimize stability problems. In this case, the liquid composition can be prepared by dissolving lyophilized tight junction modulator compound in the aqueous buffering agent. Oral dosage compositions for small intestinal delivery also include liquid compositions which may optionally contain aqueous buffering agents that prevent the therapeutic agent and tight junction modulator compound
from being significantly inactivated by gastric fluids in the stomach, thereby allowing the biologically active ingredient and tight junction modulator compound to reach the small intestines in an active form. Examples of such aqueous buffering agents which can be employed in the present invention include bicarbonate buffer (pH 5.5 to 8.7, preferably about pH 7.4).

When the oral dosage composition is a liquid composition, it is preferable that the composition be prepared just prior to administration so as to minimize stability problems. In this case, the liquid composition can be prepared by dissolving lyophilized therapeutic agent and tight junction modulator compound in the aqueous buffering agent.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. For sterile powders used in the preparation of sterile injectable solutions, the preferred methods of preparation are vacuum drying and freeze-drying which yields a powder of the active ingredient plus any additional desired ingredient from a previously sterile-filtered solution thereof.

A "nasal" delivery composition differs from an "intestinal" delivery composition in that the latter must have gastroresistent properties in order to prevent the acidic degradation of the active agents in the stomach, whereas the former generally comprises water-soluble polymers with a diameter of about 50 11 m in order to reduce the mucociliary clearance, and to achieve a reproducible bioavailability of the nasally administered agents.

An "intravenous" delivery composition differs from both the "nasal" and "intestinal" delivery compositions in that there is no need for gastroresistance or water-soluble polymers in the "intravenous" delivery composition.

Nasal dosage compositions for nasal delivery are well-known in the art. Such nasal dosage compositions generally comprise water-soluble polymers that have been used extensively to prepare pharmaceutical dosage forms (Martin et al, In: Physical Chemical Principles of 20 Pharmaceutical Sciences, 3rd Ed., pages 592-638 (1983)) that can serve as carriers for peptides for nasal administration (Davis, In: Delivery Systems for Peptide Drugs, 125:1-21 (1986)). The nasal absorption of pap tides embedded in polymer matrices has been shown to be enhanced through retardation of nasal mucociliary clearance (Ilium et al, Int. J. Pharm., 46:261-265 (1988È). Other possible enhancement mechanisms include an increased concentration gradient or 25 decreased diffusion path for peptides absorption (Ting et al, Pharm. Res., 9:1330-1335 (1992). However, reduction in mucociliary clearance rate has been predicted to be a good approach toward achievement or reproducible bioavailability of nasally administered systemic drugs (Gonda et al, Pharm. Res., 7:69-75 (1990)). Microparticles with a diameter of about 50 p m are expected to deposit in the nasal cavity (Bjork et al, Int. J. Pharm., 62:187'192 (1990È); and Illum et al, Int. J. Pharm., 39:189'199 (1987), while microparticles with a diameter under 10 pm can escape the filtering system of the nose and deposit in the lower airways. Microparticles larger than 200 p m in diameter will not be retained in the nose after nasal administration (Lewis et al, Proc. Int. Symp. Control Rel. Bioact. Mater., 17:280-290 (1990)).

The particular water-soluble polymer employed is not critical to the present invention, and can be selected from any of the well-known water-soluble polymers employed for nasal dosage forms. A typical example of a water-soluble polymer useful for nasal delivery is polyvinyl alcohol (pvA). This material is a swellable hydrophilic polymer whose physical properties depend on the molecular weight, degree of hydrolysis, cross-linking density, and crystallinity (Peppas et al, In: Hydrogels in Medicine and Pharmacy, 3:109'131 (1987E. PYA can be used in the coating of dispersed materials through phase separation, spray-drying, spray-embedding, and spray-densation (Ting et al, supra).

A "skin" delivery composition comprising a modulator compound of the invention may include in addition a therapeutic or immunogenic agent, fragrance, creams, ointments, colorings, and other compounds so long as the added component does not deleteriously affect transdermal delivery of the therapeutic or immunogenic agent. Conventional pharmaceutically acceptable emulsifiers, surfactants, suspending agents, antioxidants, osmotic enhancers, extenders, diluents and preservatives may also be added. Water soluble polymers can also be used as carriers.

The particular therapeutic or immunogenic agent employed is not critical to the present invention, and can be, e.g., any drug compound, biologically active peptide, vaccine, or any other moiety otherwise not absorbed through the transcellular pathway, regardless of size or charge.

The amount of active compound in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically 35 discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically-acceptable carrier" includes any and all solvents, dispersion media, coatings, antibacterial and antifungal agents, isotonic and absorption delaying agents, and the like that are physiologically compatible. In one embodiment, the carrier is 10 suitable for parenteral administration. A carrier may be suitable for administration into the central nervous system (e.g., intraspinally or intracerebrally). Alternatively, the carrier can be suitable for intravenous, intraperitoneal or intramuscular administration. In another embodiment, the carrier is suitable for oral administration. Pharmaceutically-acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

While specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only, and not limiting as to the scope of the invention, which is to be given the full breadth of the appended claims, and any equivalent, thereof.

EXAMPLES

The foregoing discussion may be better understood in connection with the following representative examples which are presented for purposes of illustrating the principle methods and compositions of the invention, and not by way of limitation. Various other examples will be apparent to the person skilled in the art after reading the present disclosure without departing from the spirit and scope of the invention. It is intended that all such other examples be included within the scope of the appended claims.

General Materials and Methods

All parts are by weight (e.g., % w/w), and temperatures are in degrees centigrade (° C.), unless otherwise indicated.

General Chemical Procedures

Melting points were determined with a Hoover melting point apparatus and are uncorrected. Infrared (IR) spectra for the compounds were recorded in KBr discs on a Mattson Satellite FTIR in cm$^{-1}$. $^1$H and $^{13}$C spectra were recorded in DMSO-d$_6$ on a Bruker Avance III DPX 300 MHz instrument. $^{19}$F spectra were recorded in DMSO d$_6$ on a Bruker Avance III 600 (564.6 mHz). Chemical shifts were expressed in parts per million (δ) with tetramethylsilane as internal standard. Mass spectrometry was performed on a Thermo Scientific LTQ-FT at the University of Cincinnati Mass Spectrometry facility. The purity of the compounds was monitored by HPLC using a Waters 2695 separation module and a 2487 dual λ absorbance detector with a NovaPak C18 4 μm 3.9×150 mm column. The mobile phases consisted of acetonitrile/H$_2$O using a 30 minute gradient. All compounds were ≥95%. Microanalysis was performed by Atlantic Microlab Inc., and all compounds were found to be ±0.4%. All reagents were from Sigma-Aldrich. LogS, LogP, Log BBB, human intestinal absorption, p-glycoprotein category, CYP 2C9 pKi, hERG pIC50, CYP 2D6 affinity category, oral CNS score, IV CNS score, MW, flexibility, and total polar surface area were calculated using StarDrop 5.1.1 release Build 178.

Scheme 1 illustrates the synthetic reactions used to summarize these reactions. Table 1 is a non-limiting list of aryl compounds that can be incorporated as "Ar$^1$" or "Ar$^2$" from Formula Ia, Ib, and IIa. Tables 1A and 2 illustrate the structures, names, and numbers of a variety of key compounds disclosed in this application.

TABLE 1

| Compound | Structure | Ar$^1$ or Ar$^2$ |
|---|---|---|
| a | 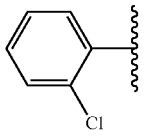 | 2-chlorophenyl |
| b | 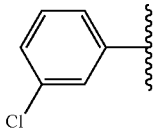 [SMILES: *c1cccc(Cl)c1] | 3-chlorophenyl |

TABLE 1-continued

| Compound | Structure | Ar¹ or Ar² |
|---|---|---|
| c | 4-Cl-C₆H₄- | 4-chlorophenyl |
| d | 2,3-Cl₂-C₆H₃- | 2,3-dichlorophenyl |
| e | 2,4-Cl₂-C₆H₃- | 2,4-dichlorophenyl |
| f | 2,5-Cl₂-C₆H₃- | 2,5-dichlorophenyl |
| g | 3-(CO₂CH₃)-C₆H₄- | 3-carboxymethylphenyl |
| h | 3,4-Cl₂-C₆H₃- | 3,4-dichlorophenyl |
| i | 3,5-Cl₂-C₆H₃- | 3,5-dichlorophenyl |
| j | 2-F-C₆H₄- | 2-fluorophenyl |
| k | 3-F-C₆H₄- | 3-fluorophenyl |
| l | 4-F-C₆H₄- | 4-fluorophenyl |
| m | 2,3-F₂-C₆H₃- | 2,3-difluorophenyl |
| n | 2,4-F₂-C₆H₃- | 2,4-difluorophenyl |
| o | 2,5-F₂-C₆H₃- | 2,5-difluorophenyl |
| p | 2,6-F₂-C₆H₃- | 2,6-difluorophenyl |
| q | 3,4-F₂-C₆H₃- | 3,4-difluorophenyl |
| r | 3,5-F₂-C₆H₃- | 3,5-difluorophenyl |
| s | 2-OMe-C₆H₄- | 2-methoxyphenyl |
| t | 3-OMe-C₆H₄- | 3-methoxyphenyl |
| u | 4-OMe-C₆H₄- | 4-methoxyphenyl |
| v | 2,3-(OMe)₂-C₆H₃- | 2,3-dimethoxyphenyl |

TABLE 1-continued

| Compound | Structure | Ar¹ or Ar² |
|---|---|---|
| w | (2,4-dimethoxyphenyl structure) | 2,4-dimethoxyphenyl |
| x | (2,5-dimethoxyphenyl structure) | 2,5-dimethoxyphenyl |
| y | (2,6-dimethoxyphenyl structure) | 2,6-dimethoxyphenyl |
| z | (3,4-dimethoxyphenyl structure) | 3,4-dimethoxyphenyl |
| aa | (3,5-dimethoxyphenyl structure) | 3-5-dimethoxyphenyl |
| ab | (2-chloro-6-fluorophenyl structure) | 2-chloro-6-fluorophenyl |
| ac | (3-chloro-4-fluorophenyl structure) | 3-chloro-4-fluorophenyl |
| ad | (2-chloro-4-fluorophenyl structure) | 2-chloro-4-fluorophenyl |
| ae | (4-chloro-3-fluorophenyl structure) | 4-chloro-3-fluorophenyl |
| af | (3-chloro-2-fluorophenyl structure) | 3-chloro-2-fluorophenyl |
| ag | (2-chloro-5-fluorophenyl structure) | 2-chloro-5-fluorophenyl |
| ah | (4-chloro-2-fluorophenyl structure) | 4-chloro-2-fluorophenyl |
| ai | (5-chloro-2-fluorophenyl structure) | 5-chloro-2-fluorophenyl |
| aj | (phenyl structure) | Ph |
| ak | (thiophene structure) | 2-thiophene |
| al | (furan structure) | 2-furan |
| am | (thiazole structure) | 2-thiazole |
| an | (1-naphthyl structure) | 1-naphthyl |
| ao | (2-naphthyl structure) | 2-napthyl |
| ap | (2-pyridyl structure) | 2-pyridyl |
| aq | (3-pyridyl structure) | 3-pyridyl |

TABLE 1-continued

| Compound | Structure | Ar¹ or Ar² |
|---|---|---|
| ar | (4-pyridyl structure) | 4-pyridyl |
| as | (2-quinolinyl structure) | 2-quinolinyl |
| at | (3-quinolinyl structure) | 3-quinolinyl |
| au | (4-quinolinyl structure) | 4-quinolinyl |
| av | (4-trifluoromethylphenyl structure) | 4-trifluoromethylphenyl |
| aw | (3-trifluoromethylphenyl structure) | 3-trifluoromethylphenyl |
| ax | (2-trifluoromethylphenyl structure) | 2-trifluoromethylphenyl |
| ay | (4-cyanophenyl structure) | 4-cyanophenyl |
| az | (3-cyanophenyl structure) | 3-cyanophenyl |

TABLE 1A

| Compound | Structure | Name |
|---|---|---|
| 1c | (structure) | 2-(4-chlorophenyl)-4-[[methylsulfonyl]oxy]-5-amino-3(2H)-furunone |
| 2c | (structure) | 2-(4-chlorophenyl)-4-[[ethylsulfonyl]oxy]-5-amino-3(2H)-furanone |
| 3c | (structure) | 2-(4-chlorophenyl)-4-[[1-propylsulfonyl]oxy]-5-amino-3(2H)-furanone |
| 4c | (structure) | 2-(4-chlorophenyl)-4-[[2-propylsulfonyl]oxyl-5-amino-3(2H)-furanone |
| 5c | (structure) | 2-(4-chlorophenyl)-4-[[1-butylsulfonyl]oxyl-5-amino-3(2H)-furanone |

TABLE 1A-continued

| Compound | Structure | Name |
|---|---|---|
| 6c | 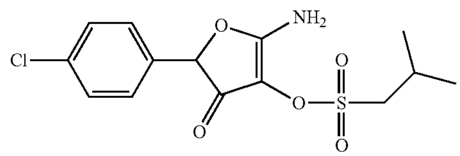 [SMILES: CC(C)CS(=O)(=O)OC1=C(N)OC(c2ccc(Cl)cc2)C1=O] | 2-(4-chlorophenyl)-4-[[3(2H)-methyl-sulfonyl]oxy]-5-amino-3(2H)-furanone |
| 7c | 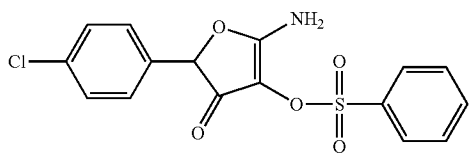 [SMILES: NC1=C(OS(=O)(=O)c2ccccc2)C(=O)C(c2ccc(Cl)cc2)O1] | 2-(4-chlorophenyl)-4-[[phenylsulfonyl]oxy]-5-amino-3(2H)-furanone |
| 8a | 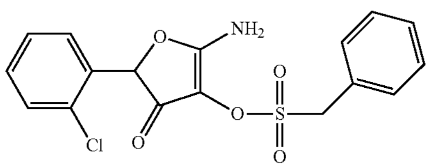 [SMILES: NC1=C(OS(=O)(=O)Cc2ccccc2)C(=O)C(c2ccccc2Cl)O1] | 2-(2-chlorophenyl)-4-[[phenylmethylsulfonyl]oxy]-5-amino-3(2H)-furanone |
| 8b | 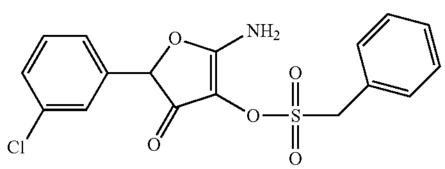 [SMILES: NC1=C(OS(=O)(=O)Cc2ccccc2)C(=O)C(c2cccc(Cl)c2)O1] | 2-(3-chlorophenyl)-4-[[phenylmethylsulfonyl]oxy]-5-amino-3(2H)-furanone |
| 8c | 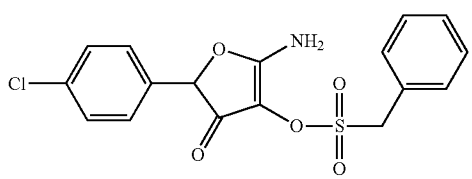 [SMILES: NC1=C(OS(=O)(=O)Cc2ccccc2)C(=O)C(c2ccc(Cl)cc2)O1] | 2-(4-chlorophenyl)-4-[[phenylmethylsulfonyl]oxy]-5-amino-3(2H)-furanone |
| 8d | 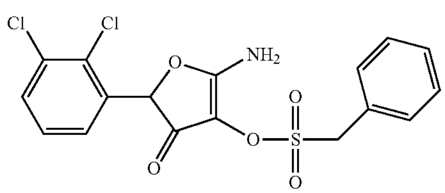 | 2-(2,3-dichlorophenyl)-4-[[phenylmethylsulfonyl]oxy]-5-amino-3(2H)-furanone |
| 8e | 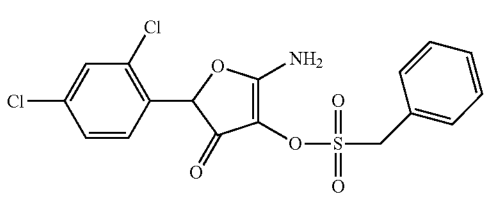 | 2-(2,4-dichlorophonyl)-4-[[phenylmethylsulfonyl]oxy]-5-amino-3(2H)-furanone |
| 8f | 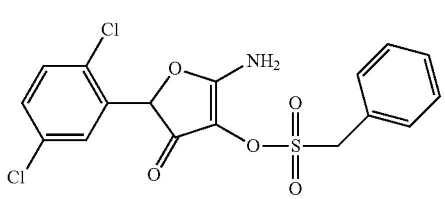 | 2-(2,5-dichlorophenyl)-4-[[phenylmethylsulfonyl]oxy]-5-amino-3(2H)-furanone |

TABLE 1A-continued

| Compound | Structure | Name |
| --- | --- | --- |
| 8g | 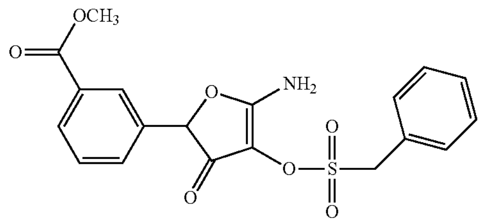 [SMILES: COC(=O)c1cccc(C2OC(N)=C(OS(=O)(=O)Cc3ccccc3)C2=O)c1] | 2-(3-carboxymethylphenyl)-4-[[phenylmethylsulfonyl]oxy]-5-amino-3(2H)-furanone |
| 8h | 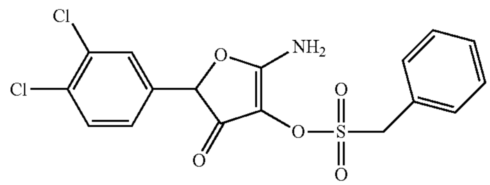 [SMILES: NC1=C(OS(=O)(=O)Cc2ccccc2)C(=O)C(c2ccc(Cl)c(Cl)c2)O1] | 2-(3,4-dichlorophenyl)-4-[[phenylmethylsulfonyl]oxy]-5-amino-3(2H)-furanone |
| 8i | 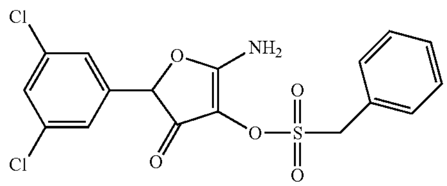 [SMILES: NC1=C(OS(=O)(=O)Cc2ccccc2)C(=O)C(c2cc(Cl)cc(Cl)c2)O1] | 2-(3,5-dichlorophenyl)-4-[[phenylmethylsulfonyl]oxy]-5-amino-3(2H)-furanone |
| 8j | 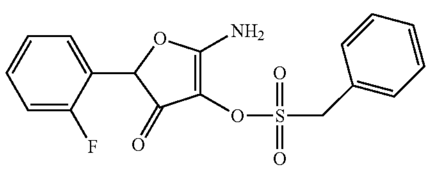 [SMILES: NC1=C(OS(=O)(=O)Cc2ccccc2)C(=O)C(c2ccccc2F)O1] | 2-(2-fluorophenyl)-4-[[phenylmethylsulfonyl]oxy]-5-amino-3(2H)-furanone |
| 8k | 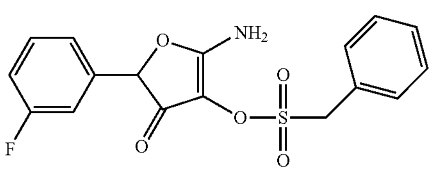 [SMILES: NC1=C(OS(=O)(=O)Cc2ccccc2)C(=O)C(c2cccc(F)c2)O1] | 2-(3-fluorophenyl)-4-[[phenylmethylsulfonyl]oxy]-5-amino-3(2H)-furanone |
| 8l | 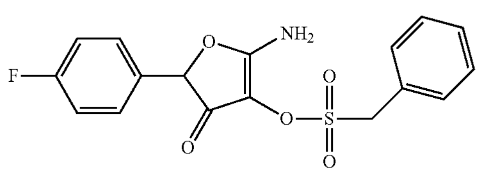 [SMILES: NC1=C(OS(=O)(=O)Cc2ccccc2)C(=O)C(c2ccc(F)cc2)O1] | 2-(4-fluorophenyl)-4-[[phenylmethylsulfonyl]oxy]-5-amino-3(2H)-furanone |
| 8m | 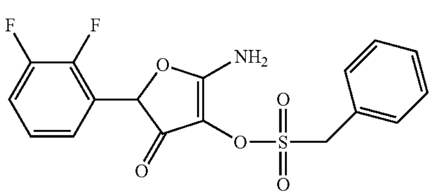 [SMILES: NC1=C(OS(=O)(=O)Cc2ccccc2)C(=O)C(c2cccc(F)c2F)O1] | 2-(2,3-difluorophonyl)-4-[[phenylmethylsulfonyl]oxy]-5-amino-3(2H)-furanone |
| 8n | 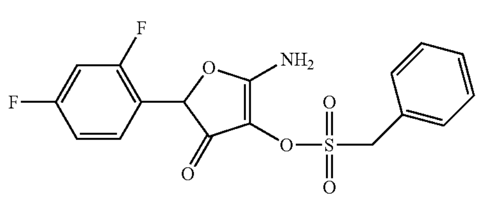 [SMILES: NC1=C(OS(=O)(=O)Cc2ccccc2)C(=O)C(c2ccc(F)cc2F)O1] | 2-(2,4-difluorophenyl)-4-[[phenylmethylsulfonyl]oxy]-5-amino-3(2H)-furanone |

TABLE 1A-continued

| Compound | Structure | Name |
|---|---|---|
| 8o | 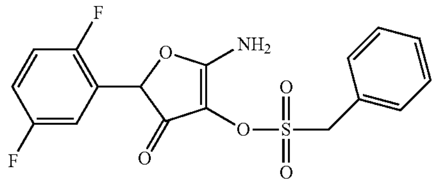 [SMILES: NC1=C(OS(=O)(=O)Cc2ccccc2)C(=O)C(c2cc(F)ccc2F)O1] | 2-(2,5-difluoropheny])-4-[[phenylmethylsulfonyl]oxy]-5-amino-3(2H)-furanone |
| 8p | 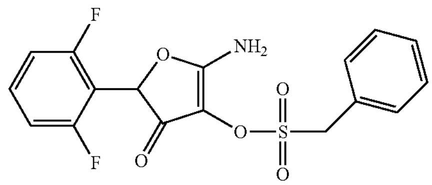 | 2-(2,6-difluorophenyl)-4-[[phenylmethylsulfonyl]oxy]-5-amino-3(2H)-furanone |
| 8q | 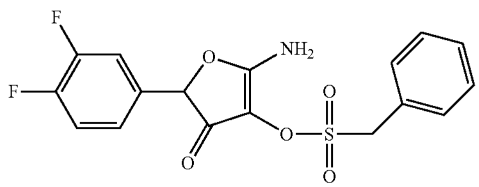 | 2-(3,4-difluorophenyl)-4-[[phenylmethylsulfonyl]oxy]-5-amino-3(2H)-furanone |
| 8r | 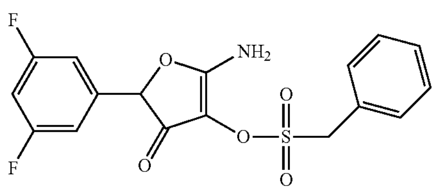 [SMILES: NC1=C(OS(=O)(=O)Cc2ccccc2)C(=O)C(c2cc(F)cc(F)c2)O1] | 2-(3,5-difluorophenyl)-4-[[phenylmethylsulfonyl]oxy]-5-amino-3(2H)-furanone |
| 8s | 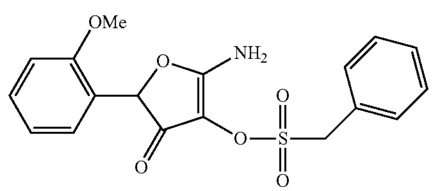 [SMILES: COc1ccccc1C1OC(N)=C(OS(=O)(=O)Cc2ccccc2)C1=O] | 2-(2-methoxyphenyl)-4-[[phenylmethylsulfonyl]oxy]-5-amino-3(2H)-furanone |
| 8t | 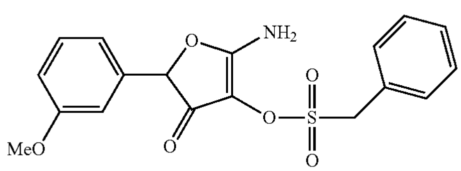 [SMILES: COc1cccc(C2OC(N)=C(OS(=O)(=O)Cc3ccccc3)C2=O)c1] | 2-(3-methoxyphenyl)-4-[[phenylmethylsulfonyl]oxy]-5-amino-3(2H)-furanone |
| 8u | 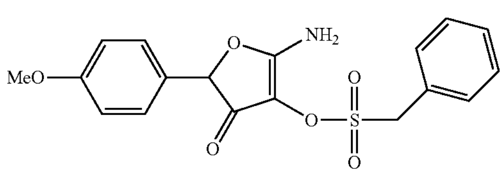 [SMILES: COc1ccc(C2OC(N)=C(OS(=O)(=O)Cc3ccccc3)C2=O)cc1] | 2-(4-methoxyphenyl)-4-[[phenylmethylsulfonyl]oxy]-5-amino-3(2H)-furanone |
| 8v | 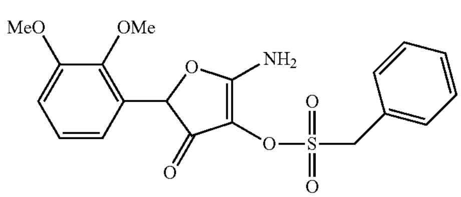 [SMILES: COc1cccc(C2OC(N)=C(OS(=O)(=O)Cc3ccccc3)C2=O)c1OC] | 2-(2,3-dimethoxyphenyl)-4-[[phenylmethylsulfonyl]oxy]-5-amino-3(2H)-furanone |

TABLE 1A-continued

| Compound | Structure | Name |
|---|---|---|
| 8w | 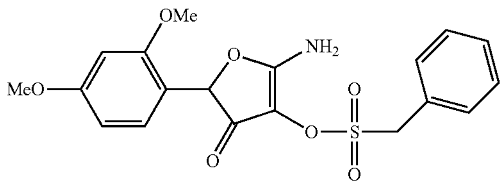 [SMILES: COc1ccc(C2OC(N)=C(OS(=O)(=O)Cc3ccccc3)C2=O)c(OC)c1] | 2-(2,4-dimethoxyphenyl)-4-[[phenylmethylsulfonyl]oxy]-5-amino-3(2H)-furanone |
| 8x | 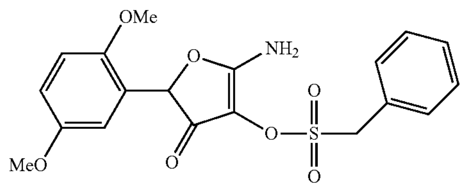 [SMILES: COc1ccc(OC)c(C2OC(N)=C(OS(=O)(=O)Cc3ccccc3)C2=O)c1] | 2-(2,5-dimethoxyphenyl)-4-[[phenylmethylsulfonyl]oxy]-5-amino-3(2H)-furanone |
| 8y | 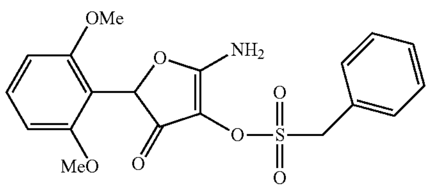 [SMILES: COc1cccc(OC)c1C1OC(N)=C(OS(=O)(=O)Cc2ccccc2)C1=O] | 2-(2,6-dimethoxyphenyl)-4-[[phenylmethylsulfonyl]oxy]-5-amino-3(2H)-furanone |
| 8z | 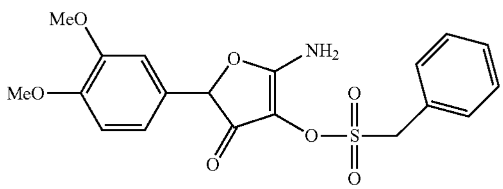 [SMILES: COc1ccc(C2OC(N)=C(OS(=O)(=O)Cc3ccccc3)C2=O)cc1OC] | 2-(3,4-dimethoxyphenyl)-4-[[phenylmethylsulfonyl]oxy]-5-amino-3(2H)-furanone |
| 8aa | 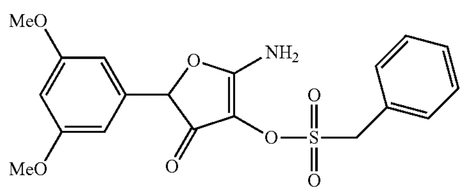 [SMILES: COc1cc(OC)cc(C2OC(N)=C(OS(=O)(=O)Cc3ccccc3)C2=O)c1] | 2-(3,5-dimethoxyphenyl)-4-[[phenylmethylsulfonyl]oxy]-5-amino-3(2H)-furanone |
| 8ab | 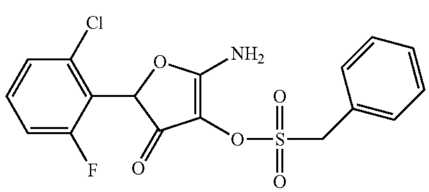 | 2-(2-chloro-6-fluorophenyl)-4-[[phenylmethylsulfonyl]oxy]-5-amino-3(2H)-furanone |
| 8ac | 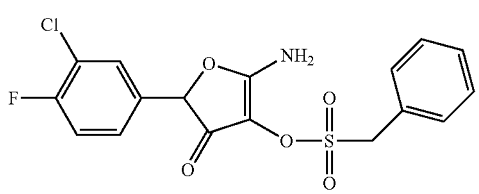 | 2-(3-chloro-4-fluorophenyl)-4-[[phenylmethylsulfonyl]oxy]-5-amino-3(2H)-furanone |
| 8ad | 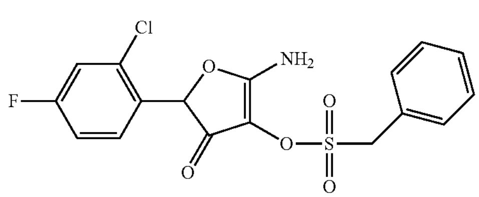 | 2-(2-chloro-4-fluorophenyl)-4-[[phenylmethylsulfonyl]oxy]-5-amino-3(2H)-furanone |

TABLE 1A-continued

| Compound | Structure | Name |
| --- | --- | --- |
| 8ae | 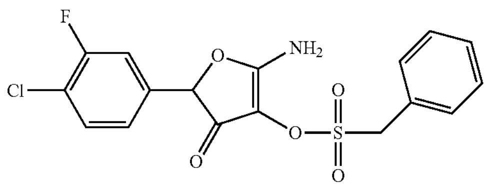 [SMILES: NC1=C(OS(=O)(=O)Cc2ccccc2)C(=O)C(c2ccc(Cl)c(F)c2)O1] | 2-(4-chloro-3-fluorophenyl)-4-[[phenylmethylsulfonyl]oxy]-5-amino-3(2H)-furanone |
| 8af | 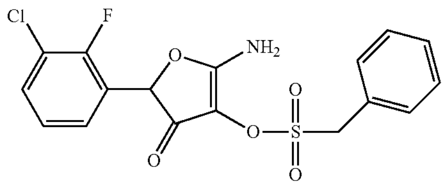 [SMILES: NC1=C(OS(=O)(=O)Cc2ccccc2)C(=O)C(c2cccc(Cl)c2F)O1] | 2-(3-chloro-2-fluorophenyl)-4-[[phenylmethylsulfonyl]oxy]-5-amino-3(2H)-furanone |
| 8ag | 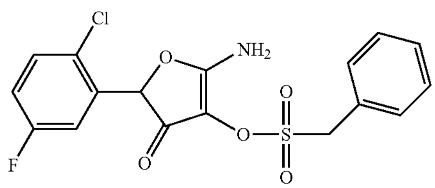 | 2-(2-chloro-5-fluorophenyl)-4-[[phenylmethylsulfonyl]oxy]-5-amino-3(2H)-furanone |
| 8ah | 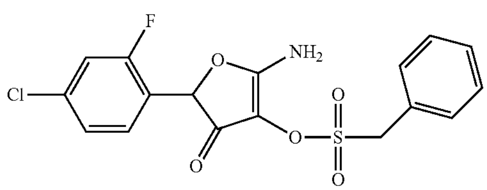 [SMILES: NC1=C(OS(=O)(=O)Cc2ccccc2)C(=O)C(c2ccc(Cl)cc2F)O1] | 2-(4-chloro-2-fluorophenyl)-4-[[phenylmethylsulfonyl]oxy]-5-amino-3(2H)-furanone |
| 8ai | 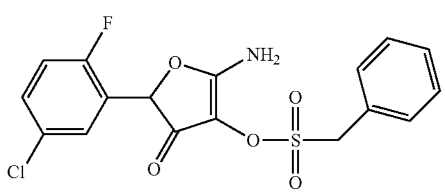 [SMILES: NC1=C(OS(=O)(=O)Cc2ccccc2)C(=O)C(c2cc(Cl)ccc2F)O1] | 2-(3-chloro-5-fluorophenyl)-4-[[phenylmethylsulfonyl]oxy]-5-amino-3(2H)-furanone |
| 8aj | 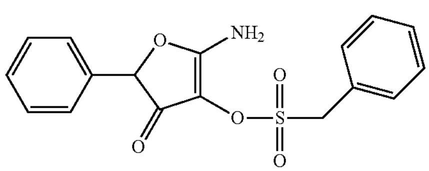 [SMILES: NC1=C(OS(=O)(=O)Cc2ccccc2)C(=O)C(c2ccccc2)O1] | 2-(phenyl)-4-[[phenylmethylsulfonyl]oxy]-5-amino-3(2H)-furanone |
| 8ak | 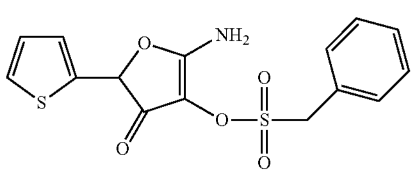 | 2-(2-thiophene)-4-[[phenylmethylsulfonyl]oxy]-5-amino)-3(2H)-furanone |
| 8al | 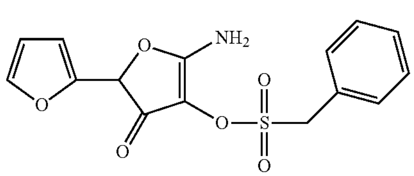 [SMILES: NC1=C(OS(=O)(=O)Cc2ccccc2)C(=O)C(c2ccco2)O1] | 2-(2-furanyl)-4-[[phenylmethylsulfonyl]oxy]-5-amino-3(2H)-furanone |

TABLE 1A-continued

| Compound | Structure | Name |
| --- | --- | --- |
| 8am | 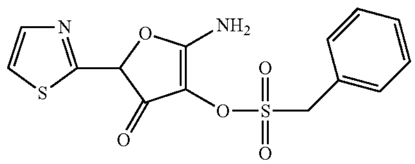 [SMILES: NC1=C(OS(=O)(=O)Cc2ccccc2)C(=O)C(c2nccs2)O1] | 2-(2-thiazolyl)-4-[[phenylmethylsulfonyl]oxy]-5-amino-3(2H)-furanone |
| 8an | 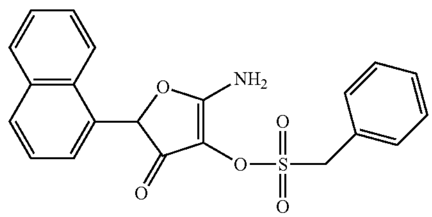 [SMILES: NC1=C(OS(=O)(=O)Cc2ccccc2)C(=O)C(c2cccc3ccccc23)O1] | 2-(1-naphthyl)-4-[[phenylmethylsulfonyl]oxy]-5-amino-3(2H)-furanone |
| 8ao | 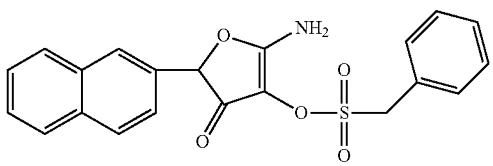 [SMILES: NC1=C(OS(=O)(=O)Cc2ccccc2)C(=O)C(c2ccc3ccccc3c2)O1] | 2-(2-naphthyl)-4-[[phenylmethylsulfonyl]oxy]-5-amino-3(2H)-furanone |
| 8ap | 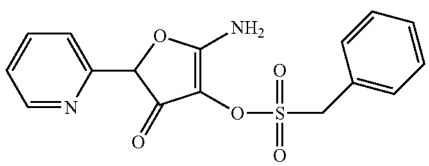 [SMILES: NC1=C(OS(=O)(=O)Cc2ccccc2)C(=O)C(c2ccccn2)O1] | 2-(2-pyridyl)-4-[[phenylmethylsulfonyl]oxy]-5-amino-3(2H)-furanone |
| 8aq | 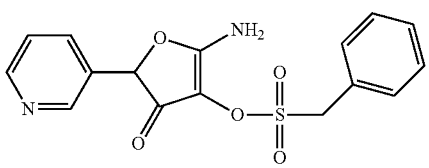 [SMILES: NC1=C(OS(=O)(=O)Cc2ccccc2)C(=O)C(c2cccnc2)O1] | 2-(3-pyridyl)-4-[[phenylmethylsulfonyl]oxy]-5-amino-3(2H)-furanone |
| 8ar | 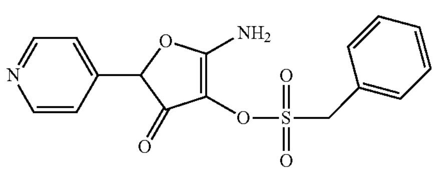 [SMILES: NC1=C(OS(=O)(=O)Cc2ccccc2)C(=O)C(c2ccncc2)O1] | 2-(4-pyridyl)-4-[[phenylmethylsulfonyl]oxy]-5-amino-3(2H)-furanone |
| 8as | 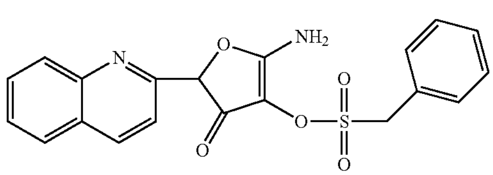 | 2-(2-quinolinyl)-4-[[phenylmethylsulfonyl]oxy]-5-amino-3(2H)-furanone |
| 8at | 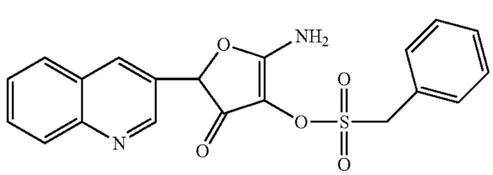 | 2-(3-quinolinyl)-4-[[phenylmethylsulfonyl]oxy]-5-amino-3(2H)-furanone |

TABLE 1A-continued

| Compound | Structure | Name |
|---|---|---|
| 8au | | 2-(4-quinolinyl)-4-[[phenylmethylsulfonyl]oxy]-5-amino-3(2H)-furanone |
| 8av | 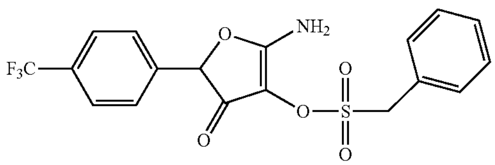 [SMILES: NC1=C(OS(=O)(=O)Cc2ccccc2)C(=O)C(c2ccc(C(F)(F)F)cc2)O1] | 2-(4-trifluoromethylphenyl)-4-[[phenylmethylsulfonyl]oxy]-5-amino-3(2H)-furanone |
| 8aw | 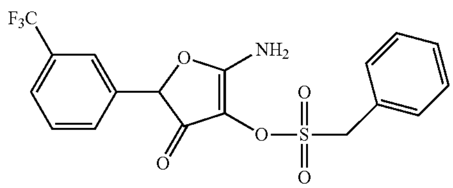 [SMILES: NC1=C(OS(=O)(=O)Cc2ccccc2)C(=O)C(c2cccc(C(F)(F)F)c2)O1] | 2-(3-trifluoromethylphenyl)-4-[[phenylmethylsulfonyl]oxy]-5-amino-3(2H)-furanone |
| 8ax | 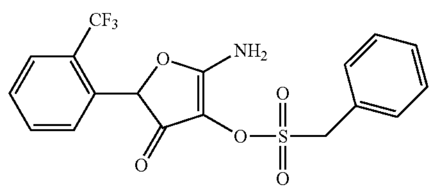 [SMILES: NC1=C(OS(=O)(=O)Cc2ccccc2)C(=O)C(c2ccccc2C(F)(F)F)O1] | 2-(2-trifluoromethylphenyl)-4-[[phenylmethylsulfonyl]oxy]-5-amino-3(2H)-furanone |
| 8ay | 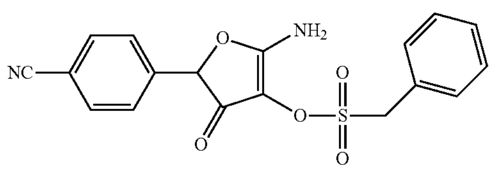 [SMILES: N#Cc1ccc(C2OC(N)=C(OS(=O)(=O)Cc3ccccc3)C2=O)cc1] | 2-(4-nitrilephenyl)-4-[[phenylmethylsulfonyl]oxy]-5-amino-3(2H)-furanone |
| 8az | 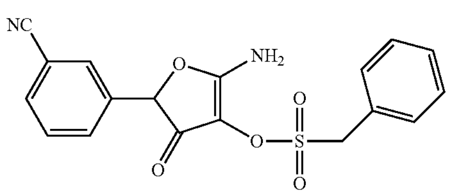 [SMILES: N#Cc1cccc(C2OC(N)=C(OS(=O)(=O)Cc3ccccc3)C2=O)c1] | 2-(3-nitrilephenyl)-4-[[phenylmethylsulfonyl]oxy]-5-amino-3(2H)-furanone |
| 9c | 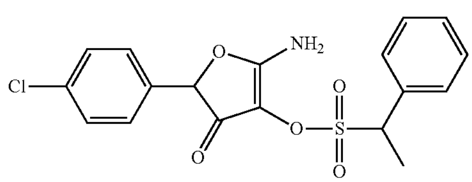 [SMILES: CC(c1ccccc1)S(=O)(=O)OC1=C(N)OC(c2ccc(Cl)cc2)C1=O] | 2-(4-chlorophenyl)-4-[[1-phenylethylsulfonyl]oxy]-5-amino-3(2H)-furanone |
| 10c | 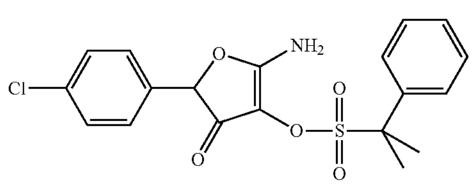 [SMILES: CC(C)(c1ccccc1)S(=O)(=O)OC1=C(N)OC(c2ccc(Cl)cc2)C1=O] | 2-(4-chlorophenyl)-4-[[1-methyl-1-phenyl]ethylsulfonyl]oxy]-5-amino-3(2H) furanone |

TABLE 1A-continued

| Compound | Structure | Name |
| --- | --- | --- |
| 11c | 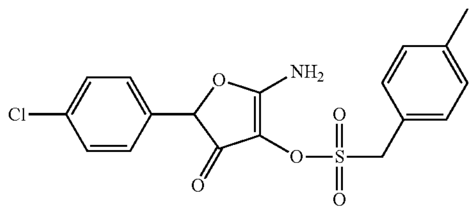 [SMILES: Cc1ccc(CS(=O)(=O)OC2=C(N)OC(c3ccc(Cl)cc3)C2=O)cc1] | 2-(4-chlorophenyl)-4-[[4-methylphenylmethylsulfonyl]oxy]-5-amino-3(2H)-furanone |
| 12c | 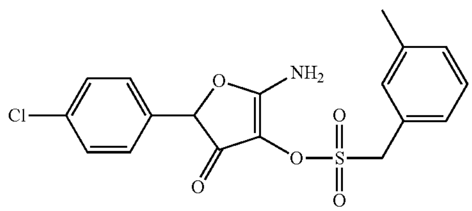 [SMILES: Cc1cccc(CS(=O)(=O)OC2=C(N)OC(c3ccc(Cl)cc3)C2=O)c1] | 2-(4-chlorophenyl)-4-[[3-methylphenylmethylsulfonyl]oxy]-5-amino-3(2H)-furanone |
| 13c | 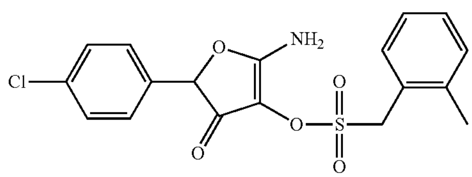 [SMILES: Cc1ccccc1CS(=O)(=O)OC1=C(N)OC(c2ccc(Cl)cc2)C1=O] | 2-(4-chlorophenyl)-4-[[2-methylphenylmethylsulfonyl]oxy]-5-amino-3(2H)-furanone |
| 14c | 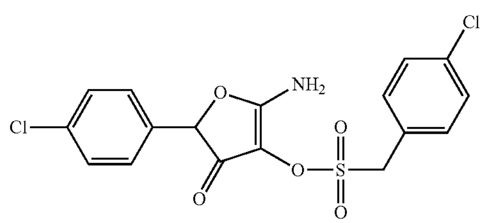 [SMILES: NC1=C(OS(=O)(=O)Cc2ccc(Cl)cc2)C(=O)C(c2ccc(Cl)cc2)O1] | 2-(4-chlorophenyl)-4-[[4-chlorophenylmethylsulfonyl]oxy]-5-amino-3(2H)-furanone |
| 15c | 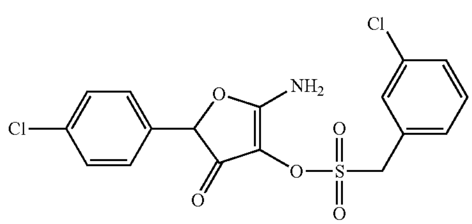 [SMILES: NC1=C(OS(=O)(=O)Cc2cccc(Cl)c2)C(=O)C(c2ccc(Cl)cc2)O1] | 2-(4-chlorophenyl)-4-[[3-chlorophenylmethylsulfonyl]oxy]-5-amino-3(2H)-furanone |
| 16c | 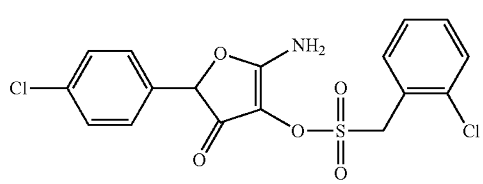 [SMILES: NC1=C(OS(=O)(=O)Cc2ccccc2Cl)C(=O)C(c2ccc(Cl)cc2)O1] | 2-(4-chlorophenyl)-4-[[2-chlorophenylmethylsulfonyl]oxy]-5-amino-3(2H)-furanone |
| 17c | 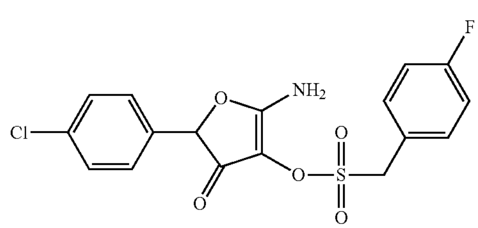 [SMILES: NC1=C(OS(=O)(=O)Cc2ccc(F)cc2)C(=O)C(c2ccc(Cl)cc2)O1] | 2-(4-chlorophenyl)-4-[[4-fluorophenylmethylsulfonyl]oxy]-5-amino-3(2H)-furanone |

TABLE 1A-continued

| Compound | Structure | Name |
| --- | --- | --- |
| 18c | 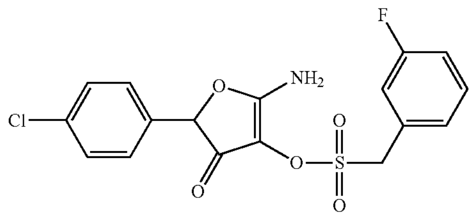 [SMILES: NC1=C(OS(=O)(=O)Cc2cccc(F)c2)C(=O)C(c2ccc(Cl)cc2)O1] | 2-(4-chlorophenyl)-4-[[3-fluorophenylmethylsulfonyl]oxy]-5-amino-3(2H)-furanone |
| 19c | 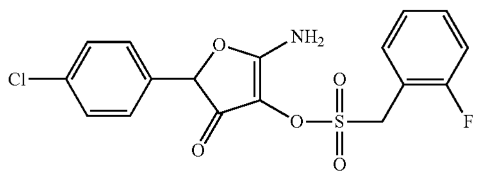 [SMILES: NC1=C(OS(=O)(=O)Cc2ccccc2F)C(=O)C(c2ccc(Cl)cc2)O1] | 2-(4-chlorophenyl)-4-[[2-fluorophenylmethylsulfonyl]oxy]-5-amino-3(2H)-furanone |
| 20c | 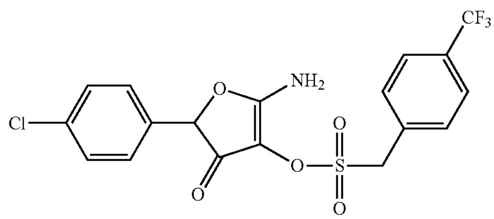 [SMILES: NC1=C(OS(=O)(=O)Cc2ccc(C(F)(F)F)cc2)C(=O)C(c2ccc(Cl)cc2)O1] | 2-(4-chlorophenyl)-4-[[4-fluoromethylphenylmethylsulfonyl]oxy]-5-amino-3(2H)-furanone |
| 21c | 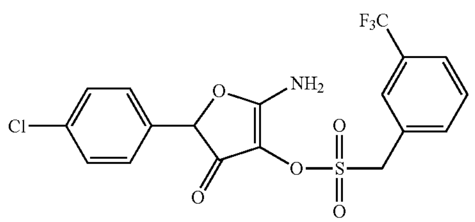 [SMILES: NC1=C(OS(=O)(=O)Cc2cccc(C(F)(F)F)c2)C(=O)C(c2ccc(Cl)cc2)O1] | 2-(4-chlorophenyl)-4-[[3-trifluoromethylphenylmethylsulfonyl]oxy]-5-amino-3(2H)-furanone |
| 22c | 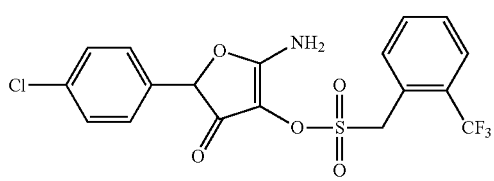 [SMILES: NC1=C(OS(=O)(=O)Cc2ccccc2C(F)(F)F)C(=O)C(c2ccc(Cl)cc2)O1] | 2-(4-chlorophenyl)-4-[[2-trifluoromethylphenylmethylsulfonyl]oxy]-5-amino-3(2H)-furanone |
| 23c | 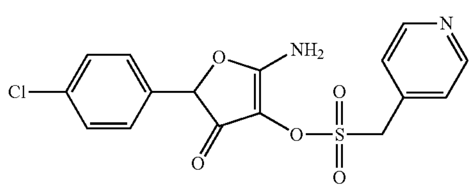 [SMILES: NC1=C(OS(=O)(=O)Cc2ccncc2)C(=O)C(c2ccc(Cl)cc2)O1] | 2-(4-chlorophenyl)-4-[[4-pyridylmethylsulfonyl]oxy]-5-amino-3(2H)-furanone |
| 24c | 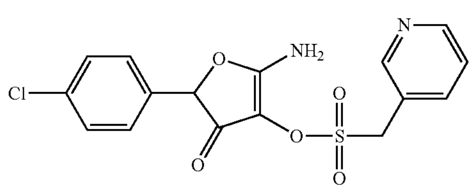 [SMILES: NC1=C(OS(=O)(=O)Cc2cccnc2)C(=O)C(c2ccc(Cl)cc2)O1] | 2-(4-chlorophenyl)-4-[[3-pyridylmethylsulfonyl]oxy]-5-amino-3(2H)-furanone |
| 25c | 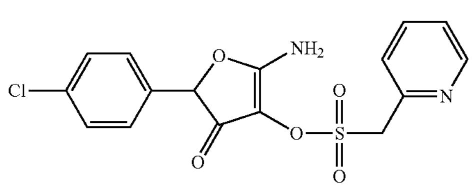 | 2-(4-chlorophenyl)-4-[[2-pyridylmethylsulfonyl]oxy]-5-amino-3(2H)-furanone |

TABLE 1A-continued

| Compound | Structure | Name |
|---|---|---|
| 26c | 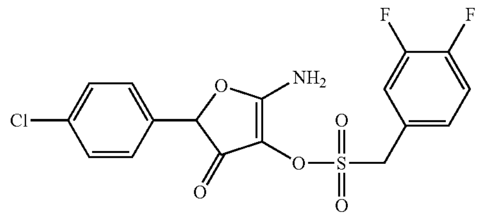 [SMILES: NC1=C(OS(=O)(=O)Cc2ccc(F)c(F)c2)C(=O)C(c2ccc(Cl)cc2)O1] | 2-(4-chlorophenyl)-4-[[3,4-difluorophenylmethylsulfonyl]oxy]-5-amino-3(2H)-furanone |
| 27c | 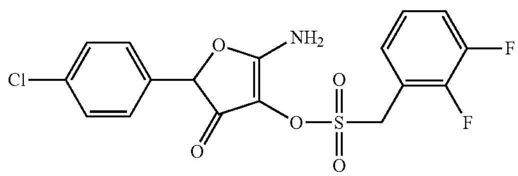 [SMILES: NC1=C(OS(=O)(=O)Cc2cccc(F)c2F)C(=O)C(c2ccc(Cl)cc2)O1] | 2-(4-chlorophenyl)-4-[[2,3-difluorophenylmethylsulfonyl]oxy]-5-amino-3(2H)-furanone |
| 28c | 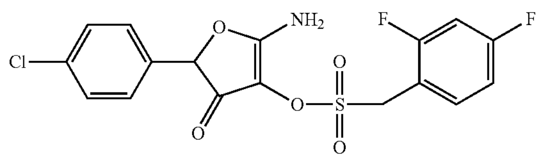 [SMILES: NC1=C(OS(=O)(=O)Cc2ccc(F)cc2F)C(=O)C(c2ccc(Cl)cc2)O1] | 2-(4-chlorophenyl)-4-[[2,4-difluorophenylmethylsulfonyl]oxy]-5-amino-3(2H)-furanone |
| 29c | 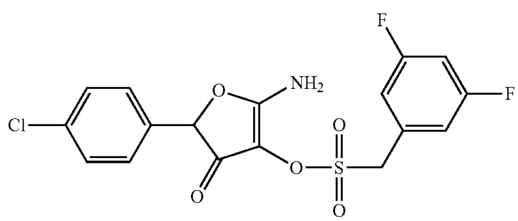 [SMILES: NC1=C(OS(=O)(=O)Cc2cc(F)cc(F)c2)C(=O)C(c2ccc(Cl)cc2)O1] | 2-(4-chlorophenyl)-4-[[3,5-difluorophenylmethylsulfonyl]oxy]-5-amino-3(2H)-furanone |
| 30c | 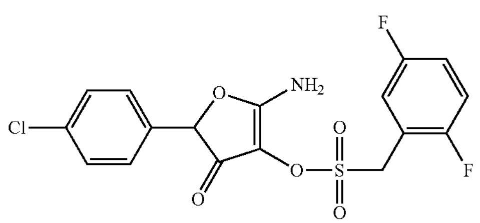 [SMILES: NC1=C(OS(=O)(=O)Cc2cc(F)ccc2F)C(=O)C(c2ccc(Cl)cc2)O1] | 2-(4-chlorophenyl)-4-[[2,5-difluorophenylmethylsulfonyl]oxy]-5-amino-3(2H)-furanone |
| 31c | 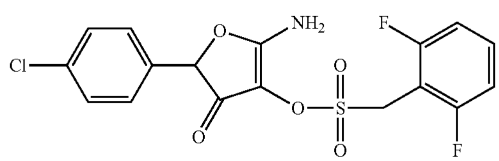 [SMILES: NC1=C(OS(=O)(=O)Cc2c(F)cccc2F)C(=O)C(c2ccc(Cl)cc2)O1] | 2-(4-chlorophenyl)-4-[[2,6-difluorophenylmethylsulfonyl]oxy]-5-amino-3(2H)-furanone |
| 32c | 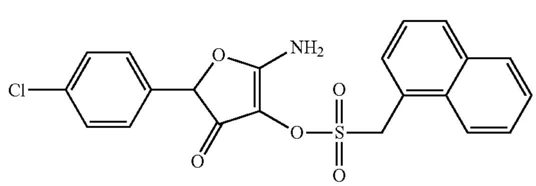 [SMILES: NC1=C(OS(=O)(=O)Cc2cccc3ccccc23)C(=O)C(c2ccc(Cl)cc2)O1] | 2-(4-chlorophenyl)-4-[[1-naphthylmethylsulfonyl]oxy]-5-amino-3(2H)-furanone |
| 33c | 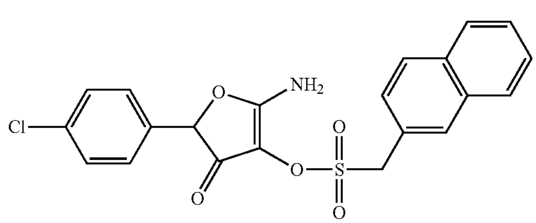 [SMILES: NC1=C(OS(=O)(=O)Cc2ccc3ccccc3c2)C(=O)C(c2ccc(Cl)cc2)O1] | 2-(4-chlorophenyl)-4-[[2-naphthylmethylsulfonyl]oxy]-5-amino-3(2H)-furanone |

TABLE 1A-continued

| Compound | Structure | Name |
|---|---|---|
| 34c | 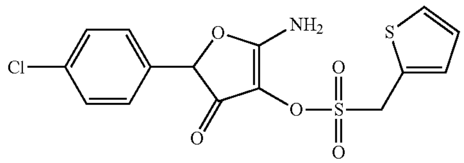 [SMILES: NC1=C(OS(=O)(=O)Cc2cccs2)C(=O)C(c2ccc(Cl)cc2)O1] | 2-(4-chlorophenyl)-4-[[2-thiophenemethylsulfonyl]oxy]-5-amino-3(2H)-furanone |
| 35c | 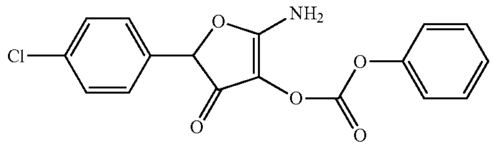 [SMILES: NC1=C(OC(=O)Oc2ccccc2)C(=O)C(c2ccc(Cl)cc2)O1] | 2-(4-chlorophenyl)-4-[[phenoxycarbonyl]oxy]-5-amino-3(2H)-furanone |
| 36c | 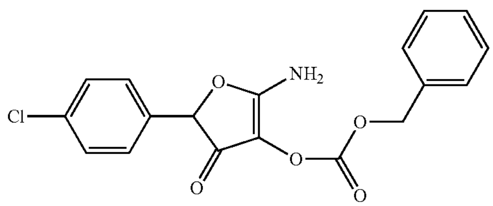 [SMILES: NC1=C(OC(=O)OCc2ccccc2)C(=O)C(c2ccc(Cl)cc2)O1] | 2-(4-chlorophenyl)-4-[[benzyloxycarbonyl]oxy]-5-amino-3(2H)-furanone |
| 37c | 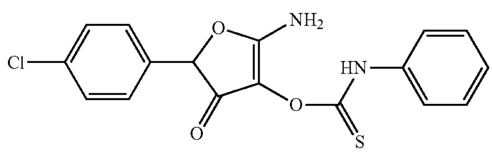 [SMILES: NC1=C(OC(=S)Nc2ccccc2)C(=O)C(c2ccc(Cl)cc2)O1] | 2-(4-chlorophenyl)-4-[[phenylaminothiocarbonyl]oxy]-5-amino-3(2H)-furanone |
| 38c | 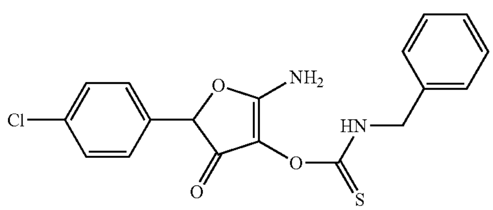 [SMILES: NC1=C(OC(=S)NCc2ccccc2)C(=O)C(c2ccc(Cl)cc2)O1] | 2-(4-chlorophenyl)-4-[[benzylaminothiocarbonyl]oxy]-5-amino-3(2H)-furanone |

TABLE 2

Structures of Key Compounds

| Structure | Name | Compound |
|---|---|---|
| 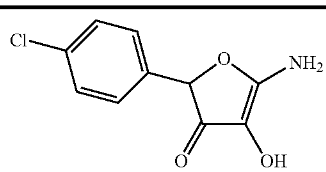 | 5-amino-4-hydroxy-2-(4-chlorophenyl)-furan-3-one | 1c |
| 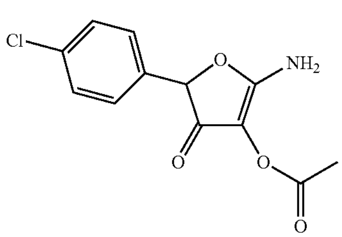 [SMILES: CC(=O)OC1=C(N)OC(c2ccc(Cl)cc2)C1=O] | 2-(4-chlorophenyl)-4-(acetoxy)-5-amino-3(2H)-furanone | 2c |

TABLE 2-continued

Structures of Key Compounds

| Structure | Name | Compound |
|---|---|---|
| 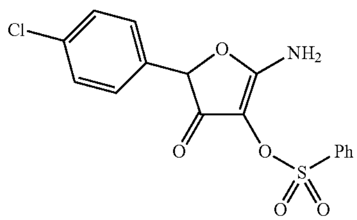 [SMILES: NC1=C(OS(=O)(=O)c2ccccc2)C(=O)C(c2ccc(Cl)cc2)O1] | 2-(4-chlorophenyl)-4-[[phenylsulfonyl]oxy]-5-amino-3(2H)-furanone | 3c |
| 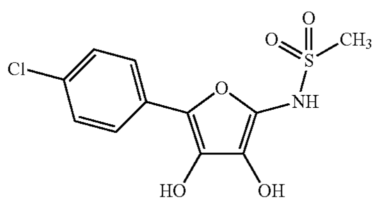 [SMILES: CS(=O)(=O)Nc1oc(-c2ccc(Cl)cc2)c(O)c1O] | N-(3,4-dihydroxy-5-(4-chlorophenyl)-2-furanyl)methanesulfonamide | 4c |
| 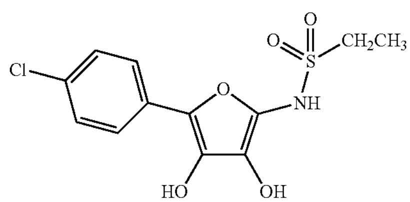 [SMILES: CCS(=O)(=O)Nc1oc(-c2ccc(Cl)cc2)c(O)c1O] | N-(3,4-dihydroxy-5-(4-chlorophenyl)-2-furanyl)ethanesulfonamide | 5c |
| 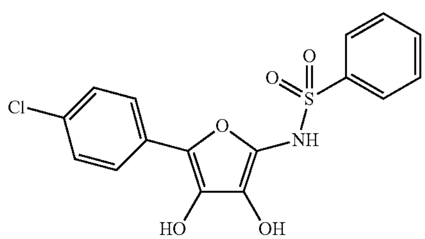 [SMILES: O=S(=O)(Nc1oc(-c2ccc(Cl)cc2)c(O)c1O)c1ccccc1] | N-(3,4-dihydroxy-5-(4-chlorophenyl)-2-furanyl)benzenesulfonamide | 6c |
| 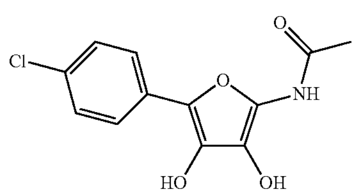 [SMILES: CC(=O)Nc1oc(-c2ccc(Cl)cc2)c(O)c1O] | N-(3,4-dihydroxy-5-(4-chlorophenyl)-2-furanyl)acetamide | 7c |
| 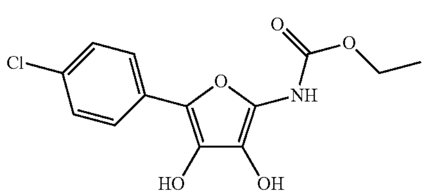 [SMILES: CCOC(=O)Nc1oc(-c2ccc(Cl)cc2)c(O)c1O] | N-(3,4-dihydroxy-5-(4-chlorophenyl)-2-furanyl)-carbamic acid ethyl ester | 8c |
| 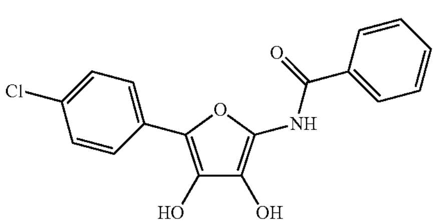 [SMILES: O=C(Nc1oc(-c2ccc(Cl)cc2)c(O)c1O)c1ccccc1] | N-(3,4-dihydroxy-5-(4-chlorophenyl)-2-furanyl)benzamide | 9c |

TABLE 2-continued

Structures of Key Compounds

| Structure | Name | Compound |
|---|---|---|
| 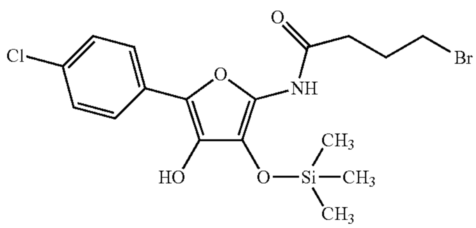 [SMILES: C[Si](C)(C)Oc1c(NC(=O)CCCBr)oc(-c2ccc(Cl)cc2)c1O] | N-(3-trimethylsilyloxy-4-dihydroxy-5-(4-chlorophenyl)-2-furanyl)-4-bromo-butanamide | 10c |
| 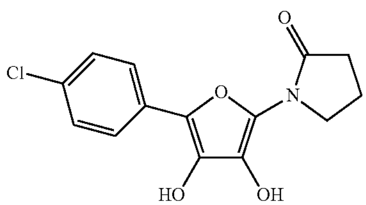 [SMILES: O=C1CCCN1c1oc(-c2ccc(Cl)cc2)c(O)c1O] | N-(3,4-dihydroxy-5-(4-chlorophenyl)-2-furanyl)-2-pyrrolidinone | 11c |
| 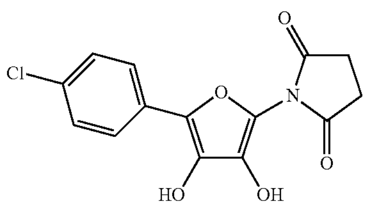 [SMILES: O=C1CCC(=O)N1c1oc(-c2ccc(Cl)cc2)c(O)c1O] | N-(3,4-dihydroxy-5-(4-chlorophenyl)-2-furanyl)succinimide | 12c |
| 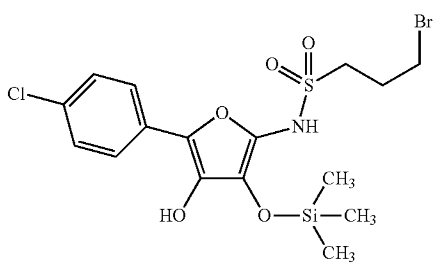 [SMILES: C[Si](C)(C)Oc1c(NS(=O)(=O)CCCBr)oc(-c2ccc(Cl)cc2)c1O] | N-(3-trimethylsilyloxy-4-dihydroxy-5-(4-chlorophenyl)-2-furanyl)-3-bromo-propylsulfonamide | 13c |
| 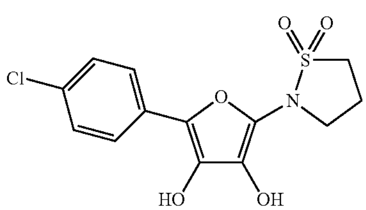 [SMILES: O=S1(=O)CCCN1c1oc(-c2ccc(Cl)cc2)c(O)c1O] | N-(3,4-dihydroxy-5-(4-chlorophenyl)-2-furanyl)-1,3-dioxide-isothiazolidine | 14c |
| 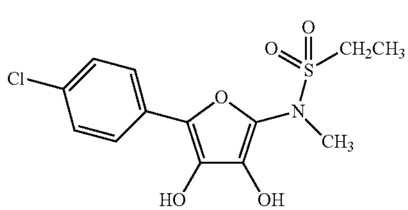 [SMILES: CCS(=O)(=O)N(C)c1oc(-c2ccc(Cl)cc2)c(O)c1O] | N-methyl-N'-(3,4-dihydroxy-5-(4-chlorophenyl)-2-furanylethanesulfonamide | 15c |

TABLE 2-continued

Structures of Key Compounds

| Structure | Name | Compound |
|---|---|---|
| 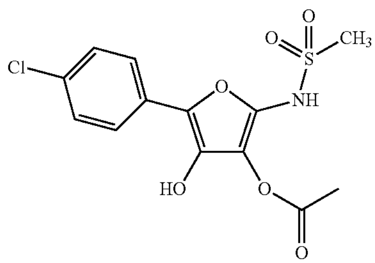 [SMILES: CC(=O)Oc1c(NS(C)(=O)=O)oc(-c2ccc(Cl)cc2)c1O] | N-(3-acetoxy-4-hydroxy-5-(4-chlorophenyl)-2-furanyl)methanesulfonamide | 16c |
| 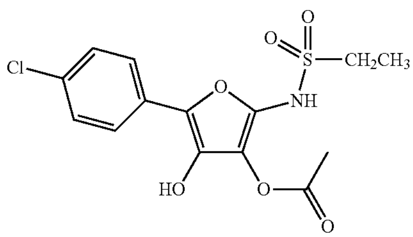 [SMILES: CCS(=O)(=O)Nc1oc(-c2ccc(Cl)cc2)c(O)c1OC(C)=O] | N-(3-acetoxy-4-hydroxy-5-(4-chlorophenyl)-2-furanyl)ethanesulfonamide | 17c |
| 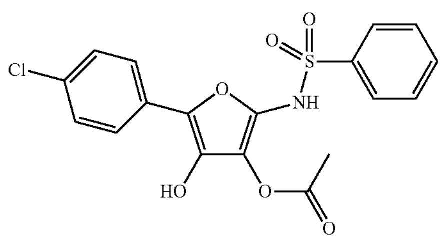 [SMILES: CC(=O)Oc1c(NS(=O)(=O)c2ccccc2)oc(-c2ccc(Cl)cc2)c1O] | N-(3-acetoxy-4-hydroxy-5-(4-chlorophenyl)-2-furanyl)benzenesulfonamide | 18c |
| 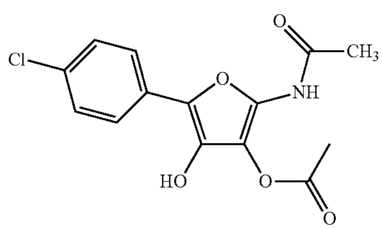 [SMILES: CC(=O)Nc1oc(-c2ccc(Cl)cc2)c(O)c1OC(C)=O] | N-(3-acetoxy-4-hydroxy-5-(4-chlorophenyl)-2-furanyl)-acetamide | 19c |
| 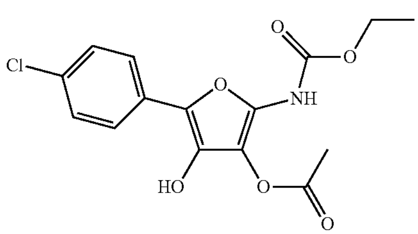 [SMILES: CCOC(=O)Nc1oc(-c2ccc(Cl)cc2)c(O)c1OC(C)=O] | N-(3-acetoxy-4-hydroxy-5-(4-chlorophenyl)-2-furanyl)-carbamic acid ethyl ester | 20c |
| 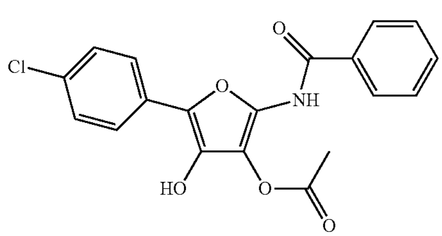 [SMILES: CC(=O)Oc1c(NC(=O)c2ccccc2)oc(-c2ccc(Cl)cc2)c1O] | N-(3-acetoxy-4-hydroxy-5-(4-chlorophenyl)-2-furanyl)benzamide | 21c |

TABLE 2-continued

Structures of Key Compounds

| Structure | Name | Compound |
|---|---|---|
| 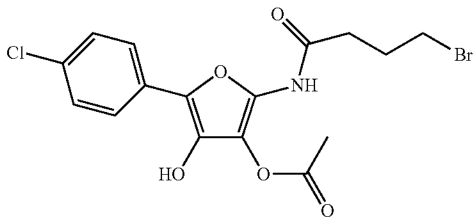 [SMILES: CC(=O)Oc1c(NC(=O)CCCBr)oc(-c2ccc(Cl)cc2)c1O] | N-(3-acetoxy-4-hydroxy-5-(4-chlorophenyl)-2-furanyl)-2-bromo-butanamide | 22c |
| 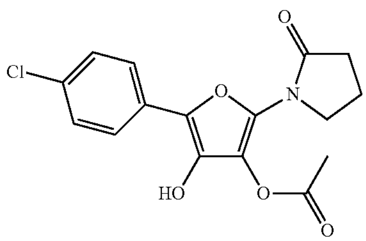 [SMILES: CC(=O)Oc1c(N2CCCC2=O)oc(-c2ccc(Cl)cc2)c1O] | N-(3-acetoxy-4-hydroxy-5-(4-chlorophenyl)-2-furanyl)-2-pyrrolidinone | 23c |
| 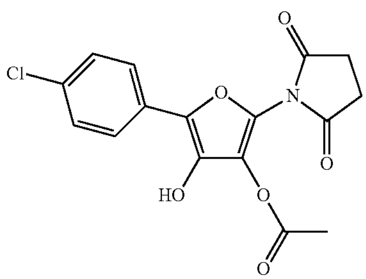 [SMILES: CC(=O)Oc1c(N2C(=O)CCC2=O)oc(-c2ccc(Cl)cc2)c1O] | N-(3-acetoxy-4-hydroxy-5-(4-chlorophenyl)-2-furanyl)succinimide | 24c |
| 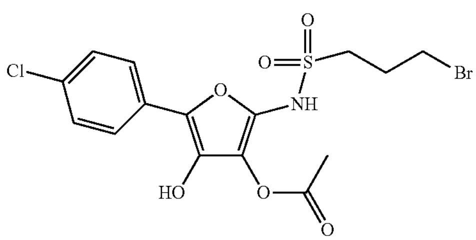 [SMILES: CC(=O)Oc1c(NS(=O)(=O)CCCBr)oc(-c2ccc(Cl)cc2)c1O] | N-(3-acetoxy-4-hydroxy-5-(4-chlorophenyl)-2-furanyl)-3-bromo-propylsulfonamide | 25c |
| 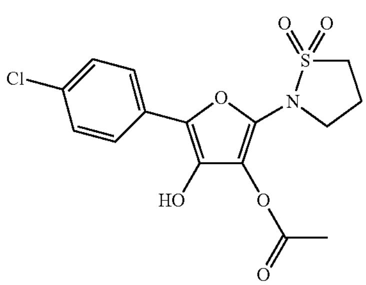 [SMILES: CC(=O)Oc1c(N2CCCS2(=O)=O)oc(-c2ccc(Cl)cc2)c1O] | N-(3-acetoxy-4-hydroxy-5-(4-chlorophenyl)-2-furanyl)-1,1-dioxide-isothiazolidine | 26c |
| 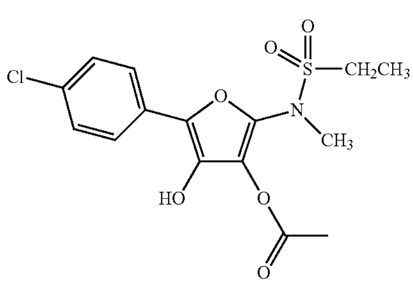 [SMILES: CCS(=O)(=O)N(C)c1oc(-c2ccc(Cl)cc2)c(O)c1OC(C)=O] | N-methyl-N'-(3-acetoxy-4-hydroxy-5-(4-chlorophenyl)-2-furanyl)ethanesulfonamide | 27c |

TABLE 2-continued

Structures of Key Compounds

| Structure | Name | Compound |
|---|---|---|
| 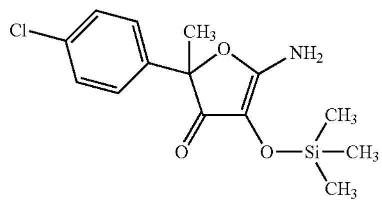 [SMILES: CC1(c2ccc(Cl)cc2)OC(N)=C(O[Si](C)(C)C)C1=O] | 5-amino-2-(4-chlorophenyl)-2-methyl-4-trimethylsilyloxy-3(2H)-furanone | 28c |
| 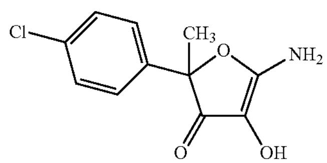 [SMILES: CC1(c2ccc(Cl)cc2)OC(N)=C(O)C1=O] | 5-amino-2-(4-chlorophenyl)-2-methyl-4-hydroxy-3(2H)-furanone | 29c |
| 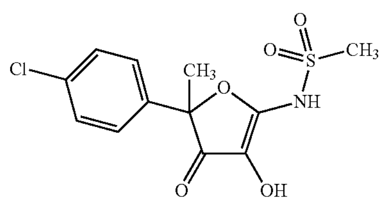 [SMILES: CC1(c2ccc(Cl)cc2)OC(NS(C)(=O)=O)=C(O)C1=O] | N-(3-hydroxy-5-(4-chlorophenyl)-5-methyl-2-3(2H)-furanonyl)-methanesulfonamide | 30c |
| 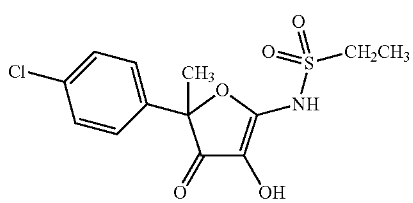 [SMILES: CCS(=O)(=O)NC1=C(O)C(=O)C(C)(c2ccc(Cl)cc2)O1] | N-(3-hydroxy-5-(4-chlorophenyl)-5-methyl-2-3(2H)-furanonyl)-ethanesulfonamide | 31c |
| 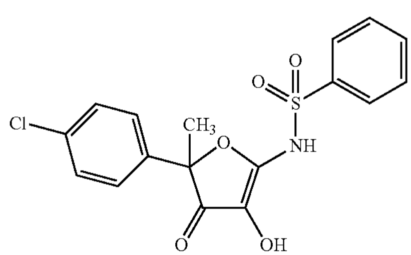 [SMILES: CC1(c2ccc(Cl)cc2)OC(NS(=O)(=O)c2ccccc2)=C(O)C1=O] | N-(3-hydroxy-5-(4-chlorophenyl)-5-methyl-2-3(2H)-furanonyl)-benzenesulfonamide | 32c |
| 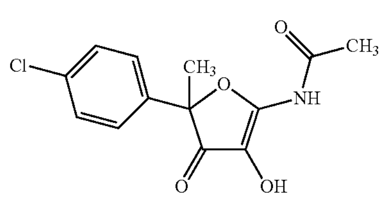 [SMILES: CC(=O)NC1=C(O)C(=O)C(C)(c2ccc(Cl)cc2)O1] | N-(3-hydroxy-5-(4-chlorophenyl)-5-methyl-2-3(2H)-furanonyl)-acetamide | 33c |
| 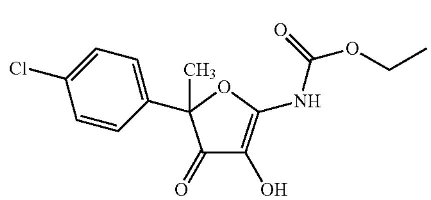 [SMILES: CCOC(=O)NC1=C(O)C(=O)C(C)(c2ccc(Cl)cc2)O1] | N-(3-hydroxy-5-(4-chlorophenyl)-5-methyl-2-3(2H)-furanonyl)-carbamic acid ethyl ester | 34c |

TABLE 2-continued

Structures of Key Compounds

| Structure | Name | Compound |
|---|---|---|
| 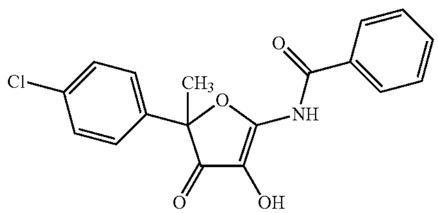 [SMILES: CC1(c2ccc(Cl)cc2)OC(NC(=O)c2ccccc2)=C(O)C1=O] | N-(3-hydroxy-5-(4-chlorophenyl)-5-methyl-2-3(2H)-furanonyl)-benzamide | 35c |
| 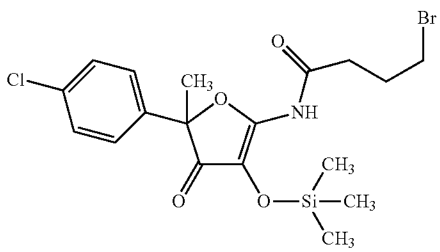 [SMILES: CC1(c2ccc(Cl)cc2)OC(NC(=O)CCCBr)=C(O[Si](C)(C)C)C1=O] | N-(3-hydroxy-5-(4-chlorophenyl)-5-methyl-2-3(2H)-furanonyl)-4-bromo-butanamide | 36c |
| 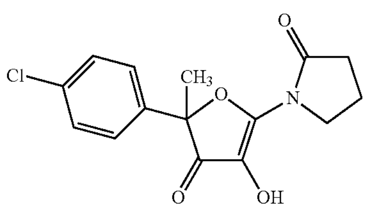 [SMILES: CC1(c2ccc(Cl)cc2)OC(N2CCCC2=O)=C(O)C1=O] | N-(3-hydroxy-5-(4-chlorophenyl)-5-methyl-2-3(2H)-furanonyl)-2-pyrrolidinone | 37c |
| 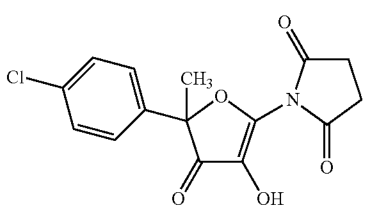 [SMILES: CC1(c2ccc(Cl)cc2)OC(N2C(=O)CCC2=O)=C(O)C1=O] | N-(3-hydroxy-5-(4-chlorophenyl)-5-methyl-2-3(2H)-furanonyl)-succinimide | 38c |
| 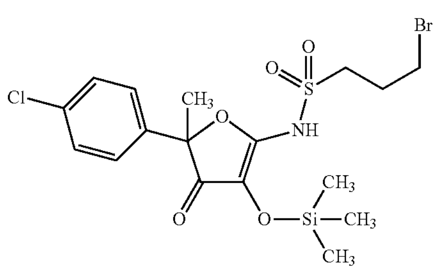 [SMILES: CC1(c2ccc(Cl)cc2)OC(NS(=O)(=O)CCCBr)=C(O[Si](C)(C)C)C1=O] | N-(3,4-dihydroxy-5-(4-chlorophenyl)-2-furanyl)-3-bromo-propylsulfonamide | 39c |
| 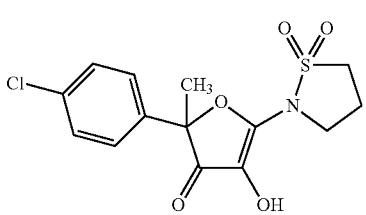 [SMILES: CC1(c2ccc(Cl)cc2)OC(N2CCCS2(=O)=O)=C(O)C1=O] | N-(3-hydroxy-5-(4-chlorophenyl)-5-methyl-2-3(2H)-furanonyl)-1,1-dioxide-isothiazolidine | 40c |

TABLE 2-continued

Structures of Key Compounds

| Structure | Name | Compound |
|---|---|---|
| 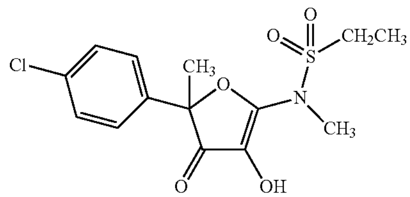 [SMILES: CCS(=O)(=O)N(C)C1=C(O)C(=O)C(C)(c2ccc(Cl)cc2)O1] | N-methyl-N'-(3-hydroxy-5-(4-chlorophenyl)-5-methyl-2-3(2H)-furanonyl)-ethanesulfonamide | 41c |
| 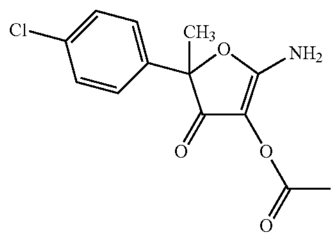 [SMILES: CC(=O)OC1=C(N)OC(C)(c2ccc(Cl)cc2)C1=O] | 5-amino-2-(4-chlorophenyl)-2-methyl-4-acetoxy-3(2H)-furanone | 42c |
| 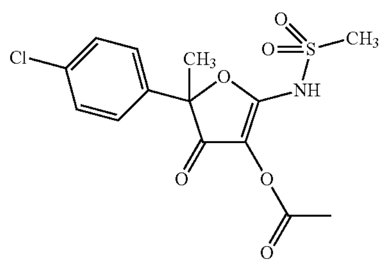 [SMILES: CC(=O)OC1=C(NS(C)(=O)=O)OC(C)(c2ccc(Cl)cc2)C1=O] | N-(3-acetoxy-5-(4-chlorophenyl)-5-methyl-2-3(2H)-furanonyl)-methanesulfonamide | 43c |
| 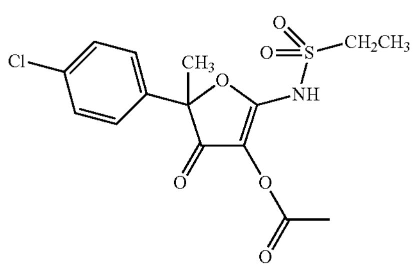 [SMILES: CCS(=O)(=O)NC1=C(OC(C)=O)C(=O)C(C)(c2ccc(Cl)cc2)O1] | N-(3-acetoxy-5-(4-chlorophenyl)-5-methyl-2-3(2H)-furanonyl)-ethanesulfonamide | 44c |
| 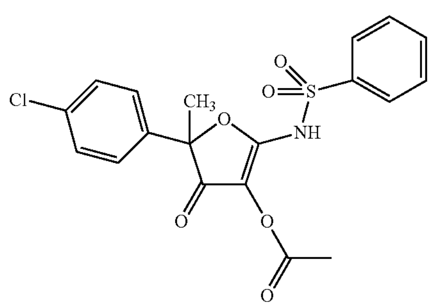 [SMILES: CC(=O)OC1=C(NS(=O)(=O)c2ccccc2)OC(C)(c2ccc(Cl)cc2)C1=O] | N-(3-acetoxy-5-(4-chlorophenyl)-5-methyl-2-3(2H)-furanonyl)-benzenesulfonamide | 45c |
| 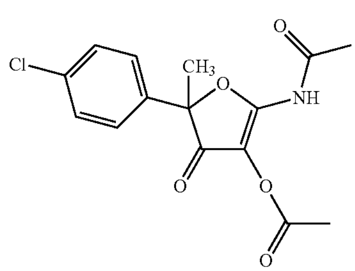 [SMILES: CC(=O)NC1=C(OC(C)=O)C(=O)C(C)(c2ccc(Cl)cc2)O1] | N-(3-acetoxy-5-(4-chlorophenyl)-5-methyl-2-3(2H)-furanonyl)-acetamide | 46c |

TABLE 2-continued

Structures of Key Compounds

| Structure | Name | Compound |
|---|---|---|
| 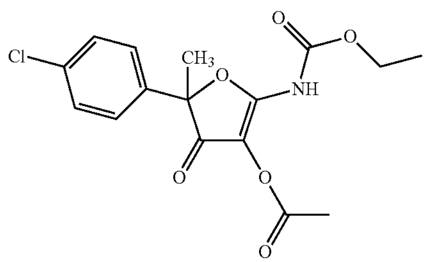 [SMILES: CCOC(=O)NC1=C(OC(C)=O)C(=O)C(C)(c2ccc(Cl)cc2)O1] | N-(3-acetoxy-5-(4-chlorophenyl)-5-methyl-2-3(2H)-furanonyl)-carbamic acid ethyl ester | 47c |
| 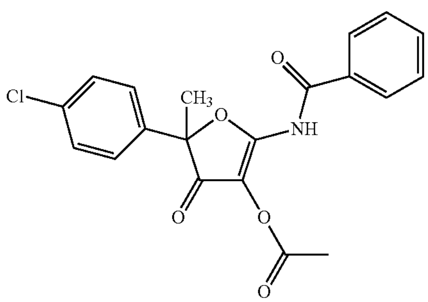 [SMILES: CC(=O)OC1=C(NC(=O)c2ccccc2)OC(C)(c2ccc(Cl)cc2)C1=O] | N-(3-acetoxy-5-(4-chlorophenyl)-5-methyl-2-3(2H)-furanonyl)-benzamide | 48c |
| 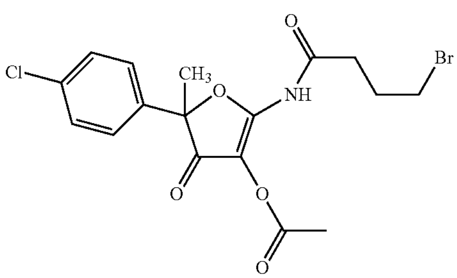 [SMILES: CC(=O)OC1=C(NC(=O)CCCBr)OC(C)(c2ccc(Cl)cc2)C1=O] | N-(3-acetoxy-5-(4-chlorophenyl)-5-methyl-2-3(2H)-furanonyl)-4-bromo-butanamide | 49c |
| 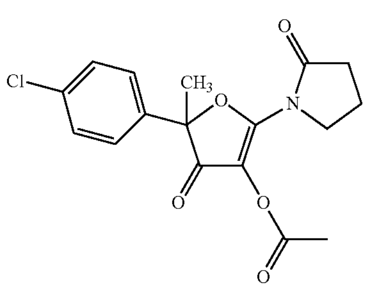 [SMILES: CC(=O)OC1=C(N2CCCC2=O)OC(C)(c2ccc(Cl)cc2)C1=O] | N-(3-acetoxy-5-(4-chlorophenyl)-5-methyl-2-3(2H)-furanonyl)-2-pyrrolidinone | 50c |
| 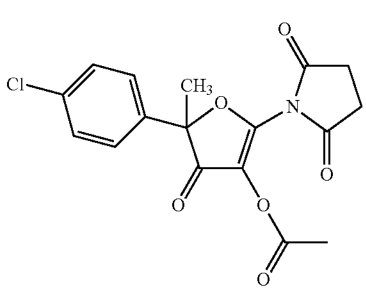 [SMILES: CC(=O)OC1=C(N2C(=O)CCC2=O)OC(C)(c2ccc(Cl)cc2)C1=O] | N-(3-acetoxy-5-(4-chlorophenyl)-5-methyl-2-3(2H)-furanonyl)-succinimide | 51c |

TABLE 2-continued

Structures of Key Compounds

| Structure | Name | Compound |
|---|---|---|
| 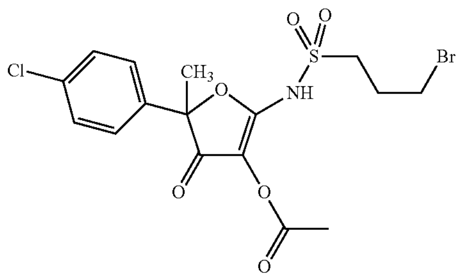 [SMILES: CC(=O)OC1=C(NS(=O)(=O)CCCBr)OC(C)(c2ccc(Cl)cc2)C1=O] | N-(3-acetoxy-5-(4-chlorophenyl)-5-methyl-2-3(2H)-furanonyl)-3-bromo-pyropylsulfonamide | 52c |
| 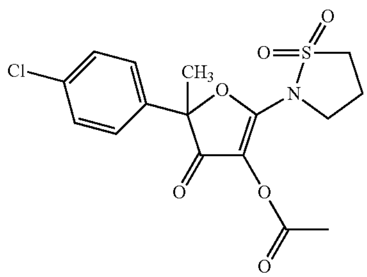 [SMILES: CC(=O)OC1=C(N2CCCS2(=O)=O)OC(C)(c2ccc(Cl)cc2)C1=O] | N-(3-acetoxy-5-(4-chlorophenyl)-5-methyl-2-3(2H)-furanonyl)-1,1-dioxide-isothiazolidine | 53c |
| 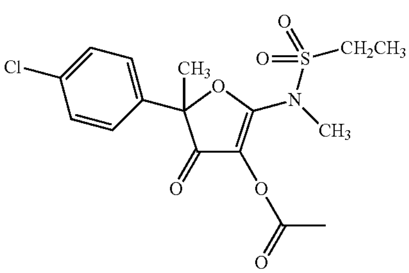 [SMILES: CCS(=O)(=O)N(C)C1=C(OC(C)=O)C(=O)C(C)(c2ccc(Cl)cc2)O1] | N-methyl-N'-(3-acetoxy-5-(4-chlorophenyl)-5-methyl-2-3(2H)-furanonyl)-ethanesulfonamide | 54c |

Example 1 Synthesis and Characterization of Compounds in Table 1A

General Procedures for Preparation of Aryltetronimides

Potassium cyanide (0.91 g) was added to sodium carbonate (1.7 g) in deionized water (30 mL) in a 3-Neck Glass Round Flask and placed in an ice bath. The system was repeatedly purged using a vacuum pump and nitrogen gas. Glyoxal (3.72 g) was then added to the system without the introduction of $O_2$ and the reactants were allowed to dissolve with stirring. In a stoppered tube, the appropriate arylaldehyde (7.11 mmoles) was added to 1,4-dioxane (5 mL), purged, and then added drop-wise to the system. The system was then removed from the ice bath and allowed to stir at room temperature for 1 hour. After 1 hour, acetic acid (5 mL) was added drop-wise until gas bubbles were no longer visible from the addition of acetic acid, or until the solution was at a pH of less than 6. The solution was vacuum filtered and washed with ice cold water (5 mL), methanol (5 mL) and ether (5 mL) and then was allowed to air dry. Crude material was recrystallized with methanol, collected by vacuum filtration and rinsed with diethyl ether and dried under vacuum.

Compound 1c: 2-(4-chlorophenyl)-4-[[methylsulfonyl]oxy]-5-amino-3(2H)-furanone

To a solution of 5 g of 5-amino-4-hydroxy-2-(4-chlorophenyl)-furan-3-one in dry THF under argon is added triethylamine in dry THF. The reaction is stirred at room temperature for 30 minutes, and 1 eq of methanesulfonyl chloride in dry THF is added dropwise. The reaction is stirred for 16 hours, followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 2c: 2-(4-chlorophenyl)-4-[[ethylsulfonyl]oxy]-5-amino-3(2H)-furanone

To a solution of 5 g of 5-amino-4-hydroxy-2-(4-chlorophenyl)-furan-3-one in dry THF under argon is added triethylamine in dry THF. The reaction is stirred at room temperature for 30 minutes, and 1 eq of ethanesulfonyl chloride in dry THF is added dropwise. The reaction is stirred for 16 hours, followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 3c: 2-(4-chlorophenyl)-4-[[1-propylsulfonyl]oxy]-5-amino-3(2H)-furanone To a solution of 5 g of 5-amino-4-hydroxy-2-(4-chlorophenyl)-furan-3-one in dry THF under argon is added triethylamine in dry THF. The reaction is stirring at room temperature for 30 minutes, and 1 eq of n-propanesulfonyl chloride in dry THF is added dropwise. The reaction is stirred for 16 hours, followed by the addition of a saturated ammonium chloride solution. The mixture is extracted 3 times with 30 mL of diethyl ether, the combined ether extracts are washed with water and brine, dried over sodium sulfate, filtered, and concentrated under reduced pressure. The solid is recrystallized with methanol.

Compound 4c: 2-(4-chlorophenyl)-4-[[2-propylsulfonyl]oxy]-5-amino-3(2H)-furanone To a solution of 5 g of 5-amino-4-hydroxy-2-(4-chlorophenyl)-furan-3-one in dry THF under argon is added triethylamine in dry THF. The reaction is stirred at room temperature for 30 minutes, and 1 eq of i-propanesulfonyl chloride in dry THF is added dropwise. The reaction is stirred for 16 hours, followed by the addition of a saturated ammonium chloride. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 5c: 2-(4-chlorophenyl)-4-[[1-butylsulfonyl]oxy]-5-amino-3(2H)-furanone

To a solution of 5 g of 5-amino-4-hydroxy-2-(4-chlorophenyl)-furan-3-one in dry THF under argon is added triethylamine in dry THF. The reaction is stirred at room temperature for 30 minutes, and 1 eq of n-butanesulfonyl chloride in dry THF is added dropwise. The reaction is stirred for 16 hours, followed by the addition of a saturated ammonium chloride solution. The mixture is extracted 3 times with 30 mL of diethyl ether, the combined ether extracts are washed with water and brine, dried over sodium sulfate, filtered, and concentrated under reduced pressure. The solid is recrystallized with methanol.

Compound 6c: 2-(4-chlorophenyl)-4-[[1-propyl-2-methyl-sulfonyl]oxy]-5-amino-3(2H)-furanone To a solution of 5 g of 5-amino-4-hydroxy-2-(4-chlorophenyl)-furan-3-one in dry THF under argon is added triethylamine in dry THF. The reaction is stirring at room temperature for 30 minutes, and 1 eq of i-butanesulfonyl chloride in dry THF is added dropwise. The reaction is stirred for 16 hours, followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 7c: 2-(4-chlorophenyl)-4-[[phenylsulfonyl]oxy]-5-amino-3(2H)-furanone 5 g of 5-amino-4-hydroxy-2-(4-chlorophenyl)-furan-3-one was stirred in 50 mL of dry THF under argon gas for 16 hours with 4.7 g $K_2CO_3$ and 4.25 mL of benzenesulfonyl chloride. The reaction was filtered, and the filtrate was acidified with 24 mL 1N HCl, and extracted 5 times with 20 mL of diethyl ether. The combined ether extracts were washed with brine and dried with $Na_2SO_4$. After filtration, 100 mL of hexanes was added to the solution, resulting in a precipitate, which was collected using vacuum filtration and recrystallized with MeOH. Yield=17%. mp 190-195° C.; FTIR 3099, 1630; $^1$H NMR (300 MHz, DMSO-$d_6$, ppm) δ 8.54 (s, 2H), 7.93 (d, J=8.1 Hz, 2H), 7.74 (t, J=7.2 Hz, 1H), 7.57 (t, J=8.1 Hz, 2H), 7.48 (d, J=8.7 Hz, 2H), 7.18 (d, J=8.4 Hz, 2H), 5.54 (s, 1H). $^{13}$C NMR (75 MHz, DMSO-$d_6$, ppm) δ 181.2, 173.4, 135.2, 135.0, 134.2, 133.9, 129.7, 129.2, 129.1, 129.0, 106.6, 82.9. Elemental Analysis Calc: C, 52.54; H, 3.31; N, 3.83; Cl, 9.69. Found: C, 52.50; H, 3.33; N, 3.79; Cl, 9.84. $C_{16}H_{12}ClNO_5S$; HPLC retention time: 32.2 min.

Compound 8a: 2-(2-chlorophenyl)-4-[[phenylmethylsulfonyl]oxy]-5-amino-3(2H)-furanone To a solution of 5 g of 5-amino-4-hydroxy-2-(2-chlorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8b: 2-(3-chlorophenyl)-4-[[phenylmethylsulfonyl]oxy]-5-amino-3(2H)-furanone To a solution of 5 g of 5-amino-4-hydroxy-2-(3-chlorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether, the combined ether extracts are washed with water and brine, dried over sodium sulfate, filtered, and concentrated under reduced pressure. The solid is recrystallized with methanol.

Compound 8c: 2-(4-chlorophenyl)-4-[[phenylmethylsulfonyl]oxy]-5-amino-3(2H)-furanone 2-(4-chlorophenyl)-4-[[phenylmethylsulfonyl]oxy]-5-amino-3(2H)-furanone 2.5 g of 5-amino-4-hydroxy-2-(4-chlorophenyl)-furan-3-one was stirred in 100 mL of dry THF. 1.31 mL of TEA was added, and 30 minutes later 2.11 g of phenylmethylsulfonylchloride was added to the reaction. The reaction was stirred for 24 hours. The reaction was filtered, and the filtrate was acidified with 24 mL 1N HCl, and extracted 5 times with 20 mL of diethyl ether. The combined ether extracts were washed with brine, and dried with $Na_2SO_4$. After filtration, the solution was concentrated under reduced pressure, and the resulting solid was recrystallized from methanol. Yield=27%. FTIR 2957, 1636; $^1$H NMR (300 MHz, DMSO-$d_6$, ppm) δ 8.79 (s, 2H), 7.60-7.49 (m, 4H), 7.43-7.35 (m, 5H), 5.80 (s, 1H), 4.97 (d, J=14.1, 1H), 4.90 (d, J=14.1, 1H). $^{13}$C NMR (75 MHz, DMSO-$d_6$, ppm) δ 181.8, 173.9, 134.3, 134.1, 131.5, 129.3, 129.1, 129.1, 129.0, 128.9, 107.9, 83.1, 57.8. Elemental Analysis Calc: C, 53.76; H, 3.72; N, 3.69. Found: C, 53.90; H, 3.68; N, 3.70. $C_{17}H_{14}ClNO_5S$; HPLC retention time: 32.2 min.

Compound 8d: 2-(2,3-dichlorophenyl)-4-[[phenylmethylsulfonyl]oxy]-5-amino-3(2H)-furanone To a solution of 5 g of 5-amino-4-hydroxy-2-(2,3-dichlorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8e: 2-(2,4-dichlorophenyl)-4-[[phenylmethylsulfonyl]oxy]-5-amino-3(2H)-furanone To a solution of 5 g of 5-amino-4-hydroxy-2-(2,4-dichlorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours, followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8f: 2-(2,5-dichlorophenyl)-4-[[phenylmethylsulfonyl]oxy]-5-amino-3(2H)-furanone To a solution of 5 g of 5-amino-4-hydroxy-2-(2,5-dichlorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8g: 2-(3-carboxymethylphenyl)-4-[[phenylmethylsulfonyl]oxy]-5-amino-3(2H)-furanone To a solution of 5 g of 5-amino-4-hydroxy-2-(3-carboxymethylphenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8h: 2-(3,4-dichlorophenyl)-4-[[phenylmethylsulfonyl]oxy]-5-amino-3(2H)-furanone To a solution of 5 g of 5-amino-4-hydroxy-2-(3,4-dichlorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8i: 2-(3,5-dichlorophenyl)-4-[[phenylmethylsulfonyl]oxy]-5-amino-3(2H)-furanone To a solution of 5 g of 5-amino-4-hydroxy-2-(3,5-dichlorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8j: 2-(2-fluorophenyl)-4-[[phenylmethylsulfonyl]oxy]-5-amino-3(2H)-furanone To a solution of 5 g of 5-amino-4-hydroxy-2-(2-fluorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8k: 2-(3-fluorophenyl)-4-[[phenylmethylsulfonyl]oxy]-5-amino-3(2H)-furanone To a solution of 5 g of 5-amino-4-hydroxy-2-(3-fluorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8l: 2-(4-fluorophenyl)-4-[[phenylmethylsulfonyl]oxy]-5-amino-3(2H)-furanone To a solution of 5 g of 5-amino-4-hydroxy-2-(4-fluorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours, followed by the addition of a saturated ammonium chloride solution. The mixture is extracted 3 times with 30 mL of diethyl ether. The combined ether extracts are washed with water and brine, dried over sodium Compound 8m: 2-(2,3-difluorophenyl)-4-[[phenylmethylsulfonyl]oxy]-5-amino-3(2H)-furanone To a solution of 5 g of 5-amino-4-hydroxy-2-(2,3-difluorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours, followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8n: 2-(2,4-difluorophenyl)-4-[[phenylmethylsulfonyl]oxy]-5-amino-3(2H)-furanone To a solution of 5 g of 5-amino-4-hydroxy-2-(2,4-difluorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8o: 2-(2,5-difluorophenyl)-4-[[phenylmethylsulfonyl]oxy]-5-amino-3(2H)-furanone To a solution of 5 g of 5-amino-4-hydroxy-2-(2,5-difluorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8p: 2-(2,6-difluorophenyl)-4-[[phenylmethylsulfonyl]oxy]-5-amino-3(2H)-furanone To a solution of 5 g of 5-amino-4-hydroxy-2-(2,6-difluorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8q: 2-(3,4-difluorophenyl)-4-[[phenylmethylsulfonyl]oxy]-5-amino-3(2H)-furanone To a solution of 5 g of 5-amino-4-hydroxy-2-(3,4-difluorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8r: 2-(3,5-difluorophenyl)-4-[[phenylmethylsulfonyl]oxy]-5-amino-3(2H)-furanone To a solution of 5 g of 5-amino-4-hydroxy-2-(3,5-difluorophenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8av 2-(4-trifluoromethylphenyl)-4-[[phenylmethylsulfonyl]oxy]-5-amino-3(2H)-furanone To a solution of 5 g of 5-amino-4-hydroxy-2-(4-trifluoromethylphenyl)-furan-3-one in dry THE under argon is added triethylamine in dry THE. The reaction is stirring at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Example 8ay: 2-(4-nitrilephenyl)-4-[[phenylmethylsulfonyl]oxy]-5-amino-3(2H)-furanone To a solution of 5 g of 5-amino-4-hydroxy-2-(4-nitrilephenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 8az: 2-(3-nitrilephenyl)-4-[[phenylmethylsulfonyl]oxy]-5-amino-3(2H)-furanone To a solution of 5 g of 5-amino-4-hydroxy-2-(3-nitrilephenyl)-furan-3-one in dry THF under argon is added triethylamine in dry THF. The reaction is stirred at room temperature for 30 minutes, and 1 eq of phenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 17c: 2-(4-chlorophenyl)-4-[[4-fluorophenylmethylsulfonyl]oxy]-5-amino-3(2H)-furanone To a solution of 5 g of 5-amino-4-hydroxy-2-(4-chlorophenyl)-furan-3-one in dry THF under argon is added triethylamine in dry THF. The reaction is stirred at room temperature for 30 minutes, and 1 eq of 4-fluorophenylmethylsulfonyl chloride in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 35c: 2-(4-chlorophenyl)-4-[[phenoxycarbonyl]oxy]-5-amino-3(2H)-furanone To a solution of 5 g of 5-amino-4-hydroxy-2-(4-chlorophenyl)-furan-3-one in dry THF under argon is added triethylamine in dry THF. The reaction is stirred at room temperature for 30 minutes, and 1 eq of phenylchloroformate in dry THF is added dropwise. The reaction is stirred for 16 hours followed by the addition of a saturated ammonium chloride solution. The mixture is extracted 3 times with 30 mL of diethyl ether. The combined ether extracts are washed with water and brine, dried over sodium sulfate, filtered, and concentrated under reduced pressure. The solid is recrystallized with methanol.

Compound 37c: 2-(4-chlorophenyl)-4-[[phenylaminothiocarbonyl]oxy]-5-amino-3(2H)-furanone To a stirring solution of 5 g of 5-amino-4-hydroxy-2-(4-chlorophenyl)-furan-3-one and sodium carbonate (1.7 g) in deionized water (30 mL) is added phenylisothiocyanate. The reaction is stirred at room temperature for 24 hours. A saturated ammonium chloride solution is added and the mixture is extracted 3 times with 30 mL of diethyl ether. The combined ether extracts are washed with water and brine, dried over sodium sulfate, filtered, and concentrated under reduced pressure. The solid is recrystallized with methanol.

Example 2 Synthesis and Characterization of Compounds in Table 2

General Procedures

Potassium cyanide (0.91 g) was added to sodium carbonate (1.7 g) in deionized water (30 mL) in a 3-Neck Glass Round Flask and placed in an ice bath. The system was repeatedly purged using a vacuum pump and nitrogen gas. Glyoxal (3.72 g) was then added to the system without the introduction of $O_2$ and the reactants were allowed to dissolve with stirring. In a stoppered tube, the appropriate arylaldehyde (7.11 mmoles) was added to 1,4-dioxane (5 mL), purged, and then added drop-wise to the system. The system was then removed from the ice bath and allowed to stir at room temperature for 1 hour. After 1 hour, acetic acid (5 mL) was added drop-wise until gas bubbles were no longer visible from the addition of acetic acid, or until the solution was at a pH of less than 6. The solution was vacuum filtered and washed with ice cold water (5 mL), methanol (5 mL) and ether (5 mL) and then was allowed to air dry. Crude material was recrystallized with methanol, collected by vacuum filtration and rinsed with diethyl ether and dried under vacuum.

Example 1c 5-amino-4-hydroxy-2-(4-chlorophenyl)-furan-3-one

Yield=70%. mp 221-2° C.; FTIR 3079, 1638; $^1$H NMR (300 MHz, DMSO-$d_6$, ppm) ι 7.82 (s, 2H), 7.46 (d, J=8.7 Hz, 2H), 7.30 (s, 1H), 7.29 (d, J=8.7 Hz, 2H), 5.43 (s, 1H). $^{13}$C NMR (75 MHz, DMSO-$d_6$, ppm) δ 182.6, 173.1, 135.7, 133.2, 128.9, 128.6, 111.7, 82.2. HRMS Calc: 248.00849, Found: 248.00852 MNa$^+$=$C_{10}H_8NO_3ClNa^+$; Elemental Analysis Calc: C, 53.23; H, 3.57; N, 6.21; Cl, 15.71. Found: C, 53.35; H, 3.61; N, 6.24; Cl, 15.83. $C_{10}H_8ClNO_3$; HPLC retention time: 16.7 min.

Example 1j 5-amino-4-hydroxy-2-(2-fluorophenyl)-furan-3-one

Yield=84%. mp 160-3° C.; FTIR 3079, 1638; $^1$H NMR (DMSO $d_6$) 5.60 (1H, s), 7.22-7.78 (4H, m); HRMS Calc: 210.05610, Found: 210.05609 MH$^+$=$C_{10}H_9$ F NO$_3^+$; Elemental Analysis Calc: C, 57.42; H, 3.85; N, 6.70; F, 9.08. Found: C, 57.50; H, 3.92; N, 6.61; F, 8.99. $C_{10}H_8FNO_3$; HPLC retention time: 11.42 min.

Example 1k 5-amino-4-hydroxy-2-(3-fluorophenyl)-furan-3-one

Yield=60%. mp 168° C.; FTIR 3356, 3129; $^1$H NMR (DMSO $d_6$) 5.44 (1H, s), 7.05-7.27 (4H, m); HRMS Calc: 210.05610, Found: 210.05609 MH$^+$=$C_{10}H_9F$ NO$_3$+; Elemental Analysis Calc: C, 57.42; H, 3.85; N, 6.70; F, 9.08. Found: C, 57.41; H, 3.87; N, 6.61; F, 8.97. $C_{10}H_8FNO_3$; HPLC retention time: 12.63 min.

Example 1l 5-amino-4-hydroxy-2-(4-fluorophenyl)-furan-3-one

Yield=68%. mp 160° C.; FTIR 3351, 3138; $^1$H NMR (DMSO $d_6$) 5.41 (1H, s), 7.22-7.78 (4H, m); HRMS Calc: 210.05610, Found: 210.05609 MH$^+$=$C_{10}H_9$ F NO$_3^+$; Elemental Analysis Calc: C, 57.42; H, 3.85; N, 6.70; F, 9.08. Found: C, 57.42; H, 3.97; N, 6.66; F, 8.90. $C_{10}H_8FNO_3$; HPLC retention time: 11.88 min.

Example 1m 5-amino-4-hydroxy-2-(2,3-difluorophenyl)-furan-3-one

Yield=76%. mp 193° C.; FTIR 3391, 3277, 1539; $^1$H NMR (DMSO $d_6$) 5.68 (1H, s), 7.05-7.85 (3H, m); HRMS Calc: 228.04668, Found: 228.04669 MH$^+$=$C_{10}H_8$ $F_2NO_3^+$; Elemental Analysis Calc: C, 52.87; H, 3.11; N, 6.17; F,

Example 1n 5-amino-4-hydroxy-2-(2,4-difluorophenyl)-furan-3-one

Yield=67%. mp 182-3° C.; FTIR 3252, 1608; $^1$H NMR (DMSO d$_6$) 5.59 (1H, s), 7.13-7.79 (3H, m); HRMS Calc: 228.04668, Found: 228.04671 MH$^+$=C$_{10}$H$_8$F$_2$NO$_3^+$; Elemental Analysis Calc: C, 52.87; H, 3.11; N, 6.17; F, 16.73. Found: C, 52.84; H, 3.00; N, 6.16; F, 16.59. C$_{10}$H$_7$F$_2$NO$_3$; HPLC retention time: 12.63 min.

Example 1o 5-amino-4-hydroxy-2-(2,5-difluorophenyl)-furan-3-one

Yield=80%. mp 196° C.; FTIR 3391, 3267; $^1$H NMR (DMSO d$_6$) 5.61 (1H, s), 7.03-7.84 (3H, m); HRMS Calc: 228.04668, Found: 228.04670 MH$^+$=C$_{10}$H$_8$F$_2$NO$_3^+$; Elemental Analysis Calc: C, 52.87; H, 3.11; N, 6.17; F, 16.73. Found: C, 52.79; H, 3.11; N, 6.15; F, 16.57. C$_{10}$H$_7$F$_2$NO$_3$; HPLC retention time: 12.09 min.

Example 1p 5-amino-4-hydroxy-2-(2,6-difluorophenyl)-furan-3-one

Yield=70%. mp 159-60° C.; FTIR 3535, 3406; $^1$H NMR (DMSO d$_6$) 5.68 (1H, s), 7.14-7.73 (3H, m); HRMS Calc: 228.04668, Found: 228.04670 MH$^+$=C$_{10}$H$_8$F$_2$NO$_3^+$; Elemental Analysis Calc: C, 52.87; H, 3.11; N, 6.17; F, 16.73. Found: C, 52.62; H, 3.10; N, 5.94; F, 16.57. C$_{10}$H$_7$F$_2$NO$_3$; HPLC retention time: 11.30 min.

Example 1q 5-amino-4-hydroxy-2-(3,4-difluorophenyl)-furan-3-one

Yield=76%. mp 190-4° C.; FTIR 3322, 3124; $^1$H NMR (DMSO d$_6$) 5.44 (1H, s), 7.13-7.85 (3H, m); HRMS Calc: 228.04668, Found: 228.04670 MH$^+$=C$_{10}$H$_8$F$_2$NO$_3^+$; Elemental Analysis Calc: C, 52.87; H, 3.11; N, 6.17; F, 16.73. Found: C, 53.13; H, 3.16; N, 6.15; F, 16.61. C$_{10}$H$_7$F$_2$NO$_3$; HPLC retention time: 13.79 min.

Example 1r 5-amino-4-hydroxy-2-(3,5-difluorophenyl)-furan-3-one

Yield=58%. mp 190-1° C.; FTIR 3346, 3143; $^1$H NMR (DMSO d$_6$) 5.68 (1H, s), 7.05-7.85 (3H, m); HRMS Calc: 228.04668, Found: 228.04670 MH$^+$=C$_{10}$H$_8$F$_2$NO$_3^+$; Elemental Analysis Calc: C, 52.87; H, 3.11; N, 6.17; F, 16.73. Found: C, 52.88; H, 3.06; N, 6.15; F, 16.70. C$_{10}$H$_7$F$_2$NO$_3$; HPLC retention time: 14.00 min.

Example 2c 2-(4-chlorophenyl)-4-(acetoxy)-5-amino-3(2H)-furanone 1 g of 5-amino-4-hydroxy-2-(4-chlorophenyl)-furan-3-one was stirred in acetic anhydride under nitrogen gas for 16 hours. The reaction was cooled to −78° C., and lyophilized. The dried mass was recrystallized from MeOH. Yield=44%. mp 221-2° C.; FTIR 3030, 1628; $^1$H NMR (300 MHz, DMSO-d$_6$, ppm) δ 8.30 (s, 2H), 7.47 (d, J=8.7 Hz, 2H), 7.35 (d, J=8.7 Hz, 2H), 5.63 (s, 1H), 2.14 (s, 3H). $^{13}$C NMR (75 MHz, DMSO-d$_6$, ppm) δ 182.4, 173.0, 168.9, 134.8, 133.8, 129.1, 129.1, 106.9, 83.2, 20.7. Elemental Analysis Calc: C, 53.85; H, 3.77; N, 5.23. Found: C, 53.76; H, 3.90; N, 5.24. C$_{12}$H$_{10}$ClNO$_4$; HPLC retention time: 19.7 min.

Example 3c 2-(4-chlorophenyl)-4-[[phenylsulfonyl]oxy]-5-amino-3(2H)-furanone 5 g of 5-amino-4-hydroxy-2-(4-chlorophenyl)-furan-3-one was stirred in 50 mL of dry THF under nitrogen gas for 16 hours with 4.7 g K$_2$CO$_3$ and 4.25 mL of benzenesulfonyl chloride. The reaction was filtered, and the filtrate was acidified with 24 mL 1N HCl, and extracted 5 times with 20 mL of diethyl ether. The combined ether extracts were washed with brine, and dried with Na$_2$SO$_4$. After filtration, 100 mL of hexanes was added to the solution, resulting in a precipitate, which was collected using vacuum filtration and recrystallized with MeOH. Yield=17%. mp 190-195° C.; FTIR 3034, 1630; $^1$H NMR (300 MHz, DMSO-d$_6$, ppm) δ 8.54 (s, 2H), 7.93 (d, J=8.1 Hz, 2H), 7.74 (t, J=7.2 Hz, 1H), 7.57 (t, J=8.1 Hz, 2H), 7.48 (d, J=8.7 Hz, 2H), 7.18 (d, J=8.4 Hz, 2H), 5.54 (s, 1H). $^{13}$C NMR (75 MHz, DMSO-d$_6$, ppm) δ 181.2, 173.4, 135.2, 135.0, 134.2, 133.9, 129.7, 129.2, 129.1, 129.0, 106.6, 82.9. Elemental Analysis Calc: C, 52.54; H, 3.31; N, 3.83; Cl, 9.69. Found: C, 52.50; H, 3.33; N, 3.79; Cl, 9.84. C$_{16}$H$_{12}$ClNO$_5$S; HPLC retention time: 32.2 min.

Example 4c

N-(3,4-dihydroxy-5-(4-chlorophenyl)-2-furanyl)methanesulfonamide 5 g of 5-amino-4-hydroxy-2-(4-chlorophenyl)-furan-3-one was stirred in 50 mL of dry THF under nitrogen gas for 16 hours with 4.6 g K$_2$CO$_3$ and 1.5 mL of methanesulfonyl chloride. The reaction was filtered, and the filtrate was acidified with 24 mL 1N HCl, and extracted 5 times with 20 mL of diethyl ether. The combined ether extracts were washed with brine, and dried with Na$_2$SO$_4$. After filtration, 100 mL of hexanes was added to the solution, resulting in a precipitate, which was collected using vacuum filtration and recrystallized with MeOH. The material was further purified by column chromatography. Yield=18%. mp 175° C.; FTIR 3169, 1616; $^1$H NMR (300 MHz, DMSO-d$_6$, ppm) δ 8.41 (s, 1H), 8.09 (s, 1H), 7.96 (d, J=8.4 Hz, 2H), 7.85 (s, 1H), 7.59 (d, J=8.4 Hz, 2H), 3.55 (s, 3H). $^{13}$C NMR (75 MHz, DMSO-d$_6$, ppm) δ 185.7, 165.1, 140.7, 136.9, 135.9, 133.5, 130.0, 129.7, 40.7. Elemental Analysis Calc: C, 43.50; H, 3.32; Cl, 11.67; N, 4.61. Found: C, 43.66; H, 3.40; Cl, 11.54; N, 4.55. C$_{11}$H$_{10}$ClNO$_5$S; HPLC retention time: 25.2 min.

Example 5c

N-(3,4-dihydroxy-5-(4-chlorophenyl)-2-furanyl)ethanesulfonamide 5 g of 5-amino-4-hydroxy-2-(4-chlorophenyl)-furan-3-one was stirred in 50 mL of dry THF under nitrogen gas for 16 hours with 4.6 g K$_2$CO$_3$ and 2.1 mL of ethanesulfonyl chloride. The reaction was filtered, and the filtrate was acidified with 24 mL 1N HCl, and extracted 5 times with 20 mL of diethyl ether. The combined ether extracts were washed with brine, and dried with $Na_2SO_4$. After filtration, 100 mL of hexanes was added to the solution, resulting in a precipitate, which was collected using vacuum filtration and recrystallized with ethyl acetate. Yield=21%. mp 183-185° C.; FTIR 3181, 1616; $^1H$ NMR (300 MHz, DMSO-$d_6$, ppm) δ 8.41 (s, 1H), 8.08 (s, 1H), 7.95 (d, J=9.3 Hz, 2H), 7.85 (s, 1H), 7.59 (d, J=9.0 Hz, 2H), 3.68 (q, J=7.2 Hz, 2H), 1.40 (t, J=6.9 Hz, 3H). $^{13}C$ NMR (75 MHz, DMSO-d6, ppm) δ 185.8, 165.1, 140.7, 136.8, 136.1, 133.5, 130.0, 129.7, 48.0, 8.6. Elemental Analysis Calc: C, 45.36; H, 3.81; Cl, 11.16; N, 4.41. Found: C, 45.42; H, 3.85; Cl, 11.06; N, 4.37. $C_{12}H_{12}ClNO_5S$; HPLC retention time: 29.9 min.

Example 4c

N-(3,4-dihydroxy-5-(4-chlorophenyl)-2-furanyl) methanesulfonamide 5 g of 5-amino-4-hydroxy-2-(4-fluorophenyl)-furan-3-one is stirring in 50 mL dry THF under dry nitrogen. The reaction is cooling in an ice bath, and 1 equivalent of triethylamine is added dropwise. The reaction is warmed to room temperature, chlorotrimethylsilane is added dropwise and the reaction is refluxing gently with a water bath for 30 minutes. 1 equivalent of methyl sulfonyl chloride is added dropwise. 1 equivalent of TEA is added dropwise, and the reaction is gently refluxing with a water bath for 1 hour. The reaction is cooling to room temperature, and 1 equivalent of tetrabutylammonium fluoride is added and stirs for 30 minutes. A saturated ammonium sulfate solution is added to quench the reaction, and the reaction is extracted 3 times with 20 mL diethyl ether. The combined ether extracts are washed with water and brine, the ether is dried with sodium sulfate, is filtered, and evaporates to yield a solid which is recrystallized with methanol.

Example 6c

N-(3,4-dihydroxy-5-(4-chlorophenyl)-2-furanyl) benzenesulfonamide 5 g of 5-amino-4-hydroxy-2-(4-fluorophenyl)-furan-3-one is stirring in 50 mL dry THF under dry nitrogen. The reaction is cooling in an ice bath, and 1 equivalent of triethylamine is added dropwise. The reaction is warmed to room temperature, chlorotrimethylsilane is added dropwise and the reaction is refluxing gently with a water bath for 30 minutes. 1 equivalent of benzene sulfonyl chloride is added dropwise. 1 equivalent of TEA is added dropwise, and the reaction is gently refluxing with a water bath for 1 hour. The reaction is cooling to room temperature, and 1 equivalent of tetrabutylammonium fluoride is added and stirs for 30 minutes. A saturated ammonium sulfate solution is added to quench the reaction, and the reaction is extracted 3 times with 20 mL diethyl ether. The combined ether extracts are washed with water and brine, the ether is dried with sodium sulfate, is filtered, and evaporates to yield a solid which is recrystallized with methanol.

Example 7c

N-(3,4-dihydroxy-5-(4-chlorophenyl)-2-furanyl) acetamide 5 g of 5-amino-4-hydroxy-2-(4-fluorophenyl)-furan-3-one is stirring in 50 mL dry THF under dry nitrogen. The reaction is cooling in an ice bath, and 1 equivalent of triethylamine is added dropwise. The reaction is warmed to room temperature, chlorotrimethylsilane is added dropwise and the reaction is refluxing gently with a water bath for 30 minutes. 1 equivalent of acetyl chloride is added dropwise. 1 equivalent of TEA is added dropwise, and the reaction is gently refluxing with a water bath for 1 hour. The reaction is cooling to room temperature, and 1 equivalent of tetrabutylammonium fluoride is added and stirs for 30 minutes. A saturated ammonium sulfate solution is added to quench the reaction, and the reaction is extracted 3 times with 20 mL diethyl ether. The combined ether extracts are washed with water and brine, the ether is dried with sodium sulfate, is filtered, and evaporates to yield a solid which is recrystallized with methanol.

Example 9c

N-(3,4-dihydroxy-5-(4-chlorophenyl)-2-furanyl) benzamide 5 g of 5-amino-4-hydroxy-2-(4-fluorophenyl)-furan-3-one is stirring in 50 mL dry THF under dry nitrogen. The reaction is cooling in an ice bath, and 1 equivalent of triethylamine is added dropwise. The reaction is warmed to room temperature, chlorotrimethylsilane is added dropwise and the reaction is refluxing gently with a water bath for 30 minutes. 1 equivalent of benzoyl chloride is added dropwise. 1 equivalent of TEA is added dropwise, and the reaction is gently refluxing with a water bath for 1 hour. The reaction is cooling to room temperature, and 1 equivalent of tetrabutylammonium fluoride is added and stirs for 30 minutes. A saturated ammonium sulfate solution is added to quench the reaction, and the reaction is extracted 3 times with 20 mL diethyl ether. The combined ether extracts are washed with water and brine, the ether is dried with sodium sulfate, is filtered, and evaporates to yield a solid which is recrystallized with methanol.

Example 12c

N-(3,4-dihydroxy-5-(4-chlorophenyl)-2-furanyl) succinimide 5 g of 5-amino-4-hydroxy-2-(4-fluorophenyl)-furan-3-one is stirring in 50 mL pyridine under dry nitrogen. 1 equivalent of succinic anhydride is added, and the reaction is refluxing with a water bath for 1 hour. A saturated ammonium sulfate solution is added to quench the reaction, and the reaction is extracted 3 times with 20 mL diethyl ether. The combined ether extracts are washed with a saturated bicarbonate solution and brine, the ether is dried with sodium sulfate, is filtered, and evaporates to yield a solid which is recrystallized with methanol.

Example 28c 5-amino-2-(4-chlorophenyl)-2-methyl-4-trimethylsilyloxy-3(2H)-furanone 5 g of 5-amino-4-hydroxy-2-(4-fluorophenyl)-furan-3-one is stirring in 50 mL dry THF under dry nitrogen. The reaction is cooling in an ice bath, and 1 equivalent of LDA in THF/Hexanes is added dropwise. The reaction is slowly warmed to room temperature for 30 minutes, and is cooled with an ice bath. 1 equivalent of chlorotrimethylsilane is added dropwise, and the reaction is slowly warmed to room temperature and stirs for 1 hour. The reaction is cooled with an ice bath, and 1 equivalent of LDA in THF/Hexanes is added dropwise, and the reaction is slowly warmed to room temperature for 30 minutes. The reaction is cooled with an ice bath, and 1 equivalent of methyl iodide in THF is added slowly dropwise. The reaction is slowly warmed to room temperature and stirs for 1 hour.

Example 29c 5-amino-2-(4-chlorophenyl)-2-methyl-4-hydroxy-3(2H)-furanone 5 g of 5-amino-2-(4-chlorophenyl)-2-methyl-4-trimethylsilyloxy-3(2H)-furanone is stirring in THF at room temperature. 1 equivalent of tetrabutylammonium fluoride is added, and the reaction stirs for 30 minutes. An ammonium sulfate solution is added to quench the reaction, and the reaction is extracted 3 times with 20 mL diethyl ether. The combined ether extracts are washed with water and brine, the ether is dried with sodium sulfate, is filtered, and evaporates to yield a solid which is recrystallized with methanol.

Example 30c

N-(3-hydroxy-5-(4-chlorophenyl)-5-methyl-2-3(2H)-furanonyl)-methanesulfonamide 5 g of 5-amino-4-hydroxy-2-(4-fluorophenyl)2-methyl-furan-3-one is stirring in 50 mL dry THF under dry nitrogen. The reaction is cooling in an ice bath, and 1 equivalent of triethylamine is added dropwise. The reaction is warmed to room temperature, chlorotrimethylsilane is added dropwise and the reaction is refluxing gently with a water bath for 30 minutes. 1 equivalent of methyl sulfonyl chloride is added dropwise. 1 equivalent of TEA is added dropwise, and the reaction is gently refluxing with a water bath for 1 hour. The reaction is cooling to room temperature and 1 equivalent of tetrabutylammonium fluoride is added and stirs for 30 minutes. A saturated ammonium sulfate solution is added to quench the reaction, and the reaction is extracted 3 times with 20 mL diethyl ether. The combined ether extracts are washed with water and brine, the ether is dried with sodium sulfate, is filtered, and evaporates to yield a solid which is recrystallized with methanol.

Example 31c

N-(3-hydroxy-5-(4-chlorophenyl)-5-methyl-2-3(2H)-furanonyl)-ethanesulfonamide 5 g of 5-amino-4-hydroxy-2-(4-fluorophenyl)2-methyl-furan-3-one is stirring in 50 mL dry THF under reaction is warmed to room temperature, chlorotrimethylsilane is added dropwise and the reaction is refluxing gently with a water bath for 30 minutes 1 equivalent of ethyl sulfonyl chloride is added dropwise. 1 equivalent of TEA is added dropwise, and the reaction is gently refluxing with a water bath for 1 hour. The reaction is cooling to room temperature and 1 equivalent of tetrabutylammonium fluoride is added and stirs for 30 minutes. A saturated ammonium sulfate solution is added to quench the reaction, and the reaction is extracted 3 times with 20 mL diethyl ether. The combined ether extracts are washed with water and brine, the ether is dried with sodium sulfate, is filtered, and evaporates to yield a solid which is recrystallized with methanol.

Example 32c

N-(3-hydroxy-5-(4-chlorophenyl)-5-methyl-2-3(2H)-furanonyl)-benzenesulfonamide 5 g of 5-amino-4-hydroxy-2-(4-fluorophenyl)2-methyl-furan-3-one is stirring in 50 mL dry THF under dry nitrogen. The reaction is cooling in an ice bath, and 1 equivalent of triethylamine is added dropwise. The reaction is warmed to room temperature, chlorotrimethylsilane is added dropwise and the reaction is refluxing gently with a water bath for 30 minutes. 1 equivalent of benzene sulfonyl chloride is added dropwise. 1 equivalent of TEA is added dropwise, and the reaction is gently refluxing with a water bath for 1 hour. The reaction is cooling to room temperature and 1 equivalent of tetrabutylammonium fluoride is added and stirs for 30 minutes. A saturated ammonium sulfate solution is added to quench the reaction, and the reaction is extracted 3 times with 20 mL diethyl ether. The combined ether extracts are washed with water and brine, the ether is dried with sodium sulfate, is filtered, and evaporates to yield a solid which is recrystallized with methanol.

Example 33c

N-(3-hydroxy-5-(4-chlorophenyl)-5-methyl-2-3(2H)-furanonyl)-acetamide 5 g of 5-amino-4-hydroxy-2-(4-fluorophenyl)2-methyl-furan-3-one is stirring in 50 mL dry THF under dry nitrogen. The reaction is cooling in an ice bath, and 1 equivalent of triethylamine is added dropwise. The reaction is warmed to room temperature, chlorotrimethylsilane is added dropwise and the reaction is refluxing gently with a water bath for 30 minutes. 1 equivalent of acetyl chloride is added dropwise. 1 equivalent of TEA is added dropwise, and the reaction is gently refluxing with a water bath for 1 hour. The reaction is cooling to room temperature and 1 equivalent of tetrabutylammonium fluoride is added and stirs for 30 minutes. A saturated ammonium sulfate solution is added to quench the reaction, and the reaction is extracted 3 times with 20 mL diethyl ether. The combined ether extracts are washed with water and brine, the ether is dried with sodium sulfate, is filtered, and evaporates to yield a solid which is recrystallized with methanol.

Example 35c

N-(3-hydroxy-5-(4-chlorophenyl)-5-methyl-2-3(2H)-furanonyl)-benzamide 5 g of 5-amino-4-hydroxy-2-(4-fluorophenyl)2-methyl-furan-3-one is stirring in 50 mL dry THF under dry nitrogen. The reaction is cooling in an ice bath, and 1 equivalent of triethylamine is added dropwise. The reaction is warmed to room temperature, chlorotrimethylsilane is added dropwise and the reaction is refluxing gently with a water bath for 30 minutes. 1 equivalent of benzoyl chloride is added dropwise. 1 equivalent of TEA is added dropwise, and the reaction is gently refluxing with a water bath for 1 hour. The reaction is cooling to room temperature and 1 equivalent of tetrabutylammonium fluoride is added and stirs for 30 minutes. A saturated ammonium sulfate solution is added to quench the reaction, and the reaction is ether is dried with sodium sulfate, is filtered, and evaporates to yield a solid which is recrystallized with methanol.

Example 38c

N-(3-hydroxy-5-(4-chlorophenyl)-5-methyl-2-3(2H)-furanonyl)-succinimide 5 g of 5-amino-4-hydroxy-2-(4-fluorophenyl)-2-methyl-furan-3-one is stirring in 50 mL dry THF under dry nitrogen. 1 equivalent of succinic anhydride and catalytic sulfamic acid is added, and the reaction is refluxing gently with a water bath for 1 hour. A saturated ammonium sulfate solution is added to quench the reaction, and the reaction is extracted 3 times with 20 mL diethyl ether. The combined ether extracts are washed with a saturated bicarbonate solution and brine, the ether is dried with sodium sulfate, is filtered, and evaporates to yield a solid which is recrystalized with methanol.

OTHER EMBODIMENTS

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A method of producing a compound of Formula Ia:

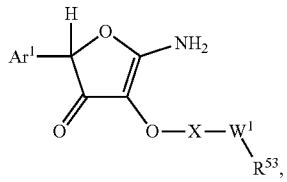

(Ia)

comprising
contacting an amine compound of Formula (IIIa)

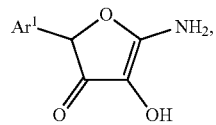

(IIIa)

with
a sulfonyl chloride of the formula $ClSO_2(CR^{50}R^{51})Ar^2$ or $ClSO_2R^{53}$;
a compound of the formula $ClCO_2Ar^2$; or
a compound of the formula $SCNAr^2$ under a suitable condition to produce the compound Formula Ia; wherein
$Ar^1$ is substituted or unsubstituted $C_6$-$C_{20}$ aryl or heteroaryl that is 5-6 membered monocyclic or 8-12 membered bicyclic aromatic ring containing 1-3 heteroatoms selected from the group consisting of O, N and S, each substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, $—S(O)_bR_a$, $—S(O)_bNR_aR_b$, and $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S; and each of $R_{S1}$ and $R_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, and 5- or 6-membered heteroaryl containing 1-3 heteroatoms selected from the group consisting of O, N and S;

$Ar^2$ is unsubstituted $C_6$-$C_{14}$ aryl, unsubstituted 5 to 12-membered heteroaryl that is 5-6 membered monocyclic or 8-12 membered bicyclic aromatic ring containing 1-3 heteroatoms selected from O, N and S, or substituted $C_6$-$C_{14}$ aryl each substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, $—S(O)_bR_a$, $—S(O)_bNR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S; and each of $R_{S1}$ and $R_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, and 5- or 6-membered heteroaryl containing 1-3 heteroatoms selected from the group consisting of O, N and S;

X is C(O), C(S), or $S(O)_2$;

$W^1$ is O when X is C(O);

$W^1$ is NH when X is C(S); and $W^1$ is a single bond or $CR^{50}R^{51}$ when X is $SO_2$;

each of $R^{50}$ or $R^{51}$, is independently selected from the group consisting of hydrogen, substituted or unsubstituted $C_1$-$C_6$ alkyl, substituted or unsubstituted $C_2$-$C_6$ alkenyl, substituted or unsubstituted $C_2$-$C_6$ alkynyl; and $R^{53}$ is selected from the group consisting of substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{20}$ aryl, substituted or unsubstituted $C_7$-$C_{26}$ arylalkyl, substituted or unsubstituted 5 to 12-membered heteroaryl that is 5-6 membered monocyclic or 8-12 membered bicyclic aromatic ring containing 1-3 heteroatoms selected from the group consisting of O, N and S, and substituted or unsubstituted 6-26 membered heteroarylalkyl, provided that when $Ar^1$ is 4-chlorophenyl, then $R^{53}$ is not methyl or unsubstituted phenyl, each substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, $—S(O)_b R_a$, $—S(O)_bNR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S; and each of $R_{S1}$ and $R_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, and 5- or 6-membered heteroaryl containing 1-3 heteroatoms selected from the group consisting of O, N and S.

2. The method of claim 1, wherein $R^{53}$ is unsubstituted $C_1$-$C_6$ alkyl or $C_1$-$C_6$ alkyl substituted with one or more substituents selected from halo, OH, CN, and amino.

3. The method of claim 1, wherein X is $S(O)_2$ and $W^1$ is $CR^{50}R^{51}$.

4. The method of claim 1, wherein X is $S(O)_2$ and $W^1$ is a single bond.

5. The method of claim 1, wherein X is C(O) and $W^1$ is O, or X is C(S) and $W^1$ is NH.

6. The method of claim 1, wherein each of $Ar^1$ and $Ar^2$ independently is phenyl, naphthyl, or 5 to 10-membered heteroaryl that is 5-6 membered monocyclic or 8-10 membered bicyclic aromatic ring containing 1-3 heteroatoms selected from O, N and S, each of which is optionally substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, $—S(O)_bR_a$, $—S(O)_bNR_aR_b$, and $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S; and each of $R_{S1}$ and $R_{S2}$, is optionally substituted with one or more substituents selected from the group consisting of halo, OH, oxo, C(O)OH, C(O)O—$C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, and 5- or 6-membered heteroaryl containing 1-3 heteroatoms selected from the group consisting of O, N and S.

7. The method of claim 1, wherein each of $Ar^1$ and $Ar^2$ independently is phenyl, naphthyl, or 5 to 10-membered heteroaryl that is 5-6 membered monocyclic or 8-10 membered bicyclic aromatic ring containing 1-3 heteroatoms selected from O, N and S, each of which is optionally substituted with one or more substituents selected from the group consisting of halo, CN, $NO_2$, NO, $N_3$, $OR_a$, $NR_aR_b$, $C(O)R_a$, $C(O)OR_a$, and $R_{S1}$, in which $R_{S1}$ is $C_1$-$C_6$ alkyl, each of $R_a$ and $R_b$, independently is H or $R_{S2}$, and $R_{S2}$ is $C_1$-$C_6$ alkyl; and each of $R_{S1}$ and $R_{S2}$, is optionally substituted with one or more substituents selected from the group consisting of halo, OH, $C_1$-$C_6$ alkoxyl, amino, mono-$C_1$-$C_6$ alkylamino, and di-$C_1$-$C_6$ alkylamino.

8. The method of claim 1, wherein each of $Ar^1$ and $Ar^2$ independently is selected from phenyl, 1-naphthyl, 2-naphthyl, 2-furanyl, 2-thiazolyl, 2-pyridyl, 3-pyridyl, 4-pyridyl, 2-quinolinyl, 3-quinolinyl, 4-quinolinyl, 2-chlorophenyl, 3-chlorophenyl, 4-chlorophenyl, 2-fluorophenyl, 3-fluorophenyl, 4-fluorophenyl, 2-trifluoromethylphenyl, 3-trifluoromethylphenyl, 4-trifluoromethylphenyl, 2-cyanophenyl, 3-cyanophenyl, 4-cyanophenyl, 3-carboxymethylphenyl, 2-methoxyphenyl, 3-methoxyphenyl, 4-methoxyphenyl, 2,3-dichlorophenyl, 2,4-dichlorophenyl, 2,5-dichlorophenyl, 3,4-dichlorophenyl, 3,5-dichlorophenyl, 2,3-difluorophenyl, 2,4-difluorophenyl, 2,5-difluorophenyl, 3,4-difluorophenyl, 3,5-difluorophenyl, 2,3-dimethoxyphenyl, 2,4-dimethoxyphenyl, 2,5-dimethoxyphenyl, 3,4-dimethoxyphenyl, 3,5-dimethoxyphenyl, 2-chloro-6-fluorophenyl, 3-chloro-4-fluorophenyl, 2-chloro-4-fluorophenyl, 4-chloro-3-fluorophenyl, 3-chloro-2-fluorophenyl, 2-chloro-5-fluorophenyl, 4-chloro-2-fluorophenyl, and 5-chloro-2-fluorophenyl.

9. The method of claim 1 wherein the compound of Formula Ia is

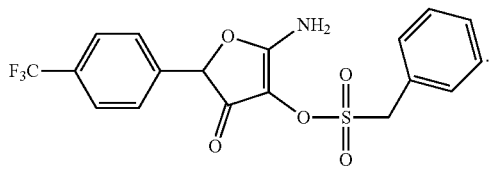 [SMILES: NC1=C(OS(=O)(=O)Cc2ccccc2)C(=O)C(c2ccc(C(F)(F)F)cc2)O1]

10. The method of claim 1, wherein the contacting is done in the presence of a base.

11. A method of producing a compound of Formula Ia:

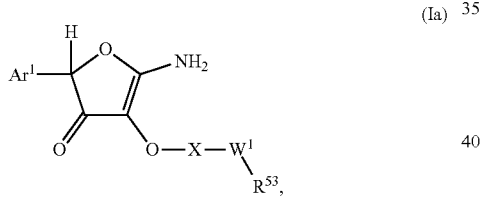

comprising
contacting an amine compound of Formula (IIIa)

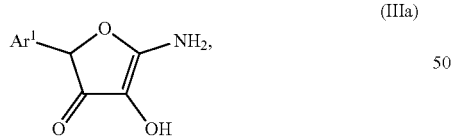

with
a compound of the formula $ClSO_2W^1R^{53}$ or $ClC(O)W^1R^{53}$; or
a compound of the formula $SCNR^{53}$ or $OCNR^{53}$; under a suitable condition to produce the compound Formula Ia; wherein
$Ar^1$ is substituted or unsubstituted $C_6$-$C_{20}$ aryl or heteroaryl that is 5-6 membered monocyclic or 8-12 membered bicyclic aromatic ring containing 1-3 heteroatoms selected from the group consisting of O, N and S, each substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, $-S(O)_bR_a$, $-S(O)_bNR_aR_b$, and $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S; and each of $R_{S1}$ and $R_{S2}$, is optionally substituted with one or more substituents selected from the group consisting of halo, OH, oxo, C(O)OH, $C(O)O-C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, and 5- or 6-membered heteroaryl containing 1-3 heteroatoms selected from the group consisting of O, N and S;

X is C(O), C(S), or $S(O)_2$;
$W^1$ is a single bond, O, $CR^{50}R^{51}$, or NH when X is C(O); a single bond or $CR^{50}R^{51}$ when X is $SO_2$; or NH when X is C(S);
each of $R^{50}$ or $R^{51}$ is independently selected from the group consisting of hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{20}$ aryl, substituted or unsubstituted $C_7$-$C_{26}$ arylalkyl, substituted or unsubstituted 5 to 12-membered heteroaryl that is 5-6 membered monocyclic or 8-12 membered bicyclic aromatic ring containing 1-3 heteroatoms selected from the group consisting of O, N and S, and substituted or unsubstituted 6-26 membered heteroarylalkyl; and
$R^{53}$ is selected from the group consisting of substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{20}$ aryl, substituted or unsubstituted $C_7$-$C_{26}$ arylalkyl, substituted or unsubstituted 5 to 12-membered heteroaryl that is 5-6 membered monocyclic or 8-12 membered bicyclic aromatic ring containing 1-3 heteroatoms selected from the group consisting of O, N and S, and substituted or unsubstituted 6-26 membered heteroarylalkyl, provided that when $Ar^1$ is 4-chlorophenyl, then $R^{53}$ is not methyl or unsubstituted phenyl, each substituted with one or more substituents selected from the group consisting of halo, CN, $NO_2$, NO, $N_3$, $OR_a$, $NR_aR_b$, $C(O)R_a$, $C(O)OR_a$, $C(O)NR_aR_b$, $NR_bC(O)R_a$, $-S(O)_bR_a$, $-S(O)_bNR_aR_b$, or $R_{S1}$, in which $R_{S1}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S, b is 0, 1, or 2, each of $R_a$ and $R_b$, independently is H or $R_{S2}$, and $R_{S2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, or 5- or 6-membered heteroaryl containing 1-3 heteroatoms selected from the group consisting of O, N and S; and each of $R_{S1}$ and $R_{S2}$, is optionally substituted with one or more substituents selected from the group consisting of halo, OH, oxo, C(O)OH, $C(O)O-C_1$-$C_6$ alkyl, CN, $C_1$-$C_6$ alkyl, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, and 5- or 6-membered heteroaryl containing 1-3 heteroatoms selected from the group consisting of O, N and S.

* * * * *